(12) United States Patent
Eckelbarger et al.

(10) Patent No.: US 9,113,629 B2
(45) Date of Patent: Aug. 25, 2015

(54) 4-AMINO-6-(4-SUBSTITUTED-PHENYL)-PICOLINATES AND 6-AMINO-2-(4-SUBSTITUTED-PHENYL)-PYRIMIDINE-4-CARBOXYLATES AND THEIR USE AS HERBICIDES

(71) Applicant: DOW AGROSCIENCES LLC, Indianapolis, IN (US)

(72) Inventors: Joseph D. Eckelbarger, Carmel, IN (US); Jeffrey B. Epp, Noblesville, IN (US); Lindsey G. Fischer, Indianapolis, IN (US); Natalie C. Giampietro, Carmel, IN (US); Nicholas M. Irvine, Westfield, IN (US); Jeremy Kister, Carmel, IN (US); William C. Lo, Fishers, IN (US); Christian T. Lowe, Westfield, IN (US); Jeffrey Petkus, Indianapolis, IN (US); Joshua Roth, Carmel, IN (US); Norbert M. Satchivi, Carmel, IN (US); Paul R. Schmitzer, Indianapolis, IN (US); Thomas L. Siddall, Zionsville, IN (US); Carla N. Yerkes, Crawfordsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/840,233

(22) Filed: Mar. 15, 2013

(65) Prior Publication Data

US 2014/0274696 A1    Sep. 18, 2014

(51) Int. Cl.
| | |
|---|---|
| *A01N 43/40* | (2006.01) |
| *A01N 43/54* | (2006.01) |
| *C07D 213/79* | (2006.01) |
| *C07D 239/42* | (2006.01) |
| *C07D 239/47* | (2006.01) |
| *C07D 213/73* | (2006.01) |

(52) U.S. Cl.
CPC .............. *A01N 43/54* (2013.01); *A01N 43/40* (2013.01); *C07D 213/79* (2013.01); *C07D 239/42* (2013.01); *C07D 239/47* (2013.01); *C07D 213/73* (2013.01)

(58) Field of Classification Search
CPC .. C07D 239/42; C07D 213/74; C07D 213/85; C07D 213/73; A61K 31/4418; A61K 31/505; A01N 43/40
USPC .......... 514/256, 344, 352, 353; 544/329, 286, 544/289
See application file for complete search history.

(56) References Cited

U.S. PATENT DOCUMENTS

| | | | |
|---|---|---|---|
| 7,498,468 B2 * | 3/2009 | Balko et al. ........................ 568/1 |
| 8,143,411 B2 * | 3/2012 | BÄRfacker et al. .......... 546/318 |
| 8,329,732 B2 * | 12/2012 | Burger et al. .................. 514/332 |
| 8,357,633 B2 | 1/2013 | Epp et al. |
| 8,658,568 B2 * | 2/2014 | Eckelbarger et al. .......... 504/193 |
| 8,658,791 B2 * | 2/2014 | Epp et al. ....................... 544/255 |
| 8,754,229 B2 * | 6/2014 | Epp et al. ....................... 546/290 |
| 8,889,694 B2 * | 11/2014 | Eckelbarger et al. ......... 514/256 |
| 2009/0088322 A1 | 4/2009 | Epp et al. |
| 2010/0137138 A1 | 6/2010 | Rosinger et al. |
| 2010/0234432 A1 * | 9/2010 | Baerfacker et al. ........... 514/350 |
| 2010/0285963 A1 * | 11/2010 | Muller et al. .................. 504/214 |
| 2011/0077156 A1 | 3/2011 | Clark et al. |
| 2011/0105325 A1 | 5/2011 | Satchivi et al. |
| 2012/0015811 A1 | 1/2012 | Dave et al. |
| 2012/0053053 A1 | 3/2012 | Boussemghoune et al. |
| 2012/0157314 A1 | 6/2012 | Ahrens et al. |
| 2012/0190548 A1 | 7/2012 | Eckelbarger et al. |
| 2012/0190549 A1 | 7/2012 | Eckelbarger et al. |
| 2012/0190551 A1 | 7/2012 | Yerkes et al. |
| 2013/0005574 A1 * | 1/2013 | Epp et al. ....................... 504/193 |

FOREIGN PATENT DOCUMENTS

| | | |
|---|---|---|
| AU | 2011317665 | 4/2013 |
| WO | WO 03/011853 A1 | 2/2003 |
| WO | WO 03011853 A1 * | 2/2003 |
| WO | WO 2005/063721 A1 | 7/2005 |
| WO | WO 2005063721 A1 * | 7/2005 |
| WO | WO 2007/082076 A1 | 7/2007 |
| WO | WO 2007/082098 A2 | 7/2007 |
| WO | WO 2007/092184 A2 | 8/2007 |
| WO | WO 2009/023438 A1 | 2/2009 |
| WO | WO 2009023438 A1 * | 2/2009 |
| WO | WO 2009/029735 A1 | 3/2009 |
| WO | WO 2009029735 A1 * | 3/2009 |
| WO | WO 2010/092339 A1 | 8/2010 |
| WO | WO 2010092339 A1 * | 8/2010 |
| WO | WO 2010/099279 A1 | 9/2010 |
| WO | WO 2010/125332 A1 | 11/2010 |
| WO | WO 2012/052410 A1 | 4/2012 |
| WO | WO 2012/080187 A1 | 6/2012 |
| WO | WO 2012103051 A2 * | 8/2012 |
| WO | WO 2013/003740 A1 | 1/2013 |
| WO | WO 2013003740 A1 * | 1/2013 |

* cited by examiner

*Primary Examiner* — Alexander R Pagano

(74) *Attorney, Agent, or Firm* — Michael J. Terapane; Meunier Carlin & Curfman LLC

(57) ABSTRACT

Provided herein are 4-amino-6-(4-substituted-phenyl)-picolinic acids and their derivatives, and 6-amino-2-(4-substituted-phenyl)-pyrimidine-4-carboxylic acids and their derivatives, compositions comprising the acids and their derivatives, and methods of use thereof as herbicides.

30 Claims, No Drawings

4-AMINO-6-(4-SUBSTITUTED-PHENYL)-PICOLINATES AND 6-AMINO-2-(4-SUBSTITUTED-PHENYL)-PYRIMIDINE-4-CARBOXYLATES AND THEIR USE AS HERBICIDES

FIELD

Provided herein are herbicidal compounds and compositions and methods for controlling undesirable vegetation.

BACKGROUND

The occurrence of undesirable vegetation, e.g., weeds, is a constant problem facing farmers in crops, pasture, and other settings. Weeds compete with crops and negatively impact crop yield. The use of chemical herbicides is an important tool in controlling undesirable vegetation.

There remains a need for new chemical herbicides that offer a broader spectrum of weed control, selectivity, minimal crop damage, storage stability, ease of handling, higher activity against weeds, and/or a means to address herbicide-tolerance that develops with respect to herbicides currently in use.

SUMMARY

Provided herein are compounds of Formula (I):

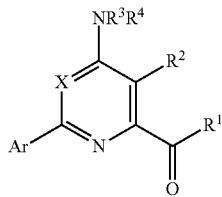

(I)

wherein

X is N or CY; wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{2''}$; wherein $R^{1'}$ is H, $C_1$-$C_8$ alkyl, or $C_7$-$C_{10}$ arylalkyl; and $R^{1''}$ and $R^{2''}$ are each independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, ($C_1$-$C_3$ alkyl)carbonyl, ($C_1$-$C_3$ haloalkyl)carbonyl, cyano, or a group of the formula —$CR^{17}$=$CR^{18}$—$SiR^{19}R^{20}R^{21}$; wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are each independently $C_1$-$C_{10}$ alkyl, $C_3$-$C_6$ cycloalkyl, $C_1$-$C_{10}$ haloalkyl, $C_3$-$C_6$ halocycloalkyl, phenyl, substituted phenyl, $C_1$-$C_{10}$ alkoxy, or OH;

$R^3$ and $R^4$ are each independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, hydroxy, $C_1$-$C_6$ alkoxy, $C_1$-$C_6$ haloalkoxy, formyl, ($C_1$-$C_3$ alkyl)carbonyl, ($C_1$-$C_3$ haloalkyl)carbonyl, ($C_1$-$C_6$ alkoxy)carbonyl, ($C_1$-$C_6$ alkyl)carbamyl, $C_1$-$C_6$ alkylsulfonyl, tri($C_1$-$C_6$ alkyl)silyl, di($C_1$-$C_6$ alkyl)phosphonyl, or $R^3$ and $R^4$ together with the nitrogen atom to which they are attached form a 5- or 6-membered saturated ring, or $R^3$ and $R^4$ taken together represent =$CR^{3'}R^{4'}$, wherein $R^{3'}$ and $R^{4'}$ are each independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino, or $R^{3'}$ and $R^{4'}$ together with the carbon atom to which they are attached form a 5- or 6-membered saturated ring;

Ar is Ar1, Ar2, Ar3, Ar4, Ar5, or Ar6:

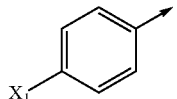
Ar1

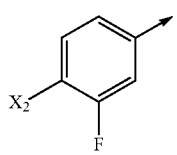
Ar2

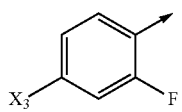
Ar3

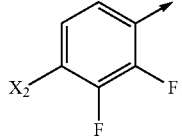
Ar4

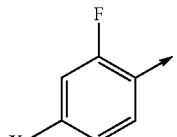
Ar5

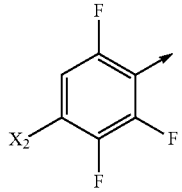
Ar6 wherein $X_1$ is H, F, Br, I, ethynyl, $CF_2H$, $OCF_2H$, $OCF_3$, CN, $CONH_2$, $CO_2H$, $CO_2CH_3$, or $NO_2$;

$X_2$ is H, F, Cl, Br, I, ethynyl, $CH_3$, $CFH_2$, $CF_2H$, $CF_3$, $OCF_2H$, $OCF_3$, CN, $CONH_2$, $CO_2H$, or $NO_2$;

$X_3$ is H, F, Br, I, ethynyl, $CH_3$, $CFH_2$, $CF_2H$, $CF_3$, $OCF_2H$, $OCF_3$, CN, $CONH_2$, $CO_2H$, or $NO_2$;

wherein a) when Ar is

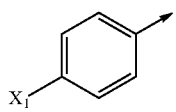

, then X is N, CH, CF, CCl, or $CCH_3$;

with provisos that:

i) $R^2$ is not Cl or vinyl, when X is N;

ii) $X_1$ is not H, F, $OCF_3$, or CN, when $R^2$ is Cl and X is CH;

iii) $X_1$ is not F, I, CN, or ethynyl, when $R^2$ is $OCH_3$ and X is CF;

iv) $X_1$ is not H, when X is CCl; and
b) when Ar is

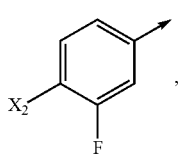

then X is N, CH, CF, CCl, or $CCH_3$;
with provisos that:
  i) $R^2$ is not Cl, when X is N;
  ii) $X_2$ is not Cl, when $R^2$ is $OCH_3$ or vinyl and X is N;
  iii) $X_2$ is not Cl, when $R^2$ is Cl and X is CH;
  iv) $X_2$ is not Cl, Br, I, or $CF_3$, when $R^2$ is $OCH_3$ and X is CF; and
c) when Ar is

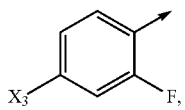

then X is N, CH, or CF;
with provisos that:
  i) $R^2$ is not Cl, when X is N;
  ii) $X_3$ is not $CH_3$, when $R^2$ is $OCH_3$ and X is N;
  iii) $X_3$ is not H, F, or $CH_3$, when $R^2$ is Cl and X is CH;
  iv) $X_3$ is not Br or I, when $R^2$ is $OCH_3$ and X is CF; and
d) when Ar is

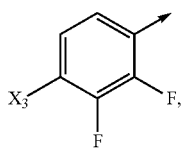

then X is N, CH, or CF;
with provisos that:
  i) $R^2$ is not Cl, when X is N;
  $X_2$ is not Cl, when $R^2$ is $OCH_3$ or vinyl and X is N;
  iii) $X_2$ is not F, when $R^2$ is Cl and X is CH;
  iv) $X_2$ is not Cl, Br, I, or $CF_3$, when $R^2$ is $OCH_3$ and X is CF;
e) when Ar is

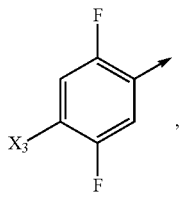

then X is N, CH, or CF;
with proviso that:
  i) $X_3$ is not $CH_3$, when $R^2$ is Cl and X is N;
  ii) $X_3$ is not Br or I, when X is CF and $R^2$ is $OCH_3$; and f) when Ar is

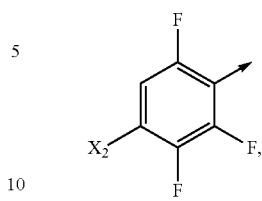

then X is N, CH, or CF;
or an N-oxide or agriculturally acceptable salt thereof.

Also provided are methods of controlling undesirable vegetation comprising (a) contacting the undesirable vegetation or area adjacent to the undesirable vegetation, or (b) pre-emergently contacting soil or water, a herbicidally effective amount of at least one compound of Formula (I) or agriculturally acceptable derivative (e.g., agriculturally acceptable salts, solvates, hydrates, esters, amides, N-oxides, or other derivatives) thereof.

DETAILED DESCRIPTION

As used herein, herbicide and herbicidal active ingredient mean a compound that controls undesirable vegetation when applied in an appropriate amount.

As used herein, control of or controlling undesirable vegetation means killing or preventing the vegetation, or causing some other adverse modifying effect to the vegetation e.g., deviations from natural growth or development, regulation, desiccation, retardation, and the like.

As used herein, a herbicidally effective or vegetation controlling amount is an amount of herbicidal active ingredient the application of which controls the relevant undesirable vegetation.

As used herein, applying an herbicide or herbicidal composition means delivering it directly to the targeted vegetation or to the locus thereof or to the area where control of undesired vegetation is desired. Methods of application include, but are not limited to, pre-emergently contacting soil or water, or post-emergently contacting the undesirable vegetation or area adjacent to the undesirable vegetation.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Suitable salts include those derived from alkali or alkaline earth metals and those derived from ammonia and amines. Preferred cations include sodium, potassium, magnesium, and aminium cations of the formula:

$R^{13}R^{14}R^{15}R^{16}N^+$ wherein $R^{13}$, $R^{14}$, $R^{15}$ and $R^{16}$ each, independently represents hydrogen or $C_1$-$C_{12}$ alkyl, $C_3$-$C_{12}$ alkenyl, or $C_3$-$C_{12}$ alkynyl, each of which is optionally substituted by one or more substituents such as hydroxy, alkoxy, $C_1$-$C_4$ alkylthio, or phenyl groups, provided that $R^{13}$, $R^{14}$, $R^{15}$ and $R^{16}$ are sterically compatible. Additionally, any two $R^{13}$, $R^{14}$, $R^{15}$ and $R^{16}$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methyl-thiopropylamine, bisallylamine, 2-butoxyethylamine, morpholine, cyclododecylamine, or benzylamine, or with a tetraalkylammonium hydroxide, such as tetramethylammonium hydroxide or choline hydroxide. Amine salts of compounds of Formula I are useful forms or derivatives of compounds of Formula I because they are water-soluble and lend themselves to the preparation of desirable aqueous based herbicidal compositions.

Other forms or derivatives of compounds of the Formula I include N-oxides of compounds of Formula I. Pyridine N-oxides can be obtained by oxidation of the corresponding pyridines. Suitable oxidation methods are described, for example, in Houben-Weyl, Methoden der organischen Chemie [Methods in organic chemistry], expanded and subsequent volumes to the 4th edition, volume E 7b, p. 565 f.

As used herein "acyl" includes formyl, ($C_1$-$C_3$ alkyl)carbonyl, and ($C_1$-$C_3$ haloalkyl)carbonyl.

As used herein, "alkyl" refers to saturated, straight-chained or branched hydrocarbon moieties. Unless otherwise specified, $C_1$-$C_{10}$ alkyl groups are intended. Examples include, but are not limited to, methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl.

As used herein, "haloalkyl" refers to straight-chained or branched alkyl groups, where in these groups the hydrogen atoms may partially or entirely be substituted with one or more halogen atom(s). Unless otherwise specified, $C_1$-$C_8$ groups are intended. Examples include, but are not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentatluoroethyl, and 1,1,1-trifluoroprop-2-yl.

As used herein, "alkenyl" refers to unsaturated, straight-chained, or branched hydrocarbon moieties containing one or more double bond(s). Unless otherwise specified, $C_2$-$C_8$ alkenyl are intended. Alkenyl groups may contain more than one unsaturated bond. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, tenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl.

As used herein, "alkynyl" represents straight-chained or branched hydrocarbon moieties containing one or more triple bond(s). Unless otherwise specified, $C_2$-$C_8$ alkynyl groups are intended. Alkynyl groups may contain more than one unsaturated bond. Examples include, but are not limited to, $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butinyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl.

As used herein, "alkoxy" refers to a group of the formula R—O—, where R is alkyl as defined above. Unless otherwise specified, alkoxy groups wherein R is a $C_1$-$C_8$ alkyl group are intended. Examples include, but are not limited to, methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, "haloalkoxy" refers to a group of the formula R—O—, where R is haloalkyl as defined above. Unless otherwise specified, haloalkoxy groups wherein R is a $C_1$-$C_8$ alkyl group are intended. Examples include, but are not limited to, chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro, 2-difluoroethoxy, 2,2-dichloro-2-fluoroethoxy, 2,2,2-trichloroethoxy, pentafluoroethoxy, and 1,1,1-trifluoroprop-2-oxy.

As used herein, "alkylthio" refers to a group of the formula R—S— where R is alkyl as defined above. Unless otherwise specified, alkylthio groups wherein R is a $C_1$-$C_8$ alkyl group are intended. Examples include, but are not limited to, methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dio-methylpropylthio, 1-ethylpropylthio, hexylthio, 1,1-dimethyl propylthio, 1,2-dimethyl propylthio, 1-methylpentylthio, 2-methylpentylthio, 3-methylpentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethylbutylthio, 1,1,2-trimethyl propylthio, 1,2,2-trimethyl propylthio, 1-ethyl-1-methyl propylthio, and 1-ethyl-2-methylpropylthio.

As used herein, "haloalkylthio" refers to an alkylthio group as defined above wherein the carbon atoms are partially or entirely substituted with one or more halogen atoms. Unless otherwise specified, haloalkylthio groups wherein R is a $C_1$-$C_8$ alkyl group are intended. Examples include, but are not limited to, chloromethylthio, bromomethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, "aryl," as well as derivative terms such as "aryloxy," refers to a phenyl, indanyl, or naphthyl group. In some embodiments, phenyl is preferred. The term "heteroaryl," as well as derivative terms such as "heteroaryloxy," refers to a 5- or 6-membered aromatic ring containing one or more heteroatoms, e.g., N, O or S; these heteroaromatic rings may be fused to other aromatic systems. The aryl or heteroaryl substituents may be unsubstituted or substituted with one or more substituents selected from, e.g., halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, ($C_1$-$C_6$ alkoxy)carbonyl, $C_1$-$C_6$ carbamoyl, hydroxycarbonyl, ($C_1$-$C_6$ alkyl)carbonyl, aminocarbonyl, ($C_1$-$C_6$ alkylamino)carbonyl, (di($C_1$-$C_6$ alkyl)amino)carbonyl, provided that the substituents are sterically compatible and the rules of chemical bonding and strain energy are satisfied. In some embodiments, preferred substituents include, for example, halogen, $C_1$-$C_2$ alkyl, and $C_1$-$C_2$ haloalkyl.

As used herein, "alkoxycarbonyl" refers to a group of the formula

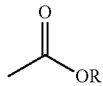

wherein R is alkyl.

As used herein, "alkylamino" or "dialkylamino" refers to an amino group substituted with one or two alkyl groups, which may be the same or different.

As used herein, "alkylcarbamyl" refers to a carbamyl group substituted on the nitrogen with an alkyl group.

As used herein, "alkylsulfonyl" refers to —$SO_2R$, wherein R is alkyl (e.g., $C_1$-$C_{10}$ alkyl).

As used herein, "carbamyl" (also referred to as carbamoyl or aminocarbonyl) refers to a group of the formula

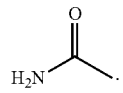

As used herein, "haloalkylamino" refers to an alkylamino group wherein the alkyl carbon atoms are partially or entirely substituted with one or more halogen atoms, As used herein, "Me" refers to a methyl group.

As used herein, the term "halogen," including derivative terms such as "halo," refers to fluorine, chlorine, bromine, or iodine (or fluoride, chloride, bromide, or iodide).

As used herein, plants and vegetation include, but are not limited to, germinant seeds, emerging seedlings, plants emerging from vegetative propagules, immature vegetation, and established vegetation.

Compounds

Provided herein are compounds of Formula (I) as defined herein (e.g., in the Summary above) and N-oxides and agriculturally acceptable salts thereof.

In some embodiments, the compound is the carboxylic acid or an agriculturally acceptable ester or salt thereof. In some embodiments, the compound is the carboxylic acid or its methyl ester.

In some embodiments:

Ar is selected from the group consisting of Ar1, Ar2, Ar3, Ar4, Ar5, and Ar6;

$R^1$ is $OR^{1'}$, wherein $R^{1'}$ is H or $C_1$-$C_8$ alkyl;

$R^2$ is halogen, $C_2$-$C_4$ alkenyl, $C_2$-$C_4$ haloalkenyl, $C_1$-$C_4$ alkoxy, haloalkoxy, $C_1$-$C_4$ alkylthio, or $C_1$-$C_4$ haloalkylthio;

$R^3$ and $R^4$ are each independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, ($C_1$-$C_3$ alkyl)carbonyl, ($C_1$-$C_3$ haloalkyl)carbonyl, ($C_1$-$C_6$ alkoxy)carbonyl, ($C_1$-$C_6$ alkyl)carbamyl, tri ($C_1$-$C_6$ alkyl)silyl, or $R^3$ and $R^4$ taken together represent =$CR^{3'}R^{4'}$, wherein $R^{3'}$ and $R^{4'}$ are each independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino; and X is N or CY, where Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio, or $C_1$-$C_3$ haloalkylthio.

In one embodiment, X is N. In one embodiment, X is CY. In one embodiment, Y is hydrogen. In one embodiment, Y is halogen (e.g., F, Cl, Br, I). In one embodiment, Y is $C_1$-$C_3$ alkyl (e.g., methyl, ethyl, n-propyl, i-propyl). In one embodiment, Y is $C_1$-$C_3$ haloalkyl (e.g., $CFH_2$, $CF_2H$, $CF_3$, $CF_2CF_3$). In one embodiment, Y is $C_1$-$C_3$ alkoxy (e.g., $OCH_3$, $OCH_2CH_3$). In one embodiment, Y is $C_1$-$C_3$ haloalkoxy (e.g., $OCFH_2$, $OCF_2H$, $OCF_3$, $OCF_2CF_3$). In one embodiment, Y is $C_1$-$C_3$ alkylthio (e.g., $SCH_3$, $SCH_2CH_3$). In one embodiment, Y is $C_1$-$C_3$ haloalkylthio (e.g., $SCFH_2$, $SCF_2H$, $SCF_3$, $SCF_2CF_3$).

In some embodiments, X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio, or $C_1$-$C_3$ haloalkylthio.

In some embodiments, X is N or CY, wherein Y is H, halo, or $C_1$-$C_3$ alkyl. In some embodiments, X is N or CY, wherein Y is H or halo. In some embodiments, X is N or CY, wherein Y is H, F, Cl, or Br. In some embodiments, X is N or CY, wherein Y is H, F, or Cl. In some embodiments, X is N or CY, wherein Y is H or $C_1$-$C_3$ alkyl. In some embodiments, X is N or CY, wherein Y is H or $CH_3$. In some embodiments, X is N or CY, wherein Y is H. In some embodiments, X is N or CY, wherein Y is H, F, Cl, Br, or $CH_3$. In some embodiments, X is N or CY, wherein Y is H, F, Cl, or $CH_3$. In some embodiments, X is N or CY, wherein Y is H or F. In some embodiments, X is N or CY, wherein Y is Br. In some embodiments, X is N or CY, wherein Y is H. In some embodiments, Y is H. In some embodiments, Y is F. In some embodiments, Y is Cl. In some embodiments, Y is Br. In some embodiments, Y is $CH_3$. In some embodiments, Y is H, halo, or $C_1$-$C_3$ alkyl. In some embodiments, Y is H or halo. In some embodiments, Y is H, F, Cl, or Br. In some embodiments, Y is H, F, or Cl. In some embodiments, Y is H or $C_1$-$C_3$ alkyl. In some embodiments, Y is H or $CH_3$. In some embodiments, Y is H, F, Cl, Br, or $CH_3$. In some embodiments, Y is H, F, Cl, or $CH_3$. In some embodiments, Y is H or F. In some embodiments, Y is halo.

In one embodiment, $R^1$ is $OR^{1'}$. In one embodiment, $R^1$ is $NR^{1''}R^{2''}$.

In one embodiment, $R^{1'}$ is H. In one embodiment, $R^1$ is $C_1$-$C_8$ alkyl (e.g., methyl, ethyl, n-propyl, i-propyl). In one embodiment, $R^1$ is $C_7$-$C_{10}$ arylalkyl (e.g., benzyl).

In one embodiment, $R^{1''}$ is hydrogen. In one embodiment, $R^{1''}$ is $C_1$-$C_{12}$ alkyl. In one embodiment, $R^{1''}$ is $C_3$-$C_{12}$ alkenyl. In one embodiment, $R^{1''}$ is $C_3$-$C_{12}$ alkynyl.

In one embodiment, $R^{2''}$ is hydrogen. In one embodiment, $R^{2''}$ is $C_1$-$C_{12}$ alkyl. In one embodiment, $R^{2''}$ is $C_3$-$C_{12}$ alkenyl. In one embodiment, $R^{2''}$ is $C_3$-$C_{12}$ alkynyl.

In some embodiments, $R^1$ is $OR^{1'}$, wherein $R^{1'}$ is H or $C_1$-$C_8$ alkyl. In some embodiments, $R^1$ is $OR^{1'}$, wherein $R^{1'}$ is H or $C_7$-$C_{10}$ arylalkyl.

In some embodiments, $R^1$ is $OR^{1'}$, wherein $R^{1'}$ is H, methyl, ethyl, or benzyl. In some embodiments, $R^1$ is $OR^{1'}$, wherein $R^{1'}$ is H, methyl, or ethyl. In some embodiments, $R^1$ is $OR^{1'}$, wherein $R^{1'}$ is H or methyl. In some embodiments, $R^1$ is $OR^{1'}$, wherein $R^{1'}$ is H or benzyl.

In one embodiment, $R^2$ is halogen (e.g., F, Cl, Br, I). In one embodiment, $R^2$ is $C_1$-$C_4$ alkyl (e.g., methyl, ethyl, propyl, butyl). In one embodiment, $R^2$ is $C_1$-$C_4$ haloalkyl (e.g., $CFH_2$, $CF_2H$, $CF_3$, $CF_2CF_3$). In one embodiment, $R^2$ is $C_2$-$C_4$ alkenyl (e.g., vinyl or ethenyl, propenyl, butenyl). In one embodiment, $R^2$ is $C_2$-$C_4$ haloalkenyl. In one embodiment, $R^2$ is $C_2$-$C_4$ alkynyl. In one embodiment, $R^2$ is $C_2$-$C_4$ haloalkynyl. In one embodiment, $R^2$ is $C_1$-$C_4$ alkoxy (e.g., $OCH_3$, $OCH_2CH_3$). In one embodiment, $R^2$ is $C_1$-$C_4$ haloalkoxy (e.g., $OCFH_2$, $OCF_2H$, $OCF_3$, $OCF_2CF_3$). In one embodiment, $R^2$ is $C_1$-$C_4$ alkylthio (e.g., $SCH_3$, $SCH_2CH_3$). In one embodiment, $R^2$ is $C_1$-$C_4$ haloalkylthio (e.g., $SCFH_2$, $SCF_2H$, $SCF_3$, $SCF_2CF_3$). In one embodiment, $R^2$ is amino. In one embodiment, $R^2$ is $C_1$-$C_4$ alkylamino. In one embodiment, $R^2$ is $C_2$-$C_4$ haloalkylamino. In one embodiment, $R^2$ is formyl. In one embodiment, $R^2$ is ($C_1$-$C_3$ alkyl)carbonyl. In one embodiment, $R^2$ is ($C_1$-$C_3$ haloalkyl)carbonyl. In one embodiment, $R^2$ is cyano.

In one embodiment, $R^2$ is —$CR^{17}$=$CR^{18}$—$SiR^{19}R^{20}R^{21}$.

In one embodiment, $R^{17}$ is hydrogen. In one embodiment, $R^{17}$ is F. In one embodiment, $R^{17}$ is Cl.

In one embodiment, $R^{18}$ is hydrogen. In one embodiment, $R^{18}$ is F. In one embodiment, $R^{18}$ is Cl. In one embodiment, $R^{18}$ is $C_1$-$C_4$ alkyl. In one embodiment, $R^{18}$ is $C_1$-$C_4$ haloalkyl.

In one embodiment, $R^{19}$ is $C_1$-$C_{10}$ alkyl. In one embodiment, $R^{19}$ is $C_3$-$C_6$ cycloalkyl. In one embodiment, $R^{19}$ is $C_1$-$C_{10}$ haloalkyl. In one embodiment, $R^{19}$ is $C_3$-$C_6$ halocycloalkyl. In one embodiment, $R^{19}$ is phenyl. In one embodiment, $R^{19}$ is substituted phenyl. In one embodiment, $R^{19}$ is $C_1$-$C_{10}$ alkoxy. In one embodiment, $R^{19}$ is OH.

In one embodiment, $R^{20}$ is $C_1$-$C_{10}$ alkyl. In one embodiment, $R^{20}$ is $C_3$-$C_6$ cycloalkyl. In one embodiment, $R^{20}$ is $C_1$-$C_{10}$ haloalkyl. In one embodiment, $R^{20}$ is $C_3$-$C_6$ halocycloalkyl. In one embodiment, $R^{20}$ is phenyl. In one embodiment, $R^{20}$ is substituted phenyl. In one embodiment, $R^{20}$ is $C_1$-$C_{10}$ alkoxy. In one embodiment, $R^{20}$ is OH.

In one embodiment, $R^{21}$ is $C_1$-$C_{10}$ alkyl. In one embodiment, $R^{21}$ is $C_3$-$C_6$ cycloalkyl. In one embodiment, $R^{21}$ is $C_1$-$C_{10}$ haloalkyl. In one embodiment, $R^{21}$ is $C_3$-$C_6$ halocycloalkyl. In one embodiment, $R^{21}$ is phenyl. In one embodiment, $R^{21}$ is substituted phenyl. In one embodiment, $R^{21}$ is $C_1$-$C_{10}$ alkoxy. In one embodiment, $R^{21}$ is OH.

In some embodiments, $R^2$ is halogen, $C_2$-$C_4$ alkenyl, $C_2$-$C_4$ haloalkenyl, $C_1$-$C_4$ alkoxy, $C_1$-$C_4$ haloalkoxy, $C_1$-$C_4$ alkylthio, or $C_1$-$C_4$ haloalkylthio. In some embodiments, $R^2$ is halogen, $C_2$-$C_4$ alkenyl, haloalkenyl, or $C_1$-$C_4$ alkoxy.

In some embodiments, $R^2$ is halogen, $C_2$-$C_4$ alkenyl, or $C_1$-$C_4$ alkoxy. In some embodiments, $R^2$ is Cl, vinyl, or $OCH_3$. In some embodiments, $R^2$ is Cl. In some embodiments, $R^2$ is vinyl. In some embodiments, $R^2$ is $OCH_3$.

In one embodiment, $R^3$ is hydrogen. In one embodiment, $R^3$ is $C_1$-$C_6$ alkyl. In one embodiment, $R^3$ is $C_1$-$C_6$ haloalkyl. In one embodiment, $R^3$ is $C_3$-$C_6$ alkenyl. In one embodiment, $R^3$ is $C_3$-$C_6$ haloalkenyl. In one embodiment, $R^3$ is $C_3$-$C_6$ alkynyl. In one embodiment, $R^3$ is hydroxy. In one embodiment, $R^3$ is $C_1$-$C_6$ alkoxy. In one embodiment, $R^3$ is $C_1$-$C_6$ haloalkoxy. In one embodiment, $R^3$ is formyl. In one embodiment, $R^3$ is ($C_1$-$C_3$ alkyl)carbonyl. In one embodiment, $R^3$ is ($C_1$-$C_3$ haloalkyl)carbonyl. In one embodiment, $R^3$ is ($C_1$-$C_6$ alkoxy)carbonyl. In one embodiment, $R^3$ is ($C_1$-$C_6$ alkyl)carbamyl. In one embodiment, $R^3$ is $C_1$-$C_6$ alkylsulfonyl. In one embodiment, $R^3$ is tri($C_1$-$C_6$ alkyl)silyl. In one embodiment, $R^3$ is di($C_1$-$C_6$ alkyl)phosphonyl.

In one embodiment, $R^4$ is hydrogen. In one embodiment, $R^4$ is $C_1$-$C_6$ alkyl. In one embodiment, $R^4$ is $C_1$-$C_6$ haloalkyl. In one embodiment, $R^4$ is $C_3$-$C_6$ alkenyl. In one embodiment, $R^4$ is $C_3$-$C_6$ haloalkenyl. In one embodiment, $R^4$ is $C_3$-$C_6$ alkynyl. In one embodiment, $R^4$ is hydroxy. In one embodiment, $R^4$ is $C_1$-$C_6$ alkoxy. In one embodiment, $R^4$ is $C_1$-$C_6$ haloalkoxy. In one embodiment, $R^4$ is formyl. In one embodiment, $R^4$ is ($C_1$-$C_3$ alkyl)carbonyl. In one embodiment, $R^4$ is ($C_1$-$C_3$ haloalkyl)carbonyl. In one embodiment, $R^4$ is ($C_1$-$C_6$ alkoxy)carbonyl. In one embodiment, $R^4$ is ($C_1$-$C_6$ alkyl)carbamyl. In one embodiment, $R^4$ is $C_1$-$C_6$ alkylsulfonyl. In one embodiment, $R^4$ is tri($C_1$-$C_6$ alkyl)silyl. In one embodiment, $R^4$ is di($C_1$-$C_6$ alkyl)phosphonyl.

In one embodiment, $R^3$ and $R^4$ together with the nitrogen atom to which they are attached form a 5-membered saturated ring. In one embodiment, $R^3$ and $R^4$ together with the nitrogen atom to which they are attached form a 6-membered saturated ring.

In one embodiment, $R^3$ and $R^4$ taken together represent =$CR^{3'}R^{4'}$.

In one embodiment, $R^{3'}$ is hydrogen. In one embodiment, $R^{3'}$ is $C_1$-$C_6$ alkyl. In one embodiment, $R^{3'}$ is $C_3$-$C_6$ alkenyl. In one embodiment, $R^{3'}$ is $C_3$-$C_6$ alkynyl. In one embodiment, $R^{3'}$ is $C_1$-$C_6$ alkoxy. In one embodiment, $R^{3'}$ is $C_1$-$C_6$ alkylamino.

In one embodiment, $R^{4'}$ is hydrogen. In one embodiment, $R^{4'}$ is $C_1$-$C_6$ alkyl. In one embodiment, $R^{4'}$ is $C_3$-$C_6$ alkenyl. In one embodiment, $R^{4'}$ is $C_3$-$C_6$ alkynyl. In one embodiment, $R^{4'}$ is $C_1$-$C_6$ alkoxy. In one embodiment, $R^{4'}$ is $C_1$-$C_6$ alkylamino.

In one embodiment, $R^{3'}$ and $R^{4'}$ together with the carbon atom to which they are attached form a 5-membered saturated ring. In one embodiment, $R^{3'}$ and $R^{4'}$ together with the carbon atom to which they are attached form a 6-membered saturated ring.

In some embodiments, $R^3$ and $R^4$ are each independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, ($C_1$-$C_3$ alkyl)carbonyl, ($C_1$-$C_3$ haloalkyl)carbonyl, ($C_1$-$C_6$ alkoxy)carbonyl, ($C_1$-$C_6$ alkyl)carbamyl, tri($C_1$-$C_6$ alkyl)silyl. In some embodiments, $R^3$ and $R^4$ taken together represent =$CR^{3'}R^{4'}$, wherein $R^{3'}$ and $R^{4'}$ are each independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino.

In some embodiments, $R^3$ is H.

In some embodiments, $R^4$ is H.

In one embodiment, Ar is Ar1.

In one embodiment, provided herein is a compound of formula (I-1), or an N-oxide or agriculturally acceptable salt thereof:

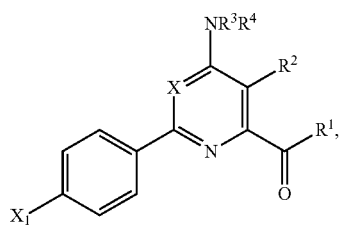
(I-1)

wherein X, $R^1$, $R^2$, $R^3$, $R^4$, and $X_1$ are defined herein elsewhere.

In one embodiment, in a compound of formula (I-1), $R^1$ is OH and $R^2$ is halogen. In one embodiment, in a compound of formula (I-1), $R^1$ is OH and $R^2$ is $C_2$-$C_4$ alkenyl. In one embodiment, in a compound of formula (I-1), $R^1$ is OH and $R^2$ is $C_1$-$C_4$ alkoxy. In one embodiment, in a compound of formula (I-1), $R^1$ is OH and $R^2$ is Cl. In one embodiment, in a compound of formula (I-1), $R^1$ is OH and $R^2$ is $OCH_3$. In one embodiment, in a compound of formula (I-1), $R^1$ is OH and $R^2$ is vinyl (or ethenyl). In one embodiment, in a compound of formula (I-1), $R^1$ is OH and $R^2$ is 1-propenyl. In one embodiment, in a compound of formula (I-1), $R^1$ is —O—($C_1$-$C_4$ alkyl) and $R^2$ is halogen. In one embodiment, in a compound of formula (I-1), $R^1$ is —O—($C_1$-$C_4$ alkyl) and $R^2$ is $C_2$-$C_4$ alkenyl. In one embodiment, in a compound of formula (I-1), $R^1$ is —O—($C_1$-$C_4$ alkyl) and $R^2$ is $C_1$-$C_4$ alkoxy. In one embodiment, in a compound of formula (I-1), $R^1$ is —O—($C_1$-$C_4$ alkyl) and $R^2$ is Cl. In one embodiment, in a compound of formula (I-1), $R^1$ is —O—($C_1$-$C_4$ alkyl) and $R^2$ is $OCH_3$. In one embodiment, in a compound of formula (I-1), $R^1$ is —O—($C_1$-$C_4$ alkyl) and $R^2$ is vinyl (or ethenyl). In one embodiment, in a compound of formula (I-1), $R^1$ is —O—($C_1$-$C_4$ alkyl) and $R^2$ is 1-propenyl. In one embodiment, in a compound of formula (I-1), $R^1$ is $OCH_3$ and $R^2$ is halogen. In one embodiment, in a compound of formula (I-1), $R^1$ is $OCH_3$ and $R^2$ is $C_2$-$C_4$ alkenyl. In one embodiment, in a compound of formula (I-1), $R^1$ is $OCH_3$ and $R^2$ is $C_1$-$C_4$ alkoxy. In one embodiment, in a compound of formula (I-1), $R^1$ is $OCH_3$ and $R^2$ is Cl. In one embodiment, in a compound of formula (I-1), $R^1$ is $OCH_3$ and $R^2$ is $OCH_3$. In one embodiment, in a compound of formula (I-1), $R^1$ is $OCH_3$ and $R^2$ is vinyl (or ethenyl). In one embodiment, in a compound of formula (I-1), $R^1$ is $OCH_3$ and $R^2$ is 1-propenyl.

In one embodiment, provided herein is a compound of formula (I-1a), (I-1b), (I-1c), (I-1d), or (I-1e), or an N-oxide or agriculturally acceptable salt thereof:

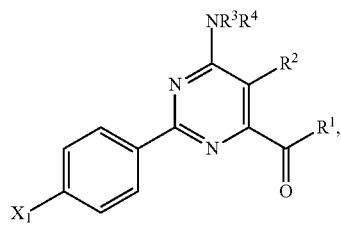
(I-1a)

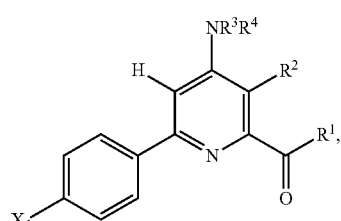
(I-1b)

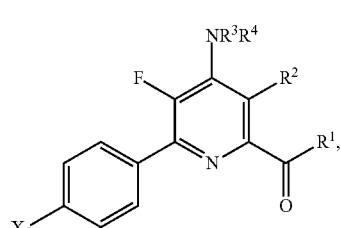
(I-1c)

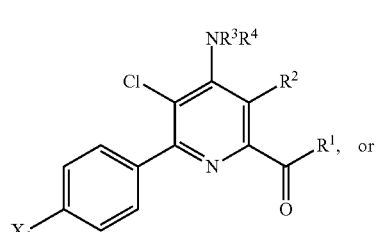
(I-1d)

or

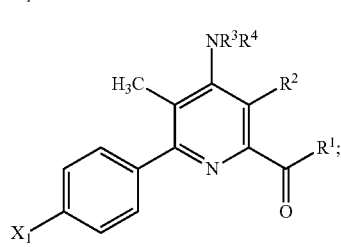
(I-1e)

wherein $R^1$, $R^2$, $R^3$, $R^4$, and $X_1$ are defined herein elsewhere.

In one embodiment, in a compound of formula (I-1a), $R^1$ is OH and $R^2$ is halogen. In one embodiment, in a compound of formula (I-1a), $R^1$ is OH and $R^2$ is $C_2$-$C_4$ alkenyl. In one embodiment, in a compound of formula (I-1a), $R^1$ is OH and $R^2$ is $C_1$-$C_4$ alkoxy. In one embodiment, in a compound of formula (I-1a), $R^1$ is OH and $R^2$ is Cl. In one embodiment, in a compound of formula (I-1a), $R^1$ is OH and $R^2$ is $OCH_3$. In one embodiment, in a compound of formula (I-1a), $R^1$ is OH and $R^2$ is vinyl (or ethenyl). In one embodiment, in a compound of formula (I-1a), $R^1$ is OH and $R^2$ is 1-propenyl. In one embodiment, in a compound of formula (I-1a), $R^1$ is —O—($C_1$-$C_4$ alkyl) and $R^2$ is halogen. In one embodiment, in a compound of formula (I-1a), $R^1$ is —O—($C_1$-$C_4$ alkyl) and $R^2$ is $C_2$-$C_4$ alkenyl. In one embodiment, in a compound of formula (I-1a), $R^1$ is —O—($C_1$-$C_4$ alkyl) and $R^2$ is $C_1$-$C_4$ alkoxy. In one embodiment, in a compound of formula (I-1a), $R^1$ is —O—($C_1$-$C_4$ alkyl) and $R^2$ is Cl. In one embodiment, in a compound of formula (I-1a), $R^1$ is —O—($C_1$-$C_4$ alkyl) and $R^2$ is $OCH_3$. In one embodiment, in a compound of formula (I-1a), $R^1$ is $—O—(C_1-C_4$ alkyl) and $R^2$ is vinyl (or ethenyl). In one embodiment, in a compound of formula (I-1a), $R^1$ is $—O—(C_1-C_4$ alkyl) and $R^2$ is 1-propenyl. In one embodiment, in a compound of formula (I-1a), $R^1$ is $OCH_3$ and $R^2$ is halogen. In one embodiment, in a compound of formula (I-1a), $R^1$ is $OCH_3$ and $R^2$ is $C_2-C_4$ alkenyl. In one embodiment, in a compound of formula (I-1a), $R^1$ is $OCH_3$ and $R^2$ is $C_1-C_4$ alkoxy. In one embodiment, in a compound of formula (I-1a), $R^1$ is $OCH_3$ and $R^2$ is Cl. In one embodiment, in a compound of formula (I-1a), $R^1$ is $OCH_3$ and $R^2$ is $OCH_3$. In one embodiment, in a compound of formula (I-1a), $R^1$ is $OCH_3$ and $R^2$ is vinyl (or ethenyl). In one embodiment, in a compound of formula (I-1a), $R^1$ is $OCH_3$ and $R^2$ is 1-propenyl.

In one embodiment, in a compound of formula (I-1b), $R^1$ is OH and $R^2$ is halogen. In one embodiment, in a compound of formula (I-1b), $R^1$ is OH and $R^2$ is $C_2-C_4$ alkenyl. In one embodiment, in a compound of formula (I-1b), $R^1$ is OH and $R^2$ is $C_1-C_4$ alkoxy. In one embodiment, in a compound of formula (I-1b), $R^1$ is OH and $R^2$ is Cl. In one embodiment, in a compound of formula (I-1b), $R^1$ is OH and $R^2$ is $OCH_3$. In one embodiment, in a compound of formula (I-1b), $R^1$ is OH and $R^2$ is vinyl (or ethenyl). In one embodiment, in a compound of formula (I-1b), $R^1$ is OH and $R^2$ is 1-propenyl. In one embodiment, in a compound of formula (I-1b), $R^1$ is $—O—(C_1-C_4$ alkyl) and $R^2$ is halogen. In one embodiment, in a compound of formula (I-1b), $R^1$ is $—O—(C_1-C_4$ alkyl) and $R^2$ is $C_2-C_4$ alkenyl. In one embodiment, in a compound of formula (I-1b), $R^1$ is $—O—(C_1-C_4$ alkyl) and $R^2$ is $C_1-C_4$ alkoxy. In one embodiment, in a compound of formula (I-1b), $R^1$ is $—O—(C_1-C_4$ alkyl) and $R^2$ is Cl. In one embodiment, in a compound of formula (I-1b), $R^1$ is $—O—(C_1-C_4$ alkyl) and $R^2$ is $OCH_3$. In one embodiment, in a compound of formula (I-1b), $R^1$ is $—O—(C_1-C_4$ alkyl) and $R^2$ is vinyl (or ethenyl). In one embodiment, in a compound of formula (I-1b), $R^1$ is $—O—(C_1-C_4$ alkyl) and $R^2$ is 1-propenyl. In one embodiment, in a compound of formula (I-1b), $R^1$ is $OCH_3$ and $R^2$ is halogen. In one embodiment, in a compound of formula (I-1b), $R^1$ is $OCH_3$ and $R^2$ is $C_2-C_4$ alkenyl. In one embodiment, in a compound of formula (I-1b), $R^1$ is $OCH_3$ and $R^2$ is $C_1-C_4$ alkoxy. In one embodiment, in a compound of formula (I-1b), $R^1$ is $OCH_3$ and $R^2$ is Cl. In one embodiment, in a compound of formula (I-1b), $R^1$ is $OCH_3$ and $R^2$ is $OCH_3$. In one embodiment, in a compound of formula (I-1b), $R^1$ is $OCH_3$ and $R^2$ is vinyl (or ethenyl). In one embodiment, in a compound of formula (I-1b), $R^1$ is $OCH_3$ and $R^2$ is 1-propenyl.

In one embodiment, in a compound of formula (I-1c), $R^1$ is OH and $R^2$ is halogen. In one embodiment, in a compound of formula (I-1c), $R^1$ is OH and $R^2$ is $C_2-C_4$ alkenyl. In one embodiment, in a compound of formula (I-1c), $R^1$ is OH and $R^2$ is $C_1-C_4$ alkoxy. In one embodiment, in a compound of formula (I-1c), $R^1$ is OH and $R^2$ is Cl. In one embodiment, in a compound of formula (I-1c), $R^1$ is OH and $R^2$ is $OCH_3$. In one embodiment, in a compound of formula (I-1c), $R^1$ is OH and $R^2$ is vinyl (or ethenyl). In one embodiment, in a compound of formula (I-1c), $R^1$ is OH and $R^2$ is 1-propenyl. In one embodiment, in a compound of formula (I-1c), $R^1$ is $—O—(C_1-C_4$ alkyl) and $R^2$ is halogen. In one embodiment, in a compound of formula (I-1c), $R^1$ is $—O—(C_1-C_4$ alkyl) and $R^2$ is $C_2-C_4$ alkenyl. In one embodiment, in a compound of formula (I-1c), $R^1$ is $—O—(C_1-C_4$ alkyl) and $R^2$ is $C_1-C_4$ alkoxy. In one embodiment, in a compound of formula (I-1c), $R^1$ is $—O—(C_1-C_4$ alkyl) and $R^2$ is Cl. In one embodiment, in a compound of formula (I-1c), $R^1$ is $—O—(C_1-C_4$ alkyl) and $R^2$ is $OCH_3$. In one embodiment, in a compound of formula (I-1c), $R^1$ is $—O—(C_1-C_4$ alkyl) and $R^2$ is vinyl (or ethenyl). In one embodiment, in a compound of formula (I-1c), $R^1$ is $—O—(C_1-C_4$ alkyl) and $R^2$ is 1-propenyl. In one embodiment, in a compound of formula (I-1c), $R^1$ is $OCH_3$ and $R^2$ is halogen. In one embodiment, in a compound of formula (I-1c), $R^1$ is $OCH_3$ and $R^2$ is $C_2-C_4$ alkenyl. In one embodiment, in a compound of formula (I-1c), $R^1$ is $OCH_3$ and $R^2$ is $C_1-C_4$ alkoxy. In one embodiment, in a compound of formula (I-1c), $R^1$ is $OCH_3$ and $R^2$ is Cl. In one embodiment, in a compound of formula (I-1c), $R^1$ is $OCH_3$ and $R^2$ is $OCH_3$. In one embodiment, in a compound of formula (I-1c), $R^1$ is $OCH_3$ and $R^2$ is vinyl (or ethenyl). In one embodiment, in a compound of formula (I-1c), $R^1$ is $OCH_3$ and $R^2$ is 1-propenyl.

In one embodiment, in a compound of formula (I-1d), $R^1$ is OH and $R^2$ is halogen. In one embodiment, in a compound of formula (I-1d), $R^1$ is OH and $R^2$ is $C_2-C_4$ alkenyl. In one embodiment, in a compound of formula (I-1d), $R^1$ is OH and $R^2$ is $C_1-C_4$ alkoxy. In one embodiment, in a compound of formula (I-1d), $R^1$ is OH and $R^2$ is Cl. In one embodiment, in a compound of formula (I-1d), $R^1$ is OH and $R^2$ is $OCH_3$. In one embodiment, in a compound of formula (I-1d), $R^1$ is OH and $R^2$ is vinyl (or ethenyl). In one embodiment, in a compound of formula (I-1 d), $R^1$ is OH and $R^2$ is 1-propenyl. In one embodiment, in a compound of formula (I-1d), $R^1$ is $—O—(C_1-C_4$ alkyl) and $R^2$ is halogen. In one embodiment, in a compound of formula (I-1d), $R^1$ is $—O—(C_1-C_4$ alkyl) and $R^2$ is $C_2-C_4$ alkenyl. In one embodiment, in a compound of formula (I-1d), $R^1$ is $—O—(C_1-C_4$ alkyl) and $R^2$ is $C_1-C_4$ alkoxy. In one embodiment, in a compound of formula (I-1d), $R^1$ is $—O—(C_1-C_4$ alkyl) and $R^2$ is Cl. In one embodiment, in a compound of formula (I-1d), $R^1$ is $—O—(C_1-C_4$ alkyl) and $R^2$ is $OCH_3$. In one embodiment, in a compound of formula (I-1d), $R^1$ is $—O—(C_1-C_4$ alkyl) and $R^2$ is vinyl (or ethenyl). In one embodiment, in a compound of formula (I-1d), $R^1$ is $—O—(C_1-C_4$ alkyl) and $R^2$ is 1-propenyl. In one embodiment, in a compound of formula (I-1d), $R^1$ is $OCH_3$ and $R^2$ is halogen. In one embodiment, in a compound of formula (I-1d), $R^1$ is $OCH_3$ and $R^2$ is $C_2-C_4$ alkenyl. In one embodiment, in a compound of formula (I-1d), $R^1$ is $OCH_3$ and $R^2$ is $C_1-C_4$ alkoxy. In one embodiment, in a compound of formula (I-1d), $R^1$ is $OCH_3$ and $R^2$ is Cl. In one embodiment, in a compound of formula (I-1d), $R^1$ is $OCH_3$ and $R^2$ is $OCH_3$. In one embodiment, in a compound of formula (I-1d), $R^1$ is $OCH_3$ and $R^2$ is vinyl (or ethenyl). In one embodiment, in a compound of formula (I-1d), $R^1$ is $OCH_3$ and $R^2$ is 1-propenyl.

In one embodiment, in a compound of formula (I-1e), $R^1$ is OH and $R^2$ is halogen. In one embodiment, in a compound of formula (I-1e), $R^1$ is OH and $R^2$ is $C_2-C_4$ alkenyl. In one embodiment, in a compound of formula (I-1e), $R^1$ is OH and $R^2$ is $C_1-C_4$ alkoxy. In one embodiment, in a compound of formula (I-1e), $R^1$ is OH and $R^2$ is Cl. In one embodiment, in a compound of formula (I-1e), $R^1$ is OH and $R^2$ is $OCH_3$. In one embodiment, in a compound of formula (I-1e), $R^1$ is OH and $R^2$ is vinyl (or ethenyl). In one embodiment, in a compound of formula (I-1e), $R^1$ is OH and $R^2$ is 1-propenyl. In one embodiment, in a compound of formula (I-1e), $R^1$ is $—O—(C_1-C_4$ alkyl) and $R^2$ is halogen. In one embodiment, in a compound of formula (I-1e), $R^1$ is $—O—(C_1-C_4$ alkyl) and $R^2$ is $C_2-C_4$ alkenyl. In one embodiment, in a compound of formula (I-1e), $R^1$ is $—O—(C_1-C_4$ alkyl) and $R^2$ is $C_1-C_4$ alkoxy. In one embodiment, in a compound of formula (I-1e), $R^1$ is $—O—(C_1-C_4$ alkyl) and $R^2$ is Cl. In one embodiment, in a compound of formula (I-1e), $R^1$ is $—O—(C_1-C_4$ alkyl) and $R^2$ is $OCH_3$. In one embodiment, in a compound of formula (I-1e), $R^1$ is $—O—(C_1-C_4$ alkyl) and $R^2$ is vinyl (or ethenyl).

In one embodiment, in a compound of formula (I-1e), R¹ is —O—(C₁-C₄ alkyl) and R² is 1-propenyl. In one embodiment, in a compound of formula (I-1e), R¹ is OCH₃ and R² is halogen. In one embodiment, in a compound of formula (I-1e), R¹ is OCH₃ and R² is C₂-C₄ alkenyl. In one embodiment, in a compound of formula (I-1e), R¹ is OCH₃ and R² is C₁-C₄ alkoxy. In one embodiment, in a compound of formula (I-1e), R¹ is OCH₃ and R² is Cl. In one embodiment, in a compound of formula (I-1e), R¹ is OCH₃ and R² is OCH₃. In one embodiment, in a compound of formula (I-1e), R¹ is OCH₃ and R² is vinyl (or ethenyl). In one embodiment, in a compound of formula (I-1e), R¹ is OCH₃ and R² is 1-propenyl.

In one embodiment, Ar is Ar2.

In one embodiment, provided herein is a compound of formula (I-2), or an N-oxide or agriculturally acceptable salt thereof:

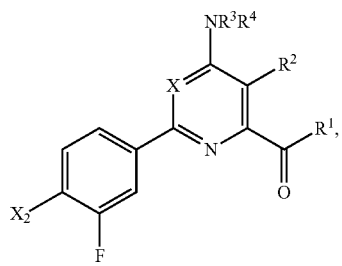
(I-2)

wherein X, R¹, R², R³, R⁴, and X₂ are defined herein elsewhere.

In one embodiment, in a compound of formula (I-2), R¹ is OH and R² is halogen. In one embodiment, in a compound of formula (I-2), R¹ is OH and R² is C₂-C₄ alkenyl. In one embodiment, in a compound of formula (I-2), R¹ is OH and R² is C₁-C₄ alkoxy. In one embodiment, in a compound of formula (I-2), R¹ is OH and R² is Cl. In one embodiment, in a compound of formula (I-2), R¹ is OH and R² is OCH₃. In one embodiment, in a compound of formula (I-2), R¹ is OH and R² is vinyl (or ethenyl). In one embodiment, in a compound of formula (I-2), R¹ is OH and R² is 1-propenyl. In one embodiment, in a compound of formula (I-2), R¹ is —O—(C₁-C₄ alkyl) and R² is halogen. In one embodiment, in a compound of formula (I-2), R¹ is —O—(C₁-C₄ alkyl) and R² is C₂-C₄ alkenyl. In one embodiment, in a compound of formula (I-2), R¹ is —O—(C₁-C₄ alkyl) and R² is C₁-C₄ alkoxy. In one embodiment, in a compound of formula (I-2), R¹ is —O—(C₁-C₄ alkyl) and R² is Cl. In one embodiment, in a compound of formula (I-2), R¹ is —O—(C₁-C₄ alkyl) and R² is OCH₃. In one embodiment, in a compound of formula (I-2), R¹ is —O—(C₁-C₄ alkyl) and R² is vinyl (or ethenyl). In one embodiment, in a compound of formula (I-2), R¹ is —O—(C₁-C₄ alkyl) and R² is 1-propenyl. In one embodiment, in a compound of formula (I-2), R¹ is OCH₃ and R² is halogen. In one embodiment, in a compound of formula (I-2), R¹ is OCH₃ and R² is C₂-C₄ alkenyl. In one embodiment, in a compound of formula (I-2), R¹ is OCH₃ and R² is C₁-C₄ alkoxy. In one embodiment, in a compound of formula (I-2), R¹ is OCH₃ and R² is Cl. In one embodiment, in a compound of formula (I-2), R¹ is OCH₃ and R² is OCH₃. In one embodiment, in a compound of formula (I-2), R¹ is OCH₃ and R² is vinyl (or ethenyl). In one embodiment, in a compound of formula (I-2), R¹ is OCH₃ and R² is 1-propenyl.

In one embodiment, provided herein is a compound of formula (I-2a), (I-2b), (I-2c), (I-2d), or (I-2e), or an N-oxide or agriculturally acceptable salt thereof:

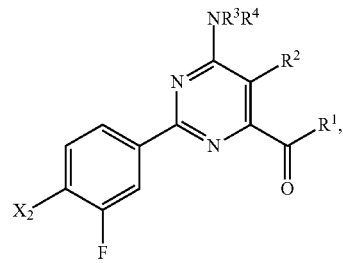
(I-2a)

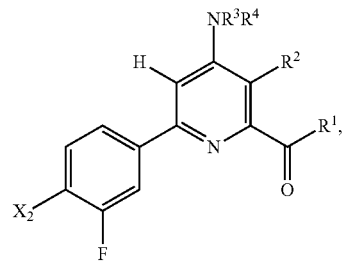
(I-2b)

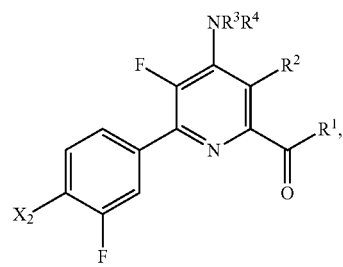
(I-2c)

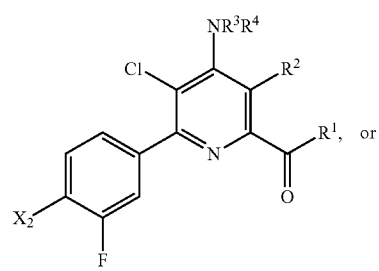
(I-2d)

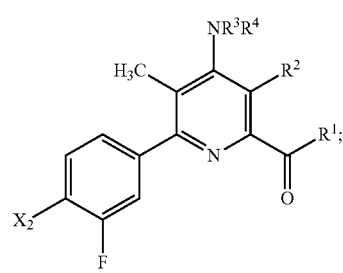
(I-2e)

wherein R¹, R², R³, R⁴, and X₂ are defined herein elsewhere.

In one embodiment, in a compound of formula (I-2a), R¹ is OH and R² is halogen. In one embodiment, in a compound of formula (I-2a), R¹ is OH and R² is C₂-C₄ alkenyl. In one embodiment, in a compound of formula (I-2a), R¹ is OH and R² is C₁-C₄ alkoxy. In one embodiment, in a compound of formula (I-2a), R¹ is OH and R² is Cl. In one embodiment, in a compound of formula (I-2a), R¹ is OH and R² is OCH₃. In one embodiment, in a compound of formula (I-2a), $R^1$ is OH and $R^2$ is vinyl (or ethenyl). In one embodiment, in a compound of formula (I-2a), $R^1$ is OH and $R^2$ is 1-propenyl. In one embodiment, in a compound of formula (I-2a), $R^1$ is —O—($C_1$-$C_4$ alkyl) and $R^2$ is halogen. In one embodiment, in a compound of formula (I-2a), $R^1$ is —O—($C_1$-$C_4$ alkyl) and $R^2$ is $C_2$-$C_4$ alkenyl. In one embodiment, in a compound of formula (I-2a), $R^1$ is —O—($C_1$-$C_4$ alkyl) and $R^2$ is $C_1$-$C_4$ alkoxy. In one embodiment, in a compound of formula (I-2a), $R^1$ is —O—($C_1$-$C_4$ alkyl) and $R^2$ is Cl. In one embodiment, in a compound of formula (I-2a), $R^1$ is —O—($C_1$-$C_4$ alkyl) and $R^2$ is $OCH_3$. In one embodiment, in a compound of formula (I-2a), $R^1$ is —O—($C_1$-$C_4$ alkyl) and $R^2$ is vinyl (or ethenyl). In one embodiment, in a compound of formula (I-2a), $R^1$ is —O—($C_1$-$C_4$ alkyl) and $R^2$ is 1-propenyl. In one embodiment, in a compound of formula (I-2a), $R^1$ is $OCH_3$ and $R^2$ is halogen. In one embodiment, in a compound of formula (I-2a), $R^1$ is $OCH_3$ and $R^2$ is $C_2$-$C_4$ alkenyl. In one embodiment, in a compound of formula (I-2a), $R^1$ is $OCH_3$ and $R^2$ is $C_1$-$C_4$ alkoxy. In one embodiment, in a compound of formula (I-2a), $R^1$ is $OCH_3$ and $R^2$ is Cl. In one embodiment, in a compound of formula (I-2a), $R^1$ is $OCH_3$ and $R^2$ is $OCH_3$. In one embodiment, in a compound of formula (I-2a), $R^1$ is $OCH_3$ and $R^2$ is vinyl (or ethenyl). In one embodiment, in a compound of formula (I-2a), $R^1$ is $OCH_3$ and $R^2$ is 1-propenyl.

In one embodiment, in a compound of formula (I-2b), $R^1$ is OH and $R^2$ is halogen. In one embodiment, in a compound of formula (I-2b), $R^1$ is OH and $R^2$ is $C_2$-$C_4$ alkenyl. In one embodiment, in a compound of formula (I-2b), $R^1$ is OH and $R^2$ is $C_1$-$C_4$ alkoxy. In one embodiment, in a compound of formula (I-2b), $R^1$ is OH and $R^2$ is Cl. In one embodiment, in a compound of formula (I-2b), $R^1$ is OH and $R^2$ is $OCH_3$. In one embodiment, in a compound of formula (I-2b), $R^1$ is OH and $R^2$ is vinyl (or ethenyl). In one embodiment, in a compound of formula (I-2b), $R^1$ is OH and $R^2$ is 1-propenyl. In one embodiment, in a compound of formula (I-2b), $R^1$ is —O—($C_1$-$C_4$ alkyl) and $R^2$ is halogen. In one embodiment, in a compound of formula (I-2b), $R^1$ is —O—($C_1$-$C_4$ alkyl) and $R^2$ is $C_2$-$C_4$ alkenyl. In one embodiment, in a compound of formula (I-2b), $R^1$ is —O—($C_1$-$C_4$ alkyl) and $R^2$ is $C_1$-$C_4$ alkoxy. In one embodiment, in a compound of formula (I-2b), $R^1$ is —O—($C_1$-$C_4$ alkyl) and $R^2$ is Cl. In one embodiment, in a compound of formula (I-2b), $R^1$ is —O—($C_1$-$C_4$ alkyl) and $R^2$ is $OCH_3$. In one embodiment, in a compound of formula (I-2b), $R^1$ is —O—($C_1$-$C_4$ alkyl) and $R^2$ is vinyl (or ethenyl). In one embodiment, in a compound of formula (I-2b), $R^1$ is —O—($C_1$-$C_4$ alkyl) and $R^2$ is 1-propenyl. In one embodiment, in a compound of formula (I-2b), $R^1$ is $OCH_3$ and $R^2$ is halogen. In one embodiment, in a compound of formula (I-2b), $R^1$ is $OCH_3$ and $R^2$ is $C_2$-$C_4$ alkenyl. In one embodiment, in a compound of formula (I-2b), $R^1$ is $OCH_3$ and $R^2$ is $C_1$-$C_4$ alkoxy. In one embodiment, in a compound of formula (I-2b), $R^1$ is $OCH_3$ and $R^2$ is Cl. In one embodiment, in a compound of formula (I-2b), $R^1$ is $OCH_3$ and $R^2$ is $OCH_3$. In one embodiment, in a compound of formula (I-2b), $R^1$ is $OCH_3$ and $R^2$ is vinyl (or ethenyl). In one embodiment, in a compound of formula (I-2b), $R^1$ is $OCH_3$ and $R^2$ is 1-propenyl.

In one embodiment, in a compound of formula (I-2c), $R^1$ is OH and $R^2$ is halogen. In one embodiment, in a compound of formula (I-2c), $R^1$ is OH and $R^2$ is $C_2$-$C_4$ alkenyl. In one embodiment, in a compound of formula (I-2c), $R^1$ is OH and $R^2$ is $C_1$-$C_4$ alkoxy. In one embodiment, in a compound of formula (I-2c), $R^1$ is OH and $R^2$ is Cl. In one embodiment, in a compound of formula (I-2c), $R^1$ is OH and $R^2$ is $OCH_3$. In one embodiment, in a compound of formula (I-2c), $R^1$ is OH and $R^2$ is vinyl (or ethenyl). In one embodiment, in a compound of formula (I-2c), $R^1$ is OH and $R^2$ is 1-propenyl. In one embodiment, in a compound of formula (I-2c), $R^1$ is —O—($C_1$-$C_4$ alkyl) and $R^2$ is halogen. In one embodiment, in a compound of formula (I-2c), $R^1$ is —O—($C_1$-$C_4$ alkyl) and $R^2$ is $C_2$-$C_4$ alkenyl. In one embodiment, in a compound of formula (I-2c), $R^1$ is —O—($C_1$-$C_4$ alkyl) and $R^2$ is $C_1$-$C_4$ alkoxy. In one embodiment, in a compound of formula (I-2c), $R^1$ is —O—($C_1$-$C_4$ alkyl) and $R^2$ is Cl. In one embodiment, in a compound of formula (I-2c), $R^1$ is —O—($C_1$-$C_4$ alkyl) and $R^2$ is $OCH_3$. In one embodiment, in a compound of formula (I-2c), $R^1$ is —O—($C_1$-$C_4$ alkyl) and $R^2$ is vinyl (or ethenyl). In one embodiment, in a compound of formula (I-2c), $R^1$ is —O—($C_1$-$C_4$ alkyl) and $R^2$ is 1-propenyl. In one embodiment, in a compound of formula (I-2c), $R^1$ is $OCH_3$ and $R^2$ is halogen. In one embodiment, in a compound of formula (I-2c), $R^1$ is $OCH_3$ and $R^2$ is $C_2$-$C_4$ alkenyl. In one embodiment, in a compound of formula (I-2c), $R^1$ is $OCH_3$ and $R^2$ is $C_1$-$C_4$ alkoxy. In one embodiment, in a compound of formula (I-2c), $R^1$ is $OCH_3$ and $R^2$ is Cl. In one embodiment, in a compound of formula (I-2c), $R^1$ is $OCH_3$ and $R^2$ is $OCH_3$. In one embodiment, in a compound of formula (I-2c), $R^1$ is $OCH_3$ and $R^2$ is vinyl (or ethenyl). In one embodiment, in a compound of formula (I-2c), $R^1$ is $OCH_3$ and $R^2$ is 1-propenyl.

In one embodiment, in a compound of formula (I-2d), $R^1$ is OH and $R^2$ is halogen. In one embodiment, in a compound of formula (I-2d), $R^1$ is OH and $R^2$ is $C_2$-$C_4$ alkenyl. In one embodiment, in a compound of formula (I-2d), $R^1$ is OH and $R^2$ is $C_1$-$C_4$ alkoxy. In one embodiment, in a compound of formula (I-2d), $R^1$ is OH and $R^2$ is Cl. In one embodiment, in a compound of formula (I-2d), $R^1$ is OH and $R^2$ is $OCH_3$. In one embodiment, in a compound of formula (I-2d), $R^1$ is OH and $R^2$ is vinyl (or ethenyl). In one embodiment, in a compound of formula (I-2d), $R^1$ is OH and $R^2$ is 1-propenyl. In one embodiment, in a compound of formula (I-2d), $R^1$ is —O—($C_1$-$C_4$ alkyl) and $R^2$ is halogen. In one embodiment, in a compound of formula (I-2d), $R^1$ is —O—($C_1$-$C_4$ alkyl) and $R^2$ is $C_2$-$C_4$ alkenyl. In one embodiment, in a compound of formula (I-2d), $R^1$ is —O—($C_1$-$C_4$ alkyl) and $R^2$ is $C_1$-$C_4$ alkoxy. In one embodiment, in a compound of formula (I-2d), $R^1$ is —O—($C_1$-$C_4$ alkyl) and $R^2$ is Cl. In one embodiment, in a compound of formula (I-2d), $R^1$ is —O—($C_1$-$C_4$ alkyl) and $R^2$ is $OCH_3$. In one embodiment, in a compound of formula (I-2d), $R^1$ is —O—($C_1$-$C_4$ alkyl) and $R^2$ is vinyl (or ethenyl). In one embodiment, in a compound of formula (I-2d), $R^1$ is —O—($C_1$-$C_4$ alkyl) and $R^2$ is 1-propenyl. In one embodiment, in a compound of formula (I-2d), $R^1$ is $OCH_3$ and $R^2$ is halogen. In one embodiment, in a compound of formula (I-2d), $R^1$ is $OCH_3$ and $R^2$ is $C_2$-$C_4$ alkenyl. In one embodiment, in a compound of formula (I-2d), $R^1$ is $OCH_3$ and $R^2$ is $C_1$-$C_4$ alkoxy. In one embodiment, in a compound of formula (I-2d), $R^1$ is $OCH_3$ and $R^2$ is Cl. In one embodiment, in a compound of formula (I-2d), $R^1$ is $OCH_3$ and $R^2$ is $OCH_3$. In one embodiment, in a compound of formula (I-2d), $R^1$ is $OCH_3$ and $R^2$ is vinyl (or ethenyl). In one embodiment, in a compound of formula (I-2d), $R^1$ is $OCH_3$ and $R^2$ is 1-propenyl.

In one embodiment, in a compound of formula (I-2e), $R^1$ is OH and $R^2$ is halogen. In one embodiment, in a compound of formula (I-2e), $R^1$ is OH and $R^2$ is $C_2$-$C_4$ alkenyl. In one embodiment, in a compound of formula (I-2e), $R^1$ is OH and $R^2$ is $C_1$-$C_4$ alkoxy. In one embodiment, in a compound of formula (I-2e), $R^1$ is OH and $R^2$ is Cl. In one embodiment, in a compound of formula (I-2e), $R^1$ is OH and $R^2$ is $OCH_3$. In one embodiment, in a compound of formula (I-2e), $R^1$ is OH and $R^2$ is vinyl (or ethenyl). In one embodiment, in a compound of formula (I-2e), $R^1$ is OH and $R^2$ is 1-propenyl. In one embodiment, in a compound of formula (I-2e), $R^1$ is —O—($C_1$-$C_4$ alkyl) and $R^2$ is halogen. In one embodiment, in a compound of formula (I-2e), $R^1$ is —O—($C_1$-$C_4$ alkyl) and $R^2$ is $C_2$-$C_4$ alkenyl. In one embodiment, in a compound of formula (I-2e), $R^1$ is —O—($C_1$-$C_4$ alkyl) and $R^2$ is $C_1$-$C_4$ alkoxy. In one embodiment, in a compound of formula (I-2e), $R^1$ is —O—($C_1$-$C_4$ alkyl) and $R^2$ is Cl. In one embodiment, in a compound of formula (I-2e), $R^1$ is —O—($C_1$-$C_4$ alkyl) and $R^2$ is $OCH_3$. In one embodiment, in a compound of formula (I-2e), $R^1$ is —O—($C_1$-$C_4$ alkyl) and $R^2$ is vinyl (or ethenyl). In one embodiment, in a compound of formula (I-2e), $R^1$ is —O—($C_1$-$C_4$ alkyl) and $R^2$ is 1-propenyl. In one embodiment, in a compound of formula (I-2e), $R^1$ is $OCH_3$ and $R^2$ is halogen. In one embodiment, in a compound of formula (I-2e), $R^1$ is $OCH_3$ and $R^2$ is $C_2$-$C_4$ alkenyl. In one embodiment, in a compound of formula (I-2e), $R^1$ is $OCH_3$ and $R^2$ is $C_1$-$C_4$ alkoxy. In one embodiment, in a compound of formula (I-2e), $R^1$ is $OCH_3$ and $R^2$ is Cl. In one embodiment, in a compound of formula (I-2e), $R^1$ is $OCH_3$ and $R^2$ is $OCH_3$. In one embodiment, in a compound of formula (I-2e), $R^1$ is $OCH_3$ and $R^2$ is vinyl (or ethenyl). In one embodiment, in a compound of formula (I-2e), $R^1$ is $OCH_3$ and $R^2$ is 1-propenyl.

In one embodiment, Ar is Ar3.

In one embodiment, provided herein is a compound of formula (I-3), or an N-oxide or agriculturally acceptable salt thereof:

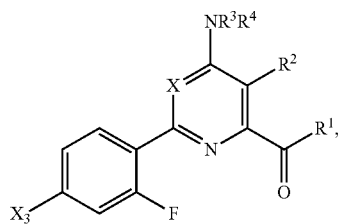

(I-3)

wherein X, $R^1$, $R^2$, $R^3$, $R^4$, and $X_3$ are defined herein elsewhere.

In one embodiment, in a compound of formula (I-3), $R^1$ is OH and $R^2$ is halogen. In one embodiment, in a compound of formula (I-3), $R^1$ is OH and $R^2$ is $C_2$-$C_4$ alkenyl. In one embodiment, in a compound of formula (I-3), $R^1$ is OH and $R^2$ is $C_1$-$C_4$ alkoxy. In one embodiment, in a compound of formula (I-3), $R^1$ is OH and $R^2$ is Cl. In one embodiment, in a compound of formula (I-3), $R^1$ is OH and $R^2$ is $OCH_3$. In one embodiment, in a compound of formula (I-3), $R^1$ is OH and $R^2$ is vinyl (or ethenyl). In one embodiment, in a compound of formula (I-3), $R^1$ is OH and $R^2$ is 1-propenyl. In one embodiment, in a compound of formula (I-3), $R^1$ is —O—($C_1$-$C_4$ alkyl) and $R^2$ is halogen. In one embodiment, in a compound of formula (I-3), $R^1$ is —O—($C_1$-$C_4$ alkyl) and $R^2$ is $C_2$-$C_4$ alkenyl. In one embodiment, in a compound of formula (I-3), $R^1$ is —O—($C_1$-$C_4$ alkyl) and $R^2$ is $C_1$-$C_4$ alkoxy. In one embodiment, in a compound of formula (I-3), $R^1$ is —O—($C_1$-$C_4$ alkyl) and $R^2$ is Cl. In one embodiment, in a compound of formula (I-3), $R^1$ is —O—($C_1$-$C_4$ alkyl) and $R^2$ is $OCH_3$. In one embodiment, in a compound of formula (I-3), $R^1$ is —O—($C_1$-$C_4$ alkyl) and $R^2$ is vinyl (or ethenyl). In one embodiment, in a compound of formula (I-3), $R^1$ is —O—($C_1$-$C_4$ alkyl) and $R^2$ is 1-propenyl. In one embodiment, in a compound of formula (I-3), $R^1$ is $OCH_3$ and $R^2$ is halogen. In one embodiment, in a compound of formula (I-3), $R^1$ is $OCH_3$ and $R^2$ is $C_2$-$C_4$ alkenyl. In one embodiment, in a compound of formula (I-3), $R^1$ is $OCH_3$ and $R^2$ is $C_1$-$C_4$ alkoxy. In one embodiment, in a compound of formula (I-3), $R^1$ is $OCH_3$ and $R^2$ is Cl. In one embodiment, in a compound of formula (I-3), $R^1$ is $OCH_3$ and $R^2$ is $OCH_3$. In one embodiment, in a compound of formula (I-3), $R^1$ is $OCH_3$ and $R^2$ is vinyl (or ethenyl). In one embodiment, in a compound of formula (I-3), $R^1$ is $OCH_3$ and $R^2$ is 1-propenyl.

In one embodiment, provided herein is a compound of formula (I-3a), (I-3b), or (I-3c), or an N-oxide or agriculturally acceptable salt thereof:

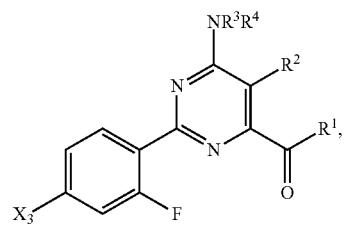

(I-3a)

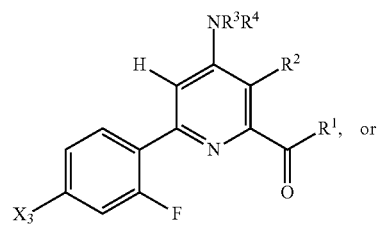

(I-3b)

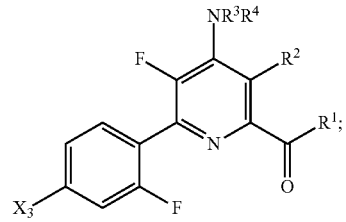

(I-3c)

wherein $R^1$, $R^2$, $R^3$, $R^4$, and $X_3$ are defined herein elsewhere.

In one embodiment, in a compound of formula (I-3a), $R^1$ is OH and $R^2$ is halogen. In one embodiment, in a compound of formula (I-3a), $R^1$ is OH and $R^2$ is $C_2$-$C_4$ alkenyl. In one embodiment, in a compound of formula (I-3a), $R^1$ is OH and $R^2$ is $C_1$-$C_4$ alkoxy. In one embodiment, in a compound of formula (I-3a), $R^1$ is OH and $R^2$ is Cl. In one embodiment, in a compound of formula (I-3a), $R^1$ is OH and $R^2$ is $OCH_3$. In one embodiment, in a compound of formula (I-3a), $R^1$ is OH and $R^2$ is vinyl (or ethenyl). In one embodiment, in a compound of formula (I-3a), $R^1$ is OH and $R^2$ is 1-propenyl. In one embodiment, in a compound of formula (I-3a), $R^1$ is —O—($C_1$-$C_4$ alkyl) and $R^2$ is halogen. In one embodiment, in a compound of formula (I-3a), $R^1$ is —O—($C_1$-$C_4$ alkyl) and $R^2$ is $C_2$-$C_4$ alkenyl. In one embodiment, in a compound of formula (I-3a), $R^1$ is —O—($C_1$-$C_4$ alkyl) and $R^2$ is $C_1$-$C_4$ alkoxy. In one embodiment, in a compound of formula (I-3a), $R^1$ is —O—($C_1$-$C_4$ alkyl) and $R^2$ is Cl. In one embodiment, in a compound of formula (I-3a), $R^1$ is —O—($C_1$-$C_4$ alkyl) and $R^2$ is $OCH_3$. In one embodiment, in a compound of formula (I-3a), $R^1$ is —O—($C_1$-$C_4$ alkyl) and $R^2$ is vinyl (or ethenyl). In one embodiment, in a compound of formula (I-3a), $R^1$ is —O—($C_1$-$C_4$ alkyl) and $R^2$ is 1-propenyl. In one embodiment, in a compound of formula (I-3a), $R^1$ is $OCH_3$ and $R^2$ is halogen. In one embodiment, in a compound of formula (I-3a), $R^1$ is $OCH_3$ and $R^2$ is $C_2$-$C_4$ alkenyl. In one embodiment, in a compound of formula (I-3a), $R^1$ is $OCH_3$ and $R^2$ is $C_1$-$C_4$ alkoxy. In one embodiment, in a compound of formula (I-3a), $R^1$ is $OCH_3$ and $R^2$ is Cl. In one embodiment, in a compound of formula (I-3a), $R^1$ is $OCH_3$ and $R^2$ is $OCH_3$. In one embodiment, in a compound of formula (I-3a), $R^1$ is $OCH_3$ and $R^2$ is vinyl (or ethenyl). In one embodiment, in a compound of formula (I-3a), $R^1$ is $OCH_3$ and $R^2$ is 1-propenyl.

In one embodiment, in a compound of formula (I-3b), $R^1$ is OH and $R^2$ is halogen. In one embodiment, in a compound of formula (I-3b), $R^1$ is OH and $R^2$ is $C_2$-$C_4$ alkenyl. In one embodiment, in a compound of formula (I-3b), $R^1$ is OH and $R^2$ is $C_1$-$C_4$ alkoxy. In one embodiment, in a compound of formula (I-3b), $R^1$ is OH and $R^2$ is Cl. In one embodiment, in a compound of formula (I-3b), $R^1$ is OH and $R^2$ is $OCH_3$. In one embodiment, in a compound of formula (I-3b), $R^1$ is OH and $R^2$ is vinyl (or ethenyl). In one embodiment, in a compound of formula (I-3b), $R^1$ is OH and $R^2$ is 1-propenyl. In one embodiment, in a compound of formula (I-3b), $R^1$ is —O—($C_1$-$C_4$ alkyl) and $R^2$ is halogen. In one embodiment, in a compound of formula (I-3b), $R^1$ is —O—($C_1$-$C_4$ alkyl) and $R^2$ is $C_2$-$C_4$ alkenyl. In one embodiment, in a compound of formula (I-3b), $R^1$ is —O—($C_1$-$C_4$ alkyl) and $R^2$ is $C_1$-$C_4$ alkoxy. In one embodiment, in a compound of formula (I-3b), $R^1$ is —O—($C_1$-$C_4$ alkyl) and $R^2$ is Cl. In one embodiment, in a compound of formula (I-3b), $R^1$ is —O—($C_1$-$C_4$ alkyl) and $R^2$ is $OCH_3$. In one embodiment, in a compound of formula (I-3b), $R^1$ is —O—($C_1$-$C_4$ alkyl) and $R^2$ is vinyl (or ethenyl). In one embodiment, in a compound of formula (I-3b), $R^1$ is —O—($C_1$-$C_4$ alkyl) and $R^2$ is 1-propenyl. In one embodiment, in a compound of formula (I-3b), $R^1$ is $OCH_3$ and $R^2$ is halogen. In one embodiment, in a compound of formula (I-3b), $R^1$ is $OCH_3$ and $R^2$ is $C_2$-$C_4$ alkenyl. In one embodiment, in a compound of formula (I-3b), $R^1$ is $OCH_3$ and $R^2$ is $C_1$-$C_4$ alkoxy. In one embodiment, in a compound of formula (I-3b), $R^1$ is $OCH_3$ and $R^2$ is Cl. In one embodiment, in a compound of formula (I-3b), $R^1$ is $OCH_3$ and $R^2$ is $OCH_3$. In one embodiment, in a compound of formula (I-3b), $R^1$ is $OCH_3$ and $R^2$ is vinyl (or ethenyl). In one embodiment, in a compound of formula (I-3b), $R^1$ is $OCH_3$ and $R^2$ is 1-propenyl.

In one embodiment, in a compound of formula (I-3c), $R^1$ is OH and $R^2$ is halogen. In one embodiment, in a compound of formula (I-3c), $R^1$ is OH and $R^2$ is $C_2$-$C_4$ alkenyl. In one embodiment, in a compound of formula (I-3c), $R^1$ is OH and $R^2$ is $C_1$-$C_4$ alkoxy. In one embodiment, in a compound of formula (I-3c), $R^1$ is OH and $R^2$ is Cl. In one embodiment, in a compound of formula (I-3c), $R^1$ is OH and $R^2$ is $OCH_3$. In one embodiment, in a compound of formula (I-3c), $R^1$ is OH and $R^2$ is vinyl (or ethenyl). In one embodiment, in a compound of formula (I-3c), $R^1$ is OH and $R^2$ is 1-propenyl. In one embodiment, in a compound of formula (I-3c), $R^1$ is —O—($C_1$-$C_4$ alkyl) and $R^2$ is halogen. In one embodiment, in a compound of formula (I-3c), $R^1$ is —O—($C_1$-$C_4$ alkyl) and $R^2$ is $C_2$-$C_4$ alkenyl. In one embodiment, in a compound of formula (I-3c), $R^1$ is —O—($C_1$-$C_4$ alkyl) and $R^2$ is $C_1$-$C_4$ alkoxy. In one embodiment, in a compound of formula (I-3c), $R^1$ is —O—($C_1$-$C_4$ alkyl) and $R^2$ is Cl. In one embodiment, in a compound of formula (I-3c), $R^1$ is —O—($C_1$-$C_4$ alkyl) and $R^2$ is $OCH_3$. In one embodiment, in a compound of formula (I-3c). $R^1$ is —O—($C_1$-$C_4$ alkyl) and $R^2$ is vinyl (or ethenyl). In one embodiment, in a compound of formula (I-3c), $R^1$ is —O—($C_1$-$C_4$ alkyl) and $R^2$ is 1-propenyl. In one embodiment, in a compound of formula (I-3c), $R^1$ is $OCH_3$ and $R^2$ is halogen. In one embodiment, in a compound of formula (I-3c), $R^1$ is $OCH_3$ and $R^2$ is $C_2$-$C_4$ alkenyl. In one embodiment, in a compound of formula (I-3c), $R^1$ is $OCH_3$ and $R^2$ is $C_1$-$C_4$ alkoxy. In one embodiment, in a compound of formula (I-3c), $R^1$ is $OCH_3$ and $R^2$ is Cl. In one embodiment, in a compound of formula (I-3c), $R^1$ is $OCH_3$ and $R^2$ is $OCH_3$. In one embodiment, in a compound of formula (I-3c), $R^1$ is $OCH_3$ and $R^2$ is vinyl (or ethenyl). In one embodiment, in a compound of formula (I-3c), $R^1$ is $OCH_3$ and $R^2$ is 1-propenyl.

In one embodiment, Ar is Ar4.

In one embodiment, provided herein is a compound of formula (I-4), or an N-oxide or agriculturally acceptable salt thereof:

(I-4)

wherein X, $R^1$, $R^2$, $R^3$, $R^4$, and $X_2$ are defined herein elsewhere.

In one embodiment, in a compound of formula (I-4), $R^1$ is OH and $R^2$ is halogen.

In one embodiment, in a compound of formula (I-4), $R^1$ is OH and $R^2$ is $C_2$-$C_4$ alkenyl. In one embodiment, in a compound of formula (I-4), $R^1$ is OH and $R^2$ is $C_1$-$C_4$ alkoxy. In one embodiment, in a compound of formula (I-4), $R^1$ is OH and $R^2$ is Cl. In one embodiment, in a compound of formula (I-4), $R^1$ is OH and $R^2$ is $OCH_3$. In one embodiment, in a compound of formula (I-4), $R^1$ is OH and $R^2$ is vinyl (or ethenyl). In one embodiment, in a compound of formula (I-4), $R^1$ is OH and $R^2$ is 1-propenyl. In one embodiment, in a compound of formula (I-4), $R^1$ is —O—($C_1$-$C_4$ alkyl) and $R^2$ is halogen. In one embodiment, in a compound of formula (I-4), $R^1$ is —O—($C_1$-$C_4$ alkyl) and $R^2$ is $C_2$-$C_4$ alkenyl. In one embodiment, in a compound of formula (I-4), $R^1$ is —O—($C_1$-$C_4$ alkyl) and $R^2$ is $C_1$-$C_4$ alkoxy. In one embodiment, in a compound of formula (I-4), $R^1$ is —O—($C_1$-$C_4$ alkyl) and $R^2$ is Cl. In one embodiment, in a compound of formula (I-4), $R^1$ is —O—($C_1$-$C_4$ alkyl) and $R^2$ is $OCH_3$. In one embodiment, in a compound of formula (I-4), $R^1$ is —O—($C_1$-$C_4$ alkyl) and $R^2$ is vinyl (or ethenyl). In one embodiment, in a compound of formula (I-4), $R^1$ is —O—($C_1$-$C_4$ alkyl) and $R^2$ is 1-propenyl. In one embodiment, in a compound of formula (I-4), $R^1$ is $OCH_3$ and $R^2$ is halogen. In one embodiment, in a compound of formula (I-4), $R^1$ is $OCH_3$ and $R^2$ is $C_2$-$C_4$ alkenyl. In one embodiment, in a compound of formula (I-4), $R^1$ is $OCH_3$ and $R^2$ is $C_1$-$C_4$ alkoxy. In one embodiment, in a compound of formula (I-4), $R^1$ is $OCH_3$ and $R^2$ is Cl. In one embodiment, in a compound of formula (I-4), $R^1$ is $OCH_3$ and $R^2$ is $OCH_3$. In one embodiment, in a compound of formula (I-4), $R^1$ is $OCH_3$ and $R^2$ is vinyl (or ethenyl). In one embodiment, in a compound of formula (I-4), $R^1$ is $OCH_3$ and $R^2$ is 1-propenyl.

In one embodiment, provided herein is a compound of formula (I-4a), (I-4b), or (I-4c), or an N-oxide or agriculturally acceptable salt thereof:

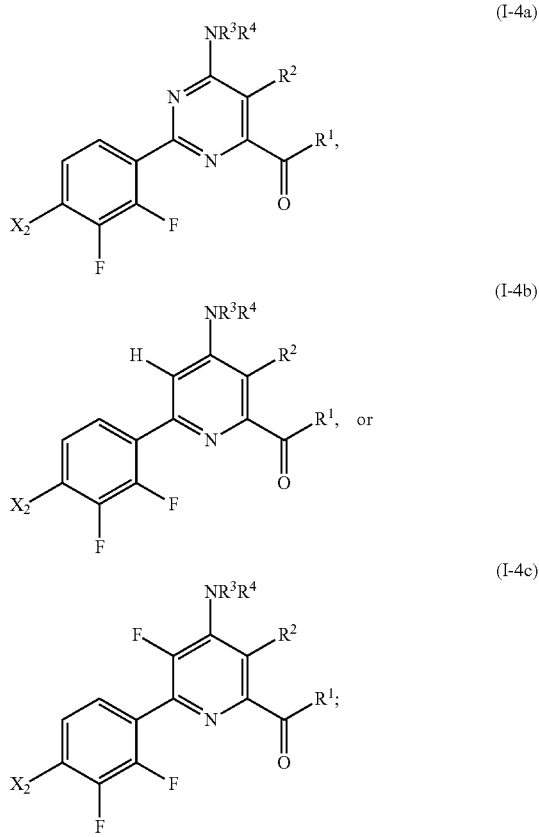

wherein $R^1$, $R^2$, $R^3$, $R^4$, and $X_2$ are defined herein elsewhere.

In one embodiment, in a compound of formula (I-4a), $R^1$ is OH and $R^2$ is halogen. In one embodiment, in a compound of formula (I-4a), $R^1$ is OH and $R^2$ is $C_2$-$C_4$ alkenyl. In one embodiment, in a compound of formula (I-4a), $R^1$ is OH and $R^2$ is $C_1$-$C_4$ alkoxy. In one embodiment, in a compound of formula (I-4a), $R^1$ is OH and $R^2$ is Cl. In one embodiment, in a compound of formula (I-4a), $R^1$ is OH and $R^2$ is $OCH_3$. In one embodiment, in a compound of formula (I-4a), $R^1$ is OH and $R^2$ is vinyl (or ethenyl). In one embodiment, in a compound of formula (I-4a), $R^1$ is OH and $R^2$ is 1-propenyl. In one embodiment, in a compound of formula (I-4a), $R^1$ is —O—($C_1$-$C_4$ alkyl) and $R^2$ is halogen. In one embodiment, in a compound of formula (I-4a), $R^1$ is —O—($C_1$-$C_4$ alkyl) and $R^2$ is $C_2$-$C_4$ alkenyl. In one embodiment, in a compound of formula (I-4a), $R^1$ is —O—($C_1$-$C_4$ alkyl) and $R^2$ is $C_1$-$C_4$ alkoxy. In one embodiment, in a compound of formula (I-4a), $R^1$ is —O—($C_1$-$C_4$ alkyl) and $R^2$ is Cl. In one embodiment, in a compound of formula (I-4a), $R^1$ is —O—($C_1$-$C_4$ alkyl) and $R^2$ is $OCH_3$. In one embodiment, in a compound of formula (I-4a), $R^1$ is —O—($C_1$-$C_4$ alkyl) and $R^2$ is vinyl (or ethenyl). In one embodiment, in a compound of formula (I-4a), $R^1$ is —O—($C_1$-$C_4$ alkyl) and $R^2$ is 1-propenyl. In one embodiment, in a compound of formula (I-4a), $R^1$ is $OCH_3$ and $R^2$ is halogen. In one embodiment, in a compound of formula (I-4a), $R^1$ is $OCH_3$ and $R^2$ is $C_2$-$C_4$ alkenyl. In one embodiment, in a compound of formula (I-4a), $R^1$ is $OCH_3$ and $R^2$ is $C_1$-$C_4$ alkoxy. In one embodiment, in a compound of formula (I-4a), $R^1$ is $OCH_3$ and $R^2$ is Cl. In one embodiment, in a compound of formula (I-4a), $R^1$ is $OCH_3$ and $R^2$ is $OCH_3$. In one embodiment, in a compound of formula (I-4a), $R^1$ is $OCH_3$ and $R^2$ is vinyl (or ethenyl). In one embodiment, in a compound of formula (I-4a), $R^1$ is $OCH_3$ and $R^2$ is 1-propenyl.

In one embodiment, in a compound of formula (I-4b), $R^1$ is OH and $R^2$ is halogen. In one embodiment, in a compound of formula (I-4b), $R^1$ is OH and $R^2$ is $C_2$-$C_4$ alkenyl. In one embodiment, in a compound of formula (I-4b), $R^1$ is OH and $R^2$ is $C_1$-$C_4$ alkoxy. In one embodiment, in a compound of formula (I-4b), $R^1$ is OH and $R^2$ is Cl. In one embodiment, in a compound of formula (I-4b), $R^1$ is OH and $R^2$ is $OCH_3$. In one embodiment, in a compound of formula (I-4b), $R^1$ is OH and $R^2$ is vinyl (or ethenyl). In one embodiment, in a compound of formula (I-4b), $R^1$ is OH and $R^2$ is 1-propenyl. In one embodiment, in a compound of formula (I-4b), $R^1$ is —O—($C_1$-$C_4$ alkyl) and $R^2$ is halogen. In one embodiment, in a compound of formula (I-4b), $R^1$ is —O—($C_1$-$C_4$ alkyl) and $R^2$ is $C_2$-$C_4$ alkenyl. In one embodiment, in a compound of formula (I-4b), $R^1$ is —O—($C_1$-$C_4$ alkyl) and $R^2$ is $C_1$-$C_4$ alkoxy. In one embodiment, in a compound of formula (I-4b), $R^1$ is —O—($C_1$-$C_4$ alkyl) and $R^2$ is Cl. In one embodiment, in a compound of formula (I-4b), $R^1$ is —O—($C_1$-$C_4$ alkyl) and $R^2$ is $OCH_3$. In one embodiment, in a compound of formula (I-4b), $R^1$ is —O—($C_1$-$C_4$ alkyl) and $R^2$ is vinyl (or ethenyl). In one embodiment, in a compound of formula (I-4b), $R^1$ is —O—($C_1$-$C_4$ alkyl) and $R^2$ is 1-propenyl. In one embodiment, in a compound of formula (I-4b), $R^1$ is $OCH_3$ and $R^2$ is halogen. In one embodiment, in a compound of formula (I-4b), $R^1$ is $OCH_3$ and $R^2$ is $C_2$-$C_4$ alkenyl. In one embodiment, in a compound of formula (I-4b), $R^1$ is $OCH_3$ and $R^2$ is $C_1$-$C_4$ alkoxy. In one embodiment, in a compound of formula (I-4b), $R^1$ is $OCH_3$ and $R^2$ is Cl. In one embodiment, in a compound of formula (I-4b), $R^1$ is $OCH_3$ and $R^2$ is $OCH_3$. In one embodiment, in a compound of formula (I-4b), $R^1$ is $OCH_3$ and $R^2$ is vinyl (or ethenyl). In one embodiment, in a compound of formula (I-4b), $R^1$ is $OCH_3$ and $R^2$ is 1-propenyl.

In one embodiment, in a compound of formula (I-4c), $R^1$ is OH and $R^2$ is halogen. In one embodiment, in a compound of formula (I-4c), $R^1$ is OH and $R^2$ is $C_2$-$C_4$ alkenyl. In one embodiment, in a compound of formula (I-4c), $R^1$ is OH and $R^2$ is $C_1$-$C_4$ alkoxy. In one embodiment, in a compound of formula (I-4c), $R^1$ is OH and $R^2$ is Cl. In one embodiment, in a compound of formula (I-4c), $R^1$ is OH and $R^2$ is $OCH_3$. In one embodiment, in a compound of formula (I-4c), $R^1$ is OH and $R^2$ is vinyl (or ethenyl). In one embodiment, in a compound of formula (I-4c), $R^1$ is OH and $R^2$ is 1-propenyl. In one embodiment, in a compound of formula (I-4c), $R^1$ is —O—($C_1$-$C_4$ alkyl) and $R^2$ is halogen. In one embodiment, in a compound of formula (I-4c), $R^1$ is —O—($C_1$-$C_4$ alkyl) and $R^2$ is $C_2$-$C_4$ alkenyl. In one embodiment, in a compound of formula (I-4c), $R^1$ is —O—($C_1$-$C_4$ alkyl) and $R^2$ is $C_1$-$C_4$ alkoxy. In one embodiment, in a compound of formula (I-4c), $R^1$ is —O—($C_1$-$C_4$ alkyl) and $R^2$ is Cl. In one embodiment, in a compound of formula (I-4c), $R^1$ is —O—($C_1$-$C_4$ alkyl) and $R^2$ is $OCH_3$. In one embodiment, in a compound of formula (I-4c), $R^1$ is —O—($C_1$-$C_4$ alkyl) and $R^2$ is vinyl (or ethenyl). In one embodiment, in a compound of formula (I-4c), $R^1$ is —O—($C_1$-$C_4$ alkyl) and $R^2$ is 1-propenyl. In one embodiment, in a compound of formula (I-4c), $R^1$ is $OCH_3$ and $R^2$ is halogen. In one embodiment, in a compound of formula (I-4c), $R^1$ is $OCH_3$ and $R^2$ is $C_2$-$C_4$ alkenyl. In one embodiment, in a compound of formula (I-4c), $R^1$ is $OCH_3$ and $R^2$ is $C_1$-$C_4$ alkoxy. In one embodiment, in a compound of formula (I-4c), $R^1$ is $OCH_3$ and $R^2$ is Cl. In one embodiment, in a compound of formula (I-4c), $R^1$ is $OCH_3$ and $R^2$ is $OCH_3$. In one embodiment, in a compound of formula (I-4c), $R^1$ is $OCH_3$ and $R^2$ is vinyl (or ethenyl). In one embodiment, in a compound of formula (I-4c), $R^1$ is $OCH_3$ and $R^2$ is 1-propenyl.

In one embodiment, Ar is Ar5.

In one embodiment, provided herein is a compound of formula (I-5), or an N-oxide or agriculturally acceptable salt thereof:

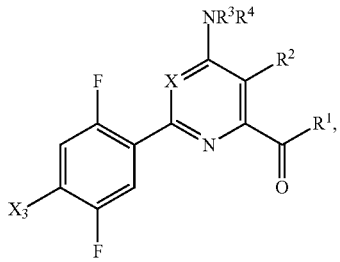

(I-5)

wherein X, $R^1$, $R^2$, $R^3$, $R^4$, and $X_3$ are defined herein elsewhere.

In one embodiment, in a compound of formula (I-5), $R^1$ is OH and $R^2$ is halogen. In one embodiment, in a compound of formula (I-5), $R^1$ is OH and $R^2$ is $C_2$-$C_4$ alkenyl. In one embodiment, in a compound of formula (I-5), $R^1$ is OH and $R^2$ is $C_1$-$C_4$ alkoxy. In one embodiment, in a compound of formula (I-5), $R^1$ is OH and $R^2$ is Cl. In one embodiment, in a compound of formula (I-5), $R^1$ is OH and $R^2$ is $OCH_3$. In one embodiment, in a compound of formula (I-5), $R^1$ is OH and $R^2$ is vinyl (or ethenyl). In one embodiment, in a compound of formula (I-5), $R^1$ is OH and $R^2$ is 1-propenyl. In one embodiment, in a compound of formula (I-5), $R^1$ is —O—($C_1$-$C_4$ alkyl) and $R^2$ is halogen. In one embodiment, in a compound of formula (I-5), $R^1$ is —O—($C_1$-$C_4$ alkyl) and $R^2$ is $C_2$-$C_4$ alkenyl. In one embodiment, in a compound of formula (I-5), $R^1$ is —O—($C_1$-$C_4$ alkyl) and $R^2$ is $C_1$-$C_4$ alkoxy. In one embodiment, in a compound of formula (I-5), $R^1$ is —O—($C_1$-$C_4$ alkyl) and $R^2$ is Cl. In one embodiment, in a compound of formula (I-5), $R^1$ is —O—($C_1$-$C_4$ alkyl) and $R^2$ is $OCH_3$. In one embodiment, in a compound of formula (I-5), $R^1$ is —O—($C_1$-$C_4$ alkyl) and $R^2$ is vinyl (or ethenyl). In one embodiment, in a compound of formula (I-5), $R^1$ is —O—($C_1$-$C_4$ alkyl) and $R^2$ is 1-propenyl. In one embodiment, in a compound of formula (I-5), $R^1$ is $OCH_3$ and $R^2$ is halogen. In one embodiment, in a compound of formula (I-5), $R^1$ is $OCH_3$ and $R^2$ is $C_2$-$C_4$ alkenyl. In one embodiment, in a compound of formula (I-5), $R^1$ is $OCH_3$ and $R^2$ is $C_1$-$C_4$ alkoxy. In one embodiment, in a compound of formula (I-5), $R^1$ is $OCH_3$ and $R^2$ is Cl. In one embodiment, in a compound of formula (I-5), $R^1$ is $OCH_3$ and $R^2$ is $OCH_3$. In one embodiment, in a compound of formula (I-5), $R^1$ is $OCH_3$ and $R^2$ is vinyl (or ethenyl). In one embodiment, in a compound of formula (I-5), $R^1$ is $OCH_3$ and $R^2$ is 1-propenyl.

In one embodiment, provided herein is a compound of formula (I-5a), (I-5b), or (I-5c), or an N-oxide or agriculturally acceptable salt thereof:

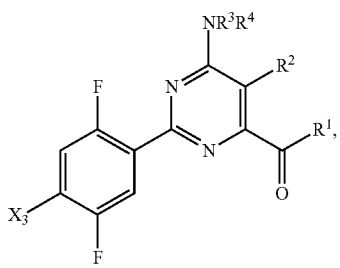

(I-5a)

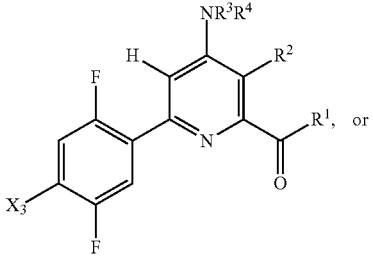

(I-5b)

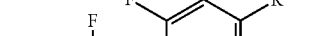

(I-5c)

wherein $R^1$, $R^2$, $R^3$, $R^4$, and $X_3$ are defined herein elsewhere.

In one embodiment, in a compound of formula (I-5a), $R^1$ is OH and $R^2$ is halogen. In one embodiment, in a compound of formula (I-5a), $R^1$ is OH and $R^2$ is $C_2$-$C_4$ alkenyl. In one embodiment, in a compound of formula (I-5a), $R^1$ is OH and $R^2$ is alkoxy. In one embodiment, in a compound of formula (I-5a), $R^1$ is OH and $R^2$ is Cl. In one embodiment, in a compound of formula (I-5a), $R^1$ is OH and $R^2$ is $OCH_3$. In one embodiment, in a compound of formula (I-5a), $R^1$ is OH and $R^2$ is vinyl (or ethenyl). In one embodiment, in a compound of formula (I-5a), $R^1$ is OH and $R^2$ is 1-propenyl. In one embodiment, in a compound of formula (I-5a), $R^1$ is —O—($C_1$-$C_4$ alkyl) and $R^2$ is halogen. In one embodiment, in a compound of formula (I-5a), $R^1$ is —O—($C_1$-$C_4$ alkyl) and $R^2$ is $C_2$-$C_4$ alkenyl. In one embodiment, in a compound of formula (I-5a), $R^1$ is —O—($C_1$-$C_4$ alkyl) and $R^2$ is $C_1$-$C_4$ alkoxy. In one embodiment, in a compound of formula (I-5a), $R^1$ is —O—($C_1$-$C_4$ alkyl) and $R^2$ is Cl. In one embodiment, in a compound of formula (I-5a), $R^1$ is —O—($C_1$-$C_4$ alkyl) and $R^2$ is $OCH_3$. In one embodiment, in a compound of formula (I-5a), $R^1$ is —O—($C_1$-$C_4$ alkyl) and $R^2$ is vinyl (or ethenyl). In one embodiment, in a compound of formula (I-5a), $R^1$ is —O—($C_1$-$C_4$ alkyl) and $R^2$ is 1-propenyl. In one embodiment, in a compound of formula (I-5a), $R^1$ is $OCH_3$ and $R^2$ is halogen. In one embodiment, in a compound of formula (I-5a), $R^1$ is $OCH_3$ and $R^2$ is $C_2$-$C_4$ alkenyl. In one embodiment, in a compound of formula (I-5a), $R^1$ is $OCH_3$ and $R^2$ is $C_1$-$C_4$ alkoxy. In one embodiment, in a compound of formula (I-5a), $R^1$ is $OCH_3$ and $R^2$ is Cl. In one embodiment, in a compound of formula (I-5a), $R^1$ is $OCH_3$ and $R^2$ is $OCH_3$. In one embodiment, in a compound of formula (I-5a), $R^1$ is $OCH_3$ and $R^2$ is vinyl (or ethenyl). In one embodiment, in a compound of formula (I-5a), $R^1$ is $OCH_3$ and $R^2$ is 1-propenyl.

In one embodiment, in a compound of formula (I-5b), $R^1$ is OH and $R^2$ is halogen. In one embodiment, in a compound of formula (I-5b), $R^1$ is OH and $R^2$ is $C_2$-$C_4$ alkenyl. In one embodiment, in a compound of formula (I-5b), $R^1$ is OH and $R^2$ is $C_1$-$C_4$ alkoxy. In one embodiment, in a compound of formula (I-5b), $R^1$ is OH and $R^2$ is Cl. In one embodiment, in a compound of formula (I-5b), $R^1$ is OH and $R^2$ is $OCH_3$. In one embodiment, in a compound of formula (I-5b), $R^1$ is OH and $R^2$ is vinyl (or ethenyl). In one embodiment, in a compound of formula (I-5b), $R^1$ is OH and $R^2$ is 1-propenyl. In one embodiment, in a compound of formula (I-5b), $R^1$ is —O—($C_1$-$C_4$ alkyl) and $R^2$ is halogen. In one embodiment, in a compound of formula (I-5b), $R^1$ is —O—($C_1$-$C_4$ alkyl) and $R^2$ is $C_2$-$C_4$ alkenyl. In one embodiment, in a compound of formula (I-5b), $R^1$ is —O—($C_1$-$C_4$ alkyl) and $R^2$ is $C_1$-$C_4$ alkoxy. In one embodiment, in a compound of formula (I-5b), $R^1$ is —O—($C_1$-$C_4$ alkyl) and $R^2$ is Cl. In one embodiment, in a compound of formula (I-5b), $R^1$ is —O—($C_1$-$C_4$ alkyl) and $R^2$ is $OCH_3$. In one embodiment, in a compound of formula (I-5b), $R^1$ is —O—($C_1$-$C_4$ alkyl) and $R^2$ is vinyl (or ethenyl). In one embodiment, in a compound of formula (I-5b), $R^1$ is —O—($C_1$-$C_4$ alkyl) and $R^2$ is 1-propenyl. In one embodiment, in a compound of formula (I-5b), $R^1$ is $OCH_3$ and $R^2$ is halogen. In one embodiment, in a compound of formula (I-5b), $R^1$ is $OCH_3$ and $R^2$ is $C_2$-$C_4$ alkenyl. In one embodiment, in a compound of formula (I-5b), $R^1$ is $OCH_3$ and $R^2$ is $C_1$-$C_4$ alkoxy. In one embodiment, in a compound of formula (I-5b), $R^1$ is $OCH_3$ and $R^2$ is Cl. In one embodiment, in a compound of formula (I-5b), $R^1$ is $OCH_3$ and $R^2$ is $OCH_3$. In one embodiment, in a compound of formula (I-5b), $R^1$ is $OCH_3$ and $R^2$ is vinyl (or ethenyl). In one embodiment, in a compound of formula (I-5b), $R^1$ is $OCH_3$ and $R^2$ is 1-propenyl.

In one embodiment, in a compound of formula (I-5c), $R^1$ is OH and $R^2$ is halogen. In one embodiment, in a compound of formula (I-5c), $R^1$ is OH and $R^2$ is $C_2$-$C_4$ alkenyl. In one embodiment, in a compound of formula (I-5c), $R^1$ is OH and $R^2$ is $C_1$-$C_4$ alkoxy. In one embodiment, in a compound of formula (I-5c), $R^1$ is OH and $R^2$ is Cl. In one embodiment, in a compound of formula (I-5c), $R^1$ is OH and $R^2$ is $OCH_3$. In one embodiment, in a compound of formula (I-5c), $R^1$ is OH and $R^2$ is vinyl (or ethenyl). In one embodiment, in a compound of formula (I-5c), $R^1$ is OH and $R^2$ is 1-propenyl. In one embodiment, in a compound of formula (I-5c), $R^1$ is —O—($C_1$-$C_4$ alkyl) and $R^2$ is halogen. In one embodiment, in a compound of formula (I-5c), $R^1$ is —O—($C_1$-$C_4$ alkyl) and $R^2$ is $C_2$-$C_4$ alkenyl. In one embodiment, in a compound of formula (I-5c), $R^1$ is —O—($C_1$-$C_4$ alkyl) and $R^2$ is $C_1$-$C_4$ alkoxy. In one embodiment, in a compound of formula (I-5c), $R^1$ is —O—($C_1$-$C_4$ alkyl) and $R^2$ is Cl. In one embodiment, in a compound of formula (I-5c), $R^1$ is —O—($C_1$-$C_4$ alkyl) and $R^2$ is $OCH_3$. In one embodiment, in a compound of formula (I-5c), $R^1$ is —O—($C_1$-$C_4$ alkyl) and $R^2$ is vinyl (or ethenyl). In one embodiment, in a compound of formula (I-5c), $R^1$ is —O—($C_1$-$C_4$ alkyl) and $R^2$ is 1-propenyl. In one embodiment, in a compound of formula (I-5c), $R^1$ is $OCH_3$ and $R^2$ is halogen. In one embodiment, in a compound of formula (I-5c), $R^1$ is $OCH_3$ and $R^2$ is $C_2$-$C_4$ alkenyl. In one embodiment, in a compound of formula (I-5c), $R^1$ is $OCH_3$ and $R^2$ is $C_1$-$C_4$ alkoxy. In one embodiment, in a compound of formula (I-5c), $R^1$ is $OCH_3$ and $R^2$ is Cl. In one embodiment, in a compound of formula (I-5c), $R^1$ is $OCH_3$ and $R^2$ is $OCH_3$. In one embodiment, in a compound of formula (I-5c), $R^1$ is $OCH_3$ and $R^2$ is vinyl (or ethenyl). In one embodiment, in a compound of formula (I-5c), $R^1$ is $OCH_3$ and $R^2$ is 1-propenyl.

In one embodiment, Ar is Ar6.

In one embodiment, provided herein is a compound of formula (I-6), or an N-oxide or agriculturally acceptable salt thereof:

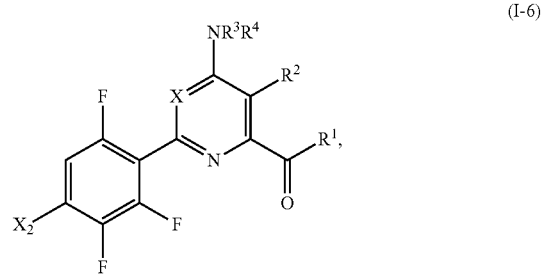

(I-6)

wherein X, $R^1$, $R^2$, $R^3$, $R^4$, and $X_2$ are defined herein elsewhere.

In one embodiment, in a compound of formula (I-6), $R^1$ is OH and $R^2$ is halogen. In one embodiment, in a compound of formula (I-6), $R^1$ is OH and $R^2$ is $C_2$-$C_4$ alkenyl. In one embodiment, in a compound of formula (I-6), $R^1$ is OH and $R^2$ is $C_1$-$C_4$ alkoxy. In one embodiment, in a compound of formula (I-6), $R^1$ is OH and $R^2$ is Cl. In one embodiment, in a compound of formula (I-6), $R^1$ is OH and $R^2$ is $OCH_3$. In one embodiment, in a compound of formula (I-6), $R^1$ is OH and $R^2$ is vinyl (or ethenyl). In one embodiment, in a compound of formula (I-6), $R^1$ is OH and $R^2$ is 1-propenyl. In one embodiment, in a compound of formula (I-6), $R^1$ is —O—($C_1$-$C_4$ alkyl) and $R^2$ is halogen. In one embodiment, in a compound of formula (I-6), $R^1$ is —O—($C_1$-$C_4$ alkyl) and $R^2$ is $C_2$-$C_4$ alkenyl. In one embodiment, in a compound of formula (I-6), $R^1$ is —O—($C_1$-$C_4$ alkyl) and $R^2$ is $C_1$-$C_4$ alkoxy. In one embodiment, in a compound of formula (I-6), $R^1$ is —O—($C_1$-$C_4$ alkyl) and $R^2$ is Cl. In one embodiment, in a compound of formula (I-6), $R^1$ is —O—($C_1$-$C_4$ alkyl) and $R^2$ is $OCH_3$. In one embodiment, in a compound of formula (I-6), $R^1$ is —O—($C_1$-$C_4$ alkyl) and $R^2$ is vinyl (or ethenyl). In one embodiment, in a compound of formula (I-6), $R^1$ is —O—($C_1$-$C_4$ alkyl) and $R^2$ is 1-propenyl. In one embodiment, in a compound of formula (I-6), $R^1$ is $OCH_3$ and $R^2$ is halogen. In one embodiment, in a compound of formula (I-6), $R^1$ is $OCH_3$ and $R^2$ is $C_2$-$C_4$ alkenyl. In one embodiment, in a compound of formula (I-6), $R^1$ is $OCH_3$ and $R^2$ is $C_1$-$C_4$ alkoxy. In one embodiment, in a compound of formula (I-6), $R^1$ is $OCH_3$ and $R^2$ is Cl. In one embodiment, in a compound of formula (I-6), $R^1$ is $OCH_3$ and $R^2$ is $OCH_3$. In one embodiment, in a compound of formula (I-6), $R^1$ is $OCH_3$ and $R^2$ is vinyl (or ethenyl). In one embodiment, in a compound of formula (I-6), $R^1$ is $OCH_3$ and $R^2$ is 1-propenyl.

In one embodiment, provided herein is a compound of formula (I-6a), (I-6b), or (I-6c), or an N-oxide or agriculturally acceptable salt thereof:

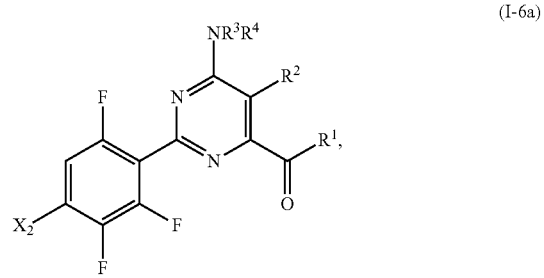

(I-6a)

(I-6b)

(I-6c)

wherein $R^1$, $R^2$, $R^3$, $R^4$, and $X_2$ are defined herein elsewhere.

In one embodiment, in a compound of formula (I-6a), $R^1$ is OH and $R^2$ is halogen. In one embodiment, in a compound of formula (I-6a), $R^1$ is OH and $R^2$ is $C_2$-$C_4$ alkenyl. In one embodiment, in a compound of formula (I-6a), $R^1$ is OH and $R^2$ is $C_1$-$C_4$ alkoxy. In one embodiment, in a compound of formula (I-6a), $R^1$ is OH and $R^2$ is Cl. In one embodiment, in a compound of formula (I-6a), $R^1$ is OH and $R^2$ is $OCH_3$. In one embodiment, in a compound of formula (I-6a), $R^1$ is OH and $R^2$ is vinyl (or ethenyl). In one embodiment, in a compound of formula (I-6a), $R^1$ is OH and $R^2$ is 1-propenyl. In one embodiment, in a compound of formula (I-6a), $R^1$ is —O—($C_1$-$C_4$ alkyl) and $R^2$ is halogen. In one embodiment, in a compound of formula (I-6a), $R^1$ is —O—($C_1$-$C_4$ alkyl) and $R^2$ is $C_2$-$C_4$ alkenyl. In one embodiment, in a compound of formula (I-6a), $R^1$ is —O—($C_1$-$C_4$ alkyl) and $R^2$ is $C_1$-$C_4$ alkoxy. In one embodiment, in a compound of formula (I-6a), $R^1$ is —O—($C_1$-$C_4$ alkyl) and $R^2$ is Cl. In one embodiment, in a compound of formula (I-6a), $R^1$ is —O—($C_1$-$C_4$ alkyl) and $R^2$ is $OCH_3$. In one embodiment, in a compound of formula (I-6a), $R^1$ is —O—($C_1$-$C_4$ alkyl) and $R^2$ is vinyl (or ethenyl). In one embodiment, in a compound of formula (I-6a), $R^1$ is —O—($C_1$-$C_4$ alkyl) and $R^2$ is 1-propenyl. In one embodiment, in a compound of formula (I-6a), $R^1$ is $OCH_3$ and $R^2$ is halogen. In one embodiment, in a compound of formula (I-6a), $R^1$ is $OCH_3$ and $R^2$ is $C_2$-$C_4$ alkenyl. In one embodiment, in a compound of formula (I-6a), $R^1$ is $OCH_3$ and $R^2$ is $C_1$-$C_4$ alkoxy. In one embodiment, in a compound of formula (I-6a), $R^1$ is $OCH_3$ and $R^2$ is Cl. In one embodiment, in a compound of formula (I-6a), $R^1$ is $OCH_3$ and $R^2$ is $OCH_3$. In one embodiment, in a compound of formula (I-6a), $R^1$ is $OCH_3$ and $R^2$ is vinyl (or ethenyl). In one embodiment, in a compound of formula (I-6a), $R^1$ is $OCH_3$ and $R^2$ is 1-propenyl.

In one embodiment, in a compound of formula (I-6b), $R^1$ is OH and $R^2$ is halogen. In one embodiment, in a compound of formula (I-6b), $R^1$ is OH and $R^2$ is $C_2$-$C_4$ alkenyl. In one embodiment, in a compound of formula (I-6b), $R^1$ is OH and $R^2$ is $C_1$-$C_4$ alkoxy. In one embodiment, in a compound of formula (I-6b), $R^1$ is OH and $R^2$ is Cl. In one embodiment, in a compound of formula (I-6b), $R^1$ is OH and $R^2$ is $OCH_3$. In one embodiment, in a compound of formula (I-6b), $R^1$ is OH and $R^2$ is vinyl (or ethenyl). In one embodiment, in a compound of formula (I-6b), $R^1$ is OH and $R^2$ is 1-propenyl. In one embodiment, in a compound of formula (I-6b), $R^1$ is —O—($C_1$-$C_4$ alkyl) and $R^2$ is halogen. In one embodiment, in a compound of formula (I-6b), $R^1$ is —O—($C_1$-$C_4$ alkyl) and $R^2$ is $C_2$-$C_4$ alkenyl. In one embodiment, in a compound of formula (I-6b), $R^1$ is —O—($C_1$-$C_4$ alkyl) and $R^2$ is $C_1$-$C_4$ alkoxy. In one embodiment, in a compound of formula (I-6b), $R^1$ is —O—($C_1$-$C_4$ alkyl) and $R^2$ is Cl. In one embodiment, in a compound of formula (I-6b), $R^1$ is —O—($C_1$-$C_4$ alkyl) and $R^2$ is $OCH_3$. In one embodiment, in a compound of formula (I-6b), $R^1$ is —O—($C_1$-$C_4$ alkyl) and $R^2$ is vinyl (or ethenyl). In one embodiment, in a compound of formula (I-6b), $R^1$ is —O—($C_1$-$C_4$ alkyl) and $R^2$ is 1-propenyl. In one embodiment, in a compound of formula (I-6b), $R^1$ is $OCH_3$ and $R^2$ is halogen. In one embodiment, in a compound of formula (I-6b), $R^1$ is $OCH_3$ and $R^2$ is $C_2$-$C_4$ alkenyl. In one embodiment, in a compound of formula (I-6b), $R^1$ is $OCH_3$ and $R^2$ is $C_1$-$C_4$ alkoxy. In one embodiment, in a compound of formula (I-6b), $R^1$ is $OCH_3$ and $R^2$ is Cl. In one embodiment, in a compound of formula (I-6b), $R^1$ is $OCH_3$ and $R^2$ is $OCH_3$. In one embodiment, in a compound of formula (I-6b), $R^1$ is $OCH_3$ and $R^2$ is vinyl (or ethenyl). In one embodiment, in a compound of formula (I-6b), $R^1$ is $OCH_3$ and $R^2$ is 1-propenyl.

In one embodiment, in a compound of formula (I-6c), $R^1$ is OH and $R^2$ is halogen. In one embodiment, in a compound of formula (I-6c), $R^1$ is OH and $R^2$ is $C_2$-$C_4$ alkenyl. In one embodiment, in a compound of formula (I-6c), $R^1$ is OH and $R^2$ is $C_1$-$C_4$ alkoxy. In one embodiment, in a compound of formula (I-6c), $R^1$ is OH and $R^2$ is Cl. In one embodiment, in a compound of formula (I-6c), $R^1$ is OH and $R^2$ is $OCH_3$. In one embodiment, in a compound of formula (I-6c), $R^1$ is OH and $R^2$ is vinyl (or ethenyl). In one embodiment, in a compound of formula (I-6c), $R^1$ is OH and $R^2$ is 1-propenyl. In one embodiment, in a compound of formula (I-6c). $R^1$ is —O—($C_1$-$C_4$ alkyl) and $R^2$ is halogen. In one embodiment, in a compound of formula (I-6c), $R^1$ is —O—($C_1$-$C_4$ alkyl) and $R^2$ is $C_2$-$C_4$ alkenyl. In one embodiment, in a compound of formula (I-6c), $R^1$ is —O—($C_1$-$C_4$ alkyl) and $R^2$ is $C_1$-$C_4$ alkoxy. In one embodiment, in a compound of formula (I-6c), $R^1$ is —O—($C_1$-$C_4$ alkyl) and $R^2$ is Cl. In one embodiment, in a compound of formula (I-6c), $R^1$ is —O—($C_1$-$C_4$ alkyl) and $R^2$ is $OCH_3$. In one embodiment, in a compound of formula (I-6c), $R^1$ is —O—($C_1$-$C_4$ alkyl) and $R^2$ is vinyl (or ethenyl). In one embodiment, in a compound of formula (I-6c), $R^1$ is —O—($C_1$-$C_4$ alkyl) and $R^2$ is 1-propenyl. In one embodiment, in a compound of formula (I-6c), $R^1$ is $OCH_3$ and $R^2$ is halogen. In one embodiment, in a compound of formula (I-6c), $R^1$ is $OCH_3$ and $R^2$ is $C_2$-$C_4$ alkenyl. In one embodiment, in a compound of formula (I-6c), $R^1$ is $OCH_3$ and $R^2$ is $C_1$-$C_4$ alkoxy. In one embodiment, in a compound of formula (I-6c), $R^1$ is $OCH_3$ and $R^2$ is Cl. In one embodiment, in a compound of formula (I-6c), $R^1$ is $OCH_3$ and $R^2$ is $OCH_3$. In one embodiment, in a compound of formula (I-6c), $R^1$ is $OCH_3$ and $R^2$ is vinyl (or ethenyl). In one embodiment, in a compound of formula (I-6c), $R^1$ is $OCH_3$ and $R^2$ is 1-propenyl.

In one embodiment, $X_1$ is H. In one embodiment, $X_1$ is F. In one embodiment, $X_1$ is Br. In one embodiment, $X_1$ is I. In one embodiment, $X_1$ is ethynyl. In one embodiment, $X_1$ is $CF_2H$. In one embodiment, $X_1$ is $OCF_2H$. In one embodiment, $X_1$ is $OCF_3$. In one embodiment, $X_1$ is CN. In one embodiment, $X_1$ is $CONH_2$. In one embodiment, $X_1$ is $CO_2H$. In one embodiment, $X_1$ is $CO_2CH_3$. In one embodiment, $X_1$ is $NO_2$.

In some embodiments, $X_1$ is H, F, Br, I, ethynyl, $CF_2H$, $OCF_2H$, $OCF_3$, CN, $CONH_2$, $CO_2CH_3$, or $NO_2$.

In some embodiments, $X_1$ is F. In some embodiments, $X_1$ is Br or I.

In one embodiment, $X_2$ is H. In one embodiment, $X_2$ is F. In one embodiment, $X_2$ is Cl. In one embodiment, $X_2$ is Br. In one embodiment, $X_2$ is I. In one embodiment, $X_2$ is ethynyl. In one embodiment, $X_2$ is $CH_3$. In one embodiment, $X_2$ is $CFH_2$. In one embodiment, $X_2$ is $CF_2H$. In one embodiment, $X_2$ is $CF_3$. In one embodiment, $X_2$ is $OCF_2H$. In one embodiment, $X_2$ is $OCF_3$. In one embodiment, $X_2$ is CN. In one embodiment, $X_2$ is $CONH_2$. In one embodiment, $X_2$ is $CO_2H$. In one embodiment, $X_2$ is $NO_2$.

In some embodiments, $X_2$ is H, Cl, Br, I, ethynyl, $CH_3$, $CF_2H$, $CF_3$, $OCF_2H$, or CN.

In some embodiments, $X_2$ is H, F, Br, I, ethynyl, $CH_3$, $CF_3$, $OCF_2H$, or CN.

In some embodiments, $X_2$ is F or Cl. In some embodiments, $X_2$ is Br or I.

In one embodiment, $X_3$ is H. In one embodiment, $X_3$ is F. In one embodiment, $X_3$ is Br. In one embodiment, $X_3$ is I. In one embodiment, $X_3$ is ethynyl. In one embodiment, $X_3$ is $CH_3$. In one embodiment, $X_3$ is $CFH_2$. In one embodiment, $X_3$ is $CF_2H$. In one embodiment, $X_3$ is $CF_3$. In one embodiment, $X_3$ is $OCF_2H$. In one embodiment, $X_3$ is $OCF_3$. In one embodiment, $X_3$ is CN. In one embodiment, $X_3$ is $CONH_2$. In one embodiment, $X_3$ is $CO_2H$. In one embodiment, $X_3$ is $NO_2$.

In some embodiments, $X_3$ is H, Br, I, ethynyl, $OCF_2H$, CN, or $NO_2$.

In some embodiments, $X_3$ is H, F, Br, I, $CH_3$, $CF_2H$, $CF_3$, $OCF_2H$, or CN.

In some embodiments, $X_3$ is F or Cl. In some embodiments, $X_3$ is Br or I.

In one embodiment, when Ar is

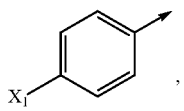

then X is N, CH, CF, CCl, or $CCH_3$, with provisos that:
  i) $R^2$ is not Cl or vinyl, when X is N;
  ii) $X_1$ is not H, F, $OCF_3$, or CN, when $R^2$ is Cl and X is CH;
  iii) $X_1$ is not F, I, CN, or ethynyl, when $R^2$ is $OCH_3$ and X is CF; and
  iv) $X_1$ is not H, when X is CCl.

In one embodiment, when Ar is

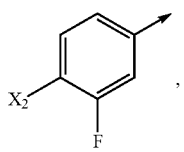

then X is N, CH, CF, CCl, or $CCH_3$, with provisos that:
  i) $R^2$ is not Cl, when X is N;
  ii) $X_2$ is not Cl, when $R^2$ is $OCH_3$ or vinyl and X is N;
  iii) $X_2$ is not Cl, when $R^2$ is Cl and X is CH; and
  iv) $X_2$ is not Cl, Br, I, or $CF_3$, when $R^2$ is $OCH_3$ and X is CF.

In one embodiment, when Ar is

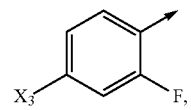

then X is N, CH, or CF, with provisos that:
  i) $R^2$ is not Cl, when X is N;
  ii) $X_3$ is not $CH_3$, when $R^2$ is $OCH_3$ and X is N;
  iii) $X_3$ is not H, F, or $CH_3$, when $R^2$ is Cl and X is CH; and
  iv) $X_3$ is not Br or I, when $R^2$ is $OCH_3$ and X is CF.

In one embodiment, when Ar is

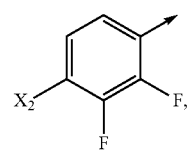

then X is N, CH, or CF, with provisos that:
  i) $R^2$ is not Cl, when X is N;
  ii) $X_2$ is not Cl, when $R^2$ is $OCH_3$ or vinyl and X is N;
  iii) $X_2$ is not F, when $R^2$ is Cl and X is CH; and
  iv) $X_2$ is not Cl, Br, I, or $CF_3$, when $R^2$ is $OCH_3$ and X is CF.

In one embodiment, when Ar is

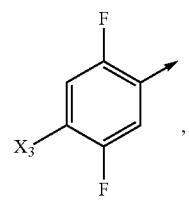

then X is N, CH, or CF, with proviso that:
  i) $X_3$ is not $CH_3$, when $R^2$ is Cl and X is N; and
  ii) $X_3$ is not Br or I, when X is CF and $R^2$ is $OCH_3$.

In one embodiment, when Ar is

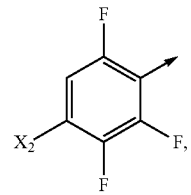

then X is N, CH, or CF.

Any of the combinations of Ar, X, Y, $R^1$, $R^2$, $R^3$, $R^4$, $R^{1'}$, $R^{1''}$, $R^{2''}$, $R^{17}$, $R^{18}$, $R^{19}$, $R^{20}$, $R^{21}$, $R^{3'}$, $R^{4'}$, Ar1, Ar2, Ar3, Ar4, Ar5, Ar6, $X_1$, $X_2$, and/or $X_3$, and/or other substituents described herein, are encompassed by this disclosure and specifically provided herein.

Methods of Preparing the Compounds

Exemplary procedures to synthesize the compounds of Formula (I) are provided below.

The 3,5-disubstituted-4-amino-6-(optionally substituted phenyl)picolinic acids of Formula (I) can be prepared in a number of ways. As depicted in Scheme I, the 4-amino-6-chloropicolinates of Formula (II) can be converted to the 4-amino-6-substituted-picolinates of Formula (III), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_1$). 4-Amino-6-substituted-picolinates of Formula (III) can be transformed into the 5-iodo-4-amino-6-substituted-picolinates of Formula (IV) via a reaction with iodinating reagents, such as periodic acid and iodine, in a polar, protic solvent, such as methyl alcohol (reaction $b_1$). Stille coupling of the 5-iodo-4-amino-6-substituted-picolinates of Formula (IV) with a stannane, such as tetramethyltin, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 5-(substituted)-4-amino-6-substituted-picolinates of Formula (I-A), wherein $Z_1$ is alkyl, alkenyl, alkynyl, haloalkenyl and alkylthio (reaction $c_1$).

Alternatively, 4-amino-6-chloropicolinates of Formula (II) can be transformed to the 5-iodo-4-amino-6-chloropicolinates of Formula (V) via a reaction with iodinating reagents, such as periodic acid and iodine, in a polar, protic solvent, such as methyl alcohol (reaction $b_2$). Stille coupling of the 5-iodo-4-amino-6-chloropicolinates of Formula (V) with a stannane, such as tetramethyltin, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 5-(substituted)-4-amino-6-chloropicolinates of Formula (VI), wherein $Z_1$ is alkyl, alkenyl, alkynyl, haloalkenyl and alkylthio (reaction $c_2$). The 5-substituted-4-amino-6-chloropicolinates of Formula (VI) can be converted to the 5-substituted-4-amino-6-substituted-picolinates of Formula (I-A), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_2$).

As depicted in Scheme II, the 4,5,6-trichloropicolinate of Formula (VII) can be converted to the corresponding isopropyl ester of Formula (VIII), via a reaction with isopropyl alcohol and concentrated sulfuric acid, e.g., at reflux temperature under Dean-Stark conditions (reaction d). The isopropyl ester of Formula (VIII) can be reacted with a fluoride ion source, such as cesium fluoride, in a polar, aprotic solvent, such as dimethyl sulfoxide, at a temperature, such as 80° C., under Dean-Stark conditions, to yield the isopropyl 4,5,6-trifluoropicolinate of Formula (IX) (reaction e). The isopropyl 4,5,6-trifluoropicolinate of Formula (IX) can be aminated with a nitrogen source, such as ammonia, in a polar, aprotic solvent, such as dimethyl sulfoxide, to produce a 4-amino-5,6-difluoropicolinate of Formula (X) (reaction f). The fluoro substituent in the 6-position of the 4-amino-5,6-difluoropicolinate of Formula (X) can be exchanged with a chloro substituent by treatment with a chloride source, such as hydrogen chloride, e.g., in dioxane, in a Parr reactor, at a temperature, such as 100° C., to produce a 4-amino-5-fluoro-6-chloropicolinate of Formula (XI) (reaction g). The 4-amino-5-fluoro-6-chloropicolinate of Formula (XI) can be transesterified to the corresponding methyl ester of Formula (XII) by reaction with titanium(IV) isopropoxide in methyl alcohol at reflux temperature (reaction h).

Scheme II

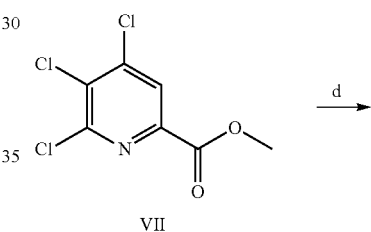

VII

Scheme I

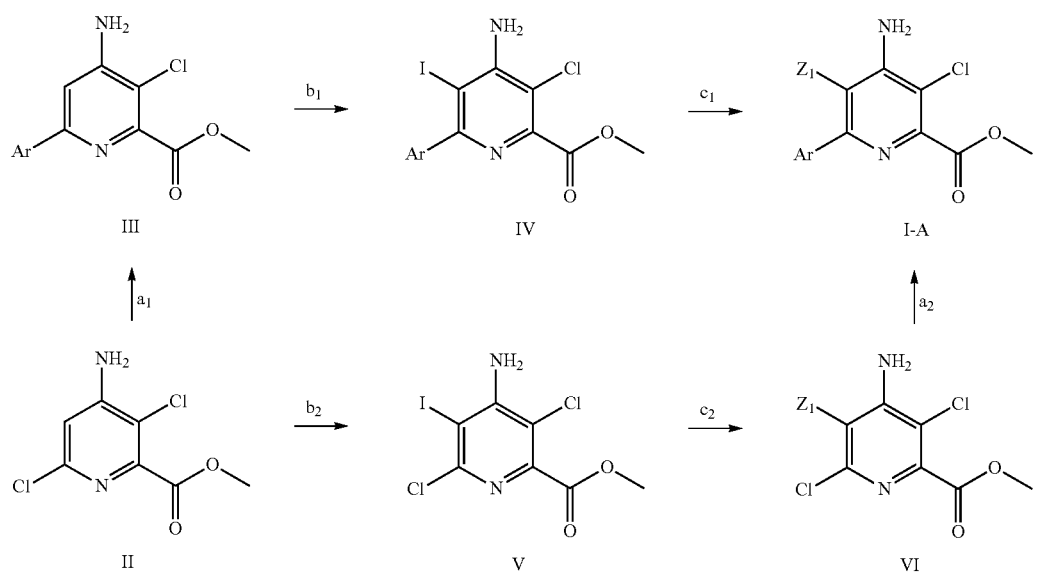

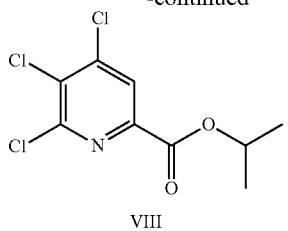

VIII

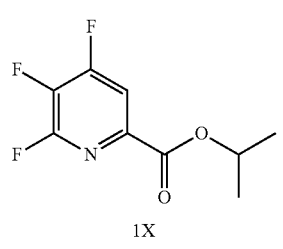

IX

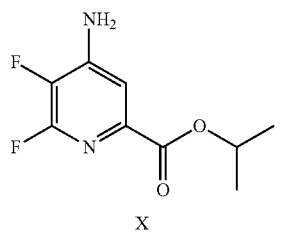

X

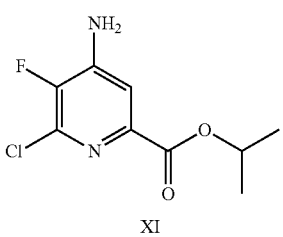

XI

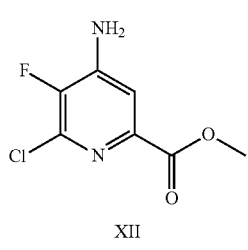

XII

As depicted in Scheme III, the 4-amino-5-fluoro-6-chloropicolinate of Formula (XII) can be transformed into the 3-iodo-4-amino-5-fluoro-6-chloropicolinate of Formula (XIII) via reaction with iodinating reagents, such as periodic acid and iodine, in a polar, protic solvent, such as methyl alcohol (reaction $b_3$). Stille coupling of the 3-iodo-4-amino-5-fluoro-6-chloropicolinates of Formula (XIII) with a stannane, such as tributyl(vinyl)stannane, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 3-(substituted)-4-amino-5-fluoro-6-chloropicolinates of Formula (XIV), wherein $R^2$ is alkyl, alkenyl, alkynyl, haloalkenyl and alkylthio (reaction $c_3$). Alternatively, the 3-iodo-4-amino-5-fluoro-6-chloropicolinates of Formula (XIII) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-chloropicolinic acids of Formula (XIV), wherein $R^2$ is alkoxy or haloalkoxy (reaction $i_1$), which can be esterified to the methyl esters, e.g., by treatment with hydrogen chloride (gas) and methyl alcohol at 50° C. (reaction $j_1$). The 3-(substituted)-4-amino-5-fluoro-6-chloropicolinates of Formula (XIV) can be converted to the 4-amino-6-substituted-picolinates of Formula (I-B), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_3$).

Alternatively, the 4-amino-5-fluoro-6-chloropicolinates of Formula (XII) can be converted to the 4-amino-5-fluoro-6-substituted-picolinates of Formula (XV), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_4$). The 4-amino-5-fluoro-6-substituted-picolinates of Formula (XV) can be transformed into the 3-iodo-4-amino-5-fluoro-6-substituted-picolinates of Formula (XVI) via reaction with iodinating reagents, such as periodic acid and iodine, in a polar, protic solvent, such as methyl alcohol (reaction $b_4$. Stille coupling of the 3-iodo-4-amino-5-fluoro-6-substituted-picolinates of Formula (XVI) with a stannane, such as tributyl(vinyl)stannane, in the presence of a catalyst, such as bis(triphenylphosphine)-palladium (II) dichloride, in a non-reactive solvent, such as 1,2-dichloroethane, at a temperature, such as 120-130° C., e.g., in a microwave reactor, provides 3-(substituted)-4-amino-5-fluoro-6-substituted-picolinates of Formula (I-B), wherein $R^2$ is alkyl, alkenyl, alkynyl, haloalkenyl and alkylthio (reaction $c_4$). Alternatively, the 3-iodo-4-amino-5-fluoro-6-substituted-picolinates of Formula (XVI) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-substituted-picolinic acids of Formula (I-B), wherein $R^2$ is alkoxy or haloalkoxy (reaction $i_2$), which can be esterified to the methyl esters, e.g., by treatment with hydrogen chloride (gas) and methyl alcohol, at a temperature, such as 50° C. (reaction $j_2$).

Scheme III

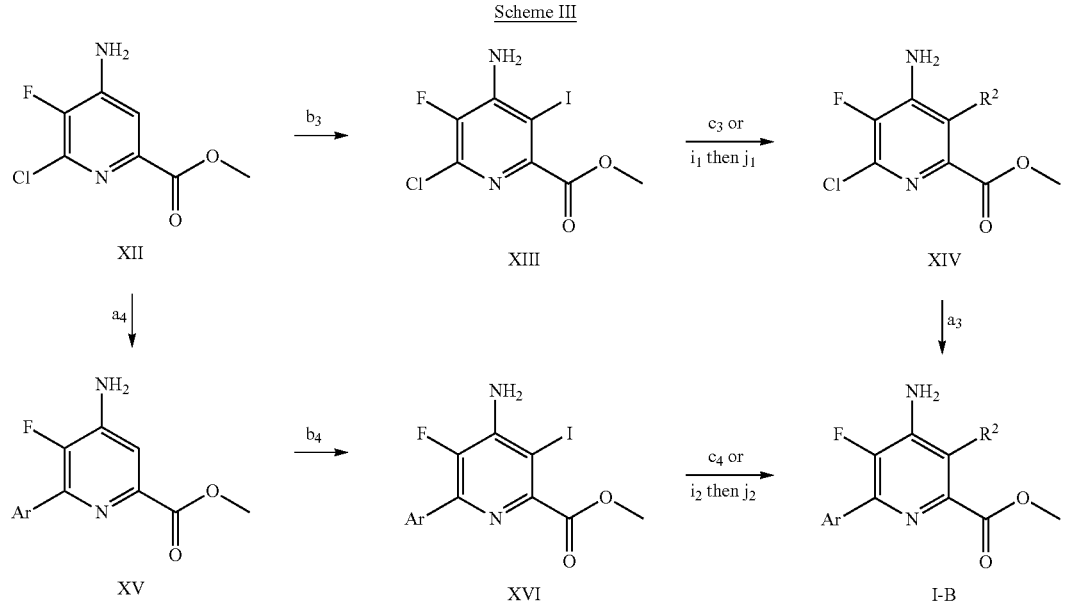

As depicted in Scheme IV, the 4-acetamido-6-(trimethylstannyl)picolinates of Formula (XVII) can be converted to the 4-acetamido-6-substituted-picolinates of Formula (XVIII), wherein Ar is as herein defined, via Stille coupling with an aryl bromide or aryl iodide, in the presence of a catalyst, such as bis(triphenylphosphine)-palladium(II) dichloride, in a solvent, such as dichloroethane, e.g., at reflux temperature (reaction k). 4-Amino-6-substituted-picolinates of Formula (I-C), wherein Ar is as herein defined, can be synthesized from 4-acetamido-6-substituted-picolinates of Formula (XVIII) via standard deprotecting methods, such as hydrochloric acid gas in methanol (reaction l).

Scheme IV

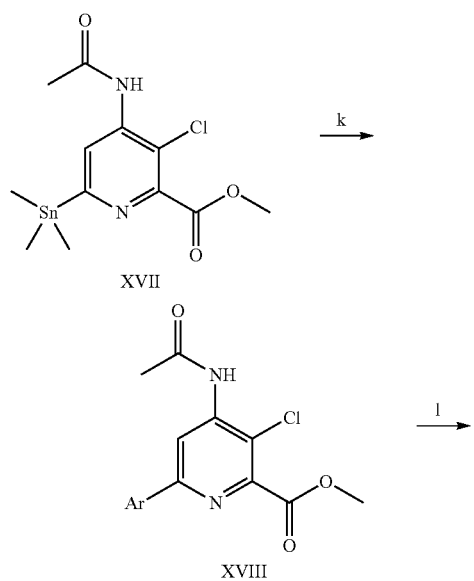

-continued

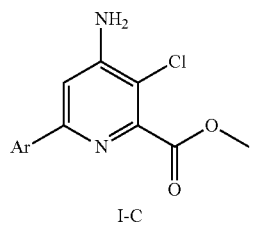

As depicted in Scheme V, 2,4-dichloro-5-methoxypyrimidine (XIX) can be transformed into 2,4-dichloro-5-methoxy-6-vinylpyrimidine (XX) via a reaction with vinyl magnesium bromide, in a polar, aprotic solvent, such as tetrahydrofuran (reaction m). 2,4-Dichloro-5-methoxy-6-vinylpyrimidine (XX) can be transformed into 2,6-dichloro-5-methoxypyrimidine-4-carboxaldehyde (XXI) via treatment with ozone, e.g., in a dichloromethane:methanol solvent mixture (reaction n). 2,6-Dichloro-5-methoxypyrimidine-4-carboxaldehyde (XXI) can be transformed into methyl 2,6-dichloro-5-methoxypyrimidine-4-carboxylate (XXII) via treatment with bromine, e.g., in a methanol:water solvent mixture (reaction o). Methyl 2,6-dichloro-5-methoxypyrimidine-4-carboxylate (XXII) can be transformed into methyl 6-amino-2-chloro-5-methoxypyrimidine-4-carboxylate (XXIII) via treatment with ammonia (e.g., 2 equivalents) in a solvent, such as DMSO (reaction p). Finally, 6-amino-2-substituted-5-methoxypyrimidine-4-carboxylates of Formula (I-D), wherein Ar is as herein defined, can be prepared via Suzuki coupling with a boronic acid or ester, with 6-amino-2-chloro-5-methoxypyrimidine-4-carboxylate (XXIII), in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_5$).

Scheme V

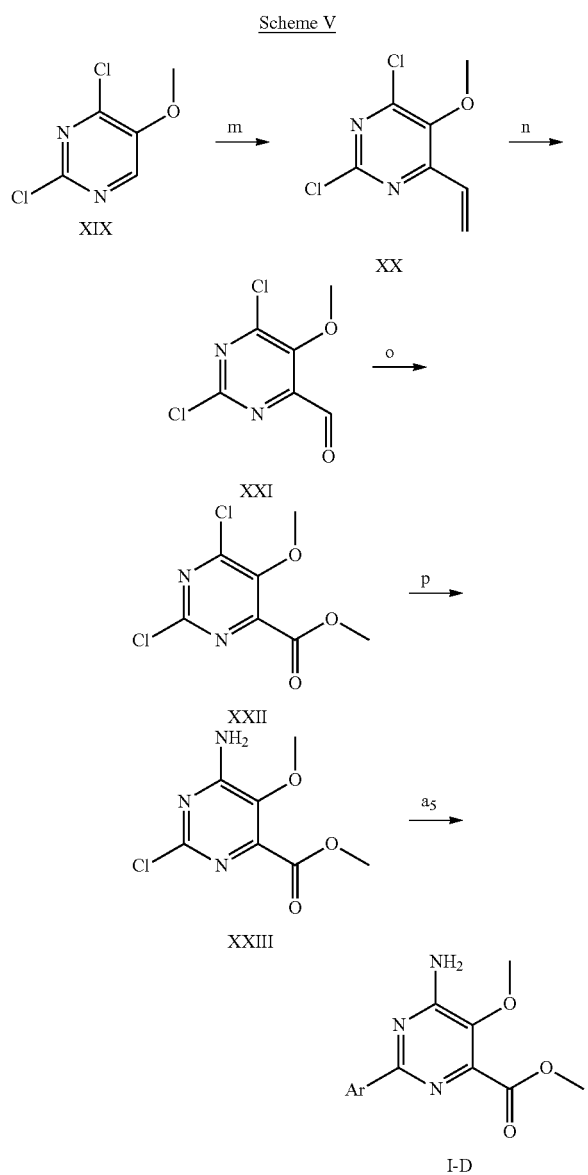

The compounds of Formulae I-A, I-B, I-C, and I-D obtained by any of these processes, can be recovered by conventional means and purified by standard procedures, such as by recrystallization or chromatography. The compounds of Formula (I) can be prepared from compounds of Formulae I-A, I-B, I-C, and I-D using standard methods well known in the art.

Compositions and Methods

In some embodiments, the compounds provided herein are employed in mixtures containing an herbicidally effective amount of the compound along with at least one agriculturally acceptable adjuvant or carrier. Exemplary adjuvants or carriers include those that are not phytotoxic or significantly phytotoxic to valuable crops, e.g., at the concentrations employed in applying the compositions for selective weed control in the presence of crops, and/or do not react or significantly react chemically with the compounds of provided herein or other composition ingredients. Such mixtures can be designed for application directly to weeds or their locus or can be concentrates or formulations that are \diluted with additional carriers and adjuvants before application. They can be solids, such as, for example, dusts, granules, water dispersible granules, or wettable powders, or liquids, such as, and for example, emulsifiable concentrates, solutions, emulsions or suspensions. They can also be provided as a pre-mix or tank-mixed.

Suitable agricultural adjuvants and carriers that are useful in preparing the herbicidal mixtures of the disclosure are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, one or more surface-active agents are utilized in the compositions of the present disclosure. Such surface-active agents are, in some embodiments, employed in both solid and liquid compositions, e.g., those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate;

soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this disclosure is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation or flood water, and by other conventional means known to those skilled in the art.

In some embodiments, the compounds and compositions described herein are applied as a post-emergence application, pre-emergence application, in-water application to flooded paddy rice or water bodies (e.g., ponds, lakes and streams), or burn-down application.

In some embodiments, the compounds and compositions provided herein are utilized to control weeds in crops, including but not limited to citrus, apple, rubber, oild palm, forestry, direct-seeded, water-seeded and transplanted rice, wheat, barley, oats, rye, sorghum, corn/maize, pastures, grasslands, rangelands, fallowland, turf, tree and vine orchards, aquatics, or row-crops, as well as non-crop settings, e.g., industrial vegetation management or rights of way. In some embodiments, the compounds and compositions are used to control woody plants, broadleaf and grass weeds, or sedges.

In some embodiments, the compounds and compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the compounds and compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* MUTT. (field violet, VIOAR), or *Viola tricolor* L. (wild violet, VIOTR).

In some embodiments, the compounds and compostions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centau-*

*rea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compounds and compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) *Moench* ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, application rates of about 1 to about 4,000 grams/hectare (g/ha) are employed in post-emergence operations. In some embodiments, rates of about 1 to about 4,000 g/ha are employed in pre-emergence operations.

In some embodiments, the compounds, compositions, and methods provided herein are used in conjunction with one or more other herbicides to control a wider variety of undesirable vegetation. When used in conjunction with other herbicides, the presently claimed compounds can be formulated with the other herbicide or herbicides, tank-mixed with the other herbicide or herbicides or applied sequentially with the other herbicide or herbicides. Some of the herbicides that can be employed in conjunction with the compounds of the present disclosure include: 4-CPA; 4-CPB; 4-CPP; 2,4-D; 2,4-D choline salt, 2,4-D esters and amines; 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halosafen, halosulfuron-methyl, haloxydine, haloxyfop-methyl, haloxyfop-P-methyl, halauxifen-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compounds and compositions of the present disclosure can generally be employed in combination with known herbicide safeners, such as benoxacor, benthiocarb, brassinolide, cloquintocet (e.g., mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

The compounds, compositions, and methods described herein be used to control undesirable vegetation on glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenylpyruvate dioxygenase (HPPD) inhibitor-tolerant-, protoporphyrinogen oxidase (PPO) inhibitor-tolerant-, triazine-tolerant-, bromoxynil-tolerant-crops (such as, but not limited to, soybean, cotton, canola/oilseed rape, rice, cereals, corn, turf, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes of action.

The compounds and compositions provided herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Synthesis of Precursors

General Considerations: Fluorine spectra were acquired at 376 MHz on a Bruker DRX400 spectrometer. The spectra were referenced to trichlorofluoromethane (CFCl$_3$) as an external standard and were typically conducted with proton decoupling.

Example 1

Preparation of methyl 4-amino-3,6-dichloropicolinate (Head A)

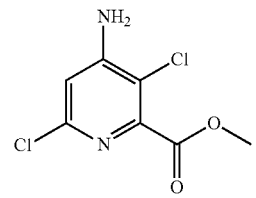

Prepared as described in Fields et al., WO 2001051468 A1.

Example 2

Preparation of methyl 4-amino-3,6-dichloro-5-fluoropicolinate (Head B)

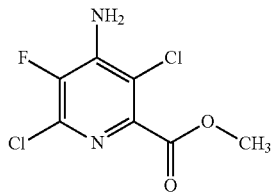

Prepared as described in Fields et al., *Tetrahedron Letters* (2010), 51(1), 79-81.

Example 3

Preparation of 2,6-dichloro-5-methoxy-4-vinyl pyrimidine

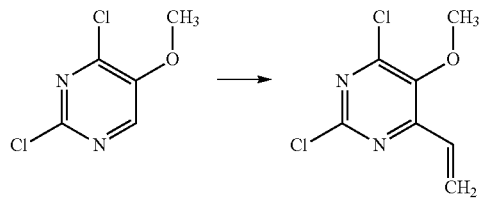

To a solution of commercially available 2,6-dichloro-5-methoxy pyrimidine (100 g, 0.55 mol) in dry tetrahydrofuran was added, dropwise, 1 M vinyl magnesium bromide in tetrahydrofuran solvent (124 g, 0.94 mol) over one hour (h) at room temperature. The mixture was then stirred for 4 h at room temperature. Excess Grignard reagent was quenched by addition of acetone (200 mL) while the temperature of the mixture was maintained at a temperature below 20° C. Thereafter, 2,3-dichloro-5,6-dicyano-p-benzoquinone (DDQ) (151 g, 0.67 mol) was added at once and stirred overnight. A yellow solid precipitated out. The solid was filtered and washed with ethyl acetate (500 mL). The filtrate was concentrated under reduced pressure and the resulting crude compound was diluted with ethyl acetate (2 L). The resulting undissolved, dark, semi-solid was separated by filtration using ethyl acetate. It was further concentrated under reduced pressure to provide a crude compound, which was purified by column chromatography. The compound was eluted with 5% to 10% ethyl acetate in hexanes mixture to provide the title compound (70 g, 60%): mp 60-61° C.; $^1$H NMR (CDCl$_3$) δ 3.99 (s, 3H), 5.85 (d, 1H), 6.75 (d, 1H), 6.95 (dd, 1H).

Example 4

Preparation of 2,6-dichloro-5-methoxy-pyrimidine-4-carbaldehyde

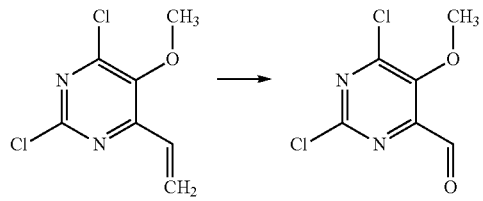

A solution of 2,6-dichloro-5-methoxy-4-vinyl pyrimidine (50 g, 0.24 mol) in dichloromethane:methanol (4:1, 2 L) was cooled to −78° C. Ozone gas was bubbled through for 5 h. The reaction was quenched with dimethyl sulfide (50 mL). The mixture was slowly warmed to room temperature and concentrated under reduced pressure at 40° C. to provide the title compound (50.5 g, 100%).

Example 5

Preparation of methyl 2,6-dichloro-5-methoxy-pyrimidine-4-carboxylate

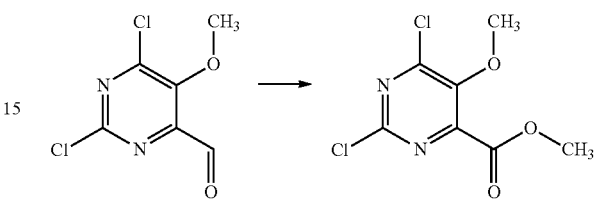

A solution of 2,6-dichloro-5-methoxy-pyrimidine-4-carbaldehyde (50 g, 0.24 mol) in methanol (1 L) and water (60 mL) was prepared. To the solution, sodium bicarbonate (400 g) was added. A 2 M solution of bromine (192 g, 1.2 mol) in methanol/water (600 mL, 9:1 v/v) was added, dropwise, to the pyrimidine solution for 45 minutes (min) at 0° C. while stirring the mixture. The stirring was continued at the same temperature for 1 h. Later, the mixture was stirred at room temperature for 4 h. While stirring, the reaction mixture was thereafter poured onto a mixture of crushed ice (2 L), sodium bisulfite (50 g), and sodium chloride (200 g). The product was extracted with ethyl acetate (1 L×2), and the combined organic layer was dried over sodium sulfate and filtered. Evaporation of the solvent under reduced pressure produced a thick material, which solidified on long standing to afford the title compound (50.8 g, 87%); ESIMS m/z 238 ([M+H]$^+$).

Example 6

Preparation of methyl 6-amino-2-chloro-5-methoxy-pyrimidine-4-carboxylate (Head C)

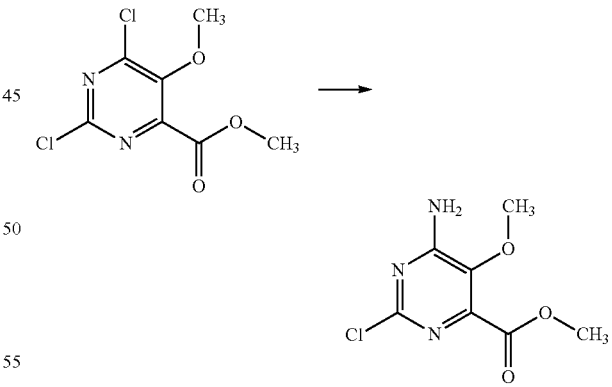

A solution of methyl 2,6-dichloro-5-methoxy-pyrimidine-4-carboxylate (25 g, 0.1 mol) and dimethyl sulfoxide (DMSO) was prepared. To this solution was added, at 0-5° C., a solution of ammonia (2 eq) in DMSO. This mixture was stirred at the same 0-5° C. temperature for 10 to 15 min. Later, the mixture was diluted with ethyl acetate, and the resulting solid was filtered off. The ethyl acetate filtrate was washed with a brine solution and dried over sodium sulfate. Upon concentration, the crude product was obtained. The crude product was stirred in a minimum amount of ethyl acetate and filtered to obtain the pure compound. Additional pure compound was obtained from the filtrate which, after concentration, was purified by flash chromatography. This produced the title compound (11 g, 50%): mp 158° C.; $^1$H NMR (DMSO-$d_6$) δ 3.71 (s, 3H), 3.86 (s, 3H), 7.65 (brs, 1H), 8.01 (brs, 1H).

Example 7

Preparation of methyl 4-amino-3,6-dichloro-5-iodopicolinate

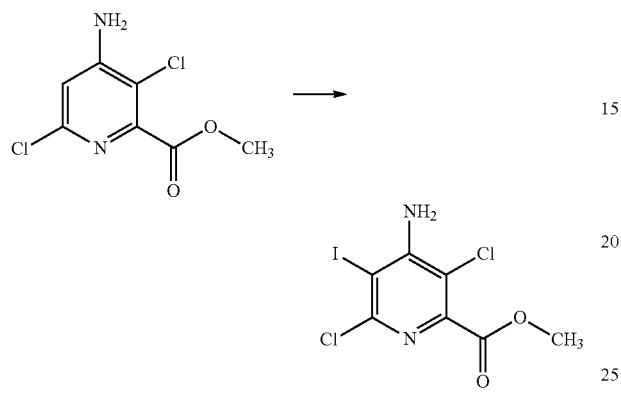

Methyl 4-amino-3,6-dichloropicolinate (10.0 g, 45.2 mmol), periodic acid (3.93 g, 17.2 mmol), and iodine (11.44 g, 45.1 mmol) were dissolved in methanol (30 mL) and refluxed at 60° C. for 27 h. The reaction mixture was concentrated, diluted with diethyl ether, and washed twice with saturated aqueous sodium bisulfite. The aqueous layers were extracted once with diethyl ether, and the combined organic layers were dried over anhydrous sodium sulfate. The product was concentrated and purified by flash chromatography (silica gel, 0-50% ethyl acetate/hexanes) to provide the title compound as a pale yellow solid (12.44 g, 35.9 mmol, 79%): mp 130.0-131.5° C.; $^1$H NMR (400 MHz, CDCl$_3$) δ 5.56 (s, 2H), 3.97 (s, 3H); $^{13}$C NMR (101 MHz, CDCl$_3$) δ 163.80, 153.00, 152.75, 145.63, 112.12, 83.91, 53.21; EIMS m/z 346.

Example 8

Preparation of Methyl 4-amino-3,6-dichloro-5-methylpicolinate (Head D)

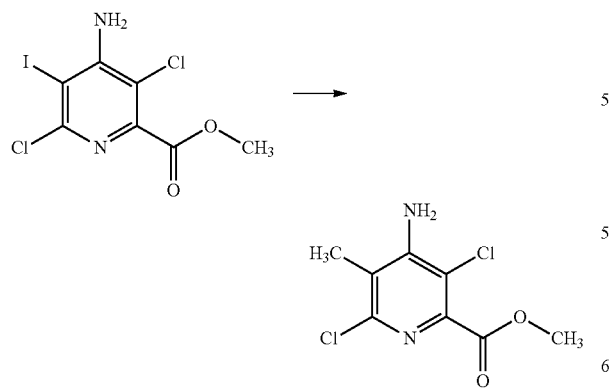

A mixture of methyl 4-amino-3,6-dichloro-5-iodopicolinate (8.1 g, 23.4 mmol), tetramethylstannane (8.35 g, 46.7 mmol), and bis(triphenylphosphine)palladium(II) chloride (2.5 g, 3.5 mmol) in 1,2-dichloroethane (40 mL) was irradiated in a Biotage Initiator™ microwave at 120° C. for 30 min, with external IR-sensor temperature monitoring from the side. The reaction mixture was loaded directly onto a silica gel cartridge and purified by flash chromatography (silica gel, 0-50% ethyl acetate/hexanes) to provide the title compound as an orange solid (4.53 g, 19.27 mmol, 83%): mp 133-136° C.; $^1$H NMR (400 MHz, CDCl$_3$) δ 4.92 (s, 2H), 3.96 (s, 3H), 2.29 (s, 3H); $^{13}$C NMR (101 MHz, CDCl$_3$) δ 164.34, 150.24, 148.69, 143.94, 117.01, 114.60, 53.02, 14.40; ESIMS m/z 236 ([M+H]$^+$), 234 ([M−H]$^−$).

Example 9

Preparation of methyl 6-amino-2,5-dichloropyrimidine-4-carboxylate (Head E)

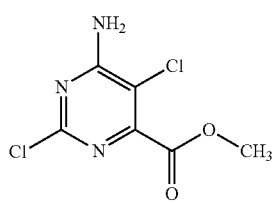

Prepared as described in Epp et al., WO 2007082076 A1.

Example 10

Preparation of methyl 4-amino-6-chloro-5-fluoro-3-methoxypicolinate (Head F)

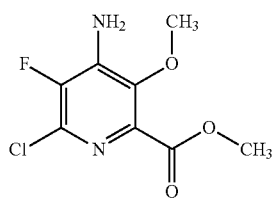

Prepared as described in Epp et al., WO 2013003740 A1.

Example 11

Preparation of methyl 4-amino-6-chloro-5-fluoro-3-vinylpicolinate (Head G)

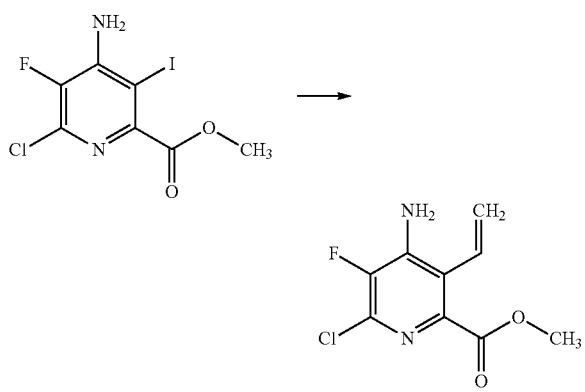

Methyl 4-amino-6-chloro-5-fluoro-3-iodopicolinate (7.05 g, 21.33 mmol, prepared as described in Epp et al., WO 2013003740 A1) and vinyl tri-n-butyl tin (7.52 mL, 25.6 mmol) were suspended in dichloroethane (71.1 mL) and the mixture was degassed with Argon for 10 min. Bis(triphenylphosphine)palladium(II) chloride (1.497 g, 2.133 mmol) was then added and the reaction mixture was stirred at 70° C. overnight (clear orange solution). The reaction was monitored by GCMS. After 20 h, the reaction mixture was concentrated, adsorbed onto Celite™, and purified by column chromatography (SiO$_2$, hexanes/ethyl acetate gradient) to afford the title compound as a light brown solid (3.23 g, 65.7%): mp 99-100° C.; $^1$H NMR (400 MHz, CDCl$_3$) δ 6.87 (dd, J=18.1, 11.6 Hz, 1H), 5.72 (dd, J=11.5, 1.3 Hz, 1H), 5.52 (dd, J=18.2, 1.3 Hz, 1H), 4.79 (s, 2H), 3.91 (s, 3H); $^{19}$F NMR (376 MHz, CDCl$_3$) δ −138.79 (s); EIMS m/z 230.

Example 12

Preparation of methyl 4-amino-3,5,6-trichloropicolinate (Head H)

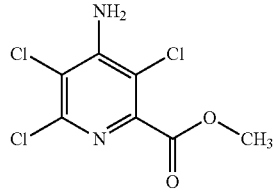

Prepared as described in Finkelstein et al., WO 2006062979 A1.

Example 13

Preparation of methyl 4-amino-6-bromo-3-chloro-5-fluoropicolinate (Head I)

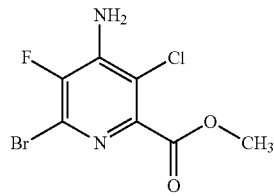

Prepared as described in Arndt et al., US 20120190857 A1.

Example 14

Preparation of methyl 4-amino-3-chloro-5-fluoro-6-(trimethylstannyl)picolinate (Head J)

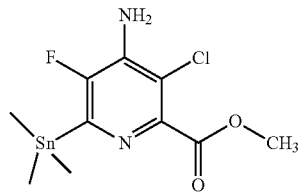

Methyl 4-amino-6-bromo-3-chloro-5-fluoropicolinate (500 mg, 1.8 mmol), 1,1,1,2,2,2-hexamethyldistannane (580 mg, 1.8 mmol) and bis(triphenylphosphine)-palladium(II) chloride (120 mg, 0.18 mmol) were combined in 6 mL dry dioxane, sparged with a stream of nitrogen for 10 min and then heated to 80° C. for 2 h. The cooled mixture was stirred with 25 mL of ethyl acetate and 25 mL of saturated NaCl for 15 min. The organic phase was separated, filtered through diatomaceous earth, dried (Na$_2$SO$_4$) and evaporated. The residue was taken up in 4 mL ethyl acetate, stirred and treated in portions with 15 mL of hexanes. The milky white solution was decanted from any solids produced, filtered through glass wool and evaporated to give the title compound as an off-white solid (660 mg, 100%): $^1$H NMR (400 MHz, CDCl$_3$) δ 4.63 (d, J=29.1 Hz, 2H), 3.97 (s, 3H), 0.39 (s, 9H); $^{19}$F NMR (376 MHz, CDCl$_3$) δ −130.28; EIMS m/z 366.

Example 15

Preparation of methyl 4-acetamido-3-chloro-6-(trimethylstannyl)-picolinate (Head K)

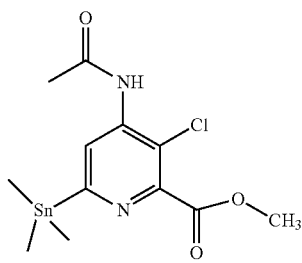

Prepared as described in Balko et al., WO 2003011853 A1.

Example 16

Preparation of methyl 4-acetamido-3,6-dichloropicolinate (Head L)

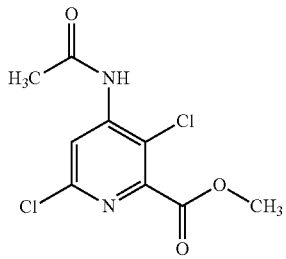 [SMILES: COC(=O)c1nc(Cl)cc(NC(C)=O)c1Cl]

Prepared as described in Fields et al., WO 2001051468 A1.

Example 17

Preparation of methyl 4-amino-3-chloro-6-iodopicolinate (Head M)

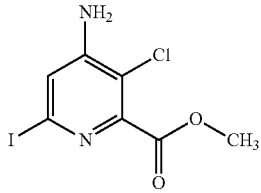

Prepared as described in Balko et al., WO 2007082098 A2.

Example 18

Preparation of methyl 4-acetamido-3-chloro-6-iodopicolinate (Head N)

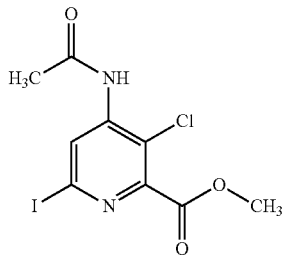 [SMILES: COC(=O)c1nc(I)cc(NC(C)=O)c1Cl]

Prepared as described in Balko et al., WO 2007082098 A2.

Example 19

Preparation of methyl 4-amino-6-bromo-3,5-difluoropicolinate (Head O)

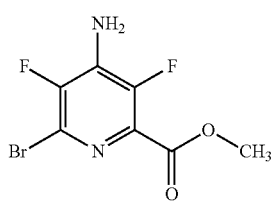

Prepared as described in Fields et al., WO 2001051468 A1.

Example 20

Preparation of methyl 6-amino-2-chloro-5-vinylpyrimidine-4-carboxylate (Head P)

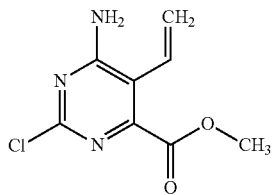

Prepared as described in Epp et al., US20090088322.

Example 22

Preparation of 4-bromo-2-fluorophenyl)trimethylsilane

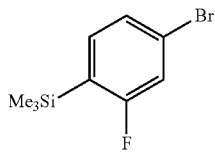

A 2.5 M solution of n-butyllithium in hexanes (900 μL, 2.2 mmol, 1.1 equiv) was added to a stirred solution of 1,4-dibromo-2-fluorobenzene (500 mg, 2.0 mmol, 1.0 equiv) in diethyl ether (10 mL) at −78° C. The resulting pale yellow solution was stirred at −78° C. for 2 h. Chlorotrimethylsilane (300 μL, 2.4 mmol, 1.2 equiv) was added and the resulting pale yellow solution was allowed to slowly warm to 23° C., by allowing the dry ice/acetone bath to melt, and stirred for 72 h. The reaction mixture was diluted with water (50 mL) and extracted with dichloromethane (3×50 mL). The combined organic layers were dried (magnesium sulfate), gravity filtered, and concentrated by rotary evaporation to afford the title compound as a pale yellow oil (350 mg, 71%): IR (thin film) 3068 (w), 2955 (m), 2927 (m), 2855 (w), 1598 (w), 1567 (w) cm$^{-1}$; $^1$H NMR (400 MHz, DMSO-d$_6$) δ 7.38-7.49 (m, 3H), 0.30 (s, 9H).

Example 23

Preparation of (2-fluoro-4-(4,4,5,5-tetramethyl-1,3,2-dioxaborolan-2-yl)phenyl)trimethylsilane

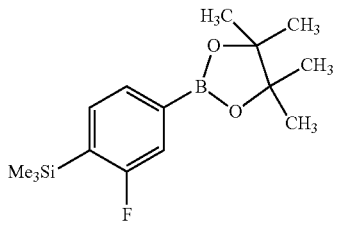 [SMILES: CC1(C)OB(c2ccc([Si](C)(C)C)c(F)c2)OC1(C)C]

A 2.5 M solution of n-butyllithium (8.5 mL, 21 mmol, 1.1 equiv) was added to a stirred solution of (4-bromo-2-fluorophenyl)trimethylsilane (4.8 g, 19 mmol, 1.0 equiv) in tetrahydrofuran (80 mL) at −78° C. The resulting orange solution was stirred at −78° C. for 15 m. 2-Isopropoxy-4,4,5,5-tetramethyl-1,3,2-dioxaborolane (4.4 mL, 21 mmol, 1.1 equiv) was added and the cloudy orange solution was allowed to slowly warm to 23° C., by allowing the dry ice/acetone bath to melt, and stirred for 20 h. The reaction mixture was diluted with water (200 mL), adjusted to approximately pH 4 using 1M hydrochloric acid, and extracted with dichloromethane (3×100 mL). The combined organic layers were dried (magnesium sulfate), gravity filtered, and concentrated by rotary evaporation to afford the title compound as a pale yellow semisolid (6.0 g, 99%): $^1$H NMR (400 MHz, CDCl$_3$) δ 7.55 (dt, J=7.5, 1 Hz, 1H), 7.38-7.42 (m, 2H), 1.34 (s, 12H), 0.29 (d, J=1 Hz, 9H).

The following compounds were made in accordance with the procedures disclosed in Example 23:

2-(4-(Difluoromethyl)phenyl)-4,4,5,5-tetramethyl-1,3,2-dioxaborolane

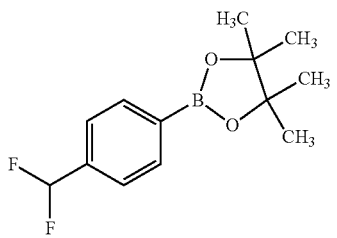 [SMILES: CC1(C)OB(c2ccc(C(F)F)cc2)OC1(C)C]

$^1$H NMR (400 MHz, CDCl$_3$) δ 7.89 (br d, J=8, 2H), 7.50 (br d, J=8, Hz, 2H), 6.65 (t, J=56 Hz, 1H), 1.35 (s, 12H).

2-(4-(Difluoromethyl)-3-fluorophenyl)-4,4,5,5-tetramethyl-1,3,2-dioxaborolane

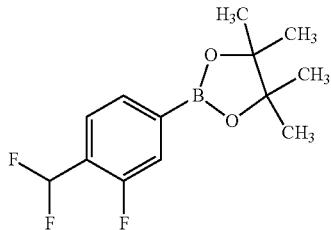 [SMILES: CC1(C)OB(c2ccc(C(F)F)c(F)c2)OC1(C)C]

$^1$H NMR (400 MHz, CDCl$_3$) δ 7.51-7.68 (m, 3H), 6.90 (t, J=55 Hz, 1H), 1.35 (s, 12H).

Example 24

Preparation of (2,3-difluoro-4-(4,4,5,5-tetramethyl-1,3,2-dioxaborolan-2-yl)phenyl)trimethylsilane

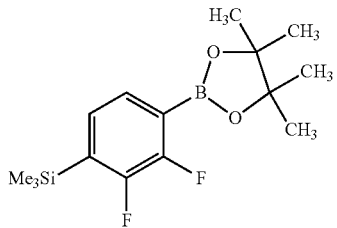 [SMILES: CC1(C)OB(c2ccc([Si](C)(C)C)c(F)c2F)OC1(C)C]

A 2.5 M solution of n-butyl lithium (9.5 mL, 24 mmol, 1.1 equiv) was added to a stirred solution of (2,3-difluorophenyl)trimethylsilane (4.0 g, 21 mmol, 1.0 equiv) in tetrahydrofuran (86 mL) at −78° C. The resulting very pale yellow solution was stirred at −78° C. for 1 h. 2-isopropoxy-4,4,5,5-tetramethyl-1,3,2-dioxaborolane (4.8 mL, 24 mmol, 1.1 equiv) was added and the pale yellow solution was allowed to slowly warm to 23° C., by allowing the dry ice/acetone bath to melt, and stirred for 20 h. The reaction mixture was diluted with water (200 mL), adjusted to approximately pH 4 using 1M hydrochloric acid, and extracted with dichloromethane (3×100 mL). The combined organic layers were dried (magnesium sulfate), gravity filtered, and concentrated by rotary evaporation to afford the title compound as a white powder (6.4 g, 96%): $^1$H NMR (400 MHz, CDCl$_3$) δ 7.42 (ddd, J=7.5, 4.5, 0.5 Hz, 1H), 7.09 (ddd, J=7.5, 4, 1 Hz, 1H), 1.34 (s, 12H), 0.29 (d, J=1 Hz, 9H).

Example 25

Preparation of (3-fluoro-4-(4,4,5,5-tetramethyl-1,3,2-dioxaborolan-2-yl)phenyl)trimethylsilane

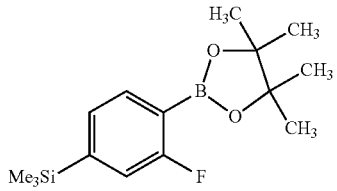 [SMILES: CC1(C)OB(c2ccc([Si](C)(C)C)cc2F)OC1(C)C]

A 2.5 M solution of n-butyllithium (3.5 mL, 8.5 mmol, 1.1 equiv) was added to a stirred solution of 1,4-dibromo-2-fluorobenzene (2.0 g, 7.9 mmol, 1.0 equiv) in tetrahydrofuran (26 mL) at −78° C. The resulting bright yellow solution was stirred at −78° C. for 15 minutes. 2-Isopropoxy-4,4,5,5-tetramethyl-1,3,2-dioxaborolane (1.8 mL, 8.7 mmol, 1.1 equiv) was added and the resulting pale yellow solution was stirred at −78° C. for 30 m. A 2.5 M solution of n-butyllithium (3.5 mL, 8.5 mmol, 1.1 equiv) was added and the resulting yellow/brown solution was stirred at −78° C. for 15 m. Chlorotrimethylsilane (2.2 mL, 17 mmol, 2.2 equiv) was added and the resulting pale yellow solution was allowed to slowly warm to 23° C., by allowing the dry ice/acetone bath to melt, and stirred for 18 h. The reaction mixture was diluted with water (150 mL) and extracted with dichloromethane (2×100 mL). The combined organic layers were dried (magnesium sulfate), gravity filtered, and concentrated by rotary evaporation to afford the title compound as a pale yellow powder (2.3 g, 99%): IR (thin film) 3058 (w), 2981 (s), 2932 (m), 1615 (m) cm$^{-1}$; $^1$H NMR (400 MHz, CDCl$_3$) δ 7.72 (dd, J=7.5, 6 Hz, 1H), 7.26 (m, 1H), 7.16 (d, J=7.5 Hz, 1H), 1.34 (s, 12H), 0.23 (s, 9H).

Example 26

Preparation of 2,3,5-trifluoro-4-iodoaniline

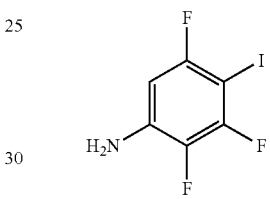

To a stirred solution of 2,3,5-trifluoro aniline (2.0 g, 13.605 mmol, 1.0 eq) in dry THF (40 mL) at −78° C., was added sec-butyl lithium (10.88 mL, 13.6 mmol, 1.0 eq) over 30 minutes. Stirring was continued at −78° C. for 2 h. A solution of iodine (4.14 g, 16.32 mmol, 1.2 eq) was added dropwise and reaction was slowly warmed to 20° C. over 1 hour (h). The reaction was quenched with 10% aq. Na$_2$S$_2$O$_3$ solution and extracted with methyl tert-butyl ether (MTBE) (3×50 mL). The combined organic extract was washed with saturated (sat.) brine solution, dried over anhydrous Na$_2$SO$_4$, filtered and evaporated to dryness under reduced pressure. The crude product was column purified over silica using 0-10% EtOAc with hexanes as eluent to afford 2,3,5-trifluoro-4-iodoaniline (1.3 g, 35%) as pink solid: $^1$H NMR (400 MHz, CDCl$_3$) δ 6.43-6.39 (m, 1H), 3.99 (brs, 2H); ESIMS m/z 274 ([M+H]$^+$).

Example 27

Preparation of 4-bromo-1-(difluoromethoxy)-2-fluorobenzene

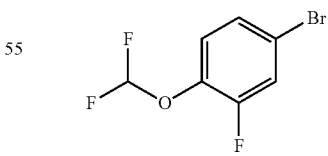

To a 100 mL flask charged with DMF (23 mL) was added sodium 2-chloro-2,2-difluoroacetate (4.79 g, 31.4 mmol), potassium carbonate (2.60 g, 18.85 mmol), 4-bromo-2-fluorophenol (3 g, 15.71 mmol). Water (5.75 mL) was added and the reaction mixture was heated to 100° C. for 3 hours. Upon cooling to room temperature, the reaction mixture was diluted with Et$_2$O (100 mL) and a 2 N NaOH solution (100 mL). The organic layer was removed and dried over anhydrous Na$_2$SO$_4$. Upon filtration the organic solution was concentrated on a rotary evaporator with the water bath at 4° C. to yield the title compound as a clear oil (1 g). NMR (400 MHz, CDCl$_3$) δ 7.35 (dd, J=9.7, 2.3 Hz, 1H), 7.27 (ddd, J=8.7, 2.3, 1.5 Hz, 1H), 7.19-7.04 (m, 1H), 6.53 (t, J=73.0 Hz, 1H); ESIMS m/z 242 ([M+H]$^+$).

The following compounds were made in accordance with the procedures disclosed in Example 27

1-Bromo-4-(difluoromethoxy)-2-fluorobenzene

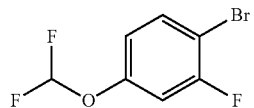

$^1$H NMR (400 MHz, CDCl$_3$) δ 7.53 (dd, J=8.8, 7.7 Hz, 1H), 6.95 (dd, J=9.1, 2.7 Hz, 1H), 6.90-6.79 (m, 1H), 6.50 (t, J=72.8 Hz, 1H); IR (thin film) 781.76, 811.23, 856.78, 945.20, 1043.80, 977.35, 1141.65, 1113.50, 1174.18, 1260.90, 1285.55, 1382.78, 1423.39, 1487.03, 1593.17, 2847.53, 2927.91, 2992.21, 3112.78 cm-1; ESIMS m/z 242 ([M+H]$^+$).

1-Bromo-4-(difluoromethoxy)-2,3-difluorobenzene

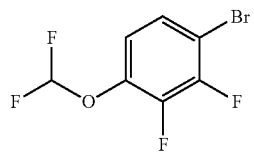

$^1$H NMR (400 MHz, CDCl$_3$) δ 7.31 (ddd, J=9.2, 6.9, 2.5 Hz, 1H), 7.02-6.93 (m, 1H), 6.56 (t, J=72.4 Hz, 1H);); IR (thin film) 776.30, 811.66, 884.39, 986.70, 1100.95, 1144.65, 1211.05, 1241.96, 1266.36, 1297.59, 1383.98, 1494.35, 1474.47, 1600.40, 1679.63, 3038.31, 3103.90 cm-1; ESIMS m/z 260 ([M+H]$^+$).

Example 28

Preparation of 2-(4-(difluoromethoxy)-3-fluorophenyl)-4,4,5,5-tetramethyl-1,3,2-dioxaborolane

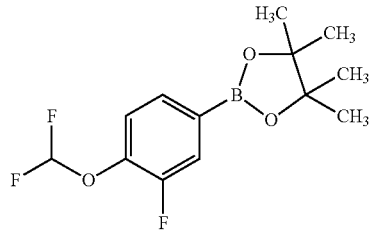 [SMILES: CC1(C)OB(c2ccc(OC(F)F)c(F)c2)OC1(C)C]

To DMSO (10 mL) was added 4,4,4',4',5,5,5',5'-octamethyl-2,2'-bi(1,3,2-dioxaborolane) (1.264 g, 4.98 mmol), PdCl$_2$(dppf) (0.304 g, 0.415 mmol), potassium acetate (1.222 g, 12.45 mmol), and 4-bromo-1-(difluoromethoxy)-2-fluorobenzene (1 g, 4.15 mmol). The reaction was heated to an external temperature of 80° C. for 18 hours. Upon cooling, the reaction was poured into 50 mL ice water. The ice water mixture was transferred to a separatory funnel and two extractions with EtOAc (50 mL) were completed. The organic layers were combined, dried over Na$_2$SO$_4$, and filtered. The solution was concentrated onto 5 g of Celite™ using EtOAc as solvent. The impregnated Celite™ was purified by silica gel chromatography using 0-30% EtOAc:hexanes to yield the title compound as a yellow oil (773 mg): $^1$H NMR (400 MHz, CDCl$_3$) δ 7.61-7.53 (m, 2H), 7.25-7.16 (m, 1H), 6.58 (t, J=73.5 Hz, 1H), 1.34 (s, 12H); ESIMS m/z 289 ([M+H]$^+$).

The following compounds were made in accordance with the procedures disclosed in Example 28:

2-(4-(Difluoromethoxy)-2-fluorophenyl)-4,4,5,5-tetramethyl-1,3,2-dioxaborolane

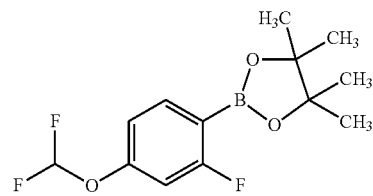 [SMILES: CC1(C)OB(c2ccc(OC(F)F)cc2F)OC1(C)C]

$^1$H NMR (400 MHz, CDCl$_3$) δ 7.74 (dd, J=8.3, 6.8 Hz, 1H), 6.89 (dd, J=8.3, 2.2 Hz, 1H), 6.81 (dd, J=9.9, 2.2 Hz, 1H), 6.54 (t, J=73.2 Hz, 1H), 1.26 (s, 12H);); IR (thin film) 848.53, 961.04, 1066.43, 1125.19, 1172.02, 1238.3, 1212.77, 1330.51, 1281.58, 1357.05, 1372.85, 1380.73, 1425.32, 1469.05, 1579.31, 1621.00, 2933.42, 2982.31 cm-1; ESIMS m/z 289 ([M+H]$^+$).

2-(4-(Difluoromethoxy)-2,3-difluorophenyl)-4,4,5,5-tetramethyl-1,3,2-dioxaborolane

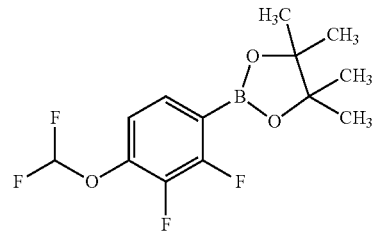 [SMILES: CC1(C)OB(c2ccc(OC(F)F)c(F)c2F)OC1(C)C]

$^1$H NMR (400 MHz, CDCl$_3$) δ 7.46 (ddd, J=8.3, 5.8, 2.3 Hz, 1H), 7.05-6.95 (m, 1H), 6.59 (t, J=72.8 Hz, 1H), 1.35 (s, 12H); IR (thin film) 673.35, 851.08, 916.78, 965.07, 1123.87, 1142.58, 1210.42, 1331.14, 1280.13, 1362.56, 1392.44, 1467.32, 1507.77, 1589.62, 1629.61, 2935.00, 2982.70 cm-1; ESIMS m/z 307 ([M+H]$^+$).

Example 29

Preparation of 1,4-difluoro-2-iodo-5-(trifluoromethyl)benzene

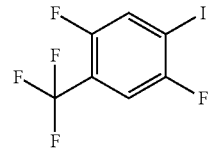 [SMILES: Fc1cc(C(F)(F)F)c(F)cc1I]

N-(2,5-difluoro-4-(trifluoromethyl)phenyl)acetamide (950 mg, 4.0 mmol) (Prepared according to Y. Tanabe et al, *J. Org. Chem.* 1988, 53, 4585-4587) was stirred in methanol (25 mL), treated with acetyl chloride (3 mL) and heated at reflux for 2 h. The volatiles were removed by evaporation and the solid residue was dissolved in 6 N HCl (50 mL), cooled to 5° C. and treated in portions with a solution of sodium nitrite (410 mg, 6.0 mmol) in water (5 mL). After 30 min, this mixture was poured into a solution of sodium iodide (2.4 g, 16 mmol) in water (50 mL) and rapidly stirred with dichloromethane (50 mL). After 30 min, solid sodium bisulfate was added to destroy the iodine color, and the separated organic phase was washed with sat. NaCl, dried (Na$_2$SO$_4$), and evaporated. The material was purified by flash chromatography (SiO$_2$, eluting with hexanes) to provide the title compound as a volatile clear liquid (250 mg, 20%): $^1$H NMR (400 MHz, CDCl$_3$) δ 7.64 (ddd, J=8.8, 4.8, 0.4 Hz, 1H), 7.28 (dd, J=11.1, 4.7 Hz, 1H); $^{19}$F NMR (376 MHz, CDCl$_3$) δ −61.92, −97.64, −97.68, −118.59, −118.63, −118.64, −118.67; EIMS m/z 308.

Example 30

Preparation of 2-(2,5-difluoro-4-(trifluoromethyl) phenyl)-4,4,5,5-tetramethyl-1,3,2-dioxaborolane

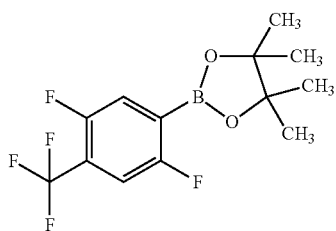 [SMILES: CC1(C)OB(c2cc(F)c(C(F)(F)F)cc2F)OC1(C)C]

1,4-difluoro-2-iodo-5-(trifluoromethyl)benzene (500 mg, 1.6 mmol) was dissolved in dry THF (7 mL), cooled to 0° C. and treated in portions with isopropyl magnesium chloride-lithium chloride complex (1.4 mL, 1.3 M, 1.8 mmol) and stirred for 40 min at 5° C. 2-Isopropoxy-4,4,5,5-tetramethyl-1,3,2-dioxaborolane (360 μl, 330 mg, 1.8 mmol) was added and stirring was continued for 1 h. After treating with sat. NH$_4$Cl, the mixture was shaken with ethyl acetate. The organic phase was washed with saturated NaCl, dried (Na$_2$SO$_4$), and evaporated to give the title compound as a light brown oil (500 mg, 100%). The material was used without further purification: $^1$H NMR (400 MHz, CDCl$_3$) δ 7.54 (dd, J=9.9, 4.3 Hz, 1H), 727 (dd, J=8.0, 5.2 Hz, 2H), 1.37 (s, 12H). $^{19}$F NMR (376 MHz, CDCl$_3$) δ −62.10, −62.13, −106.85, −106.90, −121.81, −121.87, −121.90.

Example 31

Preparation of 4-bromo-2,5-difluorobenzaldehyde

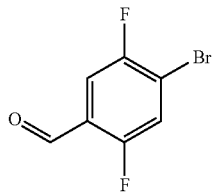 [SMILES: O=Cc1cc(F)c(Br)cc1F]

To a solution of 2,5-dibromo-1,4-difluorobenzene (10.0 g, 36.77 mmol) in diethyl ether (150 mL) at −78° C. was added n-butyl lithium (2.5 M in Hexanes, 14.86 mL, 37.15 mmol) dropwise under nitrogen. The reaction mixture was stirred at −78° C. for 30 min. Dry DMF (3.13 mL, 40.46 mmol) in diethyl ether (10 mL) was added dropwise and reaction was slowly warmed to room temperature over 2 h. The reaction was quenched with aqueous saturated ammonium chloride solution (25 mL) and extracted with diethyl ether. The organic phase was washed with saturated brine solution, dried (Na$_2$SO$_4$), filtered, and concentrated under reduced pressure (Note: Product is highly volatile). The crude product was purified by flash chromatography (SiO$_2$, eluting with 2-20% ethyl acetate in hexanes) to provide the title compound as a pale yellow solid (7.0 g, 86%): $^1$H NMR (400 MHz, CDCl$_3$): δ 7.50 (dd, J=5.08, 8.92 Hz, 1H), 7.62 (dd, J=5.80, 7.68 Hz, 1H), 10.30 (d, J=2.76 Hz, 1H).

Example 32

Preparation of (E)-4-bromo-2,5-difluorobenzaldehyde oxime

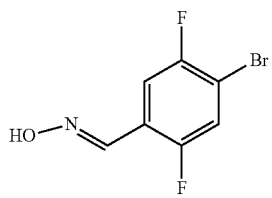 [SMILES: O/N=C/c1cc(F)c(Br)cc1F]

A solution of 4-bromo-2,5-difluorobenzaldehyde (7.0 g, 31.67 mmol), hydroxyl amine hydrochloride (2.42 g, 34.84 mmol) in pyridine (35 mL) and ethanol (35 mL) was stirred at room temperature for 30 min. The reaction mixture was diluted with saturated ammonium chloride solution and extracted with ethyl acetate. The organic phase was washed with saturated brine solution, dried (Na$_2$SO$_4$), filtered, and concentrated under reduced pressure. The crude product was purified by flash chromatography (SiO$_2$, eluting with 5-100% ethyl acetate in hexanes) to provide the title compound as a yellow solid (4.0 g, 53%): ESIMS m/z 238 [(M+2H)$^+$].

Example 33

Preparation of 4-bromo-2,5-difluorobenzonitrile

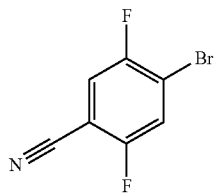 [SMILES: N#Cc1cc(F)c(Br)cc1F]

A solution of cyanuric chloride (3.12 g, 16.94 mmol) and dry DMF (8.5 mL) was stirred for 30 min or until the formation of white solid. Disappearance of cyanuric chloride was confirmed by TLC. (E)-4-bromo-2,5-difluorobenzaldehyde oxime (4.0 g, 16.94 mmol) in DMF (26 mL) was added dropwise to the suspension and stirred for 1 h. The reaction mixture was diluted with water and extracted with hexanes. The organic extract was washed with water, washed with saturated brine solution, dried (Na$_2$SO$_4$), filtered, and evaporated to dryness under reduced pressure. The crude product was purified by flash chromatography (SiO$_2$, eluting with 2-20% ethyl acetate in hexanes) to provide the title compound as a white solid (2.5 g, 68%): ¹H NMR (400 MHz, CDCl₃) δ 7.40 (dd, J=5.36, 7.10 Hz, 1H), 7.52 (dd, J=5.40, 7.66 Hz, 1H); EIMS m/z 218.

Example 34

Preparation of 1-bromo-4-(difluoromethyl)-2,5-difluorobenzene

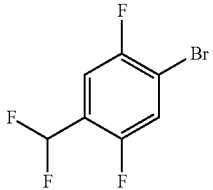

To a solution of 4-bromo-2,5-difluorobenzaldehyde (11.0 g, 49.77 mmol) in dichloromethane (55 mL) was added DAST (24.06 g, 0.15 mol) in dropwise manner at 0° C. After the addition was complete, the cooling bath was removed and stirring was continued for 2 h at rt. The reaction mixture was diluted with dichloromethane, washed with water, washed with saturated brine solution, dried (Na₂SO₄), and evaporated under reduced pressure. The crude product was purified by flash chromatography (SiO₂, eluting with 0-10% ethyl acetate in hexanes) to provide the title compound as a pale brown liquid (8.39 g, 69%): ¹H NMR (400 MHz, CDCl₃) δ 6.58 (t, J=72.32 Hz, 1H), 7.12 (t, J=7.92 Hz, 1H), 7.44 (dd, J=6.32, 9.18 Hz, 1H); EIMS m/z 244.

Example 35

Preparation of 1-bromo-4-(difluoromethoxy)-2,5-difluorobenzene

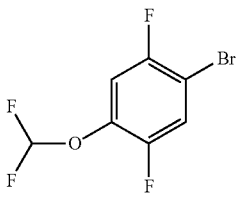

In a sealed tube, a solution of 4-bromo-2,5-difluoro phenol (5.0 g, 23.9 mmol) and potassium hydroxide (26.8 g, 479 mmol) in 1:1 mixture of acetonitrile and water (110 mL) at −78° C. was treated with bromo-difluoromethyl diethylphosphonate (12.8 g, 47.9 mmol) in one portion. The sealed tube was stirred at room temperature overnight. The reaction mixture was diluted with diethyl ether and the organic phase was separated. The aqueous phase was extracted with diethyl ether twice. The combined organic extracts were washed with a saturated brine solution, dried (Na₂SO₄), filtered, and evaporated to dryness under reduced pressure. The crude product was purified by flash chromatography (SiO₂, eluting with 0-10% ethyl acetate in hexanes) to provide the title compound as a clear liquid (4.2 g, 67.8%): ¹H NMR (300 MHz, CDCl₃) δ 6.56 (t, J=72.36 Hz, 1H), 7.11 (t, J=7.32 Hz, 1H), 7.40-7.45 (m, 1H); EIMS m/z 259.

Example 36

General Procedure for Synthesis of Boronic Acids

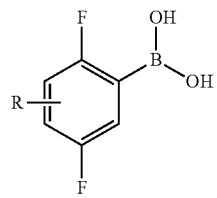

Argon was bubbled through a solution of the bromophenyl substrate (1.0 eq), potassium acetate (3.0 eq), and bis-(pinacolato)diboron (1.1 eq) in DMSO (15 vol) for 15 min in a sealed tube. Pd(dppf)Cl₂ (0.1 eq) was added and sealed tube was recapped. The reaction mixture was heated at 80° C. for 18 h. The cooled reaction mixture was diluted with water and extracted with methyl t-butyl ether. The organic extract was washed with water, washed with saturated brine solution, dried (Na₂SO₄), filtered, and evaporated to dryness under reduced pressure. The crude boronate (1.0 eq) was dissolved in diethyl ether (10 vol) and diethanolamine (1.1 eq) was added. The reaction mixture was stirred at room temperature for 30-45 min. A white solid precipitated out after 45 min. Stirring was stopped and the solvent was decanted. Fresh ether (5 vol) was added to the solids followed by an excess of 1.5 N HCl (10 vol). The resulting biphasic solution was stirred for 30 min. The organic phase was washed with saturated brine solution, dried (Na₂SO₄), filtered, and evaporated to dryness under reduced pressure. The boronic acids thus obtained were used in the next step without purification.

The following compounds were made in accordance with the procedures disclosed in Example 36:

(4-(Difluoromethoxy)-2,5-difluorophenyl)boronic acid

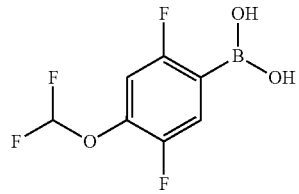 [SMILES: OB(O)c1cc(F)c(OC(F)F)cc1F]

¹H NMR (300 MHz, CDCl₃) δ 6.59 (t, J=72.78 Hz, 1H), 6.97 (dd, J=2.70, 9.14 Hz, 1H), 7.52 (dd, J=5.19, 10.29 Hz, 1H).

(4-(Difluoromethyl)-2,5-difluorophenyl)boronic acid

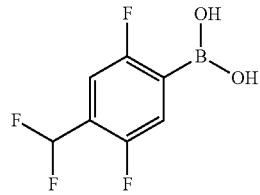 [SMILES: OB(O)c1cc(F)c(C(F)F)cc1F]

$^1$H NMR (400 MHz, CDCl$_3$) δ 6.87 (dt, J=8.48, 54.64 Hz, 1H), 7.25-7.32 (m, 1H), 7.49 (dd, J=4.08, 9.48 Hz, 1H), 7.59-7.60 (m, 1H).

Example 37

General Procedure for Synthesis of Boronic Acids (Method A)

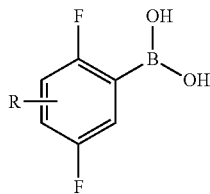

To a solution of the appropriate bromophenyl substrate (1.0 eq) in dry THF (10 vol) at −78° C., was added n-butyllithium (2.5 M in hexanes. 1.2 eq) dropwise. After addition was complete, stirring was continued for 30 min. Trimethyl borate (1.5 eq) was added in one portion and stirring was continued for 1 h at −78° C. The reaction mixture was slowly warmed to room temperature, quenched with 1.5 N HCl, and extracted with ethyl acetate. The organic extract was washed with water, washed with saturated brine solution, dried (Na$_2$SO$_4$), filtered, and evaporated to dryness under reduced pressure. The boronic acids thus obtained were used in the next step without purification.

The following compound was made in accordance with the procedures disclosed in Example 37:

(2,5-Difluoro-4-methylphenyl)boronic acid

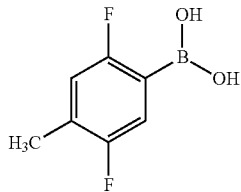

$^1$H NMR (300 MHz, CDCl$_3$): δ 2.30 (s, 3H), 5.03 (brs, 2H), 6.89 (dd, J=5.67, 10.25 Hz, 1H), 7.42 (dd, J=5.40, 9.19 Hz, 1H).

Example 38

General Procedure for Synthesis of Boronic Acids (Method B)

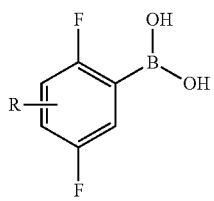

To a solution of the appropriate bromophenyl substrate (1.0 eq) in dry THF (10 vol) at −40° C. was added isopropyl magnesium chloride lithium chloride complex solution (1.3 M solution in THF, 1.05 eq) dropwise. After addition was complete, the reaction mixture was stirred at −40° C. for 45 min then slowly warmed to 0° C. Isopropoxyboronic acid pinacol ester (1.07 eq) was added dropwise and stirring was continued at 0° C. for 2 h. The reaction mixture was warmed to room temperature, quenched with aqueous saturated ammonium chloride solution, and extracted with ethyl acetate. The organic extract was washed with saturated brine solution, dried (Na$_2$SO$_4$), filtered, and evaporated under reduced pressure. The boronic acids thus obtained were used in the next step without purification.

The following compound was made in accordance with the procedures disclosed in Example 38:

(4-Cyano-2,5-difluorophenyl)boronic acid

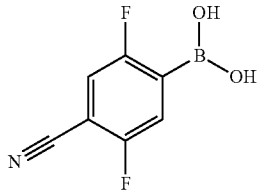 [SMILES: N#Cc1cc(F)c(B(O)O)cc1F]

$^1$H NMR (300 MHz, CDCl$_3$): δ 5.15 (br s, 2H), 7.29-7.36 (m, 1H), 7.69 (dd, J=4.80, 8.28 Hz, 1H).

Example 39

Preparation of methyl 4-amino-3-chloro-6-(3-fluoro-4-(trimethylsilyl)phenyl)picolinate

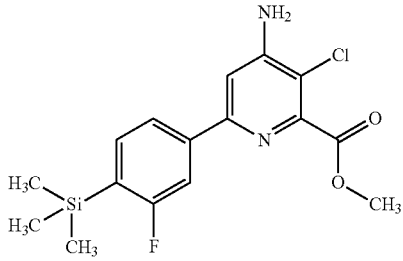

To a 20-mL microwave vessel, equipped with a stir bar, Head A (500 mg, 2.262 mmol), (2-fluoro-4-(4,4,5,5-tetramethyl-1,3,2-dioxaborolan-2-yl)phenyl)trimethylsilane (997 mg, 3.39 mmol), bis(triphenylphosphine)palladium(II) dichloride (203 mg, 3.39 mmol), and cesium fluoride (741 mg, 4.88 mmol) were charged. The vessel was placed under N$_2$ atmosphere and acetonitrile (4.0 mL) and H$_2$O (1.0 mL) were added. The vessel was placed on a Biotage Initiator™ microwave reactor for 30 min at 120° C., with external IR-sensor temperature monitoring from the side of the vessel. The reaction was poured into brine solution and extracted with ethyl acetate (3×75 mL). The combined organic layers were dried over anhydrous magnesium sulfate, filtered and concentrated. The resulting residue was purified via flash chromatography (Silica gel, 0-30% EtOAc in hexanes) to afford the title compound as a yellow solid (0.328 g, 41%): $^1$H NMR (400 MHz, DMSO-d$_6$) δ 7.68 (dd, J=7.5, 1.4 Hz, 1H), 7.61-7.47 (m, 2H), 7.30 (s, 1H), 6.78 (s, 2H), 3.88 (s, 3H), 0.30 (d, J=0.8 Hz, 9H); $^{19}$F NMR (376 MHz, DMSO-d$_6$) δ −101.12; ESIMS m/z 353 [(M+H)+].

The following compounds were prepared in accordance to the procedures disclosed in Example 39:

Methyl 4-amino-3,5-dichloro-6-(3-fluoro-4-(trimethylsilyl)phenyl)picolinate

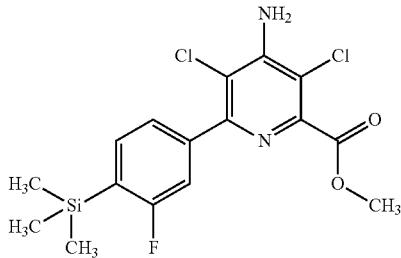

The title compound was prepared as described in Example 39 with Head H (500 mg, 1.96 mmol) and isolated as a white solid (0.381 g, 50%): $^1$H NMR (400 MHz, DMSO-$d_6$) 7.52 (dd, J=7.6, 5.9 Hz, 1H), 7.41 (dd, J=7.5, 1.3 Hz, 1H), 7.30 (dd, J=9.6, 1.4 Hz, 1H), 7.11 (s, 2H), 3.87 (s, 3H), 0.33 (d, J=0.9 Hz, 9H); $^{19}$F NMR (376 MHz, DMSO-$d_6$) δ −101.38; ESIMS m/z 387 [(M+H)$^+$].

Methyl 6-amino-2-(3-fluoro-4-(trimethylsilyl)phenyl)-5-methoxypyrimidine-4-carboxylate

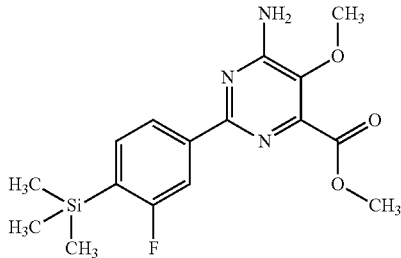

The title compound was prepared as described in Example 39 with Head C (0.510 g, 2.34 mmol) and isolated as a yellow solid (0.307 g, 38%): $^1$H NMR (400 MHz, DMSO-$d_6$) δ 8.08-7.99 (m, 1H), 7.82 (dd, J=10.3, 1.4 Hz, 1H), 7.60-7.27 (m, 3H), 3.91 (s, 3H), 3.74 (s, 3H), 0.32 (d, J=0.9 Hz, 9H); $^{19}$F NMR (376 MHz, DMSO-$d_6$) δ −101.73; ESIMS m/z 350 [(M+H)$^+$].

Methyl 4-acetamido-3-chloro-6-(3-fluoro-4-(trimethylsilyl)phenyl)picolinate

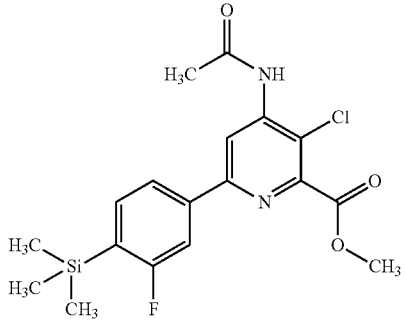

The title compound was prepared as described in Example 39 with Head L (0.500 g, 1.90 mmol), in dioxane (7.0 mL) and H$_2$O (2.0 mL) and isolated as a yellow solid (0.433 g, 58%): $^1$H NMR (400 MHz, DMSO-$d_6$) δ 9.99 (s, 1H), 8.71 (s, 1H), 7.75 (dd, J=7.6, 1.5 Hz, 1H), 7.63 (dd, J=10.1, 1.5 Hz, 1H), 7.56 (dd, =7.7, 5.9 Hz, 1H), 3.94 (s, 3H), 2.24 (s, 3H), 0.30 (d, J=0.8 Hz, 9H); $^{19}$F NMR (376 MHz, DMSO-$d_6$) δ −100.78; ESIMS m/z 396 [(M+H)$^+$].

Methyl 4-amino-3-chloro-6-(4-cyano-2-fluorophenyl)-5-fluoropicolinate (Compound 44)

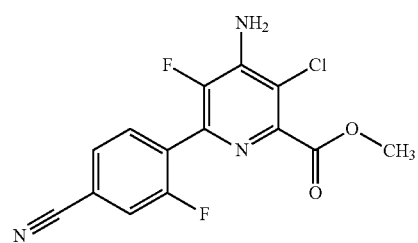 [SMILES: COC(=O)c1nc(-c2ccc(C#N)cc2F)c(F)c(N)c1Cl]

The title compound was prepared as described in Example 39 with Head B (400 mg, 1.673 mmol), and (4-cyano-2-fluorophenyl)boronic acid (400 mg, 2.425 mmol), in dioxane (4.5 mL) and H$_2$O (1.2 mL) and isolated as an off-white solid (0.451 g, 83%).

Methyl 6-amino-2-(3-fluoro-4-(trifluoromethyl)phenyl)-5-vinylpyrimidine-4-carboxylate (Compound 137)

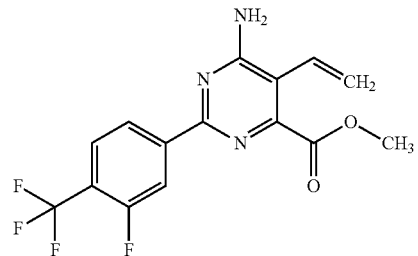 [SMILES: C=Cc1c(N)nc(-c2ccc(C(F)(F)F)c(F)c2)nc1C(=O)OC]

The title compound was prepared as described in Example 39 with Head P (350 mg, 1.64 mmol) and (3-fluoro-4-(trifluoromethyl)phenyl)boronic acid (445 mg, 2.14 mmol) in dioxane (5.0 mL) and H$_2$O (1.0 mL) and isolated as a tan solid (0.291 g, 52%).

Methyl 6-amino-2-(4-cyano-2-fluorophenyl)-5-vinylpyrimidine-4-carboxylate (Compound 98)

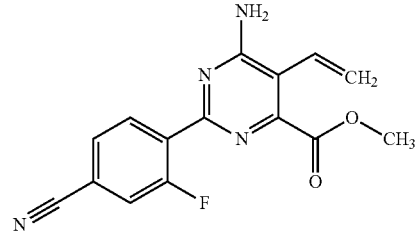 [SMILES: C=Cc1c(N)nc(-c2ccc(C#N)cc2F)nc1C(=O)OC]

The title compound was prepared as described in Example 39 with Head P (350 mg, 1.638 mmol), and (4-cyano-2- fluorophenyl)boronic acid (375 mg, 2.27 mmol) in dioxane (4.5 mL) and H₂O (1.2 mL) and isolated as an off-white solid (0.291 g, 60%).

Methyl 6-amino-2-(4-aminophenyl)-5-vinylpyrimidine-4-carboxylate

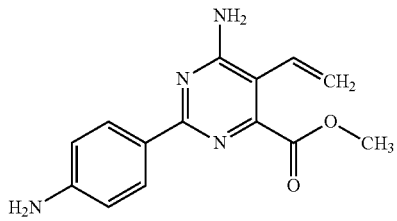 [SMILES: C=Cc1c(N)nc(-c2ccc(N)cc2)nc1C(=O)OC]

The title compound was prepared as described in Example 39 with Head P (0.800 g, 3.74 mmol), 4-(4,4,5,5-tetramethyl-1,3,2-dioxaborolan-2-yl)aniline (0.985 g, 4.49 mmol) in dioxane (15.6 mL) and H₂O (3.12 mL) and isolated as a yellow solid (0.400 g, 40%): 1H NMR (400 MHz, DMSO-d₆) δ 8.08-7.86 (m, 2H), 6.99 (s, 2H), 6.76-6.51 (m, 3H), 5.61 (s, 2H), 5.49-5.30 (m, 2H), 3.81 (s, 3H); ESIMS m/z 271 [(M+H)⁺].

Methyl 6-amino-2-(2,3,4-trifluorophenyl)-5-vinylpyrimidine-4-carboxylate (Compound 197)

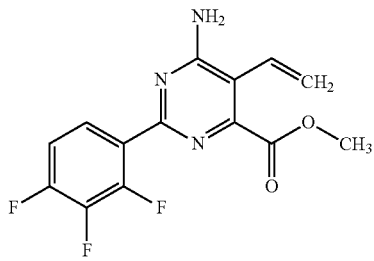 [SMILES: C=Cc1c(N)nc(-c2ccc(F)c(F)c2F)nc1C(=O)OC]

The title compound was prepared as described in Example 39 with Head P (0.350 g, 1.64 mmol) and (2,3,4-trifluorophenyl)boronic acid (0.346 g, 1.97 mmol) in dioxane (5.0 L) and H₂O (1.0 mL) and isolated as a yellow oil (0.414 g, 82%).

Example 40

Preparation of methyl 4-amino-3-chloro-6-(3-fluoro-4-(trifluoromethyl)phenyl)picolinate (Compound 29)

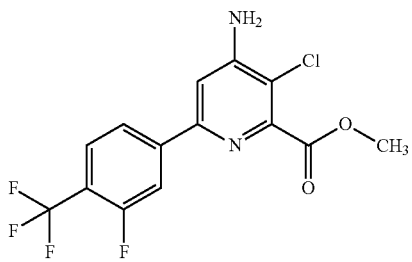 [SMILES: COC(=O)c1nc(-c2ccc(C(F)(F)F)c(F)c2)cc(N)c1Cl]

Methyl 4-amino-3,6-dichloropicolinate (630 mg, 2.85 mmol), 2-(3-fluoro-4-(trifluoromethyl)phenyl)-4,4,5,5-tetramethyl-1,3,2-dioxaborolane (1.06 g, 3.65 mmol, 1.3 equiv), bis(triphenylphosphine)palladium(II) chloride (209 mg, 0.30 mmol, 0.1 equiv), and potassium fluoride (510 mg, 8.8 mmol, 3 equiv) in acetonitrile/water (8 mL, 3:1) was capped in a 25-mL vial on a Biotage Initiator™ microwave reactor for 20 min at 115° C., with external IR-sensor temperature monitoring from the side of the vessel. The reaction mixture was diluted with ethyl acetate and washed with water. The aqueous layer was extracted with ethyl acetate and the combined organic layers were dried over anhydrous sodium sulfate, filtered, and concentrated. The crude compound was loaded onto a Celite™ cartridge and dried in vacuum oven. Purification by reverse-phase flash chromatography (0-60, 60, 60-100% acetonitrile/water) afforded the title compound as a white solid (0.57 g, 57%).

The following compounds were prepared in accordance to the procedures disclosed in Example 40:

Methyl 4-amino-3-chloro-6-(4-cyanophenyl)-5-methylpicolinate (Compound 83)

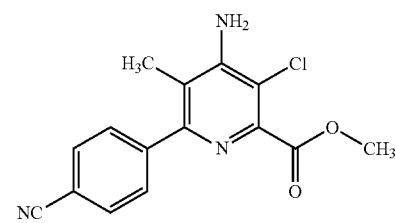 [SMILES: COC(=O)c1nc(-c2ccc(C#N)cc2)c(C)c(N)c1Cl]

The title compound was prepared as in Example 40 and isolated as an orange solid (180 mg, 55%).

Methyl 4-amino-3-chloro-6-(4-(difluoromethoxy)phenyl)-5-methylpicolinate (Compound 1H)

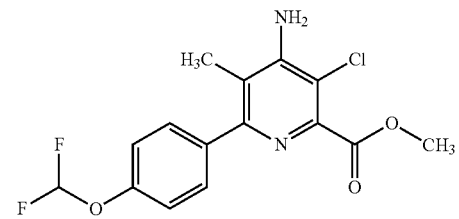 [SMILES: COC(=O)c1nc(-c2ccc(OC(F)F)cc2)c(C)c(N)c1Cl]

The title compound was prepared as in Example 40 and isolated as a waxy yellow solid (120 mg, 32%).

Methyl 4-amino-3-chloro-5-methyl-6-(4-(trimethylsilyl)phenyl)picolinate

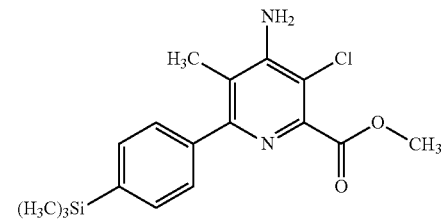

The title compound was prepared as in Example 40 and isolated as a yellow solid (1.11 g, 45%): mp 160-163° C.; ¹H NMR (400 MHz, CDCl₃) δ 7.57 (d, J=8.2 Hz, 2H), 7.42 (d, J=8.2 Hz, 2H), 4.80 (s, 2H), 3.94 (s, 3H), 2.18 (s, 3H), 0.28 (s, 9H); ¹³C NMR (101 MHz, CDCl₃) δ 167.01, 157.65, 150.16, 146.19, 141.69, 141.24, 134.39, 129.61, 117.96, 114.49, 53.95, 15.86, 1.16; ESIMS m/z 348 ([M]⁻).

Methyl 4-amino-3-chloro-6-(3-fluoro-4-(trimethylsilyl)phenyl)-5-methylpicolinate

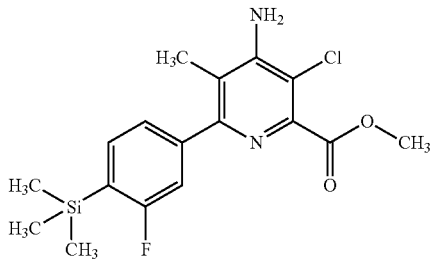

The title compound was prepared as in Example 40 and isolated as a yellow solid (346 mg, 27%): mp 167° C. (dec); ¹H NMR (400 MHz, CDCl₃) δ 7.43 (dd, J=7.4, 5.8 Hz, 1H), 7.20 (dd, J=7.4, 0.9 Hz, 1H), 7.10 (dd, J=9.2, 1.3 Hz, 1H), 4.83 (s, 2H), 3.95 (s, 3H), 2.18 (s, 3H), 0.33 (d, J=0.8 Hz, 9H); ¹⁹F NMR (376 MHz, CDCl₃) δ −100.73; ESIMS m/z 367 ([M+H]⁺).

Methyl 4-amino-3-chloro-6-(4-cyano-3-fluorophenyl)-5-methylpicolinate (Compound 155)

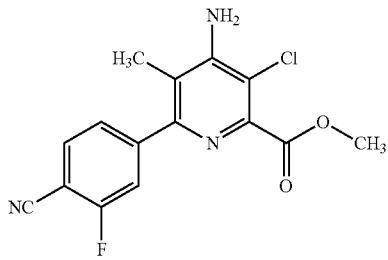 [SMILES: COC(=O)c1nc(-c2ccc(C#N)c(F)c2)c(C)c(N)c1Cl]

The title compound was prepared as in Example 40 and isolated as an off-white solid (200 mg, 49%).

Methyl 4-amino-3-chloro-6-(3-fluoro-4-formylphenyl)-5-methylpicolinate

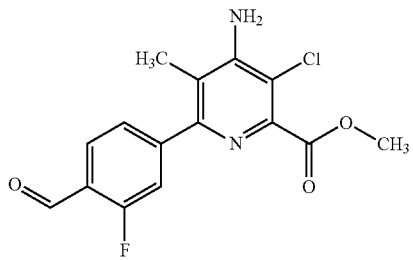 [SMILES: COC(=O)c1nc(-c2ccc(C=O)c(F)c2)c(C)c(N)c1Cl]

The title compound was prepared as in Example 40 and isolated as an orange solid (747 mg, 65%): mp 114-120° C.; ¹H NMR (400 MHz, CDCl₃) δ 10.40 (s, 1H), 7.92 (t, J=7.5 Hz, 1H), 7.38-7.29 (m, 2H), 4.97 (s, 2H), 3.97 (s, 3H), 2.18 (s, 3H); ¹⁹F NMR (376 MHz, CDCl₃) δ −121.53; ESIMS m/z 323 ([M+H]⁺).

Methyl 4-amino-3-chloro-5-fluoro-6-(2,4,5-trifluorophenyl)picolinate (Compound 200)

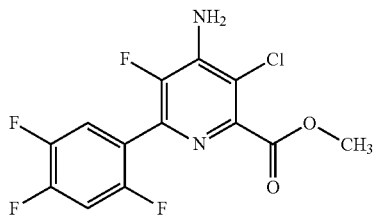

The title compound was prepared as in Example 40 and isolated as a white solid (370 mg, 73%).

Example 41

Preparation of methyl 4-amino-3-chloro-5-fluoro-6-(4-nitrophenyl)picolinate (Compound 95)

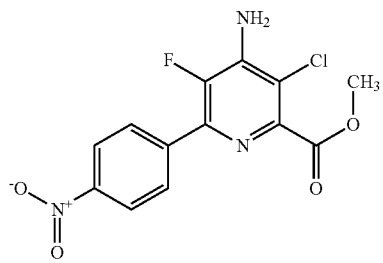

To a suspension of Head B (250 mg, 1.05 mmol), (4-nitrophenyl)boronic acid (192 mg, 1.15 mmol), cesium fluoride (CsF; 315 mg, 2.09 mmol) and tris(3-sulfonatophenyl)phosphine hydrate sodium salt (TPPTS, 60 mg, 0.11 mmol) in a water/acetonitrile mixture (2.8/0.7 mL) was added palladium acetate (12 mg, 0.05 mmol). In a Biotage™ bench top microwave the mixture was heated at 150° C. for 5 min. The reaction mixture was then filtered through Celite™, diluted with EtOAc, washed with water and brine. The organics were then dried (Na₂SO₄), filtered, concentrated in vacuo, and then purified by silica gel chromatography eluting with 0-100% EtOAc in hexanes to afford a yellow solid (150 mg, 44%).

The following compounds were made in accordance with the procedures disclosed in Example 41:

Methyl 4-acetamido-3-chloro-6-(2,3-difluoro-4-(trifluoromethyl)phenyl)picolinate

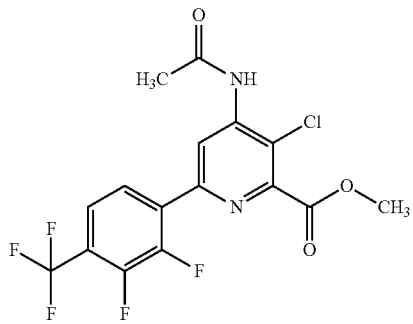 [SMILES: COC(=O)c1nc(-c2ccc(C(F)(F)F)c(F)c2F)cc(NC(C)=O)c1Cl]

$^1$H NMR (400 MHz, DMSO-d$_6$) δ 10.03 (s, 1H), 8.79 (d, J=1.0 Hz, 1H), 7.93-7.84 (m, 1H), 7.75 (dd, J=8.3, 6.3 Hz, 1H), 3.96 (s, 3H), 2.26 (s, 3H); ESIMS m/z 409 ([M+H]$^+$)

Example 42

Preparation of methyl 4-amino-3-chloro-6-(4-cyano-3-fluorophenyl)-5-fluoropicolinate (Compound 135)

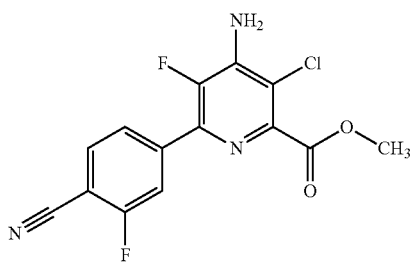 [SMILES: COC(=O)c1nc(-c2ccc(C#N)c(F)c2)c(F)c(N)c1Cl]

Head B (0.300 g, 1.255 mmol), 4-cyano-3-fluorophenylboronic acid (0.248 g, 1.506 mmol), bis(triphenylphosphine)palladium(II) chloride (0.088 g, 0.126 mmol), and cesium fluoride (0.381 g, 2.51 mmol) were combined in 1,2-dimethoxyethane (2 mL) and water (2 mL) and heated in a microwave reactor at 110° C. for 20 min. The cooled reaction mixture was partitioned between ethyl acetate and water. The organic phase was dried and concentrated. The product was purified by flash chromatography (SiO$_2$, eluting with 5-60% ethyl acetate in hexanes) to provide the title compound as a white solid (0.189 g, 46.5%).

Example 43

Preparation of methyl 4-amino-3-chloro-5-fluoro-6-(4-(methoxycarbonyl)phenyl)picolinate (Compound 190)

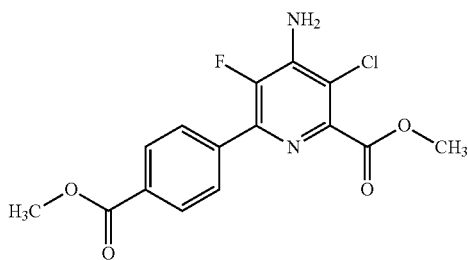

Head B (0.4 g, 1.673 mmol), 4-(methoxycarbonyl)phenylboronic acid (0.392 g, 2.175 mmol), potassium fluoride (0.253 g, 4.35 mmol), and bis(triphenylphosphine)palladium(II) chloride (0.059 g, 0.084 mmol) were combined in acetonitrile (3 mL) and water (1 mL). The reaction mixture was then irradiated in a microwave at 110° C. in a sealed vial for 20 min. The cooled reaction mixture was partitioned between ethyl acetate and water. The organic phase was dried and concentrated onto silica gel. This mixture was applied to the top of a silica gel column and the product was eluted with a 5-60% ethyl acetate in hexanes gradient solvent system. This process yielded the title compound as a white solid (0.230 g, 40.6%).

Example 44

Preparation of methyl 4-amino-6-(4-bromo-2,3-difluorophenyl)-3-chloropicolinate (Compound 114)

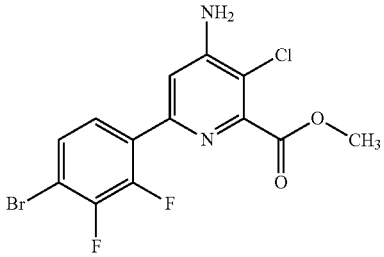 [SMILES: COC(=O)c1nc(-c2ccc(Br)c(F)c2F)cc(N)c1Cl]

Step 1:
Head N (0.600 g, 1.692 mmol), 4-bromo-2,3-difluorophenylboronic acid (0.481 g, 2.031 mmol), cesium fluoride (0.617 g, 4.06 mmol), and bis(triphenylphosphine)palladium (II) chloride (0.119 g, 0.169 mmol) were combined in 1,2-dimethoxyethane (4 mL) and water (4 mL) and heated in a microwave reactor for 20 min at 110° C. The cooled reaction mixture was partitioned between ethyl acetate and water. The organic phase was separated and concentrated onto silica gel. The product was eluted with an ethyl acetate/hexanes gradient to provide methyl 4-acetamido-6-(4-bromo-2,3-difluorophenyl)-3-chloropicolinate (0.515 g, 1.227 mmol, 72.5%) as a white solid.

Step 2:
Methyl 4-acetamido-6-(4-bromo-2,3-difluorophenyl)-3-chloropicolinate (0.515 g, 1.227 mmol) was suspended in methanol (20 mL) and acetyl chloride (1.559 mL, 21.93 mmol) was added dropwise. The reaction mixture was stirred overnight at room temperature and concentrated under vacuum. The residue was partitioned between ethyl acetate and 5% aqueous sodium bicarbonate solution. The organic phase was concentrated onto silica gel and purified by flash chromatography (SiO$_2$, eluting with 5-60% ethyl acetate in hexanes) to provide the title compound as a white solid (0.231 g, 55.8%).

Example 45

Preparation of methyl 4-amino-3-chloro-6-(2,3-difluoro-4-(trimethylsilyl)phenyl)-5-fluoropicolinate

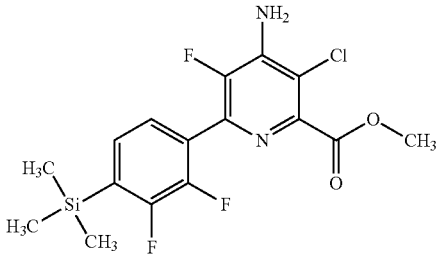

Head B (2.0 g, 8.37 mmol), (2,3-difluoro-4-(4,4,5,5-tetramethyl-1,3,2-dioxaborolan-2-yl)phenyl)trimethylsilane (3.40 g, 10.88 mmol), sodium carbonate (0.887 g, 8.37 mmol) and bis(triphenylphosphine)palladium(II) chloride (0.587 g, 0.837 mmol) were combined in acetonitrile (25 mL) and water (8 mL). The reaction mixture was then heated at reflux for 4 h. The cooled reaction mixture was partitioned between ethyl acetate and water. The organic phase was washed twice more with water then concentrated onto silica gel. This mixture was purified by silica gel chromatography and the product was eluted with a 7-60% ethyl acetate in hexanes solvent system. This process yielded the title compound as a white solid (2.7 g, 83%): mp 160-162° C.; $^1$H NMR (300 MHz, CDCl$_3$) δ 7.37-7.28 (m, 1H), 7.21 (ddd, J=7.7, 4.4, 1.3 Hz, 1H), 4.96 (br s, 2H), 3.97 (s, 3H), 0.35 (s, 9H).

Example 46

Preparation of methyl 6-amino-2-(3-fluoro-4-(trifluoromethyl)phenyl)-5-methoxypyrimidine-4-carboxylate (Compound 26)

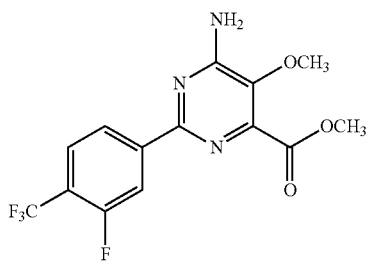

To a microwave vial was added Head C (184 mg, 0.846 mmol), 2-(3-fluoro-4-(trifluoromethyl)phenyl)-4,4,5,5-tetramethyl-1,3,2-dioxaborolane (270 mg, 0.930 mmol), potassium fluoride (128 mg, 2.198 mmol), and bis(triphenylphosphine)palladium(II) chloride (59.3 mg, 0.085 mmol). Subsequently, acetonitrile (2.789 mL) and water (2.79 mL) were added. The reaction vial was then capped and placed in a Biotage™ Initiator microwave reactor for 20 min at 115° C., with external IR-sensor temperature monitoring from the side of the vessel. The reaction mixture was cooled to room temperature, diluted with EtOAc, and washed with H$_2$O. The organics were dried over Na$_2$SO$_4$, filtered, and concentrated in vacuo. The crude product was purified via flash chromatography (silica, Hexanes/EtOAc). This yielded the title compound (172 mg, 58.9%) as a white solid.

Example 47

Preparation of methyl 4-amino-3-chloro-5-fluoro-6-(4-(trimethylsilyl)phenyl)picolinate

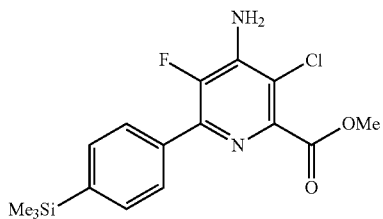 [SMILES: COC(=O)c1nc(-c2ccc([Si](C)(C)C)cc2)c(F)c(N)c1Cl]

Head B (600 mg, 2.5 mmol, 1.0 equiv) and (4-(trimethylsilyl)phenyl)boronic acid (540 mg, 2.8 mmol, 1.1 equiv) were combined in a 20 mL vial followed by cesium fluoride (420 mg, 2.8 mmol, 1.1 equiv), palladium acetate (28 mg, 0.13 mmol, 0.05 equiv), and sodium 3,3',3"-phosphinetriyltribenzenesulfonate (140 mg, 0.25 mmol, 0.10 equiv). A 3:1 mixture of water:acetonitrile (7.2 mL) was added and the resulting brown mixture was capped and placed in a Biotage Initiator™ microwave reactor for 5 min at 150° C., with external IR-sensor temperature monitoring from the side of the vessel. The cooled reaction mixture was diluted with water (150 mL) and extracted with dichloromethane (5×60 mL). The combined organic layers were dried (magnesium sulfate), gravity filtered, and concentrated by rotary evaporation. The residue was purified by silica gel column chromatography (33% ethyl acetate in hexanes) to afford the title compound as a pale yellow powder (700 mg, 79%): mp 148-150° C.; $^1$H NMR (300 MHz, CDCl$_3$) δ 7.86 (m, 2H), 7.62 (m, 2H), 4.88 (br s, 2H), 3.98 (s, 3H), 0.29 (s, 9H); ESIMS m/z 353 ([M+H]$^+$).

The following compounds were made in accordance with the procedures disclosed in Example 47:

Methyl 4-amino-3-chloro-5-fluoro-6-(2-fluoro-4-formylphenyl)picolinate

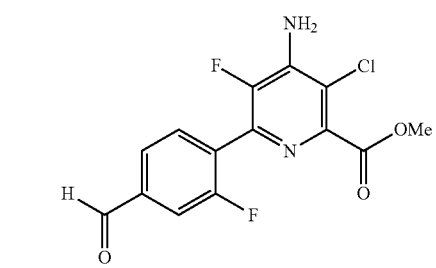 [SMILES: COC(=O)c1nc(-c2ccc(C=O)cc2F)c(F)c(N)c1Cl]

mp 151-154° C.; $^1$H NMR (400 MHz, CDCl$_3$) δ 10.06 (d, J=2 Hz, 1H), 7.79-7.84 (m, 2H), 7.67 (dd, J=10, 1 Hz, 1H), 5.00 (br s, 2H), 3.99 (s, 3H); ESIMS m/z 327 ([M+H]$^+$).

Methyl 6-amino-2-(2-fluoro-4-formylphenyl)-5-methoxypyrimidine-4-carboxylate

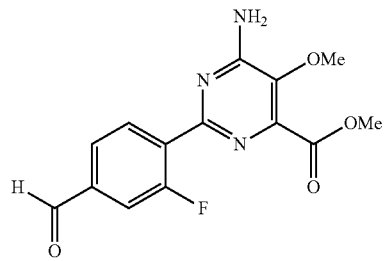 [SMILES: COC(=O)c1nc(-c2ccc(C=O)cc2F)nc(N)c1OC]

mp 176-178° C.; $^1$H NMR (400 MHz, CDCl$_3$) δ 10.03 (d, J=2 Hz, 1H), 8.10 (t, J=8 Hz, 1H), 7.73 (dd, J=8, 1.5 Hz, 1H), 7.65 (dd, J=8, 1.5 Hz, 1H), 5.45 (br s, 2H), 4.00 (s, 3H), 3.96 (s, 3H); ESIMS m/z 306 ([M+H]$^+$).

Methyl 4-amino-3-chloro-6-(2,3-difluoro-4-formylphenyl)-5-fluoropicolinate

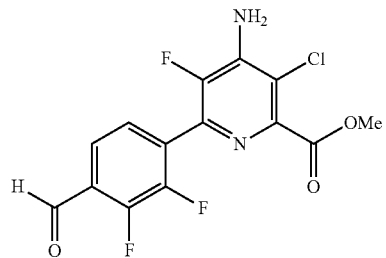 [SMILES: COC(=O)c1nc(-c2ccc(C=O)c(F)c2F)c(F)c(N)c1Cl]

¹H NMR (400 MHz, CDCl₃) δ 10.40 (d, J=1 Hz, 1H), 7.74 (m, 1H), 7.52 (m, 1H), 5.01 (br s, 2H), 3.97 (s, 3H).

Methyl 6-amino-2-(2,3-difluoro-4-formylphenyl)-5-methoxypyrimidine-4-carboxylate

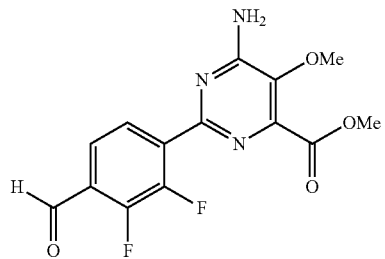 [SMILES: COC(=O)c1nc(-c2ccc(C=O)c(F)c2F)nc(N)c1OC]

mp 184-186° C.; ¹H NMR (400 MHz, CDCl₃) δ 10.38 (d, J=0.5 Hz, 1H), 7.84 (m, 1H), 7.67 (ddd, J=8, 6, 2 Hz, 1H), 5.47 (br s, 2H), 4.01 (s, 3H), 3.96 (s, 3H); ESIMS m/z 324 ([M+H]⁺).

Methyl 6-amino-2-(4-formylphenyl)-5-methoxypyrimidine-4-carboxylate

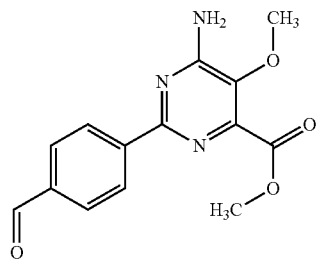 [SMILES: COC(=O)c1nc(-c2ccc(C=O)cc2)nc(N)c1OC]

mp 155-156° C.; ¹H NMR (400 MHz, CDCl₃) δ 10.1 (s, 1H), 8.54 (d, 2H), 7.99 (d, 2H), 5.56 (s, 2H), 4.08 (s, 3H), 3.99 (s, 3H); ESIMS m/z 288 ([M+H]⁺).

Methyl 4-amino-3,5-dichloro-6-(4-formylphenyl)picolinate

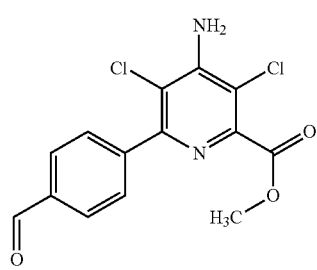 [SMILES: COC(=O)c1nc(-c2ccc(C=O)cc2)c(Cl)c(N)c1Cl]

mp 131-133° C.; ¹H NMR (400 MHz, CDCl₃) δ 10.08 (s, 1H), 7.96 (d, 2H), 7.83 (d, 2H), 5.36 (s, 2H), 3.98 (s, 3H); ESIMS m/z 325 ([M+H]⁺).

Example 48

Preparation of methyl 4-amino-3-chloro-5-fluoro-6-(3-fluoro-4-(trimethylsilyl)phenyl)picolinate

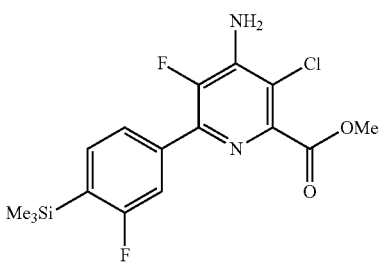 [SMILES: COC(=O)c1nc(-c2ccc([Si](C)(C)C)c(F)c2)c(F)c(N)c1Cl]

Dichloro[bis(triphenylphosphino)]-palladium(II) (150 mg, 0.21 mmol, 0.10 equiv) and sodium carbonate (270 mg, 2.5 mmol, 1.2 equiv) were sequentially added to a stirred mixture of crude (2-fluoro-4-(4,4,5,5-tetramethyl-1,3,2-dioxaborolan-2-yl)phenyl)trimethylsilane (990 mg, 2.5 mmol, 1.2 equiv) and Head B (500 mg, 2.1 mmol, 1.0 equiv) in a 1:1 mixture of water:acetonitrile (7.0 mL) at 23° C. The resulting dark orange mixture was heated to 85° C. and stirred for 4 h. The cooled reaction mixture was diluted with water (150 mL) and extracted with dichloromethane (3×80 mL). The combined organic layers were dried (magnesium sulfate), gravity filtered, and concentrated by rotary evaporation. The residue was purified by silica gel column chromatography (25% ethyl acetate in hexanes) to afford the title compound as a pale yellow powder (500 mg, 65%): mp 125-127° C.; IR (thin film) 3481 (m), 3350 (s), 2952 (w), 1728 (m), 1610 (m) cm-1; ¹H NMR (400 MHz, CDCl₃) δ 7.71 (dt, J=6.5, 1 Hz, 1H), 7.59 (dt, J=10, 1 Hz, 1H), 7.50 (dd, J=8, 6.5 Hz, 1H), 4.91 (br s, 2H), 3.99 (s, 3H), 0.33 (d, 9H); ESIMS m/z 371 ([M+H]⁺).

The following compounds were made in accordance with the procedures disclosed in Example 48:

Methyl 4-amino-3-chloro-6-(2,3-difluoro-4-(trimethylsilyl)phenyl)-5-fluoropicolinate

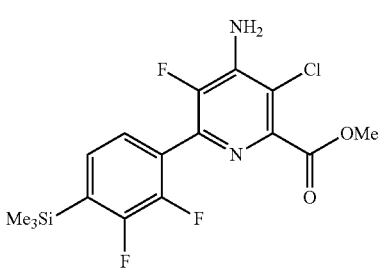 [SMILES: COC(=O)c1nc(-c2ccc([Si](C)(C)C)c(F)c2F)c(F)c(N)c1Cl]

¹H NMR (400 MHz, CDCl₃) δ 7.33 (ddd, J=8, 4.5, 1 Hz, 1H), 7.21 (ddd, J=8, 5, 1.5 Hz, 1H), 4.94 (br s, 2H), 3.96 (s, 3H), 0.33 (d, J=1 Hz, 9H); ESIMS m/z 389 ([M+H]⁺).

Methyl 4-amino-3-chloro-5-fluoro-6-(2-fluoro-4-(trimethylsilyl)phenyl)picolinate

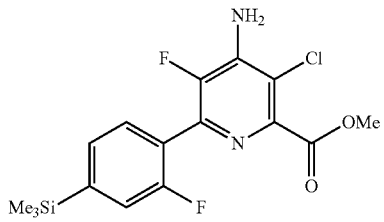

mp 175-177° C.; ¹H NMR (400 MHz, CDCl₃) δ 7.58 (t, J=8 Hz, 1H), 7.39 (dd, J=8, 1 Hz, 1H), 7.27 (m, 1H), 4.91 (br s, 2H), 3.96 (s, 3H), 0.26 (s, 9H); ESIMS m/z 371 ([M+H]⁺).

Methyl 6-amino-2-(2-fluoro-4-(trimethylsilyl)phenyl)-5-methoxypyrimidine-4-carboxylate

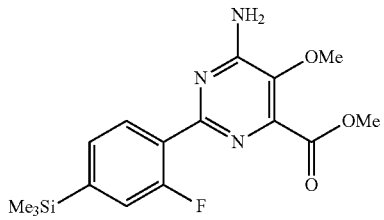 [SMILES: COC(=O)c1nc(-c2ccc([Si](C)(C)C)cc2F)nc(N)c1OC]

mp 140-142° C.; ¹H NMR (400 MHz, CDCl₃) δ 7.85 (t, J=8 Hz, 1H), 7.32 (dd, J=8, 1 Hz, 1H), 7.26 (m, 1H), 5.38 (br s, 2H), 3.99 (s, 3H), 3.94 (s, 3H), 0.26 (s, 9H); ESIMS m/z 348 ([M−H]⁻).

Methyl 4-acetamido-3-chloro-6-(2,3-difluoro-4-(trimethylsilyl)phenyl)picolinate

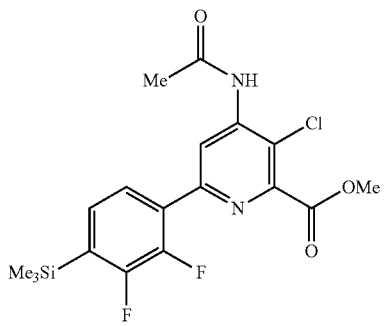 [SMILES: COC(=O)c1nc(-c2ccc([Si](C)(C)C)c(F)c2F)cc(NC(C)=O)c1Cl]

¹H NMR (400 MHz, CDCl₃) δ 9.04 (d, 1 Hz, 1H), 7.99 (br s, 1H), 7.65 (m, 1H), 7.18 (m, 1H), 4.00 (s, 3H), 2.31 (s, 3H), 0.33 (d, J=1 Hz, 9H); ESIMS m/z 413 ([M−H]).

Methyl 6-amino-5-methoxy-2-(4-(trimethylsilyl)phenyl)pyrimidine-4-carboxylate

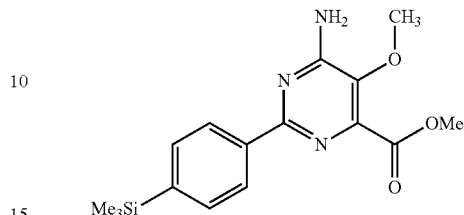

¹H NMR (400 MHz, CDCl₃) δ 8.25 (m, 2H), 7.58 m, 2H), 5.35 (br s, 2H), 4.01 (s, 3H), 3.91 (s, 3H). 0.30 (s, 9H); ESIMS m/z 330 ([M−H]⁻).

Methyl 4-acetamido-3-chloro-6-(4-(trimethylsilyl)phenyl)picolinate

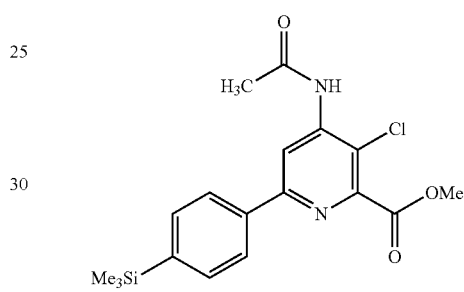

¹H NMR (400 MHz, CDCl₃) δ 9.00 (s, 1H), 7.98 (m, 2H), 7.61 (m, 2H), 7.25 (s, 1H), 4.01 (s, 3H), 2.32 (s, 3H), 0.29 (s, 9H); ESIMS m/z 375 ([M−H]⁻).

Example 49

Preparation of methyl 4-acetamido-6-(4-amino-2,3,6-trifluorophenyl)-3-chloropicolinate

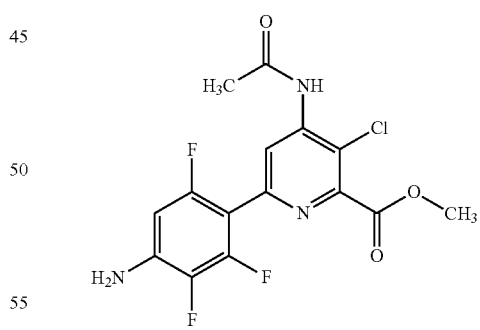

A suspension of methyl 4-acetamido-3-chloro-6-(trimethylstannyl)picolinate (Head K) (0.502 g, 1.409 mmol, 1.0 eq), 2,3,5-trifluoro-4-iodoaniline (0.5 g, 1.831 mmol, 1.3 eq), bis(triphenylphosphine)palladium(II) chloride (0.098 g, 0.1401 mmol, 0.1 eq) and CuI (26 mg, 0.1401 mmol, 0.1 eq) in dry DMF (3 mL) was irradiated with microwave at 120° C. for 1 h. Reaction mixture was cooled to 20° C. and stirred with aqueous KF solution (20 mL) for 15 m and extracted with ethyl acetate (3×100 mL). The combined organic layers were dried over anh. Na₂SO₄, filtered and evaporated to dryness under reduced pressure. The crude product was purified on silica gel (60-120) using a gradient from 0-30% EtOAc in hexanes yielded the title compound as a brown solid (280 mg, 44.8%): $^1$H NMR (400 MHz, DMSO-$d_6$) δ 9.96 (s, 1H), 8.32 (s, 1H), 6.51-6.46 (m, 1H), 6.22 (brs, 2H), 3.92 (s, 3H), 2.23 (s, 3H); ESIMS m/z 376 ([M+3H]$^+$).

Example 50

Preparation of methyl 4-amino-3-chloro-6-(2,5-difluoro-4-(trimethylsilyl)phenyl)-5-fluoropicolinate

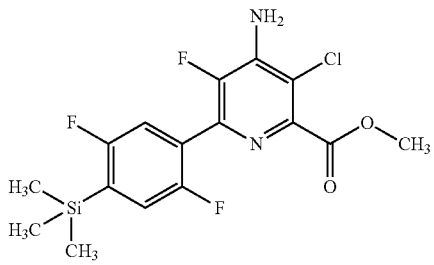

In a microwave vessel, a suspension of (2,5-difluoro-4-(4,4,5,5-tetramethyl-1,3,2-dioxaborolan-2-yl)phenyl)trimethylsilane (see, e.g., WO 2013003740 A1) (0.6 g, 1.922 mmol), methyl 4-amino-3,6-dichloro-5-fluoropicolinate (Head B) (0.383 g, 1.601 mmol), bis(triphenyl phosphine)palladium (II) chloride (0.112 g, 0.160 mmol) and sodium carbonate (0.204 g, 1.922 mmol) in a 3:1 mixture of acetonitrile (4.00 mL) and water (1.334 mL) was stirred under microwave irradiation (120° C., 20 min). The reaction mixture was poured into an half saturated brine solution and was extracted with EtOAc (3×). The combined organic layers were dried over Na$_2$SO$_4$, filtered and concentrated. The residue was purified by preparative reverse phase HPLC (water/acetonitrile gradient) to afford the title compound as a white solid (0.271 g, 0.697 mmol, 43.5%): $^1$H NMR (400 MHz, CDCl$_3$) δ 7.23 (dd, J=7.8, 5.1 Hz, 1H), 7.13 (dd, J=9.3, 4.0 Hz, 1H), 4.95 (s, 2H), 3.98 (s, 3H), 0.33 (d, J=0.8 Hz, 9H); $^{19}$F NMR (376 MHz, CDCl$_3$) δ -106.81, -106.87, -121.20, -121.25, -121.29, -121.35, -137.32, -137.41; ESIMS m/z 389 ([M+H]$^+$).

Example 51

Preparation of methyl 4-amino-3-chloro-6-(2,5-difluoro-4-(trimethylsilyl)phenyl)picolinate

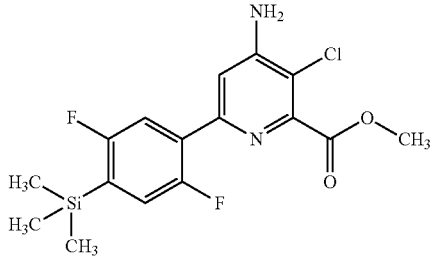

In a microwave vessel, a suspension of (2,5-difluoro-4-(4,4,5,5-tetramethyl-1,3,2-dioxaborolan-2-yl)phenyl)trimethylsilane (see, e.g., WO 2013003740 A1) (0.6 g, 1.922 mmol), methyl 4-amino-3,6-dichloropicolinate (Head A) (0.354 g, 1.601 mmol), bis(triphenyl phosphine)palladium(II) chloride (0.112 g, 0.160 mmol) and sodium carbonate (0.204 g, 1.922 mmol) in a 3:1 mixture of acetonitrile (4.00 mL) and water (1.334 mL) was stirred under microwave irradiation (120° C., 20 min). The reaction mixture was poured into an half saturated brine solution and was extracted with EtOAc (3×). The combined organic layers were dried over Na$_2$SO$_4$, filtered and concentrated. The residue was purified by preparative reverse phase HPLC (water/acetonitrile gradient) to afford the title compound as a white solid (0.234 g, 0.631 mmol, 39.4%): $^1$H NMR (400 MHz, CDCl$_3$) δ 7.66 (dd, J=8.7, 5.8 Hz, 1H), 7.25 (d, J=1.2 Hz, 1H), 7.09 (dd, J=10.8, 4.1 Hz, 1H), 4.84 (s, 2H), 4.00 (s, 3H), 0.32 (d, J=0.7 Hz, 9H); $^{19}$F NMR (376 MHz, CDCl$_3$) δ -106.56, -106.61, -124.00-124.06; ESIMS m/z 371 ([M+H]$^+$).

Example 52

Preparation of methyl 4-acetamido-3-chloro-6-(2,5-difluoro-4-(trimethylsilyl)phenyl)picolinate

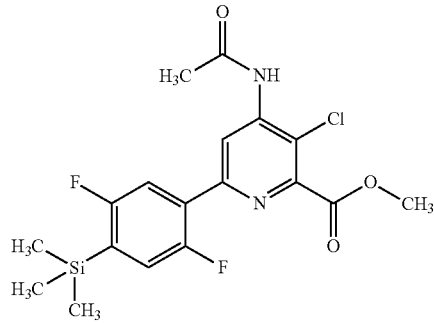

In a microwave vessel, a suspension of (2,5-difluoro-4-(4,4,5,5-tetramethyl-1,3,2-dioxaborolan-2-yl)phenyl)trimethylsilane (see, e.g., WO 2013003740 A1) (1 g, 2.56 mmol), methyl 4-acetamido-3,6-dichloropicolinate (Head L) (0.562 g, 2.135 mmol), bis(triphenyl phosphine)palladium(II) chloride (0.150 g, 0.214 mmol) and sodium carbonate (0.272 g, 2.56 mmol) in a 3:1 mixture of acetonitrile (5.34 mL) and water (1.779 mL) was stirred under microwave irradiation (120° C., 20 min). The reaction mixture was poured into an half saturated brine solution and was extracted with EtOAc (3×). The combined organic layers were dried over Na$_2$SO$_4$, filtered and concentrated. The residue was purified by preparative reverse phase HPLC (water/acetonitrile gradient) to afford the title compound as a white solid (0.481 g, 1.165 mmol, 54.6%): mp 135-137° C.; $^1$H NMR (400 MHz, CDCl$_3$) δ 9.07 (d, J=0.8 Hz, 1H), 7.96 (s, 1H), 7.62 (dd, J=8.5, 5.7 Hz, 1H), 7.13 (dd, J=10.5, 4.1 Hz, 1H), 4.02 (s, 3H), 2.33 (s, 3H), 0.33 (d, J=0.8 Hz, 9H); $^{19}$F NMR (376 MHz, CDCl$_3$) δ -106.66, -106.72, -123.42, -123.48; ESIMS m/z 411 ([M-H]$^-$).

Example 53

Preparation of methyl 6-amino-2-(2,5-difluoro-4-(trimethylsilyl)phenyl)-5-methoxypyrimidine-4-carboxylate

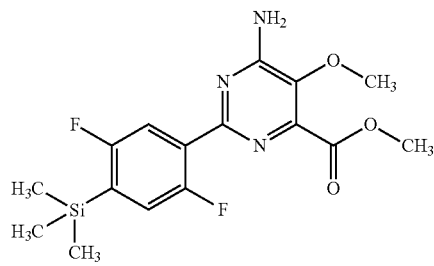

In a microwave vessel, a suspension of (2,5-difluoro-4-(4,4,5,5-tetramethyl-1,3,2-dioxaborolan-2-yl)phenyl)trimethylsilane (e.g., WO 2013003740 A1) (1.925 g, 5.05 mmol), methyl 6-amino-2-chloro-5-methoxypyrimidine-4-carboxylate (Head C) (1 g, 4.60 mmol), bis(triphenyl phosphine)palladium(II) chloride (0.323 g, 0.460 mmol) and sodium carbonate (0.584 g, 5.51 mmol) in a 3:1 mixture of acetonitrile (8.62 mL) and water (2.87 mL) was stirred under microwave irradiation (120° C., 20 min). The reaction mixture was poured into an half saturated brine solution and was extracted with EtOAc (3×). The combined organic layers were dried over Na$_2$SO$_4$, filtered and concentrated. The residue was purified by preparative reverse phase HPLC (water/acetonitrile gradient) to afford the title compound as a white solid (0.994 g, 58.9%): mp 130-131° C.; $^1$H NMR (400 MHz, CDCl$_3$) δ 7.53 (dd, J=8.4, 5.6 Hz, 1H), 7.10 (dd, J=10.2, 4.1 Hz, 1H), 5.44 (s, 2H), 4.00 (s, 3H), 3.94 (s, 3H), 0.32 (d, J=0.9 Hz, 9H); $^{19}$F NMR (376 MHz, CDCl$_3$) δ −107.45, −107.51, −122.32, −122.37; ESIMS m/z 367 ([M]$^+$).

Example 54

Preparation of methyl 4-amino-6-(2,3-difluoro-4-(trifluoromethyl)phenyl)-5-fluoro-3-vinylpicolinate (Compound 53)

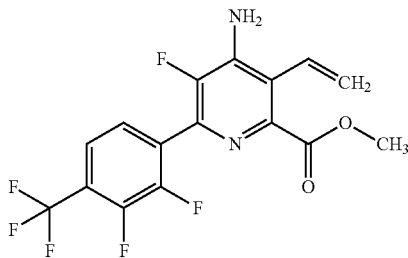 [SMILES: C=Cc1c(C(=O)OC)nc(-c2ccc(C(F)(F)F)c(F)c2F)c(F)c1N]

In a microwave vessel, a suspension of 2-(2,3-difluoro-4-(trifluoromethyl)phenyl)-4,4,5,5-tetramethyl-1,3,2-dioxaborolane (commercially available) (0.641 g, 2.081 mmol), methyl 4-amino-6-chloro-5-fluoro-3-vinylpicolinate (Head G) (0.4 g, 1.734 mmol), bis(triphenyl phosphine)palladium (II) chloride (0.122 g, 0.173 mmol) and sodium carbonate (0.368 g, 3.47 mmol) in a 3:1 mixture of acetonitrile (3.25 mL) and water (1.084 mL) was stirred under microwave irradiation (120° C., 20 min). The reaction mixture was poured into an half saturated brine solution and was extracted with EtOAc (3×). The combined organic layers were dried over Na$_2$SO$_4$, filtered and concentrated. The residue was purified by preparative reverse phase HPLC (water/acetonitrile gradient) to afford the title compound as a brown solid (0.163 g, 0.433 mmol, 24.98%).

Example 55

Preparation of methyl 4-amino-6-(4-aminophenyl)-5-fluoro-3-vinylpicolinate

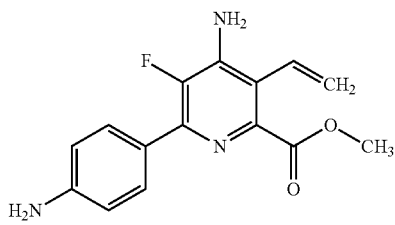 [SMILES: C=Cc1c(C(=O)OC)nc(-c2ccc(N)cc2)c(F)c1N]

In a microwave vessel, a suspension of 4-(4,4,5,5-tetramethyl-1,3,2-dioxaborolan-2-yl)aniline (commercially available) (0.617 g, 2.82 mmol), methyl 4-amino-6-chloro-5-fluoro-3-vinylpicolinate (Head G) (0.5 g, 2.168 mmol), bis (triphenyl phosphine)palladium(II) chloride (0.152 g, 0.217 mmol) and potassium fluoride (0.327 g, 5.64 mmol) in a 1:1 mixture of acetonitrile (3.61 mL) and water (3.61 mL) was stirred under microwave irradiation (120° C., 20 min). The reaction mixture was poured into a half saturated brine solution and was extracted with EtOAc (3×). The combined organic layers were dried over Na$_2$SO$_4$, filtered and concentrated. The residue was purified by flash column chromatography (SiO$_2$ 24 g, hexanes/EtOAc gradient) to afford the title compound as a yellow solid (0.552 g, 89%) as a yellow solid: $^1$H NMR (400 MHz, DMSO-d$_6$) δ 7.60-7.58 (m, 2H), 6.72 (dd, J=17.7, 11.5 Hz, 1H), 6.65-6.58 (m, 2H), 6.24 (s, 2H), 5.47 (s, 2H), 5.45 (dd, J=11.5, 1.2 Hz, 1H), 5.38 (dd, J=17.7, 1.2 Hz, 1H), 3.77 (s, 3H); $^{19}$F NMR (376 MHz, DMSO-d$_6$) δ −146.62; ESIMS m/z 286 ([M−H]$^−$).

Example 56

Preparation of methyl 6-amino-2-(4-(difluoromethoxy)phenyl)-5-methoxypyrimidine-4-carboxylate (Compound 106)

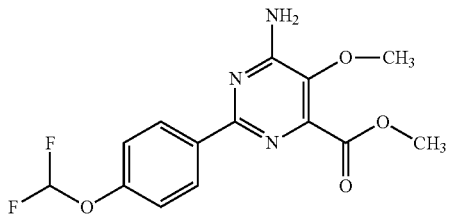 [SMILES: COC(=O)c1nc(-c2ccc(OC(F)F)cc2)nc(N)c1OC]

To a 5-mL microwave safe vial was added potassium fluoride (0.151 g, 2.59 mmol), palladium (II) acetate (0.012 g, 0.052 mmol), 2-(4-(difluoromethoxy)phenyl)-4,4,5,5-tetramethyl-1,3,2-dioxaborolane (0.28 g, 1.037 mmol), methyl 6-amino-2-chloro-5-methoxypyrimidine-4-carboxylate (0.226 g, 1.037 mmol), and 3,3',3"-phosphinetriyltribenzenesulfonate (0.052 g, 0.104 mmol). A mixture of water (1 mL) and acetonitrile (2 mL) was added and the reaction was capped and placed in a Biotage Initiator™ microwave reactor for 6 min at 160° C., with external IR-sensor temperature monitoring from the side of the vessel. Upon cooling to room temperature, the reaction mixture was diluted with EtOAc (50 mL) and water (50 mL). An additional extraction using CH$_2$Cl$_2$ (50 mL) was combined with the EtOAc and dried over of Na$_2$SO$_4$ (50 g) after the CH$_2$Cl$_2$ layer was filtered through cotton plug. The combined organics were concentrated on a rotary evaporator and the residue was purified using a Teledyne ISCO purification system with a gradient eluent system of CH$_2$Cl$_2$ and EtOAc to yield the title compound as a tan solid (134.4 mg).

Example 57

Preparation of methyl 4-amino-6-(4-cyanophenyl)-5-fluoro-3-vinylpicolinate (Compound 107)

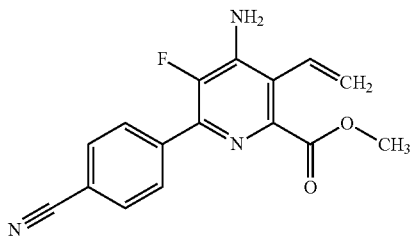 [SMILES: C=Cc1c(C(=O)OC)nc(-c2ccc(C#N)cc2)c(F)c1N]

To a 5-mL microwave safe vial was added potassium fluoride (0.227 g, 3.90 mmol), methyl 4-amino-6-chloro-5-fluoro-3-vinylpicolinate (0.3 g, 1.301 mmol), bis(triphenylphosphine)palladium (II) chloride (0.091 g, 0.130 mmol) and 4-(4,4,5,5-tetramethyl-1,3,2-dioxaborolan-2-yl)benzonitrile (0.313 g, 1.366 mmol. A mixture of water (1 mL) and acetonitrile (2 mL) was added and the reaction was capped and placed in a Biotage Initiator™ microwave reactor for 20 min at 115° C., with external IR-sensor temperature monitoring from the side of the vessel. Upon cooling to room temperature, the reaction mixture was diluted with CH$_2$Cl$_2$ (25 mL) and water (25 mL) and the organic layer was filtered through cotton plug. An additional extraction using EtOAc (25 mL) was combined with the CH$_2$Cl$_2$ and dried over of Na$_2$SO$_4$ (50 g). Following filtration of the combined organics through a cotton plug and concentration on a rotary evaporator, the residue was purified using a Teledyne ISCO purification system with a gradient eluent system of CH$_2$Cl$_2$ and EtOAc to yield the title compound as a tan solid (297 mg).

Example 58

Preparation of methyl 4-amino-5-fluoro-6-(4-formylphenyl)-3-vinylpicolinate

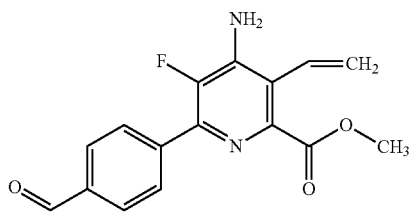 [SMILES: C=Cc1c(C(=O)OC)nc(-c2ccc(C=O)cc2)c(F)c1N]

To a 5-mL microwave safe vial was added potassium fluoride (0.378 g, 6.50 mmol), methyl 4-amino-6-chloro-5-fluoro-3-vinylpicolinate (0.5 g, 2.168 mmol), bis(triphenylphosphine)palladium(II) chloride (0.152 g, 0.217 mmol) and 4-(4,4,5,5-tetramethyl-1,3,2-dioxaborolan-2-yl)benzaldehyde (0.528 g, 2.276 mmol). A mixture of water (1 mL) and acetonitrile (2 mL) was added and the reaction was capped and placed in a Biotage Initiator™ microwave reactor for 20 min at 115° C., with external IR-sensor temperature monitoring from the side of the vessel. Upon cooling to room temperature, the reaction mixture was diluted with CH$_2$Cl$_2$ (25 mL) and water (25 mL) and the organic layer was filtered through a cotton plug. An additional extraction using EtOAc (25 mL) was combined with the CH$_2$Cl$_2$ and dried over Na$_2$SO$_4$ (50 g). Following filtration of the combined organics through a cotton plug and concentration on a rotary evaporator, the residue was purified using a Teledyne ISCO purification system with a gradient eluent system of CH$_2$Cl$_2$ and EtOAc to yield the title compound as a white solid (635 mg): $^1$H NMR (400 MHz, CDCl$_3$) δ 10.08 (s, 1H), 8.13 (dd, J=8.3, 1.6 Hz, 2H), 8.03-7.93 (m, 2H), 6.91 (ddd, J=18.1, 11.6, 0.5 Hz, 1H), 5.73 (dd, J=11.5, 1.4 Hz, 1H), 5.60 (dd, J=18.1, 1.4 Hz, 1H), 4.77 (s, 2H), 3.94 (s, 3H); $^{19}$F NMR (376 MHz, CDCl$_3$) δ −143.49; ESIMS m/z 301 ([M+H]$^+$).

Example 59

Preparation of methyl 4-amino-3-chloro-6-(2,5-difluoro-4-(trifluoromethyl)phenyl)picolinate (Compound 70)

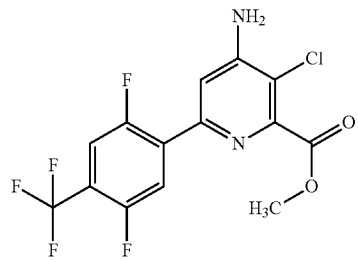 [SMILES: COC(=O)c1nc(-c2cc(F)c(C(F)(F)F)cc2F)cc(N)c1Cl]

1,4-Difluoro-2-iodo-5-(trifluoromethyl)benzene (250 mg, 0.81 mmol), Head K (318 mg, 0.81 mmol), copper(I)iodide (0.08 mmol) and bis(triphenylphosphine)palladium(II) chloride (57 mg, 0.08 mmol) were combined in dry DMF (5 mL), deaerated with a stream of nitrogen for 10 min and heated to 75° C. After 2 h, the mixture was cooled and partitioned between ethyl acetate and water. The organic phase was washed with saturated NaCl, dried (Na$_2$SO$_4$), and evaporated. The crude product was purified by flash chromatography (SiO$_2$, eluting with 0-30% ethyl acetate in hexanes) to provide 100 mg of the acetamide intermediate. This material was taken up in methanol (20 mL), treated with acetyl chloride (3 mL) and stirred for 3 days at 20° C. After removal of volatiles under vacuum, the mixture was stirred with sat. NaHCO$_3$ and ethyl acetate. The organic phase was washed with saturated NaCl, dried (Na$_2$SO$_4$), and evaporated to provide the title compound as a white solid (77 mg, 24%).

Example 60

Preparation of methyl 6-amino-2-(2,5-difluoro-4-(trifluoromethyl)phenyl)-5-methoxypyrimidine-4-carboxylate (Compound 148)

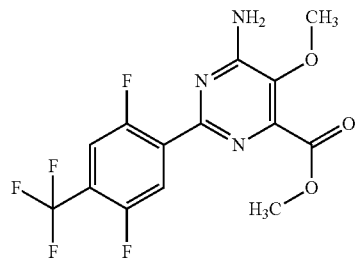 [SMILES: COC(=O)c1nc(-c2cc(F)c(C(F)(F)F)cc2F)nc(N)c1OC]

2-(2,5-Difluoro-4-(trifluoromethyl)phenyl)-4,4,5,5-tetramethyl-1,3,2-dioxaborolane (400 mg, 1.2 mmol), Head C (250 mg 1.2 mmol), cesium fluoride (360 mg, 2.3 mmol) and bis(triphenylphosphine)palladium(II) chloride (82 mg, 0.12 mmol) were combined in 4 mL 1:1 v/v acetonitrile-water and heated at 115° C. for 30 min in a microwave reactor. The mixture was partitioned between water and ethyl acetate. The organic phase was washed with saturated NaCl, dried (Na$_2$SO$_4$), and evaporated. The material was purified by flash chromatography (SiO$_2$, eluting with 0-30% ethyl acetate in hexanes) to provide a brown oil which was triturated with hexanes-dichloromethane to provide the title compound as a white solid (40 mg, 8.8%).

Example 61

Preparation of methyl 6-amino-2-(2,3-difluoro-4-(trimethylsilyl)phenyl)-5-methoxypyrimidine-4-carboxylate

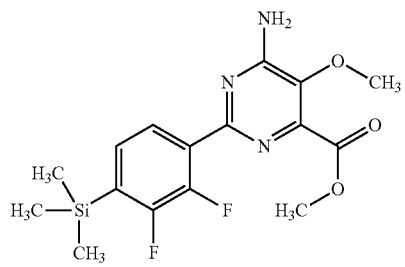

(2,3-Difluoro-4-(4,4,5,5-tetramethyl-1,3,2-dioxaborolan-2-yl)phenyl)trimethylsilane (1.3 g, 4.2 mmol) (e.g., WO 2013003740 A1), Head C (750 mg, 3.5 mmol) and bis(triphenylphosphine)palladium(II) chloride (240 mg, 0.34 mmol) were combined in 10 mL 1:1 v/v acetonitrile-water and heated to 115° C. for 30 min via microwave. The cooled mixture was partitioned between saturated NaCl and ethyl acetate. The organic phase was washed with sat. NaCl, dried ($Na_2SO_4$), and evaporated. The material was purified by flash chromatography ($SiO_2$, eluting with 0-20% ethyl acetate in hexanes) to provide the title compound as a white solid (330 mg, 26%): $^1$H NMR (400 MHz, $CDCl_3$) δ 7.60 (ddd, J=7.5, 6.0, 1.2 Hz, 1H), 7.14 (ddd, J=7.7, 4.5, 1.5 Hz, 1H), 5.48 (s, 2H), 4.00 (s, 3H), 3.95 (s, 3H), 0.34 (d, J=0.7 Hz, 9H). $^{19}$F NMR (376 MHz, $CDCl_3$) δ −127.10 to −127.25 (m), −142.40 (dd, J=22.6, 3.6 Hz); mp 157-159° C.; ESIMS m/z 368 [(M+H)+].

The following compound was made in accordance with the procedures disclosed in Example 61 from commercially available (4,4,5,5-tetramethyl-1,3,2-dioxaborolan-2-yl)phenyl)trimethylsilane:

Methyl 4-amino-3,5-dichloro-6-(4-(trimethylsilyl)phenyl)picolinate (prepared utilizing Head H)

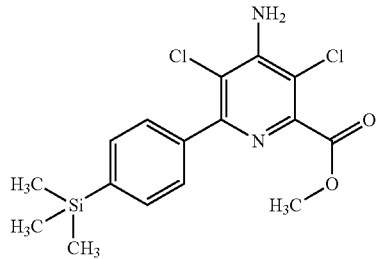 [SMILES: COC(=O)c1nc(-c2ccc([Si](C)(C)C)cc2)c(Cl)c(N)c1Cl]

$^1$H NMR (400 MHz, $CDCl_3$) δ 6.36 (m, 4H), 5.33 (2, 2H), 3.99 (s, 3H), 0.307 (s, 9H); mp 171-174° C.; ESIMS m/z 369 [(M+H)+].

The following compounds were made in accordance with the procedures disclosed in Example 61 from commercially available 2-fluoro-4-(4,4,5,5-tetramethyl-1,3,2-dioxaborolan-2-yl)phenyl)trimethylsilane (prepared according to WO 2013003740 A1):

Methyl 4-amino-3-chloro-6-(2-fluoro-4-(trimethylsilyl)phenyl)picolinate (prepared utilizing Head A)

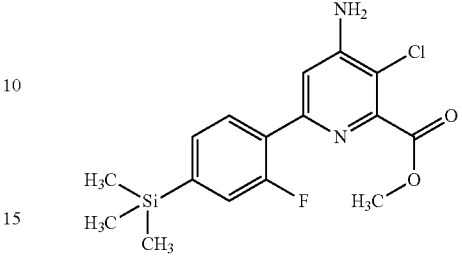

$^1$H NMR (400 MHz, $CDCl_3$) δ 7.97 (m, 1H), 7.30 (m, 3H), 4.84 (s, 2H), 4.01 (s, 3H), 0.293 (s, 9H); mp 154-156° C.; ESIMS m/z 353 [(M+H)+].

Methyl 4-amino-3,5-dichloro-6-(2-fluoro-4-(trimethylsilyl)phenyl)picolinate (prepared utilizing Head H)

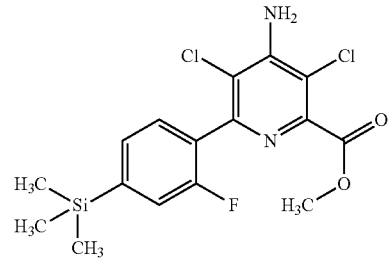

$^1$H NMR (400 MHz, $CDCl_3$) δ 7.35 (m, 3H), 5.33 (s, 2H), 3.96 (s, 3H), 0.290 (s, 9H); mp 184-185° C.; ESIMS m/z 387 [(M+H)+].

Example 62

General Procedure for Suzuki Coupling (Method A)

Argon was bubbled through a solution of Head A, Head B, or Head C (1.0 eq), a boronic acid (1.0 eq), $Na_2CO_3$ (2.0 eq) and Pd(PPh$_3$)$_4$ (0.1 eq) in 1:1 toluene:ethanol (20 vol) for 15 min in a sealed tube. The reaction mixture was then heated in the sealed tube at 110° C. for 18 h. The cooled reaction mixture was diluted with water and extracted with ethyl acetate. (Note: The aqueous layer contained carboxylic acid products that were isolated as described below). The organic extracts was washed with water, washed with saturated brine solution, dried ($Na_2SO_4$), filtered, and evaporated to dryness under reduced pressure. The crude product was purified by preparative TLC to get the pure esters. The aqueous layer was acidified to pH 2 using 1.5 N HCl and extracted with ethyl acetate. The organic extract was washed with saturated brine solution, dried ($Na_2SO_4$), filtered, and evaporated to dryness under reduced pressure. The crude product was purified by preparative TLC to get the pure carboxylic acid derivatives.

Example 63

General Procedure for Suzuki Coupling (Method B)

Argon was bubbled through a solution of Head A, Head B or Head C (0.8 eq), a boronic acid (1.0 eq), $NaHCO_3$ (2 M solution, 1.0 eq) and Pd(PPh$_3$)$_4$ (0.1 eq) in dry dioxane (20 vol) for 15 min in a sealed tube. The sealed tube was heated at 80° C. for 18 h. The cooled reaction mixture was diluted with water and extracted with ethyl acetate. The organic extract was washed with water, washed with saturated brine solution, dried (Na$_2$SO$_4$), filtered, and evaporated to dryness under reduced pressure. The crude product was purified by flash chromatography (SiO$_2$, eluting with 5-40% ethyl acetate in hexanes) to provide the pure compound.

Example 64

Preparation of methyl 4-amino-3-chloro-6-(3-fluoro-4-iodophenyl)picolinate (Compound 66)

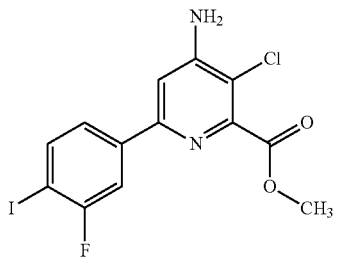 [SMILES: COC(=O)c1nc(-c2ccc(I)c(F)c2)cc(N)c1Cl]

To a 250-mL round bottom flask, equipped with a stir bar, was added methyl 4-amino-3-chloro-6-(3-fluoro-4-(trimethylsilyl)phenyl)picolinate (0.328 g, 0.930 mmol), and dichloromethane (5.0 mL). To this solution iodine monochloride (0.141 mL, 2.79 mmol) was added. The reaction mixture was allowed to stir at room temperature for 18 hrs. Another portion of iodine monochloride (0.141 mL, 2.79 mmol) was added, and the reaction was allowed to stir at room temperature for an additional 4.5 hrs. The reaction mixture was poured into 1 M Na$_2$SO$_3$, and the layers were partitioned. The aqueous phase was extracted with additional ethyl acetate (2×100 mL). The combined organic layers were dried over anhydrous magnesium sulfate, filtered and concentrated to afford the title compound as a white solid (0.375 g, 99%):

The following compounds were made in accordance with the procedures disclosed in Example 64:

Methyl 4-amino-3,5-dichloro-6-(3-fluoro-4-iodophenyl)picolinate (Compound 13)

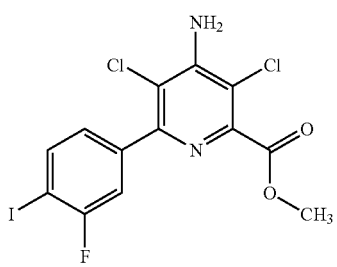 [SMILES: COC(=O)c1nc(-c2ccc(I)c(F)c2)c(Cl)c(N)c1Cl]

The title compound was prepared as described in Example 64 with methyl 4-amino-3,5-dichloro-6-(3-fluoro-4-(trimethylsilyl)phenyl)picolinate (0.381 g, 0.984 mmol) and isolated as a white solid (0.360 g, 83%).

Methyl 6-amino-2-(3-fluoro-4-iodophenyl)-5-methoxypyrimidine-4-carboxylate (Compound 27)

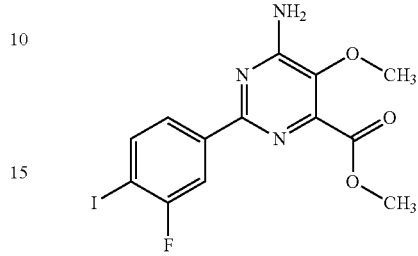

The title compound was prepared as described in Example 64 with methyl 6-amino-2-(3-fluoro-4-(trimethylsilyl)phenyl)-5-methoxypyrimidine-4-carboxylate (0.307 g, 0.879 mmol) and isolated as an off-white solid (0.368 g).

Example 65

Preparation of methyl 4-amino-3-chloro-6-(4-iodophenyl)-5-methylpicolinate (Compound 136)

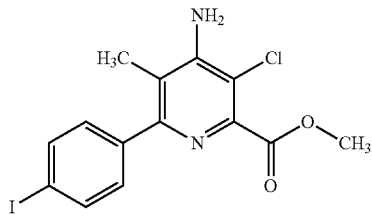 [SMILES: COC(=O)c1nc(-c2ccc(I)cc2)c(C)c(N)c1Cl]

To methyl 4-amino-3-chloro-5-methyl-6-(4-(trimethylsilyl)phenyl)picolinate (0.95 g, 2.72 mmol) in dichloromethane (9 mL) was added iodine monochloride (920 mg, 5.67 mmol) in dichloromethane (4.5 mL) dropwise. The reaction was stirred at room temperature for 4 h, then quenched with saturated aqueous sodium thiosulfate, diluted with water, and extracted with dichloromethane (3×). The organic layers were dried over anhydrous sodium sulfate, filtered and concentrated. Purification by flash chromatography (0-30% ethyl acetate/hexanes) afforded the title compound as a red-orange solid (618 mg, 56%).

The following compound was made in accordance with the procedures disclosed in Example 65:

Methyl 4-amino-3-chloro-6-(3-fluoro-4-iodophenyl)-5-methylpicolinate (Compound 79)

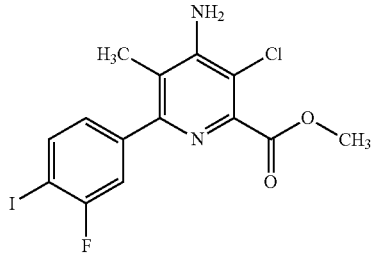 [SMILES: COC(=O)c1nc(-c2ccc(I)c(F)c2)c(C)c(N)c1Cl]

The title compound was prepared as in Example 65 and isolated as an off-white solid (54 mg, 59%).

Example 66

Methyl 4-amino-6-(4-iodophenyl)-3-chloro-5-fluoropicolinate (Compound 118)

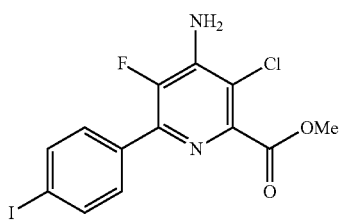 [SMILES: COC(=O)c1nc(-c2ccc(I)cc2)c(F)c(N)c1Cl]

Iodine monochloride (280 mg, 1.7 mmol, 2.0 equiv) was added to a stirred solution of methyl 4-amino-3-chloro-5-fluoro-6-(4-(trimethylsilyl)phenyl)picolinate (300 mg, 0.85 mmol, 1.0 equiv) in 1,2-dichloroethane (5.7 mL) at 23° C. The resulting brown solution was stirred at 23° C. for 17 h. The reaction mixture was diluted with saturated solution of sodium thiosulfate (100 mL) and extracted with dichloromethane (4×40 mL). The combined organic layers were dried (magnesium sulfate), gravity filtered, and concentrated by rotary evaporation. The residue was purified by silica gel column chromatography (33% ethyl acetate in hexanes) to afford the title compound as a pale purple powder (250 mg, 71%).

The following compounds were made in accordance with the procedures disclosed in Example 66:

Methyl 4-acetamido-3-chloro-6-(2,3-difluoro-4-iodophenyl)picolinate

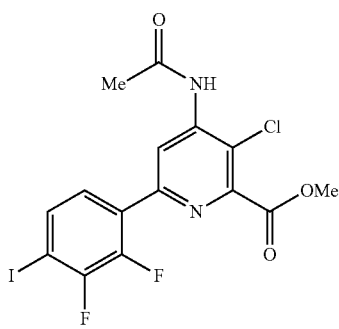 [SMILES: COC(=O)c1nc(-c2ccc(I)c(F)c2F)cc(NC(C)=O)c1Cl]

$^1$H NMR (400 MHz, CDCl$_3$) δ 9.06 (d, J=1.5 Hz, 1H), 7.98 (br s, 1H), 7.60 (ddd, J=9, 5, 2 Hz, 1H), 7.53 (ddd, J=9, 7, 2 Hz, 1H), 4.03 (s, 3H), 2.34 (s, 3H); ESIMS m/z 467 ([M+H]$^+$).

Methyl 4-acetamido-3-chloro-6-(4-iodophenyl)picolinate

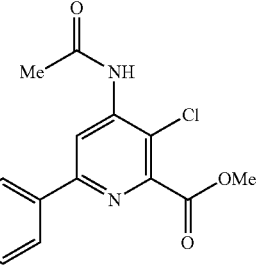

$^1$H NMR (400 MHz, CDCl$_3$) δ 9.00 (s, 1H), 7.77 (m, 4H), 7.25 (s, 1H), 4.03 (s, 3H), 2.33 (s, 3H); ESIMS m/z 431 ([M+H]$^+$).

Example 67

Preparation of methyl 4-amino-3-chloro-6-(2,5-difluoro-4-iodophenyl)-5-fluoropicolinate (Compound 55)

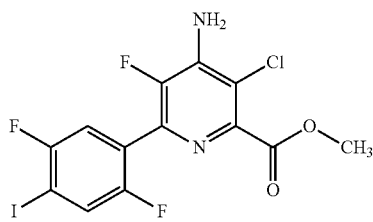

To a solution of methyl 4-amino-3-chloro-6-(2,5-difluoro-4-(trimethylsilyl)phenyl)-5-fluoropicolinate (0.280 g, 0.720 mmol) in CH$_2$Cl$_2$ (2.88 mL) at 20° C. was added iodine monochloride (0.144 mL, 2.880 mmol). The reaction mixture was stirred at 20° C. overnight. The mixture was then poured into a 10% aqueous solution of Na$_2$SO$_3$, extracted with EtOAc (3×), dried over Na$_2$SO$_4$, filtered and concentrated. The residue was purified by flash column chromatography (SiO$_2$, hexanes/EtOAc gradient) to afford the title compound as a white solid (0.237 g, 0.536 mmol, 74.4%).

The following compound was made in accordance with the procedures disclosed in Example 67:

Methyl 4-acetamido-3-chloro-6-(2,5-difluoro-4-iodophenyl)picolinate

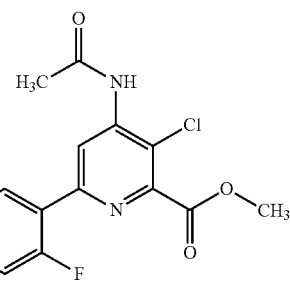

¹H NMR (400 MHz, CDCl₃) δ 9.10 (d, J=0.7 Hz, 1H), 7.96 (s, 1H), 7.76 (dd, J=8.4, 6.4 Hz, 1H), 7.57 (dd, J=9.8, 5.0 Hz, 1H), 4.03 (s, 3H), 2.33 (s, 3H); ¹⁹F NMR (376 MHz, CDCl₃) δ −99.95, −100.00, −119.90, −119.95; ESIMS m/z 465 ([M−H]⁻).

Example 68

Preparation of methyl 6-amino-2-(2,3-difluoro-4-iodophenyl)-5-methoxypyrimidine-4-carboxylate (Compound 24)

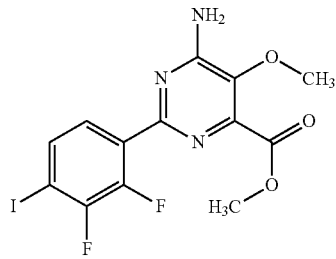 [SMILES: COC(=O)c1nc(-c2ccc(I)c(F)c2F)nc(N)c1OC]

Methyl 6-amino-2-(2,3-difluoro-4-(trimethylsilyl)phenyl)-5-methoxypyrimidine-4-carboxylate (330 mg, 0.90 mmol) was stirred in 1,2-dichloroethane (5 mL), treated with iodine monochloride (1.0 g, 6.9 mmol), and heated to 70° C. for 21 h. After cooling, the mixture was diluted with ethyl acetate, washed with 15% sodium bisulfite, washed with saturated NaCl, dried (Na₂SO₄), and evaporated. The material was purified by RP-HPLC using 70% acetonitrile to provide the title compound as a white solid (250 mg, 66%).

Example 69

Preparation of methyl 4-acetamido-6-(4-bromo-3-fluorophenyl)-3-chloropicolinate

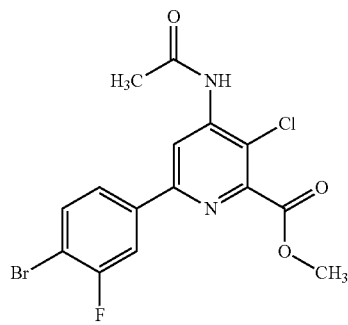 [SMILES: COC(=O)c1nc(-c2ccc(Br)c(F)c2)cc(NC(C)=O)c1Cl]

To a 100-mL round bottom flask, equipped with a stir bar was added methyl 4-acetamido-3-chloro-6-(3-fluoro-4-(trimethylsilyl)phenyl)picolinate (433 mg, 1.11 mmol), dichloromethane (10 mL) and bromine (0.225 mL, 4.39 mmol). The reaction was allowed to stir at room temperature for 18 hrs. The reaction was then poured into 1 N Na₂SO₃ and extracted with ethyl acetate (3×50 mL). The combined organic layers were dried over anhydrous magnesium sulfate, filtered and concentrated. The resulting residue was purified by flash chromatography (0-50% EtOAc in Hexanes) to afford the title compound as a light tan solid (0.440 g, 100%): ¹H NMR (400 MHz, DMSO-d₆) δ 10.02 (s, 1H), 8.71 (s, 1H), 7.98-7.81 (m, 2H), 7.74 (dd, J=8.4, 2.1 Hz, 1H), 3.94 (s, 3H), 2.23 (s, 3H); ¹⁹F NMR (376 MHz, DMSO-d₆) δ −107.44; ESIMS m/z 402 [(M+H)⁺].

The following compounds were made in accordance with the procedures disclosed in Example 69.

Methyl 4-amino-6-(4-bromo-3-fluorophenyl)-3,5-dichloropicolinate (Compound 73)

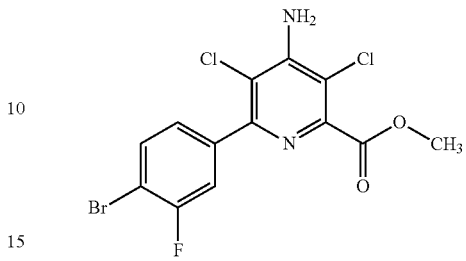

The title compound was prepared as described in Example 69 with methyl 4-amino-3,5-dichloro-6-(3-fluoro-4-(trimethylsilyl)phenyl)picolinate (0.290 g, 0.749 mmol) and isolated as a white solid (0.250 g, 85%).

Methyl 6-amino-2-(4-bromo-3-fluorophenyl)-5-methoxypyrimidine-4-carboxylate (Compound 171)

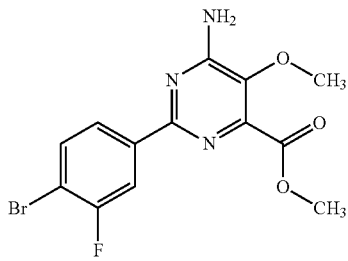

The title compound was prepared as described in Example 69 with methyl 6-amino-2-(3-fluoro-4-(trimethylsilyl)phenyl)-5-methoxypyrimidine-4-carboxylate (0.250 g, 0.715 mmol) and isolated as a white solid (0.200 g, 78%).

Example 70

Preparation of methyl 4-amino-6-(4-bromophenyl)-3-chloro-5-methylpicolinate (Compound 81)

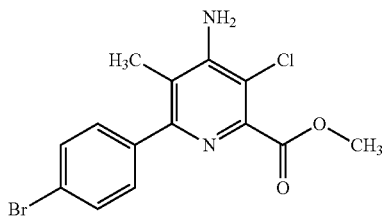 [SMILES: COC(=O)c1nc(-c2ccc(Br)cc2)c(C)c(N)c1Cl]

To methyl 4-amino-3-chloro-5-methyl-6-(4-(trimethylsilyl)phenyl)picolinate (150 mg, 0.43 mmol) and potassium carbonate (215 mg, 1.56 mmol) in 1,2-dichloroethane (DCE, 2.9 mL) was added bromine (0.03 mL, 0.58 mmol) and stirred at room temperature for 18 h. The DCE was concentrated off under vacuum and the crude material was partitioned between ethyl acetate and aqueous potassium carbonate. The aqueous layer was extracted with ethyl acetate (3×), washed with water, dried over anhydrous magnesium sulfate, filtered, and adsorbed onto silica gel. Purification by flash chromatography (0-40% ethyl acetate/hexanes) afforded the title compound as a yellow solid (68 mg, 45%).

The following compound was made in accordance with the procedures disclosed in Example 70:

Methyl 4-amino-6-(4-bromo-3-fluorophenyl)-3-chloro-5-methylpicolinate (Compound 112)

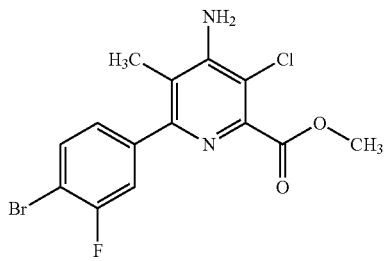 [SMILES: COC(=O)c1nc(-c2ccc(Br)c(F)c2)c(C)c(N)c1Cl]

The title compound was prepared as in Example 70 and isolated as an off-white solid (96 mg, 52%).

Example 71

Preparation of methyl 4-amino-6-(4-bromo-2,3-difluorophenyl)-3-chloro-5-fluoropicolinate (Compound 109)

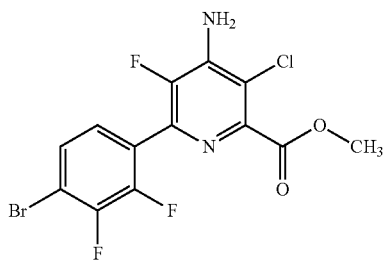 [SMILES: COC(=O)c1nc(-c2ccc(Br)c(F)c2F)c(F)c(N)c1Cl]

Methyl 4-amino-3-chloro-6-(2,3-difluoro-4-(trimethylsilyl)phenyl)-5-fluoropicolinate (2.5 g, 6.43 mmol) was dissolved in acetonitrile (32 mL) and bromine (3.31 mL, 64.3 mmol) was added. The reaction mixture was stirred at room temperature for 4 h at which time LCMS indicated the reaction was mostly complete. The reaction mixture was partitioned between dichloromethane and water and sodium thiosulfate (10.17 g, 64.3 mmol) was added. The aqueous phase was extracted with dichloromethane and the organic extracts were combined and concentrated under vacuum. The product was purified by flash chromatography (SiO$_2$, eluting with 5-40% ethyl acetate in hexanes) to provide the title compound as a light yellow solid (1.62 g, 63.7%).

Example 72

Methyl 4-amino-6-(4-bromophenyl)-3-chloro-5-fluoropicolinate (Compound 138)

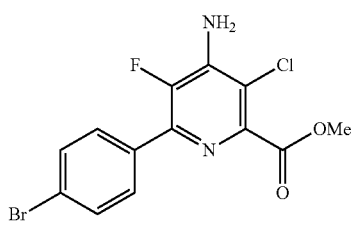 [SMILES: COC(=O)c1nc(-c2ccc(Br)cc2)c(F)c(N)c1Cl]

Bromine (47 µL, 0.92 mmol, 1.2 equiv) was added to a stirred solution of methyl 4-amino-3-chloro-5-fluoro-6-(4-(trimethylsilyl)phenyl)picolinate (270 mg, 0.77 mmol, 1.0 equiv) in 1,2-dichloroethane (5.1 mL) at 23° C. The resulting dark orange solution was stirred at 23° C. for 24 h. The reaction mixture was quenched with a saturated solution of sodium thiosulfate (5 mL) and then adjusted to pH 10 using 2 M sodium hydroxide. The reaction mixture was diluted with water (50 mL) and extracted with dichloromethane (3×30 mL). The combined organic layers were dried (magnesium sulfate), gravity filtered, and concentrated by rotary evaporation. The residue was purified by reverse phase column chromatography (5% acetonitrile to 100% acetonitrile gradient) to afford the title compound as a tan powder (160 mg, 57%).

The following compound was made in accordance with the procedures disclosed in Example 72.

Methyl 4-acetamido-6-(4-bromophenyl)-3-chloropicolinate

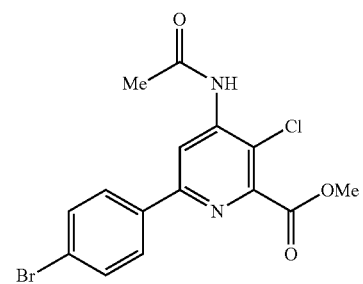 [SMILES: COC(=O)c1nc(-c2ccc(Br)cc2)cc(NC(C)=O)c1Cl]

$^1$H NMR (400 MHz, CDCl$_3$) δ 9.01 (s, 1H), 7.90 (m, 2H), 7.49 (m, 2H), 7.25 (s, 1H), 4.03 (s, 3H), 2.34 (s, 3H); ESIMS m/z 385 ([M+H]$^+$).

Example 73

Preparation of methyl 4-amino-6-(4-bromo-2,5-difluorophenyl)-3-chloro-5-fluoropicolinate (Compound 51)

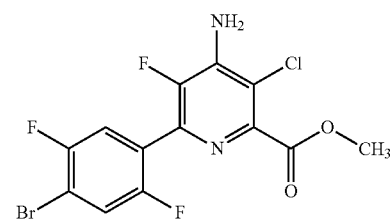 [SMILES: COC(=O)c1nc(-c2cc(F)c(Br)cc2F)c(F)c(N)c1Cl]

To a solution of methyl 4-amino-3-chloro-6-(2,5-difluoro-4-(trimethylsilyl)phenyl)-5-fluoropicolinate (0.240 g, 0.617 mmol) in CH$_2$Cl$_2$ (2.469 mL) at 20° C. was added bromine (0.127 mL, 2.469 mmol). After 24 h, the reaction mixture was poured into a saturated aqueous solution of Na$_2$S$_2$O$_3$ and was extracted with EtOAc (3×). The combined organic layers were dried over Na$_2$SO$_4$, filtered and concentrated. The residue was purified by flash column chromatography (SiO$_2$, hexanes/EtOAc gradient) to afford the title compound as a white solid (0.187 g, 0.473 mmol, 77%).

The following compound was made in accordance with the procedures disclosed in Example 73:

Methyl 4-acetamido-6-(4-bromo-2,5-difluorophenyl)-3-chloropicolinate

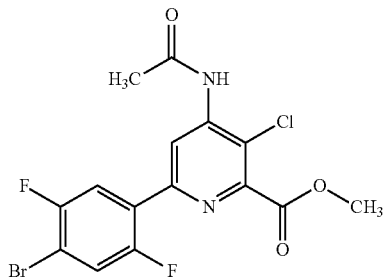 [SMILES: COC(=O)c1nc(-c2cc(F)c(Br)cc2F)cc(NC(C)=O)c1Cl]

mp 177-179° C.; ESIMS m/z 418 ([M−H]−); $^1$H NMR (400 MHz, CDCl$_3$) δ 9.10 (d, J=0.7 Hz, 1H), 7.97 (s, 1H), 7.85 (dd, J=9.1, 6.6 Hz, 1H), 7.40 (dd, J=9.9, 5.5 Hz, 1H), 4.03 (s, 3H), 2.33 (s, 3H); $^{19}$F NMR (376 MHz, CDCl$_3$) δ −112.76, −112.80, −119.21, −119.26.

Example 74

Preparation of methyl 6-amino-2-(4-bromo-2,3-difluorophenyl)-5-methoxypyrimidine-4-carboxylate (Compound 122)

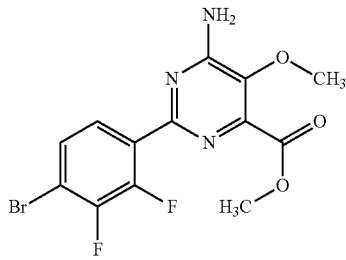 [SMILES: COC(=O)c1nc(-c2ccc(Br)c(F)c2F)nc(N)c1OC]

Methyl 6-amino-2-(2,3-difluoro-4-(trimethylsilyl)phenyl)-5-methoxypyrimidine-4-carboxylate (350 mg, 0.95 mmol) was stirred in 4 mL 1,2-dichloroethane, treated with bromine (1.0 g, 6.3 mmol) and heated to 60° C. for 6 h. After cooling, the mixture was stirred with 15% sodium bisulfite solution until negative to starch-iodine paper. The mixture was diluted with ethyl acetate, washed with saturated NaCl, dried (Na$_2$SO$_4$), and evaporated. Purification by flash chromatography (SiO$_2$, eluting with 0-30% ethyl acetate in hexanes) provided the title compound as white solid (75 mg, 23%).

Example 75

Preparation of methyl 4-amino-6-(4-bromo-3-fluorophenyl)-3-chloropicolinate (Compound 115)

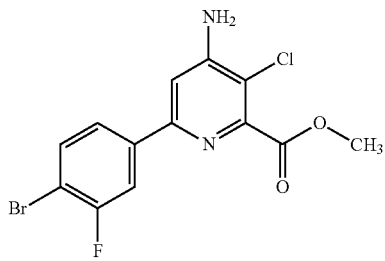 [SMILES: COC(=O)c1nc(-c2ccc(Br)c(F)c2)cc(N)c1Cl]

To a 100-mL round bottom flask, equipped with a stir bar, was added methyl 4-acetamido-6-(4-bromo-3-fluorophenyl)-3-chloropicolinate (0.411 g, 1.023 mmol), methanol (5.12 mL) and acetyl chloride (1.45 mL, 20.5 mmol). The reaction was allowed to stir at room temperature for 18 hours. The solvent was removed with a rotary evaporator. The resulting solid was dissolved in 1 N NaHCO$_3$ and extracted with ethyl acetate (3×75 mL). The combined organic layers were dried over anhydrous magnesium sulfate, filtered and concentrated to afford the title compound as a white solid (0.324 g, 88%).

Example 76

Methyl 4-amino-3-chloro-6-(2,3-difluoro-4-iodophenyl)picolinate (Compound 129)

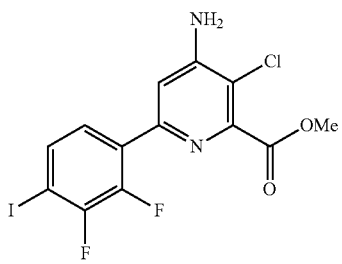 [SMILES: COC(=O)c1nc(-c2ccc(I)c(F)c2F)cc(N)c1Cl]

Acetyl chloride (1.3 mL, 18 mmol, 10 equiv) was slowly added to methanol (12 mL) and stirred at 23° C. for 30 m. Methyl 4-acetamido-3-chloro-6-(2,3-difluoro-4-iodophenyl)picolinate (830 mg, 1.8 mmol, 1.0 equiv) was added and the heterogeneous white mixture was stirred at 23° C. for 18 h. The reaction mixture was concentrated by rotary evaporation. The residue was diluted with saturated sodium bicarbonate (200 mL) and extracted with dichloromethane (3×75 mL). The organic layer was dried (magnesium sulfate), gravity filtered, and concentrated by rotary evaporation to afford the title compound as a white powder (720 mg, 95%).

Example 77

Preparation of methyl 4-amino-6-(4-bromo-2,5-difluorophenyl)-3-chloropicolinate (Compound 127)

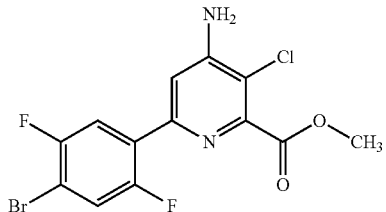 [SMILES: COC(=O)c1nc(-c2cc(F)c(Br)cc2F)cc(N)c1Cl]

To a solution of methyl 4-acetamido-6-(4-bromo-2,5-difluorophenyl)-3-chloropicolinate (0.300 g, 0.715 mmol) in a mixture of MeOH (3.57 mL) and THF (3.57 mL) was slowly added acetyl chloride (1.017 mL, 14.30 mmol). The reaction mixture was stirred at 20° C. for 2 h. The mixture was then poured into a saturated aqueous solution of NaHCO$_3$ and extracted with EtOAc (3×). The combined organic layers were dried over Na$_2$SO$_4$, filtered, concentrated and dried in vacuo to afford methyl 4-amino-6-(4-bromo-2,5-difluorophenyl)-3-chloropicolinate (0.257 g, 0.681 mmol, 95%) as a white solid.

Example 78

Preparation of methyl 4-(N-acetylacetamido)-3-chloro-6-(2,5-difluoro-4-(trimethylsilyl)phenyl)picolinate

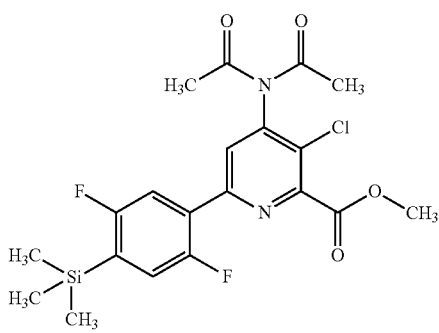

To a solution of methyl 4-amino-3-chloro-6-(2,5-difluoro-4-(trimethylsilyl)phenyl)picolinate (0.280 g, 0.755 mmol) in dichloroethane (3.02 mL) was added N,N-diisopropylethylamine (0.396 mL, 2.265 mmol) and acetyl chloride (0.107 mL, 1.510 mmol). The reaction stirred at 20° C. for 4 h and then at 60° C. for 2 h. The mixture was poured into a saturated aqueous solution of NH$_4$Cl and extracted with EtOAc (3×). The combined organic layers were washed with brine, dried over Na$_2$SO$_4$, filtered and concentrated. The residue was purified by flash column chromatography (SiO$_2$, hexanes/EtOAc gradient) to afford the title compound as a light yellow solid (104 mg, 0.229 mmol, 30.3%): mp 121-123° C.; $^1$H NMR (400 MHz, CDCl$_3$) δ 7.88 (d, J=0.7 Hz, 1H), 7.79 (dd, J=8.5, 5.8 Hz, 1H), 7.15 (dd, J=10.9, 4.1 Hz, 1H), 4.05 (s, 3H), 2.35 (s, 6H), 0.35 (d, J=0.8 Hz, 9H); ESIMS m/z 455 ([M+H]$^+$).

Example 79

Preparation of methyl 4-amino-6-(4-bromophenyl)-5-fluoro-3-vinylpicolinate (Compound 57)

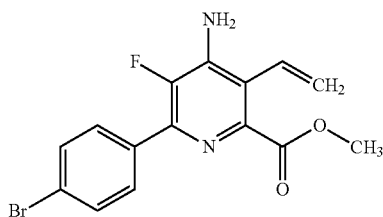 [SMILES: C=Cc1c(C(=O)OC)nc(-c2ccc(Br)cc2)c(F)c1N]

To a 0° C. suspension of nitrosyl tetrafluoroborate (0.122 g, 1.044 mmol) in CH$_2$Cl$_2$ (2 mL) was added a solution of methyl 4-amino-6-(4-aminophenyl)-5-fluoro-3-vinylpicolinate (0.3 g, 1.044 mmol) in a 1:1 mixture of CH$_2$Cl$_2$ and CH$_3$CN (10 mL). The reaction mixture was stirred at 0° C. for 30 min, then was added dropwise to a suspension of potassium bromide (0.497 g, 4.18 mmol), 18-crown-6 (0.028 g, 0.104 mmol), copper(II) bromide (0.023 g, 0.104 mmol), copper(I) bromide (0.015 g, 0.104 mmol), and 1,10-phenanthroline (0.019 g, 0.104 mmol). The mixture was stirred at 20° C. for 1 h. Additional copper (I) bromide (0.749 g, 5 equiv) was added and the reaction was stirred at 20° C. for an additional 1 h. The reaction mixture was diluted with Et$_2$O and filtered on a short pad of Celite™. The supernatant was concentrated and purified by flash column chromatography (SiO$_2$, hexanes/EtOAc gradient) followed by preparative reverse phase HPLC (water/acetonitrile gradient) to afford the title compound as a light brown solid (130 mg, 0.370 mmol, 35.5%).

The following compound was made in accordance with the procedures disclosed in Example 79:

Methyl 4-acetamido-6-(4-bromo-2,3,6-trifluorophenyl)-3-chloropicolinate

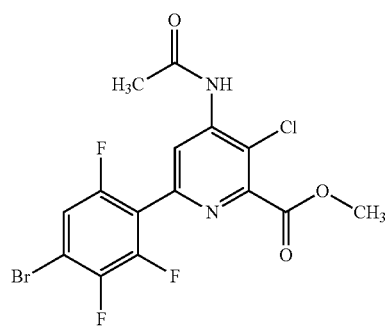 [SMILES: COC(=O)c1nc(-c2c(F)cc(Br)c(F)c2F)cc(NC(C)=O)c1Cl]

$^1$H NMR (400 MHz, DMSO-d$_6$) δ 10.08 (s, 1H), 8.48 (s, 1H), 7.87-7.84 (m, 1H), 3.93 (s, 3H), 2.25 (s, 3H); ESIMS m/z 437 ([M+2H]$^+$).

Example 80

Preparation of methyl 6-amino-2-(4-iodophenyl)-5-vinylpyrimidine-4-carboxylate (Compound 164)

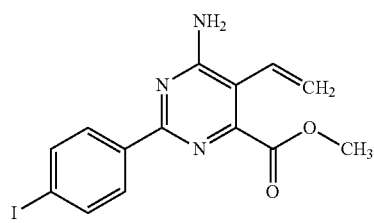 [SMILES: C=Cc1c(N)nc(-c2ccc(I)cc2)nc1C(=O)OC]

To a 50-mL round bottom flask, equipped with a stir bar, was added nitrosyl tetrafluoroborate (78 mg, 0.67 mmol) and dichloromethane (2.0 mL). The flask was cooled in a ice water bath and placed under N$_2$ atmosphere. Then methyl 6-amino-2-(4-aminophenyl)-5-vinylpyrimidine-4-carboxylate (180 mg, 0.666 mmol) in dichloromethane (2.5 mL) was added dropwise. The reaction was allowed to stir for 60 min. Then sodium iodide (499 mg, 3.33 mmol) in a minimal amount of H$_2$O was added, followed by dioxane (1.0 mL). The reaction was allowed to stir for 18 hrs at room temperature. The reaction mixture was poured into saturated Na$_2$SO$_3$ solution and extracted with ethyl acetate (3×50 L). The combined organic layers were dried over anhydrous magnesium sulfate, filtered and concentrated. The resulting residue was purified by flash chromatography (Silica gel, 0-30% EtOAc in Hexanes), and reverse phase chromatography to afford the title compound as a light yellow solid (0.068 g, 27%).

Example 81

Preparation of methyl 4-amino-5-fluoro-6-(4-iodophenyl)-3-vinylpicolinate (Compound 139)

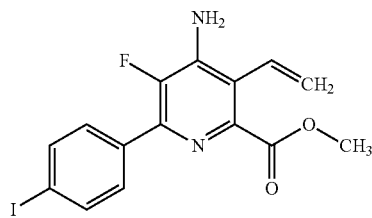

To a 0° C. suspension of nitrosyl tetrafluoroborate (0.041 g, 0.348 mmol) in $CH_2Cl_2$ (1 mL) was added a solution of methyl 4-amino-6-(4-aminophenyl)-5-fluoro-3-vinylpicolinate (0.1 g, 0.348 mmol) in a 1:1 mixture of $CH_2Cl_2$ and $CH_3CN$ (4 mL). The reaction mixture was stirred at 0° C. for 30 min, then a solution of sodium iodide (0.261 g, 1.740 mmol) dissolved in a minimum of water was added and the reaction was stirred at 20° C. for 30 min. The mixture was then poured into a 10% aqueous solution of sodium sulfite and extracted with EtOAc (3×). The combined organic layers were dried over $Na_2SO_4$, filtered and concentrated. The residue was purified by flash column chromatography ($SiO_2$, hexanes/EtOAc gradient) followed by preparative reverse phase HPLC (water/acetonitrile gradient) to afford the title compound as a white solid (32 mg, 0.080 mmol, 23.09%).

The following compound was made in accordance with the procedures disclosed in Example 81.

Methyl 4-acetamido-3-chloro-6-(2,3,6-trifluoro-4-iodophenyl)picolinate

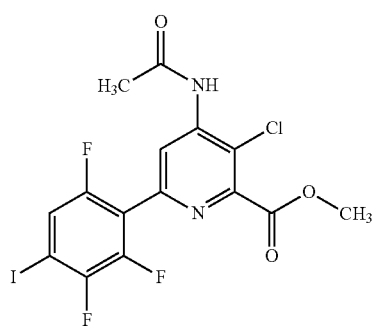 [SMILES: COC(=O)c1nc(-c2c(F)cc(I)c(F)c2F)cc(NC(C)=O)c1Cl]

$^1$H NMR (400 MHz, DMSO-$d_6$) δ 10.07 (s, 1H), 8.46 (s, 1H), 7.89-7.85 (m, 1H), 3.93 (s, 3H), 2.25 (s, 3H); ESIMS m/z 487 ([M+3H]$^+$).

Example 82

Preparation of methyl 4-amino-3-chloro-5-methyl-6-(4-((trimethylsilyl)ethynyl)phenyl)picolinate

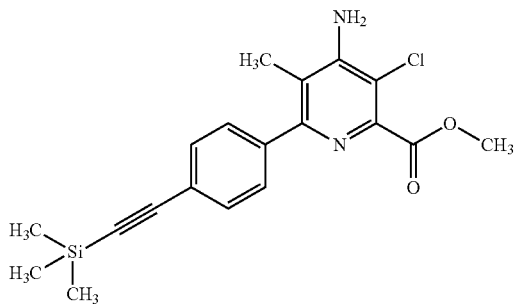

A mixture of methyl 4-amino-3-chloro-6-(4-iodophenyl)-5-methylpicolinate (264 mg, 0.66 mmol), trimethyl((tributylstannyl)ethynyl)silane (280 mg, 0.72 mmol), tetrakis(triphenylphosphine)palladium(0) (75 mg, 0.065 mmol) in anhydrous DMF (1.3 mL) was heated at 90° C. for 16 h. The reaction was cooled, diluted water, and extracted with ethyl acetate (2×). The organic layers were dried over anhydrous magnesium sulfate, filtered, and adsorbed onto silica gel. Purification by flash chromatography (0-100% ethyl acetate/hexanes) afforded the title compound as a brown solid (52 mg, 21%): mp 158-164° C.; $^1$H NMR (400 MHz, CDCl$_3$) δ 7.52 (d, J=8.5 Hz, 2H), 7.40 (d, J=8.5 Hz, 2H), 4.83 (s, 2H), 3.96 (s, 3H), 2.14 (s, 3H), 0.26 (s, 9H); IR (neat film) 3325, 3227, 2955, 2157, 1729, 1629, 1246 cm$^{-1}$; ESIMS m/z 372 ([M]$^+$).

Example 83

Preparation of methyl 4-amino-3-chloro-6-(4-ethynylphenyl)-5-methylpicolinate (Compound 40)

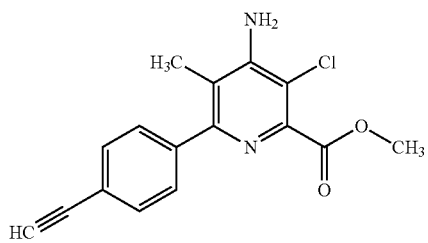 [SMILES: C#Cc1ccc(-c2nc(C(=O)OC)c(Cl)c(N)c2C)cc1]

To methyl 4-amino-3-chloro-5-methyl-6-(4-((trimethylsilyl)ethynyl)phenyl)picolinate (50 mg, 0.13 mmol) in methanol (0.7 mL) was added potassium carbonate (24 mg, 0.17 mmol). The reaction was stirred at room temperature for 40 min, then diluted with water and extracted with dichloromethane (4×). The organic layers were dried over anhydrous magnesium sulfate, filtered and concentrated to afford the title compound as a brown oil (34 mg, 84%).

Example 84

Preparation of methyl 4-amino-3-chloro-5-fluoro-6-(4-((trimethylsilyl)ethynyl)phenyl)picolinate

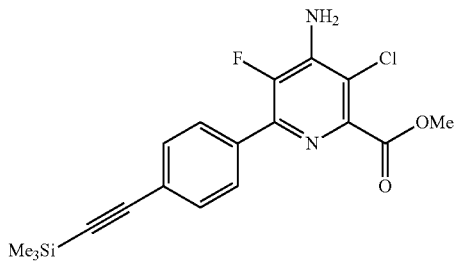 [SMILES: COC(=O)c1nc(-c2ccc(C#C[Si](C)(C)C)cc2)c(F)c(N)c1Cl]

Trimethyl((tributylstannyl)ethynyl)silane (510 mg, 1.3 mmol, 1.1 equiv) was added to a stirred mixture of methyl 4-amino-3-chloro-5-fluoro-6-(4-iodophenyl)picolinate (490 mg, 1.2 mmol, 1.0 equiv) and tetrakis(triphenylphosphine)palladium(0) (140 mg, 0.12 mmol, 0.10 equiv) in N,N-dimethylformamide (2.4 mL) at 23° C. The reaction mixture was heated to 90° C., resulting in a homogeneous yellow solution, and stirred for 20 h. The cooled reaction mixture was diluted with water (200 mL) and extracted with diethyl ether (4×100 mL). Hexanes (100 mL) was added to the combined organic layers and the turbid solution was washed with water (200 mL). The organic layer was dried (magnesium sulfate), gravity filtered, and concentrated by rotary evaporation. The residue was purified by silica gel column chromatography (25% ethyl acetate in hexanes) to afford the title compound as a tan powder (330 mg, 73%): mp 83-86° C.; IR (thin film) 3487 (m), 3375 (s), 2958 (s), 2159 (m), 1739 (s), 1618 (s) cm$^{-1}$; $^1$H NMR (300 MHz, CDCl$_3$) δ 7.89 (m, 2H), 7.55 (m, 2H), 4.89 (br s, 2H), 3.99 (s, 3H), 0.26 (s, 9H); ESIMS m/z 377 ([M+H]$^+$).

Example 85

Preparation of methyl 4-amino-3-chloro-6-(4-ethynylphenyl)-5-fluoropicolinate (Compound 7)

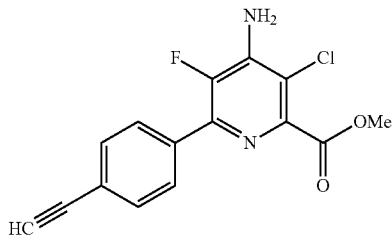 [SMILES: C#Cc1ccc(-c2nc(C(=O)OC)c(Cl)c(N)c2F)cc1]

Potassium carbonate (100 mg, 0.74 mmol, 1.0 equiv) was added to a stirred mixture of methyl 4-amino-3-chloro-5-fluoro-6-(4-((trimethylsilyl)ethynyl)phenyl)picolinate (280 mg, 0.74 mmol, 0.10 equiv) in methanol (3.7 mL) at 23° C. The heterogeneous pale yellow mixture was stirred at 23° C. for 30 m. The reaction mixture was diluted with water (200 mL) and extracted with dichloromethane (5×50 mL). The organic layers were dried (magnesium sulfate), gravity filtered, and concentrated by rotary evaporation to afford the title compound as a tan powder (220 mg, 96%).

Example 86

Preparation of methyl 4-amino-3-chloro-6-(4-ethynyl-3-fluorophenyl)-5-fluoropicolinate (Compound 133)

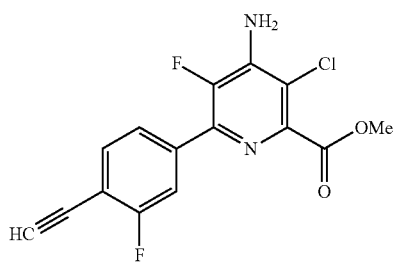 [SMILES: C#Cc1ccc(-c2nc(C(=O)OC)c(Cl)c(N)c2F)cc1F]

Dimethyl 1-diazo-2-oxopropylphosphonate (290 mg, 1.5 mmol, 1.2 equiv) was added to a stirred mixture of methyl 4-amino-3-chloro-5-fluoro-6-(3-fluoro-4-formylphenyl)picolinate (410 mg, 1.3 mmol, 1.0 equiv) and solid potassium carbonate (350 mg, 2.5 mmol, 2.0 equiv) in methanol (12 mL) at 23° C. The resulting cloudy pale yellow mixture was stirred at 23° C. for 2 h. The reaction mixture was diluted with water (150 mL) and extracted with dichloromethane (4×60 mL). The organic layers were dried (magnesium sulfate), gravity filtered, and concentrated by rotary evaporation. The residue was purified by silica gel column chromatography (33% ethyl acetate in hexanes) to afford the title compound as a white powder (150 mg, 38%).

Example 87

Preparation of methyl 4-amino-3-chloro-6-(4-ethynyl-3-fluorophenyl)-5-methylpicolinate (Compound 151)

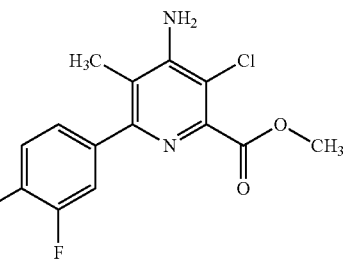

To a solution of methyl 4-amino-3-chloro-6-(3-fluoro-4-formylphenyl)-5-methylpicolinate (358 mg, 1.1 mmol) and potassium carbonate (537 mg, 3.9 mmol) in methanol (11 mL) at room temperature was added 1 mL of dimethyl(1-diazo-2-oxopropyl)phosphonate (Bestmann-Ohira reagent, crude reagent) for 3 h. The reaction was quenched with saturated aqueous sodium bicarbonate and extracted with ethyl acetate (3×). The combined organic layers were dried organics over anhydrous sodium sulfate, filtered, and adsorbed onto

Example 88

Preparation of methyl 4-amino-6-(4-ethynylphenyl)-5-fluoro-3-vinylpicolinate (Compound 60)

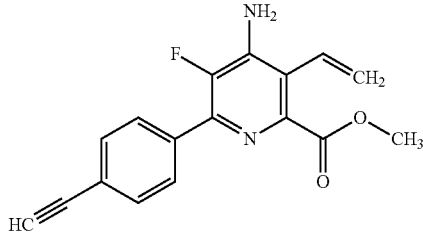 [SMILES: C#Cc1ccc(-c2nc(C(=O)OC)c(C=C)c(N)c2F)cc1]

To a 20 mL reaction vial was added methyl 4-amino-5-fluoro-6-(4-formylphenyl)-3-vinylpicolinate (0.41 g, 1.365 mmol), potassium carbonate (0.377 g, 2.73 mmol) and MeOH (10 mL). Dimethyl(1-diazo-2-oxopropyl)phosphonate (0.315 g, 1.638 mmol) was added in one portion. After stirring for 4 h, the reaction mixture was diluted with $Et_2O$ (50 mL) and washed with a 5% solution of $NaHCO_3$ (25 mL) The organic layer was dried over $MgSO_4$ (5 g), filtered, and concentrated on a rotary evaporator. The resulting reside was purified using a Teledyne ISCO purification system with a gradient eluent system of $CH_2Cl_2$ and EtOAc to yield the title compound as a white solid (250 mg).

Example 89

Preparation of methyl 4-((tert-butoxycarbonyl)amino)-3-chloro-6-(1-chloro-3-fluorophenyl)-5-fluoropicolinate

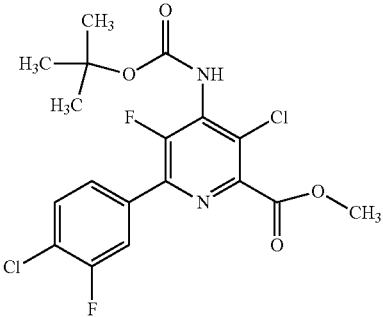 [SMILES: COC(=O)c1nc(-c2ccc(Cl)c(F)c2)c(F)c(NC(=O)OC(C)(C)C)c1Cl]

Step 1:
Methyl 4-amino-3-chloro-6-(4-chloro-3-fluorophenyl)-5-fluoropicolinate (1.43 g, 4.29 mmol) was combined with di-tert-butyl dicarbonate (2.99 mL, 12.88 mmol) and N,N-dimethylpyridin-4-amine (0.079 g, 0.644 mmol) in dichloromethane (30 mL). The reaction mixture was stirred overnight at rt. The reaction mixture was concentrated under a stream of nitrogen and applied directly to a column of silica gel. The compound was eluted with a 2-20% ethyl acetate/hexanes gradient solvent system to provide methyl 4-(bis(tert-butoxycarbonyl)amino)-3-chloro-6-(4-chloro-3-fluorophenyl)-5-fluoropicolinate (2.1 g, 3.94 mmol, 92%) as a white solid.

Step 2:
Methyl 4-(bis(tert-butoxycarbonyl)amino)-3-chloro-6-(4-chloro-3-fluorophenyl)-5-fluoropicolinate (2.1 g, 3.94 mmol) was dissolved in dichloroethane (20 mL) and trifluoroacetic acid (0.598 mL, 7.76 mmol) was added at rt. The reaction mixture was stirred overnight at room temperature then concentrated under vacuum. The product was purified by flash chromatography (SiO2, eluting with 2-20% ethyl acetate in dichloromethane) to provide the title compound as a white solid (1.64 g, 98%): $^1H$ NMR (300 MHz, $CDCl_3$) δ 7.80 (dd, J=22.0, 8.5 Hz, 2H), 7.50 (dd, J=8.3, 7.6 Hz, 1H), 6.51 (s, 1H), 4.02 (s, 3H), 1.56 (s, 9H); ESIMS m/z 431 ($[M-H]^-$).

Example 90

Preparation of methyl 4-amino-6-(4-chloro-3-fluorophenyl)-5-fluoro-3-vinylpicolinate (Compound 215)

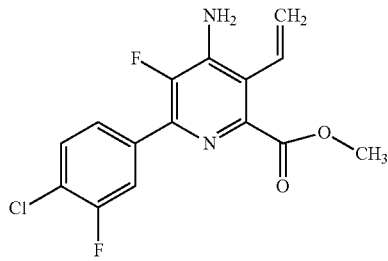 [SMILES: C=Cc1c(C(=O)OC)nc(-c2ccc(Cl)c(F)c2)c(F)c1N]

Step 1:
Methyl 4-(tert-butoxycarbonylamino)-3-chloro-6-(4-chloro-3-fluorophenyl)-5-fluoropicolinate (1.5 g, 3.46 mmol), tributyl(vinyl)stannane (2.196 g, 6.92 mmol), and bis(triphenylphosphine)palladium(II) chloride (0.365 g, 0.519 mmol) were combined in 1,2-dichloroethane (4.62 mL) and irradiated in a microwave at 130° C. in a sealed vial for 30 min. The cooled reaction mixture was applied directly to a silica gel column and eluted with a 5-40% ethyl acetate/hexanes gradient to provide methyl 4-(tert-butoxycarbonylamino)-6-(4-chloro-3-fluorophenyl)-5-fluoro-3-vinylpicolinate (0.966 g, 2.274 mmol, 65.7%) as a white solid.

Step 2:
Methyl 4-(tert-butoxycarbonylamino)-6-(4-chloro-3-fluorophenyl)-5-fluoro-3-vinylpicolinate (0.966 g, 2.274 mmol) was dissolved in dichloroethane (11 mL) and trifluoroacetic acid (3.50 mL, 45.5 mmol) was added. After 4 h at room temperature, the reaction mixture was concentrated under vacuum then coevaporated with additional dichloroethane twice more. The residue was purified by flash chromatography ($SiO_2$, eluting with 7-60% ethyl acetate in hexanes) to provide the title compound as a white solid (0.705 g, 95%).

Example 91

Preparation of methyl 4-amino-5-bromo-3-chloro-6-(2,5-difluoro-4-(trimethylsilyl)phenyl)picolinate

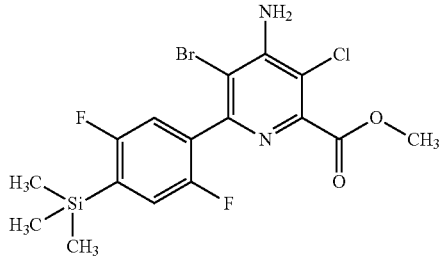

To a solution of methyl 4-amino-3-chloro-6-(2,5-difluoro-4-(trimethylsilyl)phenyl)picolinate (0.210 g, 0.566 mmol) in CH$_2$Cl$_2$ (2.265 mL) at 20° C. was added bromine (0.117 mL, 2.265 mmol). The reaction mixture was stirred at 20° C. overnight. The mixture was then poured into a saturated aqueous solution of Na$_2$S$_2$O$_3$ and extracted with EtOAc (3×). The combined organic layers were dried over Na$_2$SO$_4$, filtered and concentrated. The residue was purified by flash column chromatography (SiO$_2$, hexanes/EtOAc gradient) to provide the title compound as a white solid (0.125 g, 49.1%): mp 165-166° C.; $^1$H NMR (400 MHz, CDCl$_3$) δ 7.10 (dd, J=8.9, 4.0 Hz, 1H), 7.03 (dd, J=7.6, 5.1 Hz, 1H), 5.43 (s, 2H), 3.96 (s, 3H), 0.33 (d, J=0.7 Hz, 9H); ESIMS m/z 450 ([M+H]$^+$).

Example 92

Preparation of 4-amino-3-chloro-6-(3-fluoro-4-iodophenyl)picolinic acid (Compound 77)

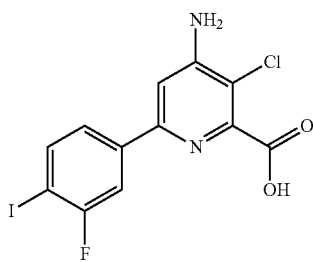 [SMILES: Nc1cc(-c2ccc(I)c(F)c2)nc(C(=O)O)c1Cl]

To a 100-mL round bottom flask, equipped with a stir bar was added methyl 4-amino-3-chloro-6-(3-fluoro-4-iodophenyl)picolinate (0.284 g, 0.699 mmol), 1.0 N sodium hydroxide (2.79 mL, 2.79 mmol) and methanol (5.0 mL). The reaction was allowed to stir for 18 hours at room temperature. The solvent was then removed with a rotary evaporator. The resulting solid was diluted with H$_2$O, which was adjusted to pH-3.0 with 1 N HCl, and extracted with ethyl acetate (3×50 mL). The combined organic layers were dried over anhydrous magnesium sulfate, filtered and concentrated to afford the title compound as a white solid (0.056 g, 21%).

The following compounds were made in accordance with the procedures disclosed in Example 92:

4-Amino-3,5-dichloro-6-(3-fluoro-4-iodophenyl)picolinic acid (Compound 145)

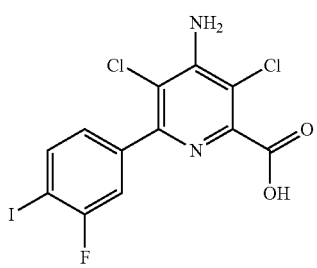 [SMILES: Nc1c(Cl)c(C(=O)O)nc(-c2ccc(I)c(F)c2)c1Cl]

The title compound was prepared as described in Example 92 with methyl 4-amino-3,5-dichloro-6-(3-fluoro-4-iodophenyl)picolinate (0.197 g, 0.447 mmol) and isolated as a white solid (0.133 g, 70%).

6-Amino-2-(3-fluoro-4-iodophenyl)-5-methoxypyrimidine-4-carboxylic acid (Compound 37)

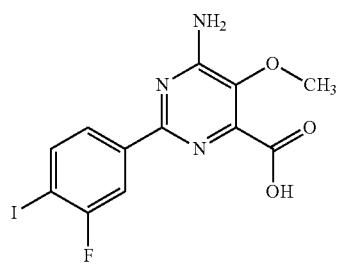 [SMILES: COc1c(N)nc(-c2ccc(I)c(F)c2)nc1C(=O)O]

The title compound was prepared as described in Example 92 with methyl 6-amino-2-(3-fluoro-4-iodophenyl)-5-methoxypyrimidine-4-carboxylate (0.309 g, 0.766 mmol) and isolated as a white solid (0.065 g, 22%).

4-Amino-6-(4-bromo-3-fluorophenyl)-3-chloropicolinic acid (Compound 110)

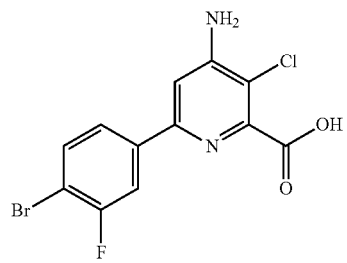 [SMILES: Nc1cc(-c2ccc(Br)c(F)c2)nc(C(=O)O)c1Cl]

The title compound was prepared as described in Example 92 with methyl 4-amino-6-(4-bromo-3-fluorophenyl)-3-chloropicolinate (291 mg, 0.809 mmol) and isolated as a white solid (0.247 g, 88%).

4-Amino-6-(4-bromo-3-fluorophenyl)-3,5-dichloropicolinic acid (Compound 43)

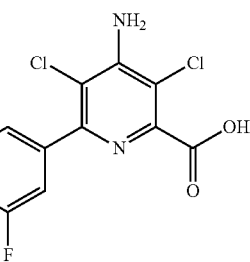

The title compound was prepared as described in Example 92 with methyl 4-amino-6-(4-bromo-3-fluorophenyl)-3,5-dichloropicolinate (225 mg, 0.571 mmol) and isolated as a white solid (0.219 g, 100%).

6-Amino-2-(4-bromo-3-fluorophenyl)-5-methoxypyrimidine-4-carboxylic acid (Compound 113)

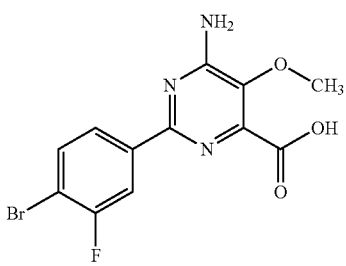 [SMILES: COc1c(N)nc(-c2ccc(Br)c(F)c2)nc1C(=O)O]

The title compound was prepared as described in Example 92 with methyl 6-amino-2-(4-bromo-3-fluorophenyl)-5-methoxypyrimidine-4-carboxylate (166 mg, 0.466 mmol) and isolated as a white solid (0.056 g, 35%).

6-Amino-2-(4-cyano-2-fluorophenyl)-5-vinylpyrimidine-4-carboxylic acid (Compound 5)

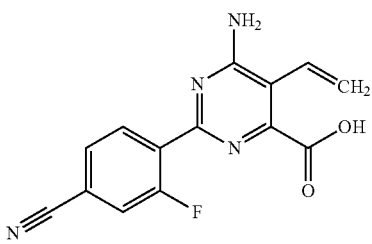 [SMILES: C=Cc1c(N)nc(-c2ccc(C#N)cc2F)nc1C(=O)O]

The title compound was prepared as described in Example 92 with methyl 6-amino-2-(4-cyano-2-fluorophenyl)-5-vinylpyrimidine-4-carboxylate (294 mg, 0.986 mmol) and isolated as a an orange solid (0.202 g, 72%).

6-Amino-2-(3-fluoro-4-(trifluoromethyl)phenyl)-5-vinylpyrimidine-4-carboxylic acid (Compound 32)

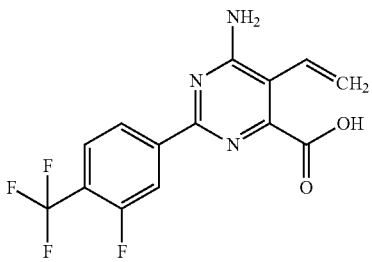 [SMILES: C=Cc1c(N)nc(-c2ccc(C(F)(F)F)c(F)c2)nc1C(=O)O]

The title compound was prepared as described in Example 92 with methyl 6-amino-2-(3-fluoro-4-(trifluoromethyl)phenyl)-5-vinylpyrimidine-4-carboxylate (265 mg, 0.777 mmol) and isolated as a light yellow solid (0.234 g, 92%).

6-Amino-2-(2,3,4-trifluorophenyl)-5-vinylpyrimidine-4-carboxylic acid (Compound 191)

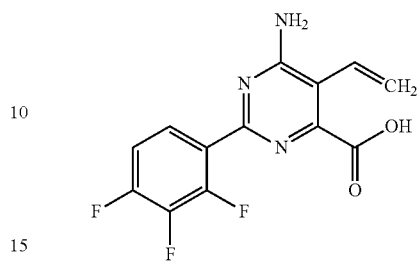

The title compound was prepared as described in Example 92 with methyl 6-amino-2-(2,3,4-trifluorophenyl)-5-vinylpyrimidine-4-carboxylate (335 mg, 1.08 mmol) and isolated as a yellow solid (0.275 g, 86%).

Example 93

Preparation of 4-amino-3-chloro-6-(4-cyano-2-fluorophenyl)-5-fluoropicolinic acid (Compound 65)

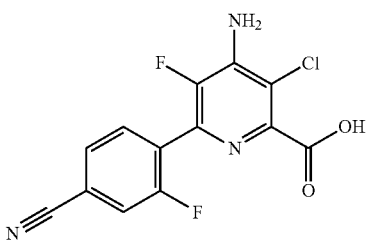 [SMILES: N#Cc1ccc(-c2nc(C(=O)O)c(Cl)c(N)c2F)c(F)c1]

In a 50-mL round bottom flask, equipped with a stir bar, methyl 4-amino-3-chloro-6-(4-cyano-2-fluorophenyl)-5-fluoropicolinate (351 mg, 1.084 mmol) and lithium hydroxide hydrate (100 mg, 2.383 mmol) were dissolved in tetrahydrofuran (2.0 mL), methanol (2.0 mL) and $H_2O$ (1.0 mL). The reaction was stirred at room temperature for 2 hours. The solvent was then removed by rotary evaporator. The resulting solid was treated with $H_2O$, which was then adjusted to pH-3.0 with 1 N HCl, and extracted with ethyl acetate (3× 50 mL). The combined organic layers were dried over anhydrous magnesium sulfate, filtered and concentrated. The resulting residue was purified by reverse phase chromatography (150 g $C_{18}$, 0-100% acetonitrile in $H_2O$), as needed, to afford the title compound as a white solid (0.058 g, 20%).

The following compound was made in accordance with the procedures disclosed in Example 93:

6-Amino-2-(4-iodophenyl)-5-vinylpyrimidine-4-carboxylic acid (Compound 123)

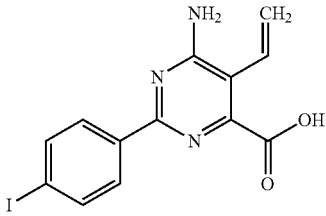 [SMILES: C=Cc1c(N)nc(-c2ccc(I)cc2)nc1C(=O)O]

The title compound was prepared as described in Example 93 with 6-amino-2-(4-iodophenyl)-5-vinylpyrimidine-4-carboxylic acid (65 mg, 0.177 mmol) and isolated as an off-white solid (60 mg, 92%).

Example 94

Preparation of 4-amino-3-chloro-6-(3-fluoro-4-(trifluoromethyl)phenyl)-5-methylpicolinic acid (Compound 161)

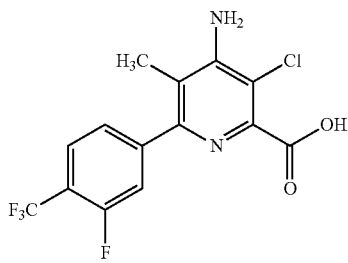 [SMILES: Cc1c(-c2ccc(C(F)(F)F)c(F)c2)nc(C(=O)O)c(Cl)c1N]

To methyl 4-amino-3-chloro-6-(3-fluoro-4-(trifluoromethyl)phenyl)-5-methylpicolinate (0.35 g, 0.96 mmol) in methanol (6.4 mL) was added 2 N NaOH (1.93 mL, 3.9 mmol), and the reaction was stirred at room temperature for 18 h. The solution was acidified with 2 N HCl and the precipitate was vacuum filtered to afford the title compound as a white powder (199 mg, 59%).

The following compounds were made in accordance with the procedures disclosed in Example 94

4-Amino-3-chloro-6-(4-(difluoromethoxy)phenyl)-5-methylpicolinic acid (Compound 94)

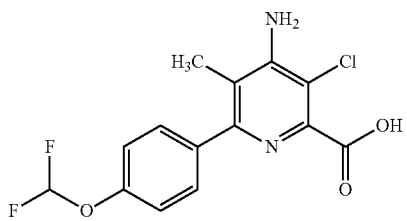

The title compound was prepared as in Example 94 and isolated as a yellow solid (36 mg, 68%).

4-Amino-6-(4-bromophenyl)-3-chloro-5-methylpicolinic acid (Compound 78)

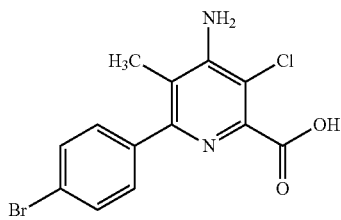

The title compound was prepared as in Example 94 and isolated as a white solid (24 mg, 71%).

4-Amino-3-chloro-6-(4-iodophenyl)-5-methylpicolinic acid (Compound 116)

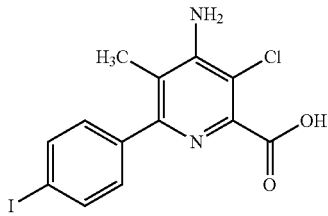 [SMILES: Cc1c(-c2ccc(I)cc2)nc(C(=O)O)c(Cl)c1N]

The title compound was prepared as in Example 94 and isolated as an orange powder (86 mg, 83%).

4-Amino-3-chloro-6-(3-fluoro-4-iodophenyl)-5-methylpicolinic acid (Compound 87)

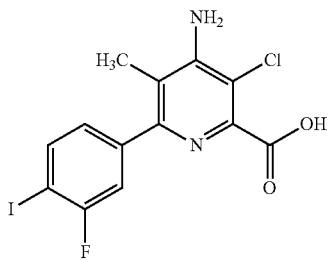 [SMILES: Cc1c(-c2ccc(I)c(F)c2)nc(C(=O)O)c(Cl)c1N]

The title compound was prepared as in Example 94 and isolated as a white solid (120.5 mg, 88%).

4-Amino-3-chloro-6-(4-ethynyl-3-fluorophenyl)-5-methylpicolinic acid (Compound 6)

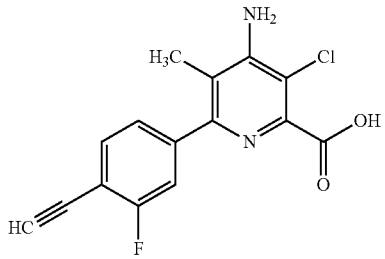

The title compound was prepared as in Example 94 and isolated as a yellow powder (147 mg, 82%).

Example 95

Preparation of 4-amino-3-chloro-5-fluoro-6-(4-nitrophenyl)picolinic acid (Compound 31)

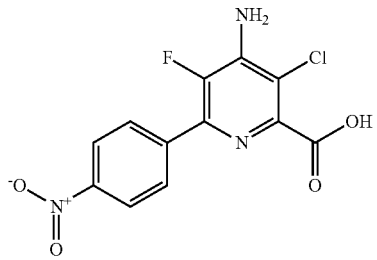

To a solution of methyl 4-amino-3-chloro-5-fluoro-6-(4-nitrophenyl)picolinate (88 mg, 0.27 mmol) in methanol (MeOH; 3 mL) was added 1 Normal (N) aqueous sodium hydroxide solution (NaOH; 3 mL, 3 mmol). The reaction mixture was stirred for 24 hours (h) at ambient temperature. The solution was then concentrated and acidified with 2 N aqueous hydrochloric acid (HCl) solution. The desired product precipitated out of solution, was collected in a Buchner funnel, and allowed to dry overnight to afford a white solid (84 mg, 100%).

Example 96

Preparation of 4-amino-3-chloro-6-(2,3-difluoro-4-(trifluoromethyl)phenyl)picolinic acid (Compound 172)

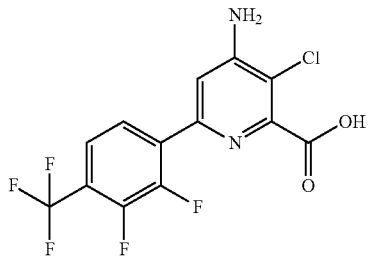 [SMILES: Nc1cc(-c2ccc(C(F)(F)F)c(F)c2F)nc(C(=O)O)c1Cl]

To a mixture of methyl 4-acetamido-3-chloro-6-(2,3-difluoro-4-(trifluoromethyl)phenyl)picolinate (115 mg, 0.28 mmol) in methanol (1 mL) was added 2 Normal (N) aqueous sodium hydroxide solution (NaOH; 1.4 mL, 2.81 mmol). The reaction solution was stirred at ambient temperature for 15 h. The solution was then concentrated, and acidified with a 2 N aqueous HCl solution. The desired product precipitated out of solution. This mixture was extracted (3×) with dichloromethane, the organics were combined, dried (Na$_2$SO$_4$), filtered and the concentrated in vacuo to afford a white solid (94 mg, 90%).

Example 97

Preparation of 4-amino-3-chloro-5-fluoro-6-(4-iodophenyl)picolinic acid (Compound 45)

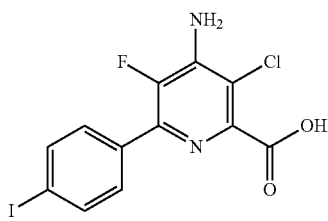

A 2 M solution of sodium hydroxide (740 µL, 1.5 mmol, 4.0 equiv) was added to a stirred solution of methyl 4-amino-6-(4-iodophenyl)-3-chloro-5-fluoropicolinate (150 mg, 0.37 mmol, 1.0 equiv) in methanol (3.7 mL) at 23° C. The resulting pink solution was stirred at 23° C. for 3 h. The reaction mixture adjusted to pH 3, using concentrated hydrochloric acid, and concentrated by rotary evaporation. The residue was slurried in water and vacuum filtered to afford the title compound as a pale pink powder (110 mg, 79%).

Example 98

Preparation of 4-amino-3-chloro-6-(2,3-difluoro-4-iodophenyl)-5-fluoropicolinic acid (Compound 141)

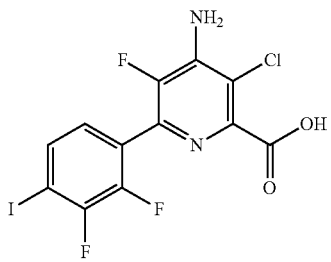 [SMILES: Nc1c(F)c(-c2ccc(I)c(F)c2F)nc(C(=O)O)c1Cl]

A 2 M solution of aqueous sodium hydroxide (270 L, 0.54 mmol, 2.0 equiv) was added to a stirred suspension of methyl 4-amino-3-chloro-6-(2,3-difluoro-4-iodophenyl)-5-fluoropicolinate (120 mg, 0.27 mmol, 1.0 equiv) in methanol (2.7 mL) at 23° C. The heterogeneous white mixture was stirred at 23° C. for 18 h. The reaction mixture was adjusted to approximately pH 4 via dropwise addition of concentrated hydrochloric acid and concentrated via rotary evaporation. The residue was dissolved in dichloromethane (250 mL), passed through a hydrophobic membrane phase separator, dried (magnesium sulfate), gravity filtered, and concentrated by rotary evaporation to afford the title compound as a white powder (110 mg, 92%).

Example 99

Preparation of 4-amino-6-(4-bromo-2,3,6-trifluorophenyl)-3-chloropicolinic acid (Compound 162)

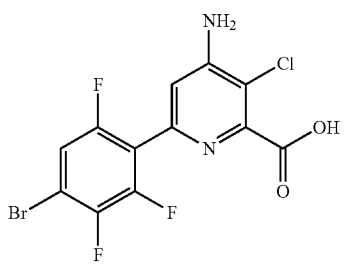 [SMILES: Nc1cc(-c2c(F)cc(Br)c(F)c2F)nc(C(=O)O)c1Cl]

A solution of methyl 4-acetamido-6-(4-bromo-2,3,6-trifluorophenyl)-3-chloropicolinate (50 mg, 0.122 mmol, 1.0 eq) and sodium hydroxide (14 mg, 0.366 mmol, 3.0 eq) in THF:MeOH:H$_2$O (1:1:0.5, 2.5 mL) was stirred at 20° C. for 2 h. The reaction mixture was acidified to pH 4-5 using 1.5 N HCl and extracted with EtOAc (2×). The combined organic extract was dried over anhydrous Na$_2$SO$_4$ and evaporated to dryness

Example 100

Preparation of 4-amino-6-(4-bromo-2,5-difluorophenyl)-3-chloro-5-fluoropicolinic acid (Compound 42)

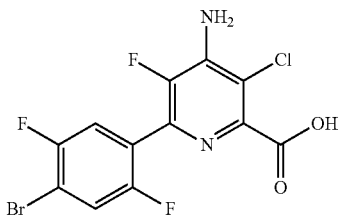 [SMILES: Nc1c(F)c(-c2cc(F)c(Br)cc2F)nc(C(=O)O)c1Cl]

To a solution of methyl 4-amino-6-(4-bromo-2,5-difluorophenyl)-3-chloro-5-fluoropicolinate (0.160 g, 0.404 mmol) in a 1:1 mixture of MeOH (0.674 mL) and acetone (0.674 mL) was added a 2 N aqueous solution of sodium hydroxide (0.607 mL, 1.213 mmol). The reaction mixture was stirred at 20° C. overnight. The reaction mixture was concentrated, poured into a 2 N aqueous solution of HCl, and extracted with EtOAc (3×). The combined organic layers were dried over $Na_2SO_4$, filtered, concentrated and dried in vacuo to afford the title compound as a light brown solid (126 mg, 82%).

Example 101

Preparation of 4-amino-3-chloro-6-(4-(difluoromethoxy)-3-fluorophenyl)-5-fluoropicolinic acid (Compound 92)

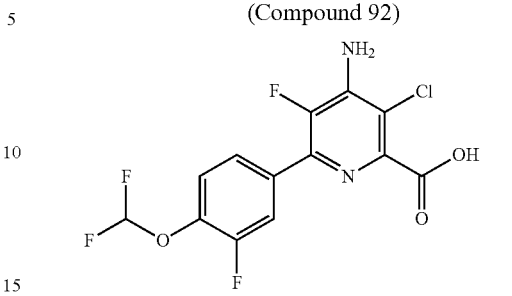

To a flask charged with MeOH (2 mL) was added methyl 4-amino-3-chloro-6-(4-(difluoromethoxy)-3-fluorophenyl)-5-fluoropicolinate (190 mg, 0.52 mmol) and sodium hydroxide 2 M solution (1 mL, 1 mmol). Following 12 h of mechanical stirring, the reaction mixture was concentrated using a rotary evaporator with a water bath temperature of 40° C. Water was added to the resulting oil and the solution was slowly acidified by the addition of concentrated HCl until a tan precipitate formed. Filtration using filter paper and a Büchner funnel afforded the title compound as a tan solid (108 mg).

TABLE 1

Compound Number, Structure, Preparation and Appearance

| Cmpd. No. | Structure | Appearance | Prepared as in Example: |
|---|---|---|---|
| 1 | (structure: 4-amino-3,5-dichloro-6-(4-cyanophenyl)picolinic acid methyl ester) | White Solid | 42 |
| 2 | (structure: pyrimidine with NH₂, OCH₃, CO₂CH₃, and 4-bromo-2,5-difluorophenyl) | White Solid | 73 |
| 3 | (structure: 4-amino-6-(4-bromo-2,5-difluorophenyl)-3-chloropicolinic acid) | White Solid | 100 |

(text above tables, continuation from previous page:)
under reduced pressure to provide the title compound as a pale brown solid (30 mg, 65%).

TABLE 1-continued
Compound Number, Structure, Preparation and Appearance
| Cmpd. No. | Structure | Appearance | Prepared as in Example: |
|---|---|---|---|
| 4 | 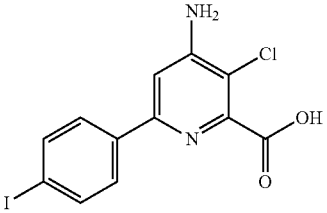 [SMILES: Nc1cc(-c2ccc(I)cc2)nc(C(=O)O)c1Cl] | Brown Solid | 97 |
| 5 | 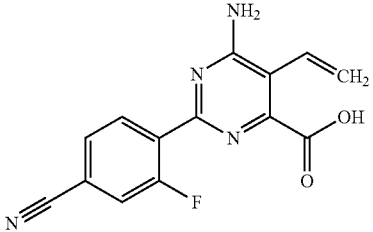 [SMILES: C=Cc1c(N)nc(-c2ccc(C#N)cc2F)nc1C(=O)O] | Orange Solid | 92 |
| 6 | 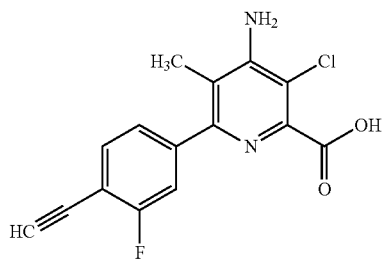 [SMILES: C#Cc1ccc(-c2nc(C(=O)O)c(Cl)c(N)c2C)cc1F] | Yellow Powder | 94 |
| 7 | 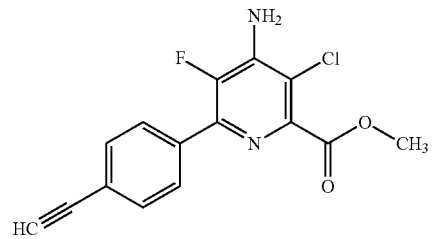 [SMILES: C#Cc1ccc(-c2nc(C(=O)OC)c(Cl)c(N)c2F)cc1] | Tan Powder | 85 |
| 8 | 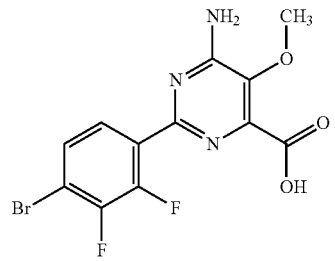 [SMILES: COc1c(N)nc(-c2ccc(Br)c(F)c2F)nc1C(=O)O] | | 98 |
| 9 | 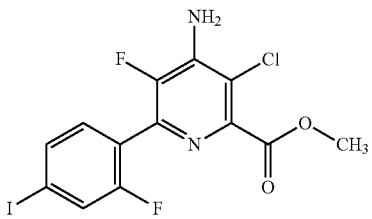 [SMILES: COC(=O)c1nc(-c2ccc(I)cc2F)c(F)c(N)c1Cl] | Off-White Powder | 66 |

TABLE 1-continued

Compound Number, Structure, Preparation and Appearance

| Cmpd. No. | Structure | Appearance | Prepared as in Example: |
|---|---|---|---|
| 10 | 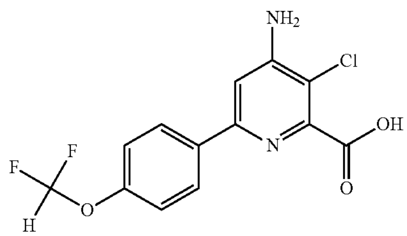 [SMILES: Nc1cc(-c2ccc(OC(F)F)cc2)nc(C(=O)O)c1Cl] | White Solid | 98 |
| 11 | 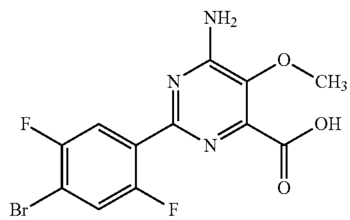 [SMILES: COc1c(N)nc(-c2cc(F)c(Br)cc2F)nc1C(=O)O] | White Solid | 100 |
| 12 | 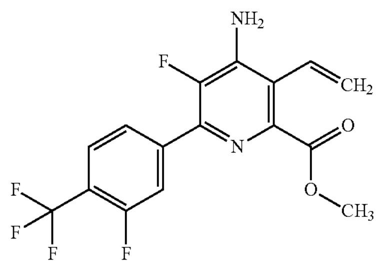 [SMILES: C=Cc1c(C(=O)OC)nc(-c2ccc(C(F)(F)F)c(F)c2)c(F)c1N] | Tan Solid | 42 |
| 13 | 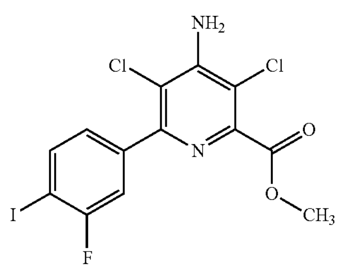 [SMILES: COC(=O)c1nc(-c2ccc(I)c(F)c2)c(Cl)c(N)c1Cl] | Yellow Solid | 64 |
| 14 | 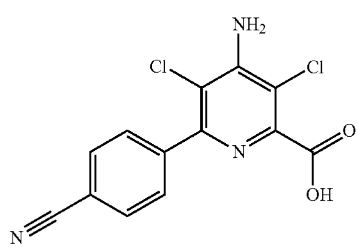 [SMILES: N#Cc1ccc(-c2nc(C(=O)O)c(Cl)c(N)c2Cl)cc1] | White Solid | 98 |
| 15 | 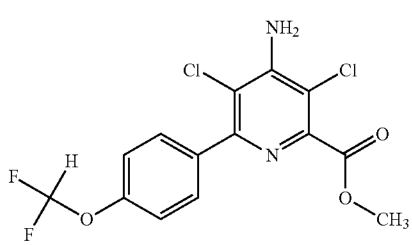 [SMILES: COC(=O)c1nc(-c2ccc(OC(F)F)cc2)c(Cl)c(N)c1Cl] | Yellow Solid | 42 |

TABLE 1-continued

Compound Number, Structure, Preparation and Appearance

| Cmpd. No. | Structure | Appearance | Prepared as in Example: |
|---|---|---|---|
| 16 | 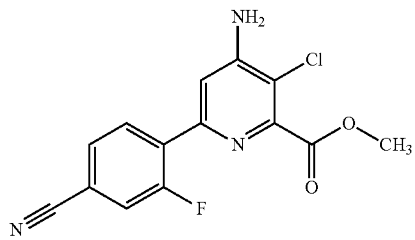 [SMILES: COC(=O)c1nc(-c2ccc(C#N)cc2F)cc(N)c1Cl] | Off-White Solid | 42 |
| 17 | 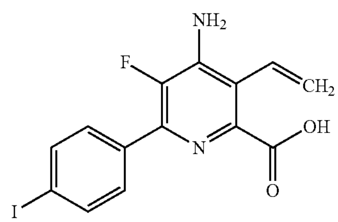 [SMILES: C=Cc1c(C(=O)O)nc(-c2ccc(I)cc2)c(F)c1N] | Yellow Solid | 100 |
| 18 | 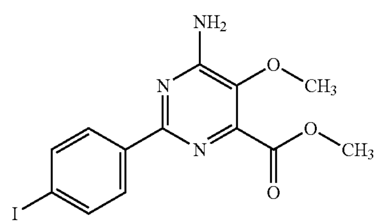 [SMILES: COC(=O)c1nc(-c2ccc(I)cc2)nc(N)c1OC] | Light Yellow Oil | 66 |
| 19 | 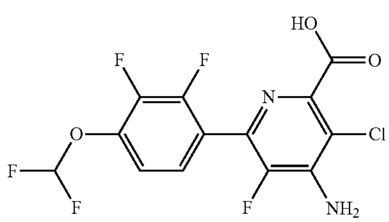 [SMILES: Nc1c(F)c(-c2ccc(OC(F)F)c(F)c2F)nc(C(=O)O)c1Cl] | White Solid | 101 |
| 20 | 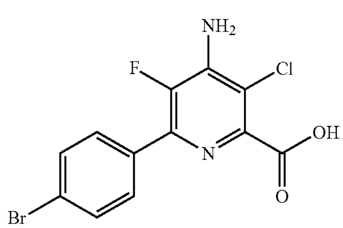 [SMILES: Nc1c(F)c(-c2ccc(Br)cc2)nc(C(=O)O)c1Cl] | Orange-Tinged White Solid | 97 |
| 21 | 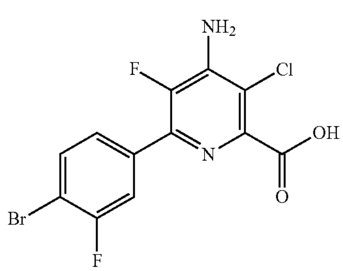 | Off-White Powder | 97 |

TABLE 1-continued

Compound Number, Structure, Preparation and Appearance

| Cmpd. No. | Structure | Appearance | Prepared as in Example: |
|---|---|---|---|
| 22 | 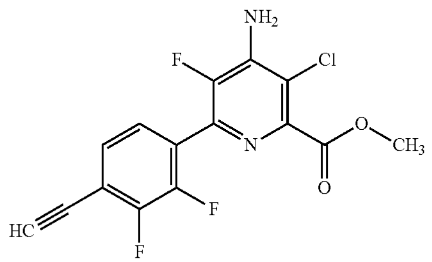 [SMILES: C#Cc1ccc(-c2nc(C(=O)OC)c(Cl)c(N)c2F)c(F)c1F] | White Powder | 86 |
| 23 | 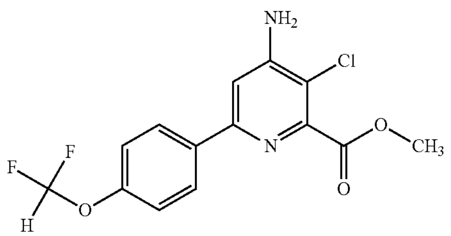 [SMILES: COC(=O)c1nc(-c2ccc(OC(F)F)cc2)cc(N)c1Cl] | Yellow Solid | 42 |
| 24 | 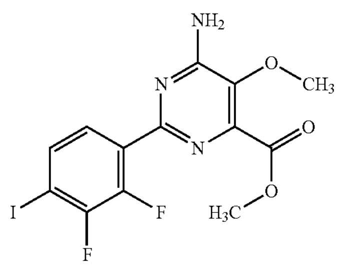 [SMILES: COC(=O)c1nc(-c2ccc(I)c(F)c2F)nc(N)c1OC] | White Solid | 68 |
| 25 | 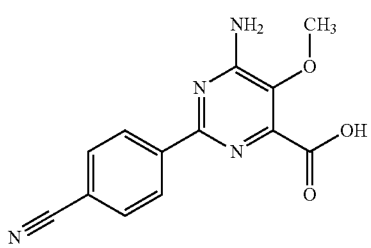 [SMILES: COc1c(N)nc(-c2ccc(C#N)cc2)nc1C(=O)O] | Yellow Solid | 98 |
| 26 | 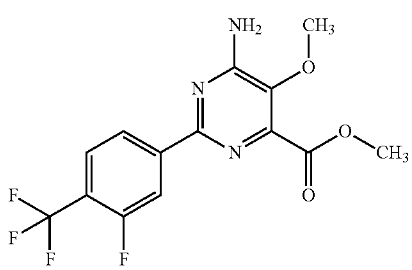 [SMILES: COC(=O)c1nc(-c2ccc(C(F)(F)F)c(F)c2)nc(N)c1OC] | White Solid | 46 |
| 27 | 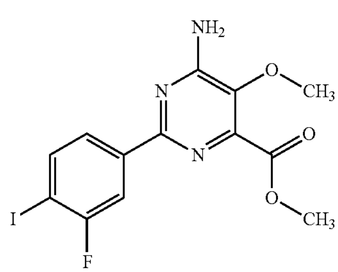 [SMILES: COC(=O)c1nc(-c2ccc(I)c(F)c2)nc(N)c1OC] | Yellow Solid | 64 |

TABLE 1-continued
Compound Number, Structure, Preparation and Appearance
| Cmpd. No. | Structure | Appearance | Prepared as in Example: |
|---|---|---|---|
| 28 | 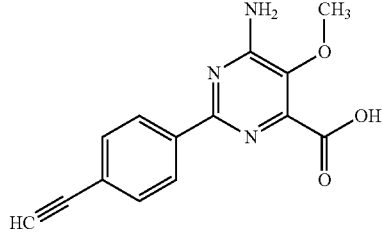 [SMILES: C#Cc1ccc(-c2nc(N)c(OC)c(C(=O)O)n2)cc1] | White Solid | 98 |
| 29 | 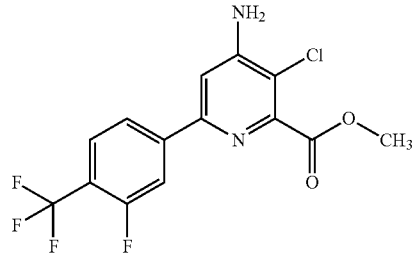 [SMILES: COC(=O)c1nc(-c2ccc(C(F)(F)F)c(F)c2)cc(N)c1Cl] | White Solid | 40 |
| 30 | 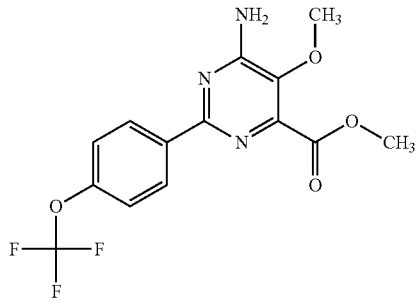 [SMILES: COC(=O)c1nc(-c2ccc(OC(F)(F)F)cc2)nc(N)c1OC] | Yellow Solid | 42 |
| 31 | 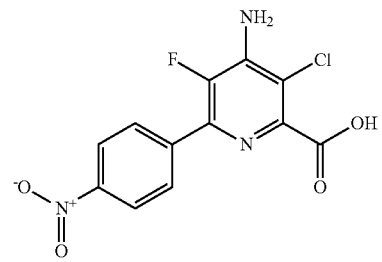 | Tan Solid | 95 |
| 32 | 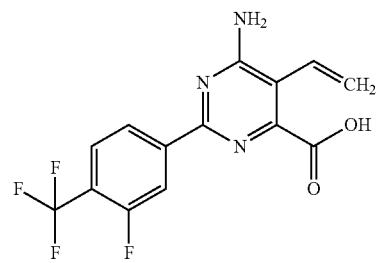 [SMILES: C=Cc1c(N)nc(-c2ccc(C(F)(F)F)c(F)c2)nc1C(=O)O] | Light Yellow Solid | 92 |

TABLE 1-continued

Compound Number, Structure, Preparation and Appearance

| Cmpd. No. | Structure | Appearance | Prepared as in Example: |
|---|---|---|---|
| 33 | 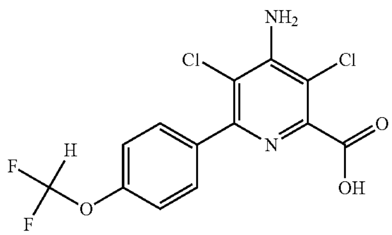 [SMILES: Nc1c(Cl)c(C(=O)O)nc(-c2ccc(OC(F)F)cc2)c1Cl] | White Solid | 98 |
| 34 | 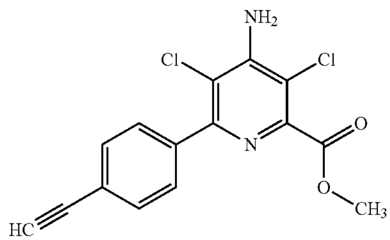 [SMILES: C#Cc1ccc(-c2nc(C(=O)OC)c(Cl)c(N)c2Cl)cc1] | Yellow Solid | 86 |
| 35 | 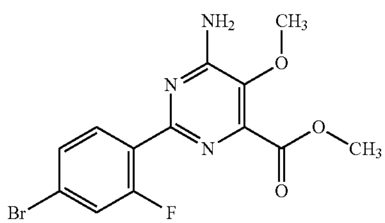 [SMILES: COC(=O)c1nc(-c2ccc(Br)cc2F)nc(N)c1OC] | Off-White Powder | 72 |
| 36 | 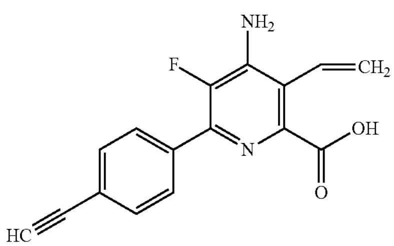 [SMILES: C#Cc1ccc(-c2nc(C(=O)O)c(C=C)c(N)c2F)cc1] | Off White Solid | 101 |
| 37 | 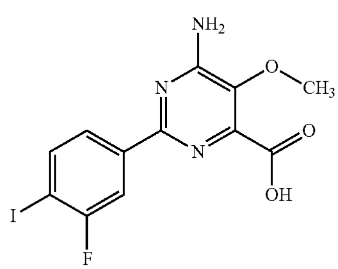 [SMILES: COc1c(N)nc(-c2ccc(I)c(F)c2)nc1C(=O)O] | White Solid | |
| 38 | 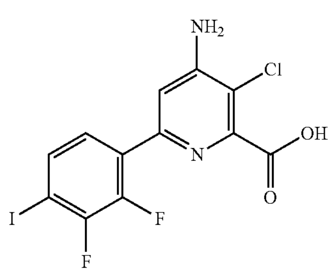 [SMILES: Nc1cc(-c2ccc(I)c(F)c2F)nc(C(=O)O)c1Cl] | White Powder | 97 |

TABLE 1-continued

Compound Number, Structure, Preparation and Appearance

| Cmpd. No. | Structure | Appearance | Prepared as in Example: |
|---|---|---|---|
| 39 | 4-amino-3-chloro-6-(4-cyanophenyl)-5-fluoropyridine-2-carboxylic acid | White Solid | 98 |
| 40 | methyl 4-amino-3-chloro-6-(4-ethynylphenyl)-5-methylpyridine-2-carboxylate | Brown Oil | 83 |
| 41 | 6-amino-2-(4-ethynyl-2-fluorophenyl)-5-methoxypyrimidine-4-carboxylic acid | Tan Powder | 98 |
| 42 | 4-amino-6-(4-bromo-2,5-difluorophenyl)-3-chloro-5-fluoropyridine-2-carboxylic acid | Light Brown Solid | 100 |
| 43 | 4-amino-6-(4-bromo-3-fluorophenyl)-3,5-dichloropyridine-2-carboxylic acid | White Solid | 92 |
| 44 | methyl 4-amino-3-chloro-6-(4-cyano-2-fluorophenyl)-5-fluoropyridine-2-carboxylate | Off White Solid | 39 |

TABLE 1-continued

Compound Number, Structure, Preparation and Appearance

| Cmpd. No. | Structure | Appearance | Prepared as in Example: |
|---|---|---|---|
| 45 | 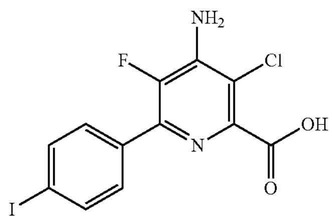 [SMILES: Nc1c(F)c(-c2ccc(I)cc2)nc(C(=O)O)c1Cl] | Pale Pink Powder | 97 |
| 46 | 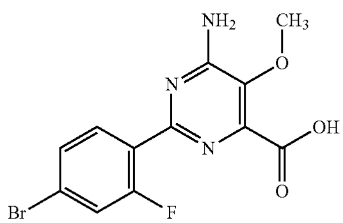 [SMILES: COc1c(N)nc(-c2ccc(Br)cc2F)nc1C(=O)O] | Off-White Powder | 98 |
| 47 | 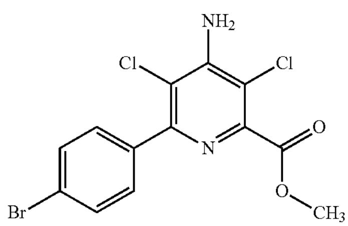 [SMILES: COC(=O)c1nc(-c2ccc(Br)cc2)c(Cl)c(N)c1Cl] | White Solid | 74 |
| 48 | 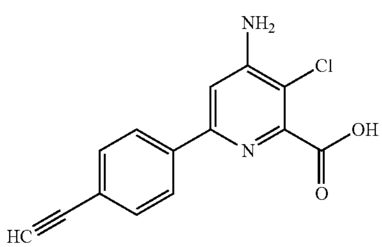 [SMILES: C#Cc1ccc(-c2cc(N)c(Cl)c(C(=O)O)n2)cc1] | White Solid | 98 |
| 49 | 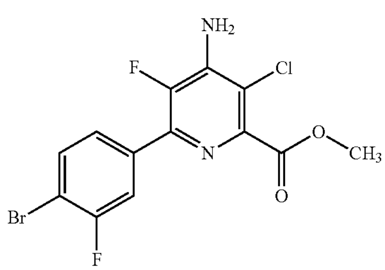 | Off-White Powder | 72 |
| 50 | 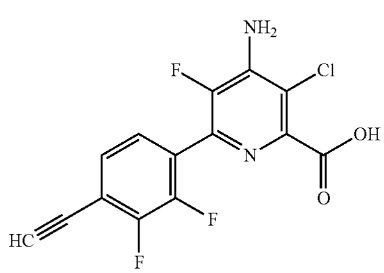 [SMILES: C#Cc1ccc(-c2nc(C(=O)O)c(Cl)c(N)c2F)c(F)c1F] | Off-White Powder | 98 |

TABLE 1-continued

Compound Number, Structure, Preparation and Appearance

| Cmpd. No. | Structure | Appearance | Prepared as in Example: |
|---|---|---|---|
| 51 | 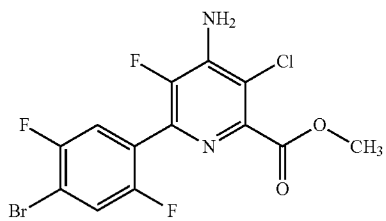 [SMILES: COC(=O)c1nc(-c2cc(F)c(Br)cc2F)c(F)c(N)c1Cl] | White Solid | 73 |
| 52 | 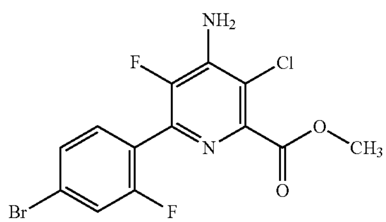 [SMILES: COC(=O)c1nc(-c2ccc(Br)cc2F)c(F)c(N)c1Cl] | White Powder | 72 |
| 53 | 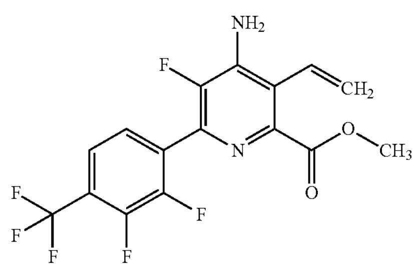 [SMILES: C=Cc1c(C(=O)OC)nc(-c2ccc(C(F)(F)F)c(F)c2F)c(F)c1N] | Brown Solid | 54 |
| 54 | 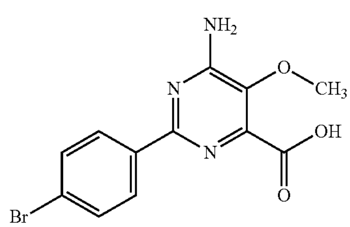 [SMILES: COc1c(N)nc(-c2ccc(Br)cc2)nc1C(=O)O] | White Solid | 97 |
| 55 | 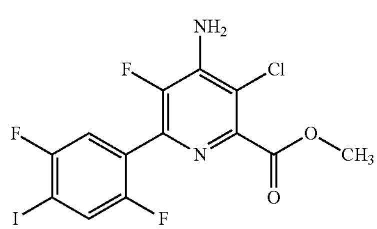 | White Solid | 67 |
| 56 | 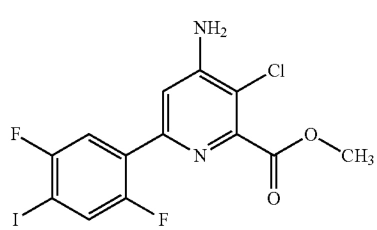 [SMILES: COC(=O)c1nc(-c2cc(F)c(I)cc2F)cc(N)c1Cl] | Orange Solid | 77 |

TABLE 1-continued

Compound Number, Structure, Preparation and Appearance

| Cmpd. No. | Structure | Appearance | Prepared as in Example: |
|---|---|---|---|
| 57 | 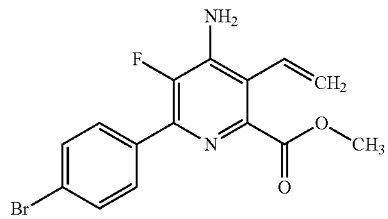 [SMILES: C=Cc1c(C(=O)OC)nc(-c2ccc(Br)cc2)c(F)c1N] | Light Brown Solid | 79 |
| 58 | 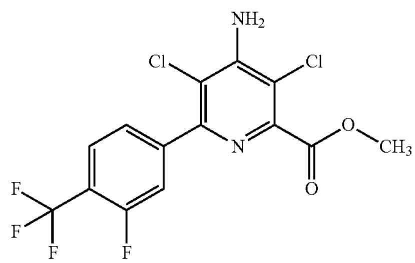 [SMILES: COC(=O)c1nc(-c2ccc(C(F)(F)F)c(F)c2)c(Cl)c(N)c1Cl] | Off White Solid | 46 |
| 59 | 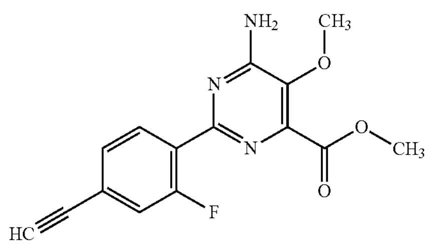 [SMILES: C#Cc1ccc(-c2nc(N)c(OC)c(C(=O)OC)n2)c(F)c1] | White Powder | 86 |
| 60 | 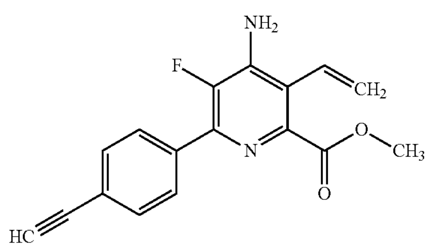 [SMILES: C#Cc1ccc(-c2nc(C(=O)OC)c(C=C)c(N)c2F)cc1] | White Solid | 88 |
| 61 | 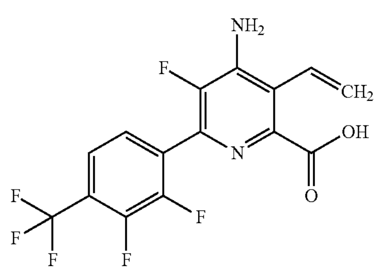 [SMILES: C=Cc1c(C(=O)O)nc(-c2ccc(C(F)(F)F)c(F)c2F)c(F)c1N] | Brown Gummy Oil | 100 |
| 62 | 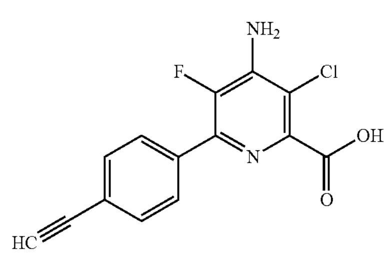 [SMILES: C#Cc1ccc(-c2nc(C(=O)O)c(Cl)c(N)c2F)cc1] | Tan Powder | 97 |

TABLE 1-continued
Compound Number, Structure, Preparation and Appearance
| Cmpd. No. | Structure | Appearance | Prepared as in Example: |
|---|---|---|---|
| 63 | 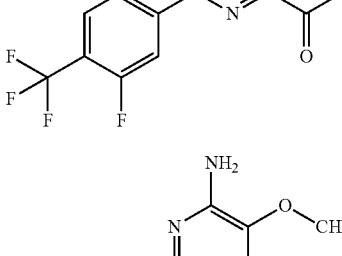 | White Solid | 96 |
| 64 | 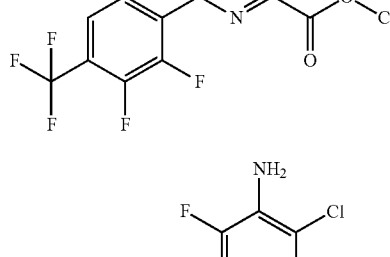 | White Solid | 41 |
| 65 | 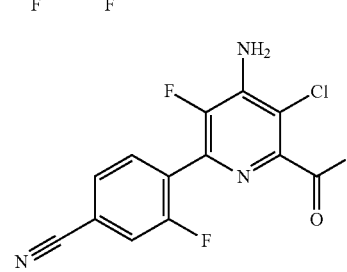 | Brown Solid | 93 |
| 66 | 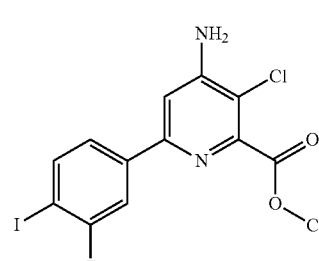 | Brown Solid | 64 |
| 67 | 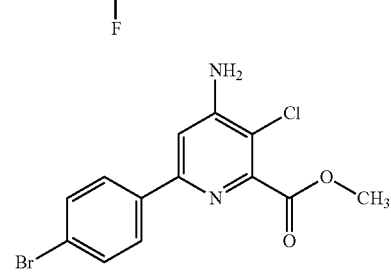 | Dark Brown Viscous Oil | 76 |
| 68 | 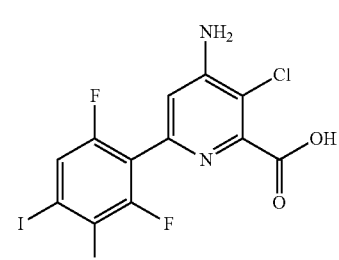 | Offwhite Soid | 100 |

US 9,113,629 B2
TABLE 1-continued
Compound Number, Structure, Preparation and Appearance
| Cmpd. No. | Structure | Appearance | Prepared as in Example: |
|---|---|---|---|
| 69 | 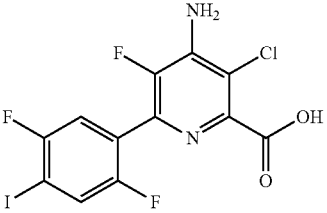 [SMILES: Nc1c(F)c(-c2cc(F)c(I)cc2F)nc(C(=O)O)c1Cl] | White Solid | 100 |
| 70 | 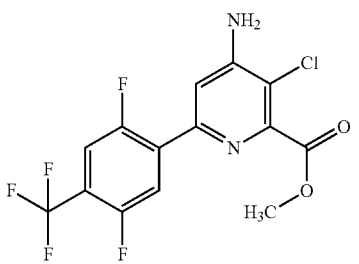 [SMILES: COC(=O)c1nc(-c2cc(F)c(C(F)(F)F)cc2F)cc(N)c1Cl] | White Solid | 59 |
| 71 | 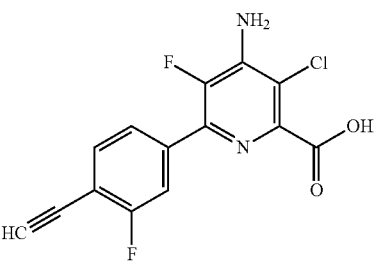 [SMILES: C#Cc1ccc(-c2nc(C(=O)O)c(Cl)c(N)c2F)cc1F] | Off-White Powder | 98 |
| 72 | 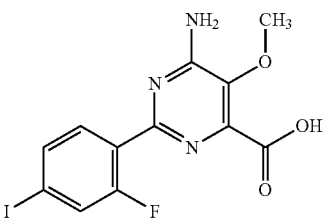 [SMILES: COc1c(N)nc(-c2ccc(I)cc2F)nc1C(=O)O] | Yellow Powder | 98 |
| 73 | 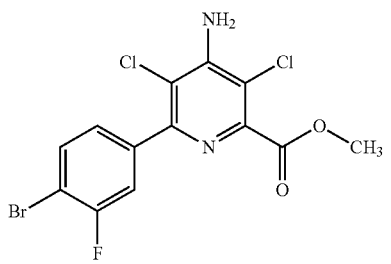 | White Solid | 69 |
| 74 | 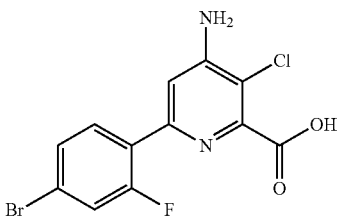 [SMILES: Nc1cc(-c2ccc(Br)cc2F)nc(C(=O)O)c1Cl] | White Solid | 98 |

TABLE 1-continued

Compound Number, Structure, Preparation and Appearance

| Cmpd. No. | Structure | Appearance | Prepared as in Example: |
|---|---|---|---|
| 76 | 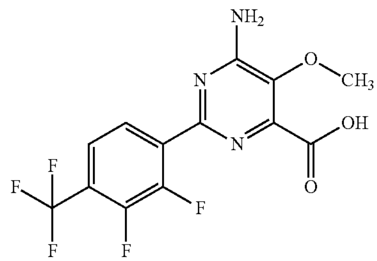 [SMILES: COc1c(N)nc(-c2ccc(C(F)(F)F)c(F)c2F)nc1C(=O)O] | White Solid | 95 |
| 77 | 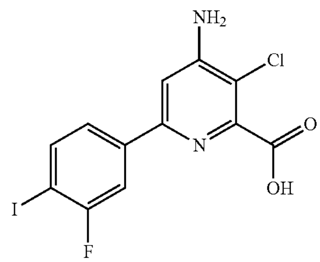 [SMILES: Nc1cc(-c2ccc(I)c(F)c2)nc(C(=O)O)c1Cl] | White Solid | 92 |
| 78 | 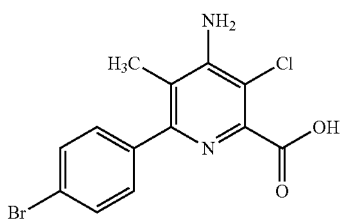 | White Solid | 94 |
| 79 | 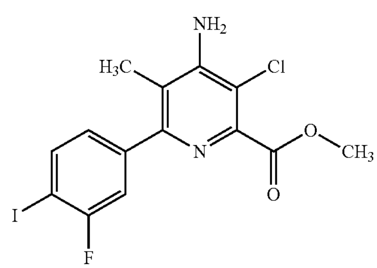 [SMILES: COC(=O)c1nc(-c2ccc(I)c(F)c2)c(C)c(N)c1Cl] | Off-White Solid | 65 |
| 80 | 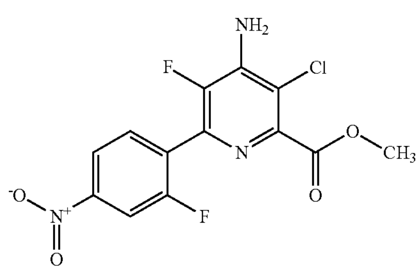 | Yellow Solid | 41 |
| 81 | 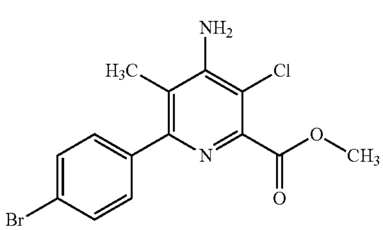 [SMILES: COC(=O)c1nc(-c2ccc(Br)cc2)c(C)c(N)c1Cl] | Pale Orange Powder | 70 |

TABLE 1-continued

Compound Number, Structure, Preparation and Appearance

| Cmpd. No. | Structure | Appearance | Prepared as in Example: |
|---|---|---|---|
| 82 | 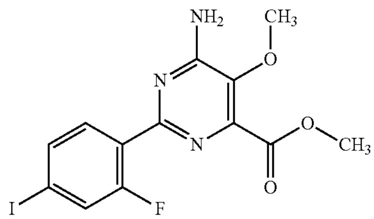 [SMILES: COC(=O)c1nc(-c2ccc(I)cc2F)nc(N)c1OC] | Yellow Powder | 66 |
| 83 | 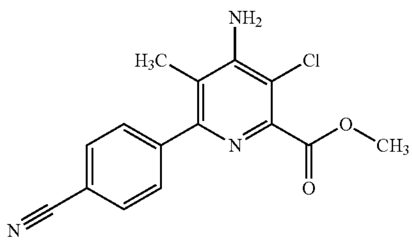 [SMILES: COC(=O)c1nc(-c2ccc(C#N)cc2)c(C)c(N)c1Cl] | Orange Solid | 40 |
| 84 | 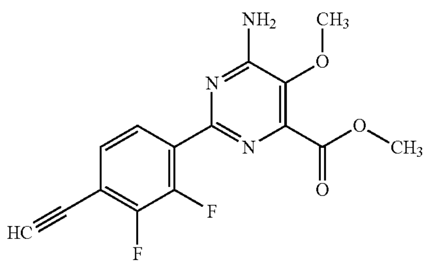 [SMILES: C#Cc1ccc(-c2nc(N)c(OC)c(C(=O)OC)n2)c(F)c1F] | White Powder | 86 |
| 85 | 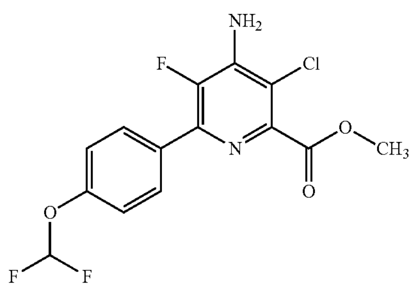 [SMILES: COC(=O)c1nc(-c2ccc(OC(F)F)cc2)c(F)c(N)c1Cl] | White Solid | 42 |
| 86 | 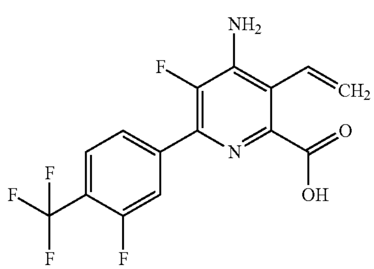 [SMILES: C=Cc1c(C(=O)O)nc(-c2ccc(C(F)(F)F)c(F)c2)c(F)c1N] | White Solid | 98 |
| 87 | 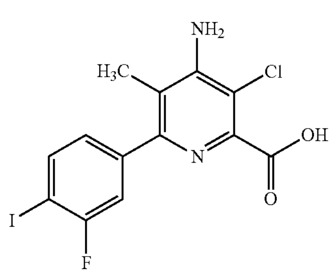 [SMILES: Cc1c(-c2ccc(I)c(F)c2)nc(C(=O)O)c(Cl)c1N] | White Powder | 94 |

TABLE 1-continued
Compound Number, Structure, Preparation and Appearance
| Cmpd. No. | Structure | Appearance | Prepared as in Example: |
|---|---|---|---|
| 88 | 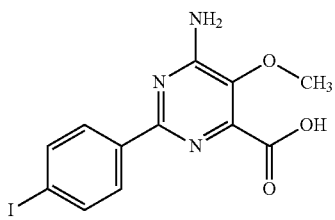 [SMILES: COc1c(N)nc(-c2ccc(I)cc2)nc1C(=O)O] | White Solid | 97 |
| 89 | 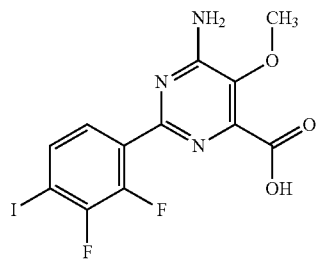 [SMILES: COc1c(N)nc(-c2ccc(I)c(F)c2F)nc1C(=O)O] | White Solid | 98 |
| 90 | 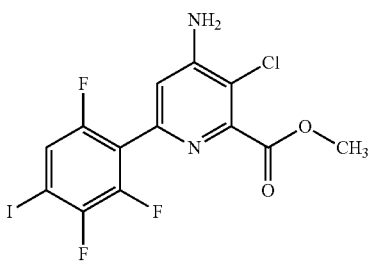 [SMILES: COC(=O)c1nc(-c2c(F)cc(I)c(F)c2F)cc(N)c1Cl] | White Solid | 77 |
| 91 | 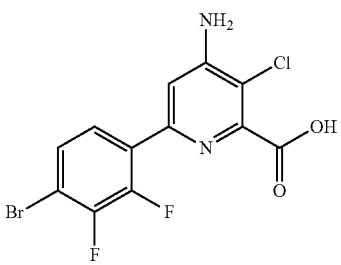 [SMILES: Nc1cc(-c2ccc(Br)c(F)c2F)nc(C(=O)O)c1Cl] | White Solid | 97 |
| 92 | 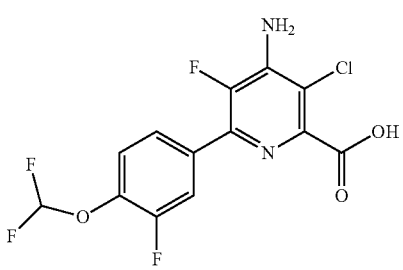 [SMILES: Nc1c(F)c(-c2ccc(OC(F)F)c(F)c2)nc(C(=O)O)c1Cl] | Tan Solid | 101 |
| 93 | 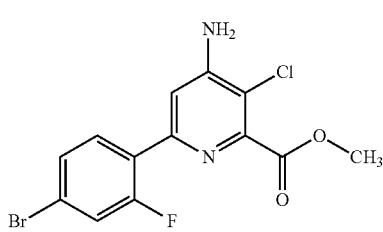 [SMILES: COC(=O)c1nc(-c2ccc(Br)cc2F)cc(N)c1Cl] | White Solid | 74 |

TABLE 1-continued

Compound Number, Structure, Preparation and Appearance

| Cmpd. No. | Structure | Appearance | Prepared as in Example: |
|---|---|---|---|
| 94 | 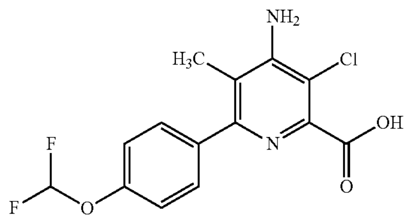 [SMILES: Cc1c(-c2ccc(OC(F)F)cc2)nc(C(=O)O)c(Cl)c1N] | Yellow Solid | 94 |
| 95 | 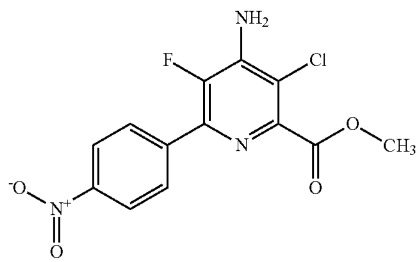 | Yellow Solid | 41 |
| 96 | 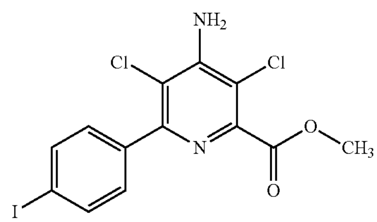 [SMILES: COC(=O)c1nc(-c2ccc(I)cc2)c(Cl)c(N)c1Cl] | Gray Solid | 68 |
| 97 | 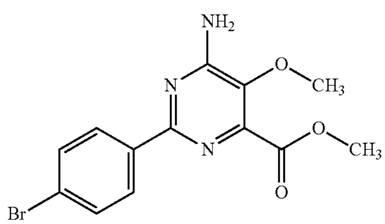 [SMILES: COC(=O)c1nc(-c2ccc(Br)cc2)nc(N)c1OC] | Off-White Solid | 72 |
| 98 | 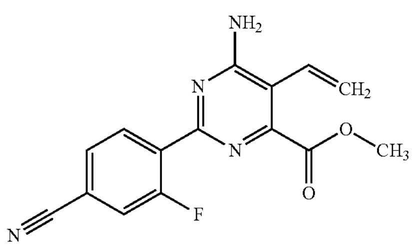 [SMILES: C=Cc1c(N)nc(-c2ccc(C#N)cc2F)nc1C(=O)OC] | Yellow Solid | 39 |
| 99 | 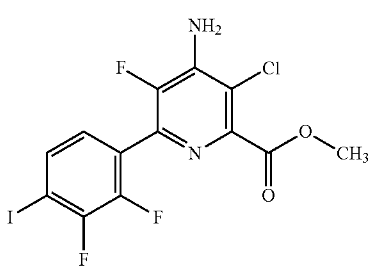 [SMILES: COC(=O)c1nc(-c2ccc(I)c(F)c2F)c(F)c(N)c1Cl] | White Powder | 66 |

TABLE 1-continued

Compound Number, Structure, Preparation and Appearance

| Cmpd. No. | Structure | Appearance | Prepared as in Example: |
|---|---|---|---|
| 100 | 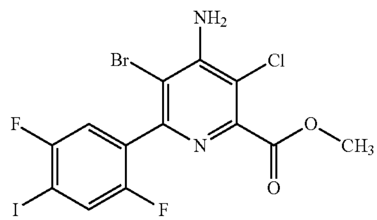 [SMILES: COC(=O)c1nc(-c2cc(F)c(I)cc2F)c(Br)c(N)c1Cl] | Light Brown solid | 67 |
| 101 | 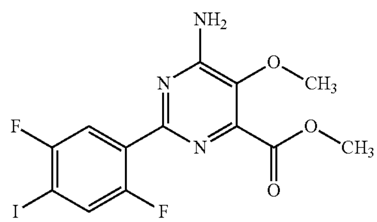 [SMILES: COC(=O)c1nc(-c2cc(F)c(I)cc2F)nc(N)c1OC] | White Solid | 67 |
| 102 | 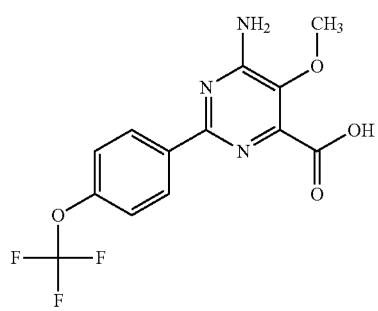 [SMILES: COc1c(N)nc(-c2ccc(OC(F)(F)F)cc2)nc1C(=O)O] | Yellow Solid | 98 |
| 103 | 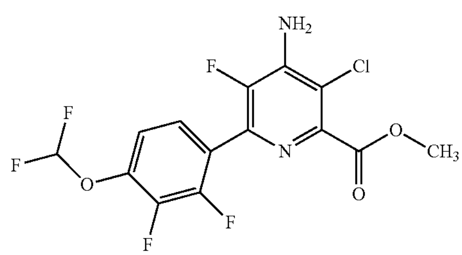 [SMILES: COC(=O)c1nc(-c2ccc(OC(F)F)c(F)c2F)c(F)c(N)c1Cl] | Tan Solid | 56 |
| 104 | 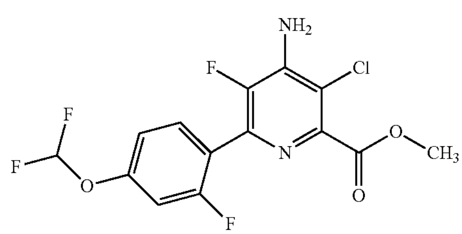 [SMILES: COC(=O)c1nc(-c2ccc(OC(F)F)cc2F)c(F)c(N)c1Cl] | Yellow Solid | 56 |
| 105 | 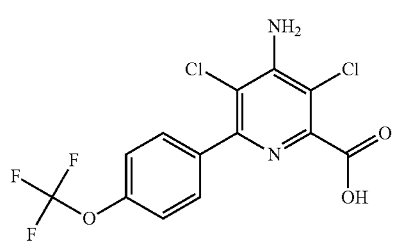 | White Solid | 98 |

TABLE 1-continued

Compound Number, Structure, Preparation and Appearance

| Cmpd. No. | Structure | Appearance | Prepared as in Example: |
|---|---|---|---|
| 106 | 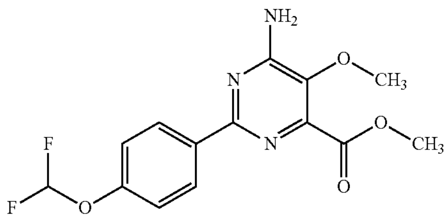 [SMILES: COC(=O)c1nc(-c2ccc(OC(F)F)cc2)nc(N)c1OC] | White Solid | 56 |
| 107 | 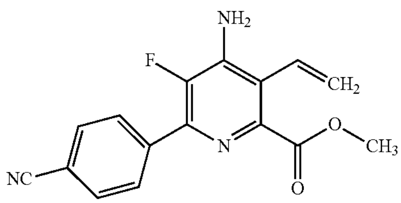 [SMILES: C=Cc1c(C(=O)OC)nc(-c2ccc(C#N)cc2)c(F)c1N] | Tan Solid | 57 |
| 108 | 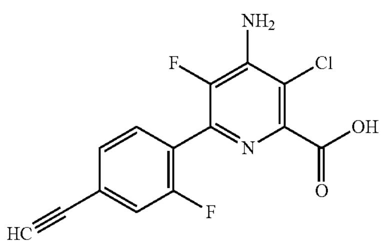 [SMILES: C#Cc1ccc(-c2nc(C(=O)O)c(Cl)c(N)c2F)c(F)c1] | Pale Orange Powder | 98 |
| 109 | 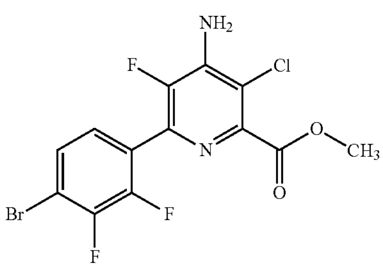 [SMILES: COC(=O)c1nc(-c2ccc(Br)c(F)c2F)c(F)c(N)c1Cl] | Light Yellow Solid | 71 |
| 110 | 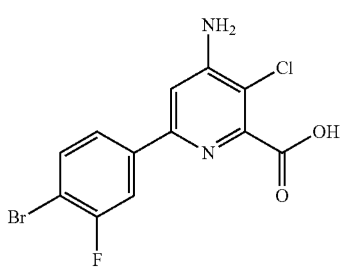 [SMILES: Nc1cc(-c2ccc(Br)c(F)c2)nc(C(=O)O)c1Cl] | Off White Solid | 92 |
| 111 | 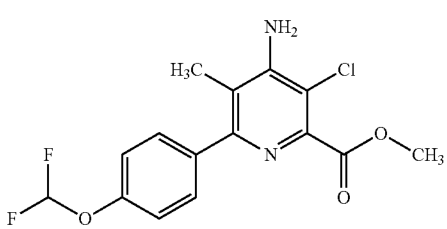 [SMILES: COC(=O)c1nc(-c2ccc(OC(F)F)cc2)c(C)c(N)c1Cl] | Waxy Yellow Solid | 40 |

TABLE 1-continued

Compound Number, Structure, Preparation and Appearance

| Cmpd. No. | Structure | Appearance | Prepared as in Example: |
|---|---|---|---|
| 112 | 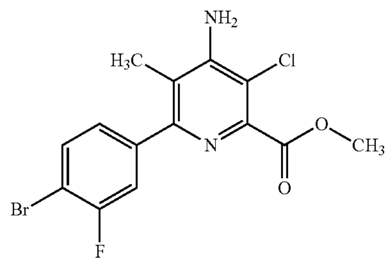 [SMILES: COC(=O)c1nc(-c2ccc(Br)c(F)c2)c(C)c(N)c1Cl] | Off-White Solid | 70 |
| 113 | 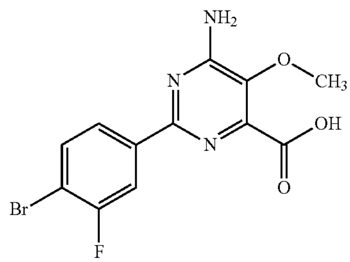 [SMILES: COc1c(N)nc(-c2ccc(Br)c(F)c2)nc1C(=O)O] | White Solid | 92 |
| 114 | 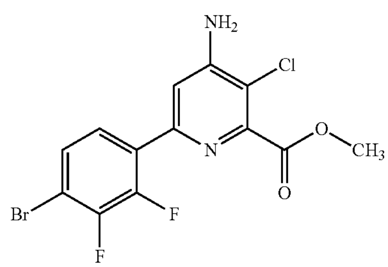 | White Solid | 44 |
| 115 | 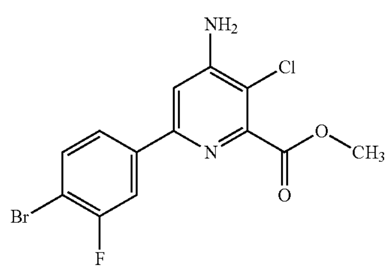 [SMILES: COC(=O)c1nc(-c2ccc(Br)c(F)c2)cc(N)c1Cl] | White Solid | 75 |
| 116 | 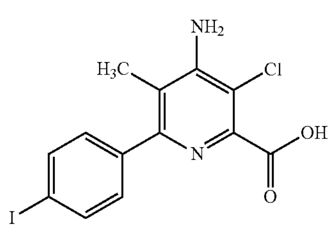 | Orange Powder | 94 |
| 117 | 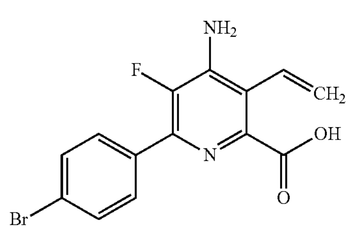 [SMILES: C=Cc1c(C(=O)O)nc(-c2ccc(Br)cc2)c(F)c1N] | Light Brown Solid | 100 |

TABLE 1-continued

Compound Number, Structure, Preparation and Appearance

| Cmpd. No. | Structure | Appearance | Prepared as in Example: |
|---|---|---|---|
| 118 | 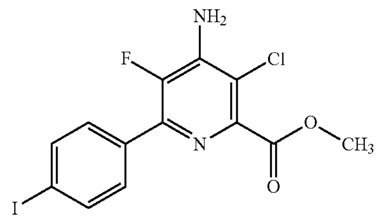 [SMILES: COC(=O)c1nc(-c2ccc(I)cc2)c(F)c(N)c1Cl] | Purple Powder | 66 |
| 119 | 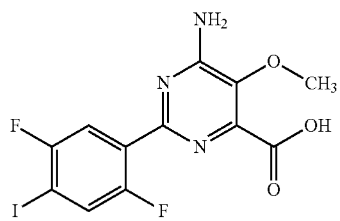 [SMILES: COc1c(N)nc(-c2cc(F)c(I)cc2F)nc1C(=O)O] | Yellow Solid | 100 |
| 121 | 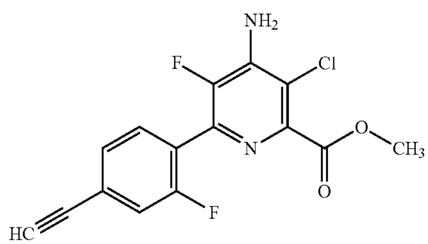 [SMILES: C#Cc1ccc(-c2nc(C(=O)OC)c(Cl)c(N)c2F)c(F)c1] | White Powder | 86 |
| 122 | 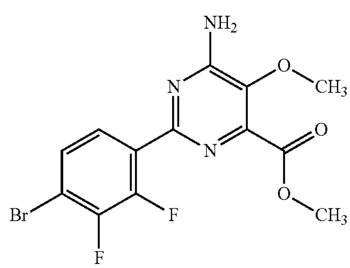 [SMILES: COC(=O)c1nc(-c2ccc(Br)c(F)c2F)nc(N)c1OC] | White Solid | 74 |
| 123 | 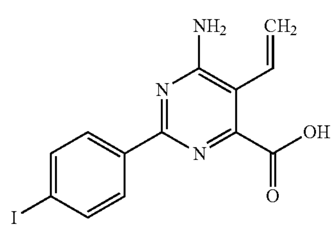 [SMILES: C=Cc1c(N)nc(-c2ccc(I)cc2)nc1C(=O)O] | Off White Solid | 93 |
| 124 | 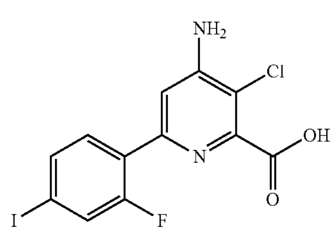 [SMILES: Nc1cc(-c2ccc(I)cc2F)nc(C(=O)O)c1Cl] | Yellow Solid | 98 |

TABLE 1-continued

Compound Number, Structure, Preparation and Appearance

| Cmpd. No. | Structure | Appearance | Prepared as in Example: |
|---|---|---|---|
| 125 | 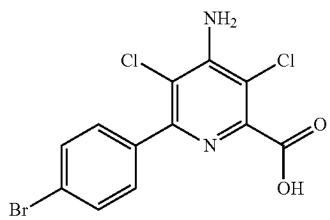 [SMILES: Nc1c(Cl)c(C(=O)O)nc(-c2ccc(Br)cc2)c1Cl] | White Solid | 98 |
| 126 | 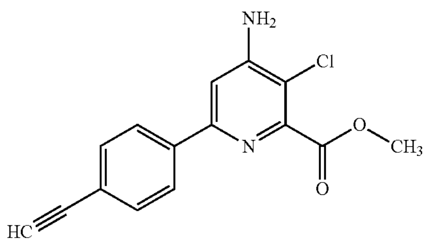 [SMILES: C#Cc1ccc(-c2cc(N)c(Cl)c(C(=O)OC)n2)cc1] | Yellow Solid | 86 |
| 127 | 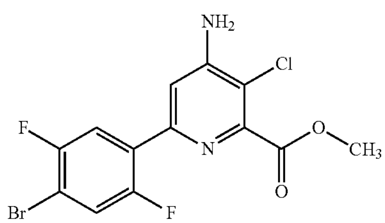 [SMILES: COC(=O)c1nc(-c2cc(F)c(Br)cc2F)cc(N)c1Cl] | White Solid | 77 |
| 128 | 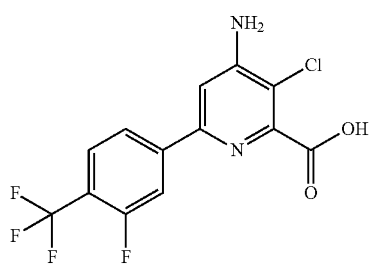 [SMILES: Nc1cc(-c2ccc(C(F)(F)F)c(F)c2)nc(C(=O)O)c1Cl] | White Solid | 96 |
| 129 | 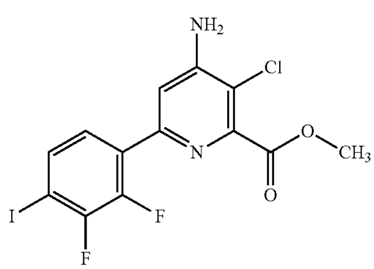 [SMILES: COC(=O)c1nc(-c2ccc(I)c(F)c2F)cc(N)c1Cl] | White Powder | 76 |
| 130 | 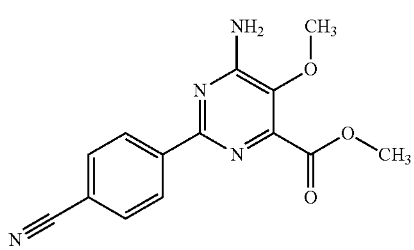 [SMILES: COC(=O)c1nc(-c2ccc(C#N)cc2)nc(N)c1OC] | White Solid | 42 |

TABLE 1-continued

Compound Number, Structure, Preparation and Appearance

| Cmpd. No. | Structure | Appearance | Prepared as in Example: |
|---|---|---|---|
| 131 | 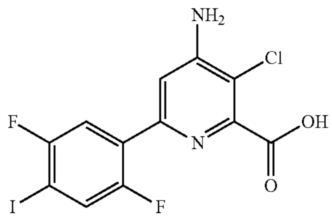 [SMILES: Nc1cc(-c2cc(F)c(I)cc2F)nc(C(=O)O)c1Cl] | Light Brown Solid | 100 |
| 132 | 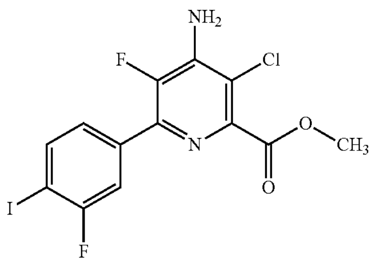 [SMILES: COC(=O)c1nc(-c2ccc(I)c(F)c2)c(F)c(N)c1Cl] | Tan Powder | 66 |
| 133 | 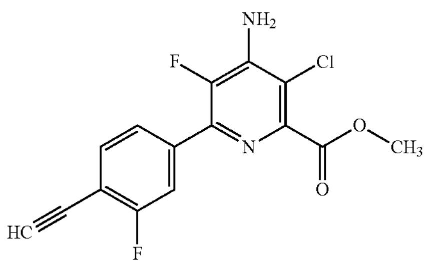 [SMILES: C#Cc1ccc(-c2nc(C(=O)OC)c(Cl)c(N)c2F)cc1F] | White Powder | 86 |
| 134 | 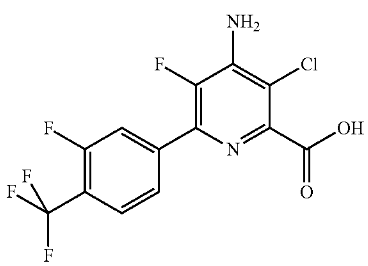 [SMILES: Nc1c(F)c(-c2ccc(C(F)(F)F)c(F)c2)nc(C(=O)O)c1Cl] | White Solid | 95 |
| 135 | 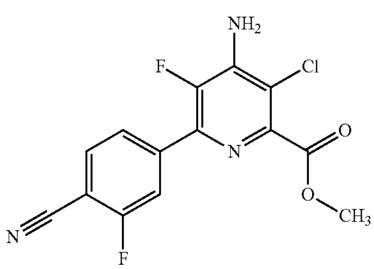 [SMILES: COC(=O)c1nc(-c2ccc(C#N)c(F)c2)c(F)c(N)c1Cl] | White Solid | 42 |
| 136 | 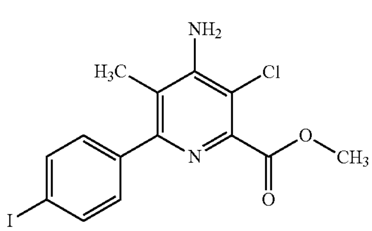 [SMILES: COC(=O)c1nc(-c2ccc(I)cc2)c(C)c(N)c1Cl] | Red-Orange Solid | 65 |

TABLE 1-continued

Compound Number, Structure, Preparation and Appearance

| Cmpd. No. | Structure | Appearance | Prepared as in Example: |
|---|---|---|---|
| 137 | 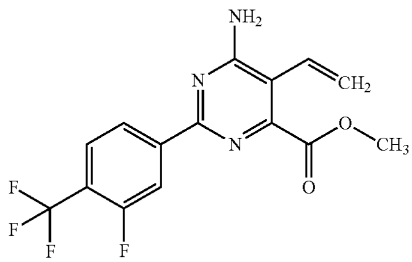 [SMILES: C=Cc1c(N)nc(-c2ccc(C(F)(F)F)c(F)c2)nc1C(=O)OC] | Light Tan Solid | 39 |
| 138 | 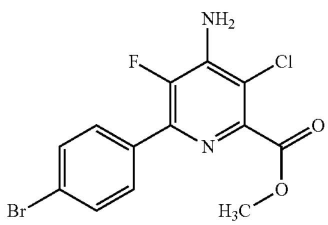 [SMILES: COC(=O)c1nc(-c2ccc(Br)cc2)c(F)c(N)c1Cl] | Tan Powder | 72 |
| 139 | 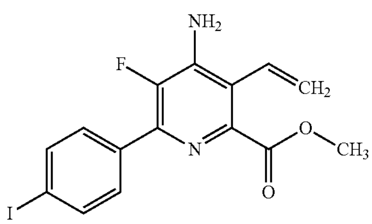 [SMILES: C=Cc1c(C(=O)OC)nc(-c2ccc(I)cc2)c(F)c1N] | White Solid | 81 |
| 140 | 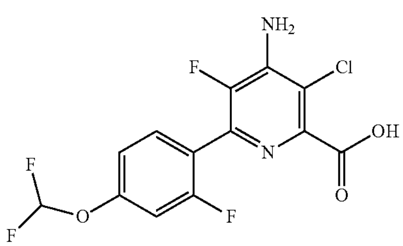 [SMILES: Nc1c(F)c(-c2ccc(OC(F)F)cc2F)nc(C(=O)O)c1Cl] | Off White Solid | 101 |
| 141 | 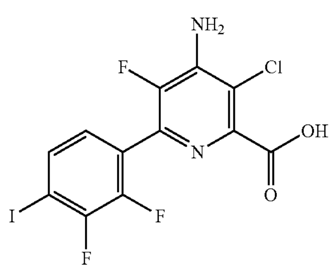 [SMILES: Nc1c(F)c(-c2ccc(I)c(F)c2F)nc(C(=O)O)c1Cl] | White Powder | 98 |
| 142 | 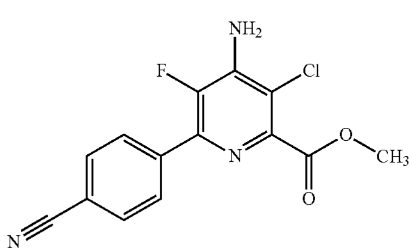 [SMILES: COC(=O)c1nc(-c2ccc(C#N)cc2)c(F)c(N)c1Cl] | Solid | 42 |

TABLE 1-continued

Compound Number, Structure, Preparation and Appearance

| Cmpd. No. | Structure | Appearance | Prepared as in Example: |
|---|---|---|---|
| 143 | 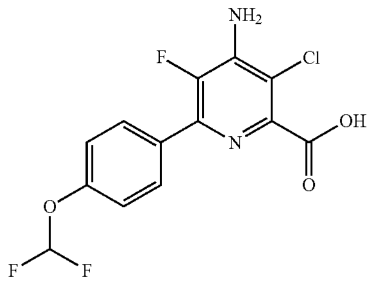 [SMILES: Nc1c(F)c(-c2ccc(OC(F)F)cc2)nc(C(=O)O)c1Cl] | White Solid | 98 |
| 144 | 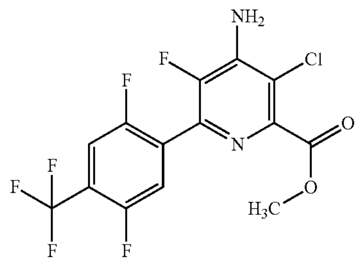 [SMILES: COC(=O)c1nc(-c2cc(F)c(C(F)(F)F)cc2F)c(F)c(N)c1Cl] | White Solid | 60 |
| 145 | 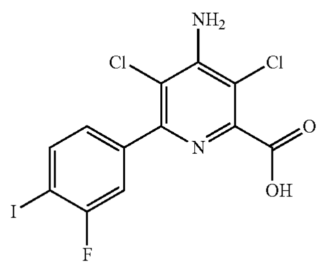 [SMILES: Nc1c(Cl)c(C(=O)O)nc(-c2ccc(I)c(F)c2)c1Cl] | White Solid | 92 |
| 146 | 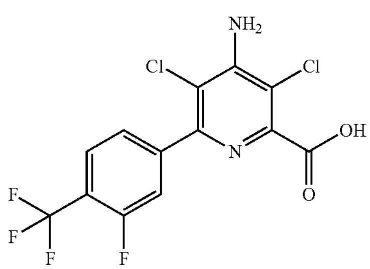 [SMILES: Nc1c(Cl)c(C(=O)O)nc(-c2ccc(C(F)(F)F)c(F)c2)c1Cl] | White Solid | 94 |
| 147 | 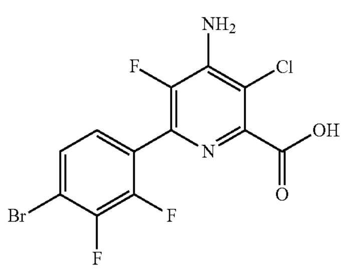 [SMILES: Nc1c(F)c(-c2ccc(Br)c(F)c2F)nc(C(=O)O)c1Cl] | Tan Solid | 98 |

TABLE 1-continued

Compound Number, Structure, Preparation and Appearance

| Cmpd. No. | Structure | Appearance | Prepared as in Example: |
|---|---|---|---|
| 148 | 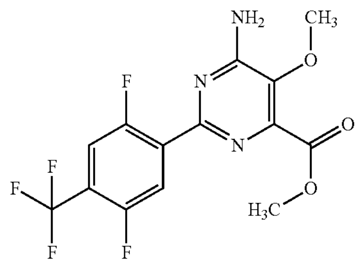 [SMILES: COC(=O)c1nc(-c2cc(F)c(C(F)(F)F)cc2F)nc(N)c1OC] | White Solid | 60 |
| 149 | 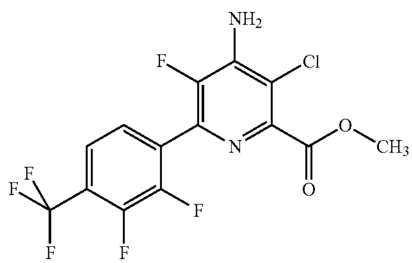 [SMILES: COC(=O)c1nc(-c2ccc(C(F)(F)F)c(F)c2F)c(F)c(N)c1Cl] | White Solid | 41 |
| 150 | 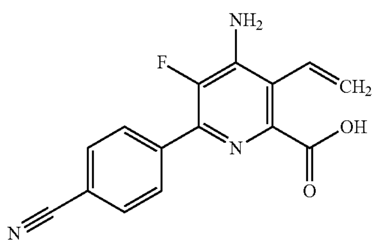 [SMILES: C=Cc1c(C(=O)O)nc(-c2ccc(C#N)cc2)c(F)c1N] | Tan Solid | 101 |
| 151 | 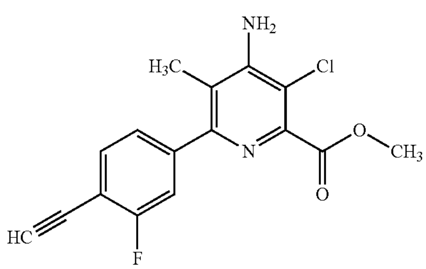 [SMILES: C#Cc1ccc(-c2nc(C(=O)OC)c(Cl)c(N)c2C)cc1F] | Yellow Solid | 87 |
| 152 | 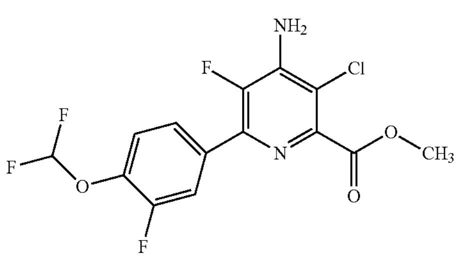 [SMILES: COC(=O)c1nc(-c2ccc(OC(F)F)c(F)c2)c(F)c(N)c1Cl] | White Solid | 56 |
| 153 | 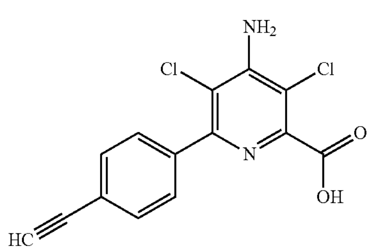 [SMILES: C#Cc1ccc(-c2nc(C(=O)O)c(Cl)c(N)c2Cl)cc1] | Yellow Solid | 98 |

TABLE 1-continued

Compound Number, Structure, Preparation and Appearance

| Cmpd. No. | Structure | Appearance | Prepared as in Example: |
|---|---|---|---|
| 154 | 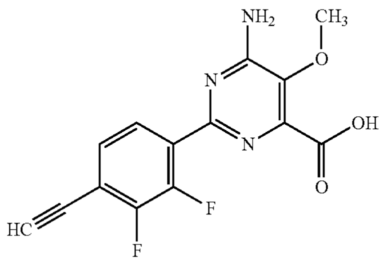 [SMILES: C#Cc1ccc(-c2nc(N)c(OC)c(C(=O)O)n2)c(F)c1F] | Tan Powder | 98 |
| 155 | 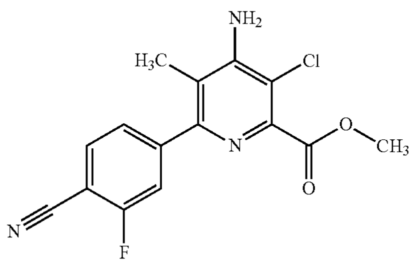 [SMILES: COC(=O)c1nc(-c2ccc(C#N)c(F)c2)c(C)c(N)c1Cl] | White Flaky Solid | 40 |
| 156 | 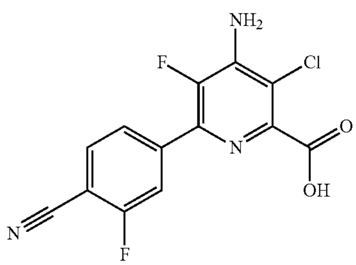 [SMILES: N#Cc1ccc(-c2nc(C(=O)O)c(Cl)c(N)c2F)cc1F] | White Solid | 98 |
| 157 | 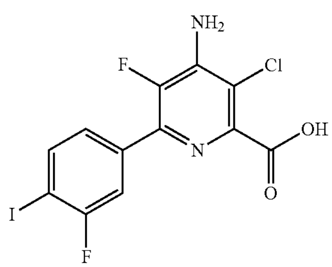 [SMILES: Nc1c(F)c(-c2ccc(I)c(F)c2)nc(C(=O)O)c1Cl] | Tan Powder | 97 |
| 158 | 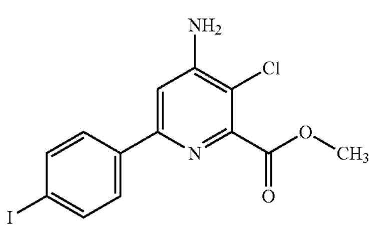 [SMILES: COC(=O)c1nc(-c2ccc(I)cc2)cc(N)c1Cl] | Dark Brown Semi Solid | 76 |
| 159 | 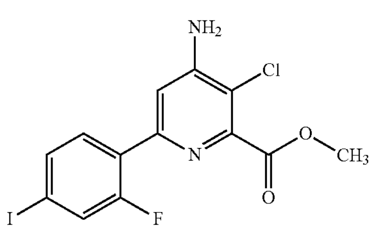 [SMILES: COC(=O)c1nc(-c2ccc(I)cc2F)cc(N)c1Cl] | White Solid | 68 |

TABLE 1-continued

Compound Number, Structure, Preparation and Appearance

| Cmpd. No. | Structure | Appearance | Prepared as in Example: |
|---|---|---|---|
| 160 | 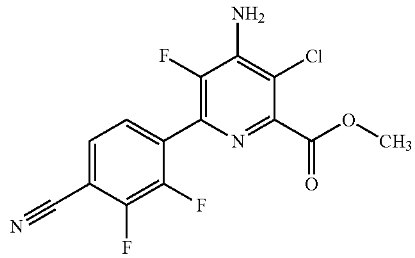 [SMILES: COC(=O)c1nc(-c2ccc(C#N)c(F)c2F)c(F)c(N)c1Cl] | White Solid | 41 |
| 161 | 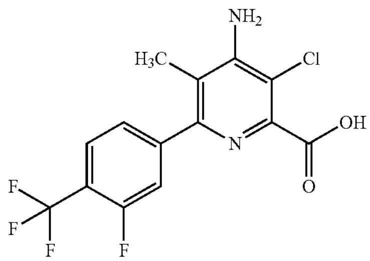 [SMILES: Cc1c(-c2ccc(C(F)(F)F)c(F)c2)nc(C(=O)O)c(Cl)c1N] | White Powder | 94 |
| 162 | 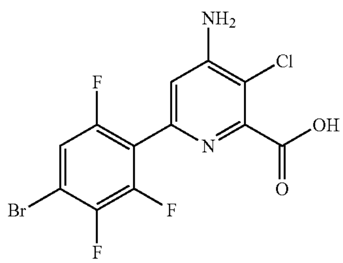 [SMILES: Nc1cc(-c2c(F)cc(Br)c(F)c2F)nc(C(=O)O)c1Cl] | Brown Solid | 99 |
| 163 | 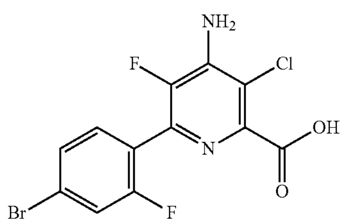 [SMILES: Nc1c(F)c(-c2ccc(Br)cc2F)nc(C(=O)O)c1Cl] | Off-White Powder | 98 |
| 164 | 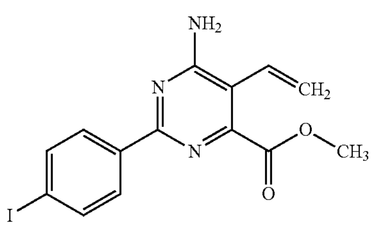 [SMILES: C=Cc1c(N)nc(-c2ccc(I)cc2)nc1C(=O)OC] | Light Yellow Solid | 80 |
| 165 | 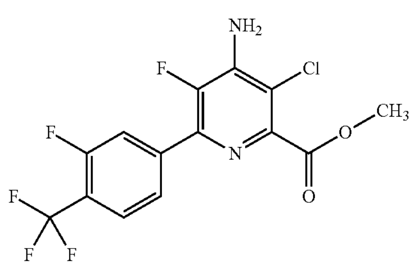 [SMILES: COC(=O)c1nc(-c2ccc(C(F)(F)F)c(F)c2)c(F)c(N)c1Cl] | White Solid | 41 |

TABLE 1-continued

Compound Number, Structure, Preparation and Appearance

| Cmpd. No. | Structure | Appearance | Prepared as in Example: |
|---|---|---|---|
| 166 | 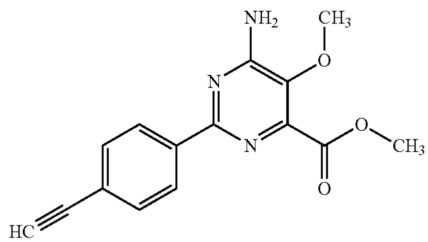 [SMILES: C#Cc1ccc(-c2nc(N)c(OC)c(C(=O)OC)n2)cc1] | Yellow Solid | 86 |
| 167 | 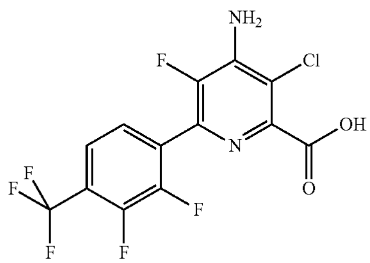 [SMILES: Nc1c(F)c(-c2ccc(C(F)(F)F)c(F)c2F)nc(C(=O)O)c1Cl] | White Solid | 95 |
| 168 | 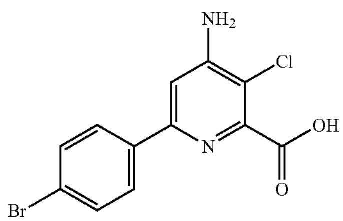 [SMILES: Nc1cc(-c2ccc(Br)cc2)nc(C(=O)O)c1Cl] | Brown Solid | 97 |
| 169 | 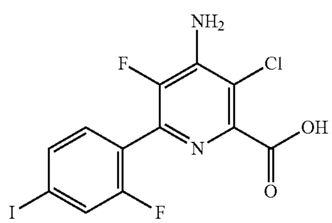 [SMILES: Nc1c(F)c(-c2ccc(I)cc2F)nc(C(=O)O)c1Cl] | Off-White Powder | 98 |
| 170 | 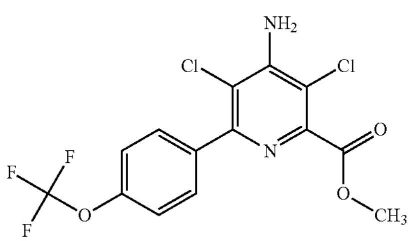 | White Solid | 42 |
| 171 | 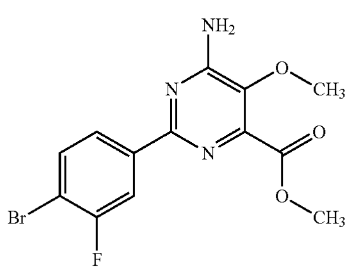 [SMILES: COC(=O)c1nc(-c2ccc(Br)c(F)c2)nc(N)c1OC] | White Solid | 69 |

TABLE 1-continued

Compound Number, Structure, Preparation and Appearance

| Cmpd. No. | Structure | Appearance | Prepared as in Example: |
|---|---|---|---|
| 172 | 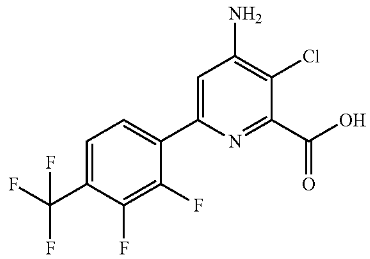 [SMILES: Nc1cc(-c2ccc(C(F)(F)F)c(F)c2F)nc(C(=O)O)c1Cl] | White Solid | 96 |
| 173 | 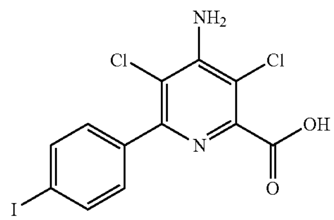 [SMILES: Nc1c(Cl)c(C(=O)O)nc(-c2ccc(I)cc2)c1Cl] | Yellow Solid | 98 |
| 174 | 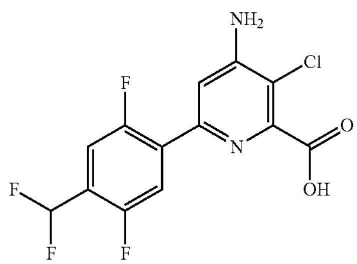 [SMILES: Nc1cc(-c2cc(F)c(C(F)F)cc2F)nc(C(=O)O)c1Cl] | Off White Solid | 62 |
| 175 | 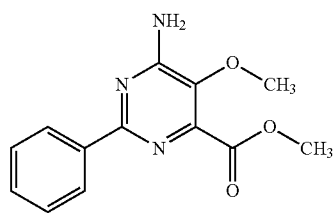 [SMILES: COC(=O)c1nc(-c2ccccc2)nc(N)c1OC] | Tan Solid | 57 |
| 176 | 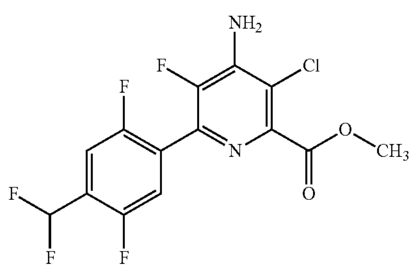 [SMILES: COC(=O)c1nc(-c2cc(F)c(C(F)F)cc2F)c(F)c(N)c1Cl] | White Solid | 63 |
| 177 | 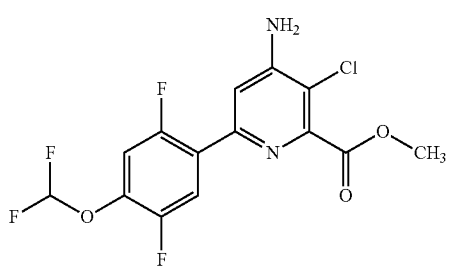 [SMILES: COC(=O)c1nc(-c2cc(F)c(OC(F)F)cc2F)cc(N)c1Cl] | White Solid | 63 |

TABLE 1-continued
Compound Number, Structure, Preparation and Appearance
| Cmpd. No. | Structure | Appearance | Prepared as in Example: |
|---|---|---|---|
| 178 | 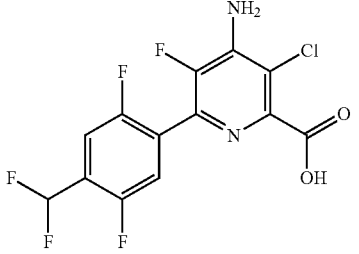 [SMILES: Nc1c(F)c(-c2cc(F)c(C(F)F)cc2F)nc(C(=O)O)c1Cl] | Off White Solid | 62 |
| 179 | 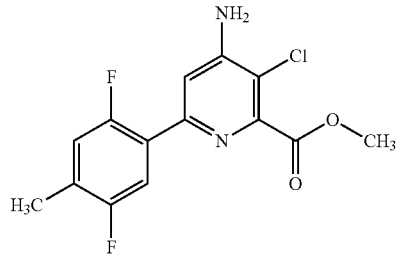 | White Solid | 63 |
| 180 | 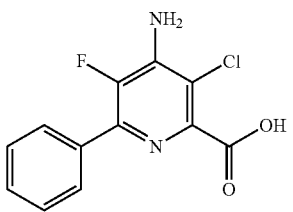 [SMILES: Nc1c(F)c(-c2ccccc2)nc(C(=O)O)c1Cl] | White Solid | 101 |
| 181 | 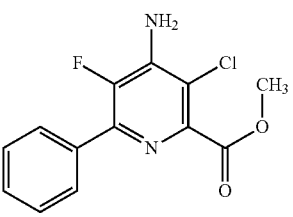 [SMILES: COC(=O)c1nc(-c2ccccc2)c(F)c(N)c1Cl] | | 57 |
| 183 | 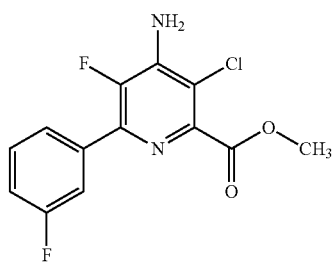 [SMILES: COC(=O)c1nc(-c2cccc(F)c2)c(F)c(N)c1Cl] | Pale Yellow Oil | 46 |
| 184 | 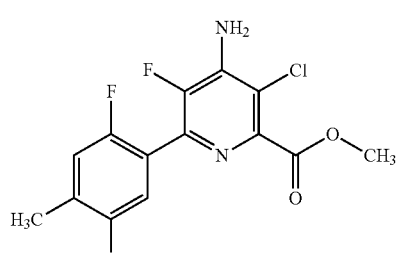 | White Solid | 63 |

TABLE 1-continued

Compound Number, Structure, Preparation and Appearance

| Cmpd. No. | Structure | Appearance | Prepared as in Example: |
|---|---|---|---|
| 185 | 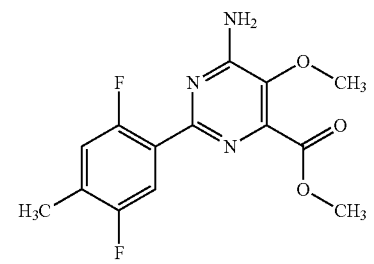 | White Solid | 63 |
| 186 | 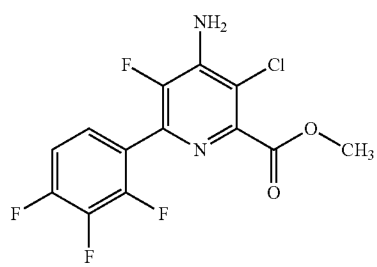 [SMILES: COC(=O)c1nc(-c2ccc(F)c(F)c2F)c(F)c(N)c1Cl] | White Solid | 41 |
| 187 | 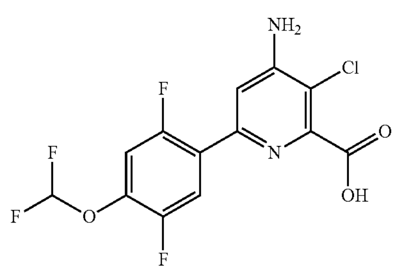 [SMILES: Nc1cc(-c2cc(F)c(OC(F)F)cc2F)nc(C(=O)O)c1Cl] | White Solid | 98 |
| 188 | 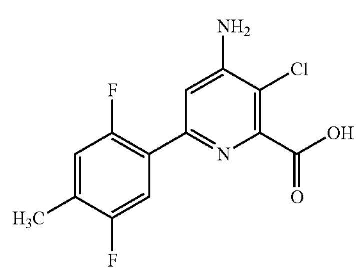 [SMILES: Cc1cc(F)c(-c2cc(N)c(Cl)c(C(=O)O)n2)cc1F] | White Solid | 62 |
| 189 | 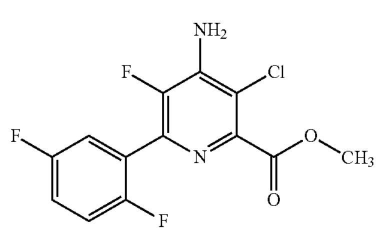 [SMILES: COC(=O)c1nc(-c2cc(F)ccc2F)c(F)c(N)c1Cl] | White Solid | 46 |

TABLE 1-continued

Compound Number, Structure, Preparation and Appearance

| Cmpd. No. | Structure | Appearance | Prepared as in Example: |
|---|---|---|---|
| 190 | 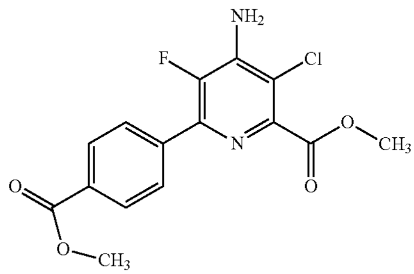 [SMILES: COC(=O)c1ccc(-c2nc(C(=O)OC)c(Cl)c(N)c2F)cc1] | White Solid | 43 |
| 191 | 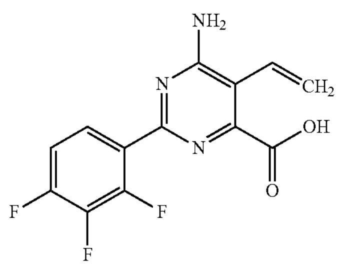 [SMILES: C=Cc1c(N)nc(-c2ccc(F)c(F)c2F)nc1C(=O)O] | Yellow Solid | 92 |
| 192 | 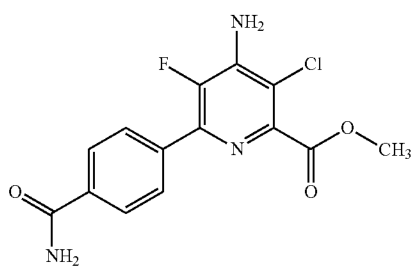 [SMILES: COC(=O)c1nc(-c2ccc(C(N)=O)cc2)c(F)c(N)c1Cl] | White Solid | 43 |
| 193 | 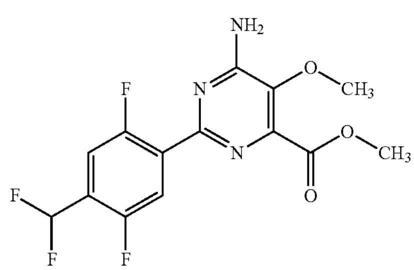 [SMILES: COC(=O)c1nc(-c2cc(F)c(C(F)F)cc2F)nc(N)c1OC] | White Solid | 63 |
| 194 | 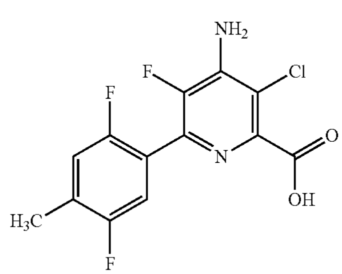 [SMILES: Cc1cc(F)c(-c2nc(C(=O)O)c(Cl)c(N)c2F)cc1F] | White Solid | 62 |

TABLE 1-continued

Compound Number, Structure, Preparation and Appearance

| Cmpd. No. | Structure | Appearance | Prepared as in Example: |
|---|---|---|---|
| 195 | 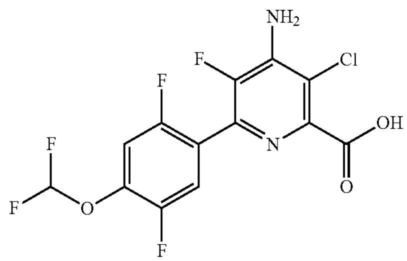 [SMILES: Nc1c(F)c(-c2cc(F)c(OC(F)F)cc2F)nc(C(=O)O)c1Cl] | White Solid | 98 |
| 196 | 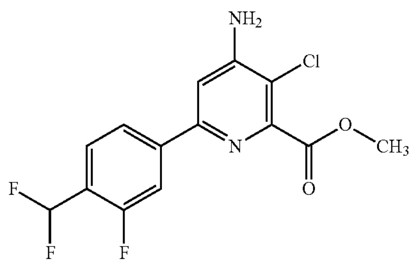 [SMILES: COC(=O)c1nc(-c2ccc(C(F)F)c(F)c2)cc(N)c1Cl] | White Powder | 47 |
| 197 | 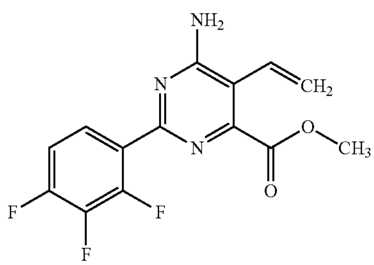 [SMILES: C=Cc1c(N)nc(-c2ccc(F)c(F)c2F)nc1C(=O)OC] | Yellow Solid | 39 |
| 198 | 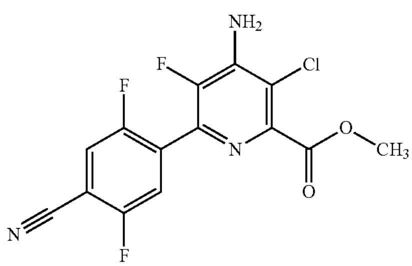 [SMILES: COC(=O)c1nc(-c2cc(F)c(C#N)cc2F)c(F)c(N)c1Cl] | White Solid | 63 |
| 199 | 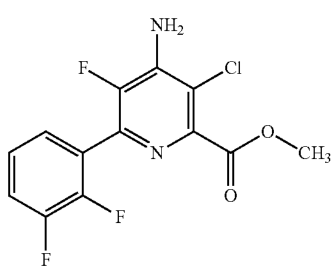 [SMILES: COC(=O)c1nc(-c2cccc(F)c2F)c(F)c(N)c1Cl] | Tan Solid | 57 |
| 200 | 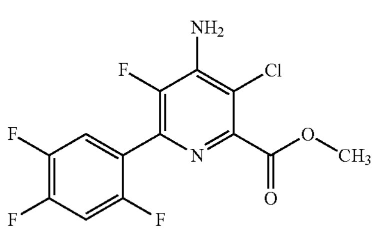 | White Powder | 40 |

TABLE 1-continued

Compound Number, Structure, Preparation and Appearance

| Cmpd. No. | Structure | Appearance | Prepared as in Example: |
|---|---|---|---|
| 201 | 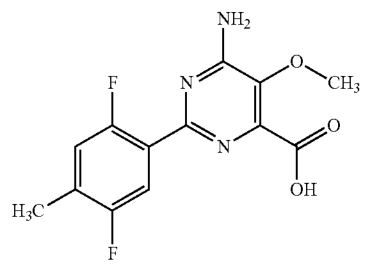 | White Solid | 62 |
| 202 | 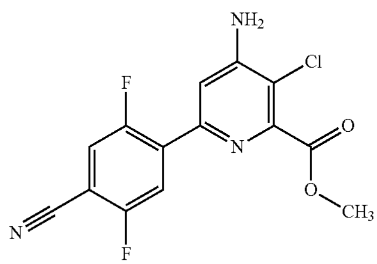 [SMILES: COC(=O)c1nc(-c2cc(F)c(C#N)cc2F)cc(N)c1Cl] | White Solid | 63 |
| 203 | 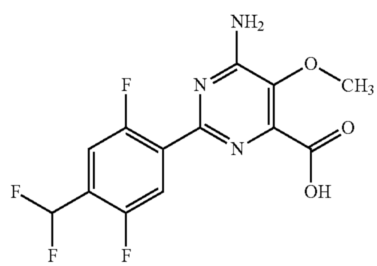 [SMILES: COc1c(N)nc(-c2cc(F)c(C(F)F)cc2F)nc1C(=O)O] | White Solid | 62 |
| 204 | 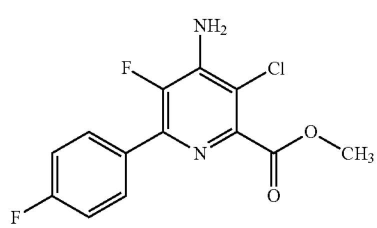 | White Solid | 41 |
| 205 | 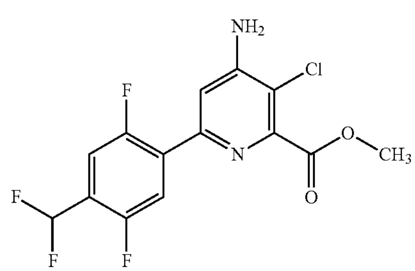 [SMILES: COC(=O)c1nc(-c2cc(F)c(C(F)F)cc2F)cc(N)c1Cl] | White Solid | 62 |
| 206 | 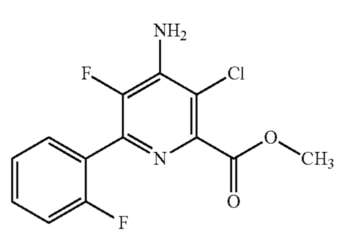 [SMILES: COC(=O)c1nc(-c2ccccc2F)c(F)c(N)c1Cl] | Tan Solid | 57 |

TABLE 1-continued

Compound Number, Structure, Preparation and Appearance

| Cmpd. No. | Structure | Appearance | Prepared as in Example: |
|---|---|---|---|
| 207 | 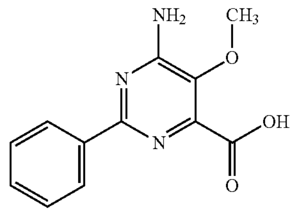 [SMILES: COc1c(N)nc(-c2ccccc2)nc1C(=O)O] | Tan Solid | 101 |
| 208 | 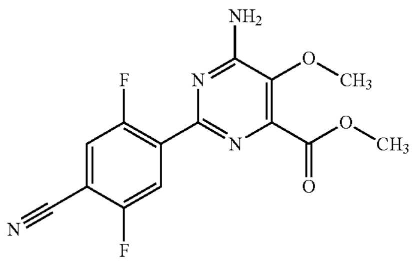 [SMILES: COC(=O)c1nc(-c2cc(F)c(C#N)cc2F)nc(N)c1OC] | White Solid | 63 |
| 209 | 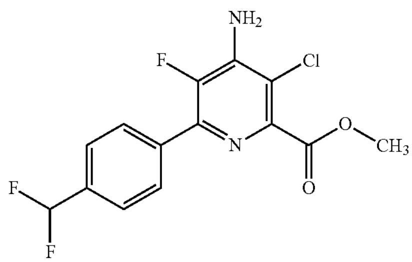 [SMILES: COC(=O)c1nc(-c2ccc(C(F)F)cc2)c(F)c(N)c1Cl] | White Powder | 47 |
| 210 | 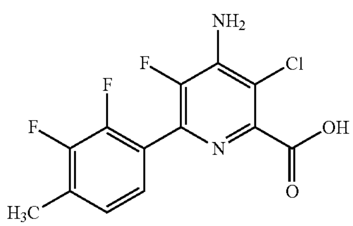 [SMILES: Cc1ccc(-c2nc(C(=O)O)c(Cl)c(N)c2F)c(F)c1F] | | 95 |
| 211 | 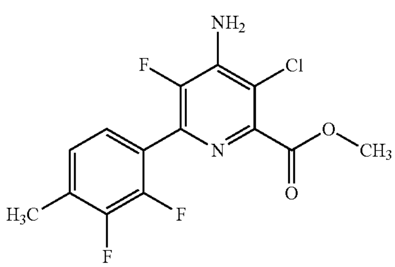 | White Solid | 41 |
| 212 | 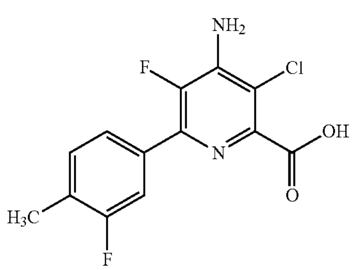 [SMILES: Cc1ccc(-c2nc(C(=O)O)c(Cl)c(N)c2F)cc1F] | | 95 |

TABLE 1-continued

Compound Number, Structure, Preparation and Appearance

| Cmpd. No. | Structure | Appearance | Prepared as in Example: |
|---|---|---|---|
| 213 | 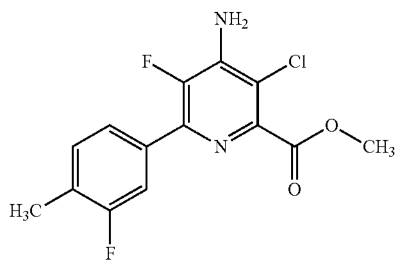 | White Solid | 41 |
| 214 | 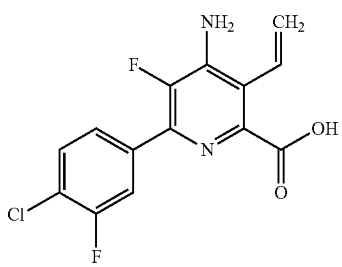 [SMILES: C=Cc1c(C(=O)O)nc(-c2ccc(Cl)c(F)c2)c(F)c1N] | White Solid | 98 |
| 215 | 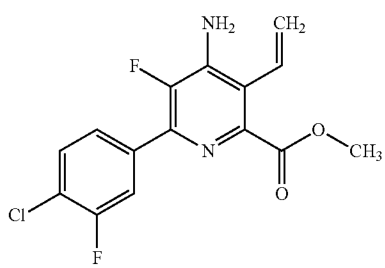 [SMILES: C=Cc1c(C(=O)OC)nc(-c2ccc(Cl)c(F)c2)c(F)c1N] | White Solid | 90 |
| 216 | 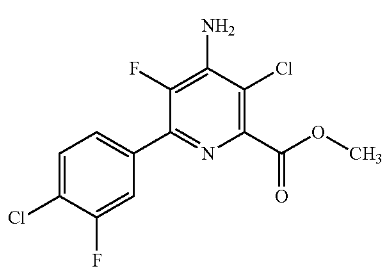 [SMILES: COC(=O)c1nc(-c2ccc(Cl)c(F)c2)c(F)c(N)c1Cl] | White Solid | 42 |
| 217 | 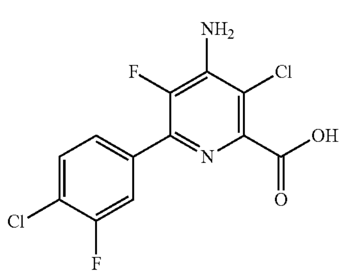 [SMILES: Nc1c(F)c(-c2ccc(Cl)c(F)c2)nc(C(=O)O)c1Cl] | Off-White Solid | 97 |

TABLE 2

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 1 | 133.4-134.8 | | ESIMS m/z 322 ([M + H]$^+$) | $^1$H NMR (400 MHz, CDCl$_3$) δ 7.81 (m, 4H), 5.42 (s, 2H), 4.02 (s, 3H) | |
| 2 | 186-187 | | ESIMS m/z 373 ([M − H]$^-$) | $^1$H NMR (400 MHz, CDCl$_3$) δ 7.78 (dd, J = 9.0, 6.5 Hz, 1H), 7.37 (dd, J = 9.6, 5.6 Hz, 1H), 5.43 (s, 2H), 4.01 (s, 3H), 3.95 (s, 3H) | $^{19}$F NMR (376 MHz, CDCl$_3$) δ −113.66, −113.70, −117.53, −117.58 |
| 3 | 172-174 | | ESIMS m/z 364 ([M + H]$^+$) | $^1$H NMR (400 MHz, DMSO-d$_6$) δ 7.89-7.84 (m, 2H), 7.26 (d, J = 1.2 Hz, 1H), 6.85 (s, 2H) | $^{19}$F NMR (376 MHz, DMSO-d$_6$) δ −108.94, −108.99, −114.18, −114.22 |
| 4 | | | ESIMS m/z 375 ([M + H]$^+$) | $^1$H NMR (400 MHz, DMSO-d$_6$) δ 7.85 (m, 2H), 7.69 (m, 2H), 7.24 (s, H1), 6.73 (br s, 2H) | |
| 5 | 164-168 | | | $^1$H NMR (400 MHz, DMSO-d$_6$) δ 13.65 (s, 1H), 8.12-7.89 (m, 2H), 7.80 (dd, J = 8.0, 1.6 Hz, 1H), 7.32 (d, J = 4.8 Hz, 2H), 6.66 (dd, J = 17.7, 11.4 Hz, 1H), 5.75-5.41 (m, 2H) | $^{19}$F NMR (376 MHz, DMSO-d$_6$) δ −111.46 |
| 6 | 175.0-176.5 | | ESIMS m/z 303 ([M − H]$^-$) | $^1$H NMR (400 MHz, DMSO-d$_6$) δ 13.38 (s, 1H), 7.62 (t, J = 7.7 Hz, 1H), 7.40 (dd, J = 10.4, 1.5 Hz, 1H), 7.31 (dd, J = 7.9, 1.6 Hz, 1H), 6.51 (s, 2H), 4.59 (s, 1H), 2.09 (s, 3H) | $^{19}$F NMR (376 MHz, DMSO-d$_6$) δ −111.32 |
| 7 | 127-130 | IR (thin film) 3478 (s), 3374 (s), 3239 (s), 2955 (w), 1731 (m), 1624 (m) cm$^{-1}$ | ESIMS m/z 305 ([M + H]$^+$) | $^1$H NMR (400 MHz, CDCl$_3$) δ 7.91 (m, 2H), 7.58 (m, 2H), 4.90 (br s, 2H), 3.99 (s, 3H), 3.16 (s, 1H) | |
| 8 | 126-128 (dec) | | ESIMS m/z 360 ([M + H]$^+$) | $^1$H NMR (400 MHz, DMSO-d$_6$) δ 13.64 (s, 1H), 7.74-7.56 (m, 2H), 7.45 (s, 2H), 3.76 (s, 3H) | $^{19}$F NMR (376 MHz, DMSO) δ −131.53, −131.58, −136.08, −136.14. |
| 9 | 136-138 | IR (thin film) 3489 (s), 3381 (s), 3233 (m), 3199 (m), 3083 (w), 3000 (w), 2954 (m), 2853 (w), 1737 (s), 1622 (s) cm$^{-1}$ | ESIMS m/z 425 ([M + H]$^+$) | $^1$H NMR (400 MHz, CDCl$_3$) δ 7.88 (dd, J = 8, 1.5 Hz, 1H), 7.55 (dd, J = 10, 1.5 Hz, 1H), 7.33 (dd, J = 8.5, 8 Hz, 1H), 4.94 (br s, 2H), 3.96 (s, 3H) | |
| 10 | 170.4-172.1 | | ESIMS m/z 315 ([M + H]$^+$) | $^1$H NMR (400 MHz, DMSO-d$_6$) δ 7.97 (d, 2H), 7.30 (m, 5H), 6.72 (s, 2H) | |
| 11 | 132-133 | | ESIMS m/z 359 ([M − H]$^-$) | $^1$H NMR (400 MHz, DMSO-d$_6$) δ 7.86-7.73 (m, 2H), 7.43 (s, 2H), 3.75 (s, 3H) | $^{19}$F NMR (376 MHz, DMSO-d$_6$) δ −114.36, −114.40, −116.52, −116.57. |
| 12 | 77-78 | | ESIMS m/z 359 ([M + H]$^+$) | $^1$H NMR (400 MHz, CDCl$_3$) δ 7.86 (dd, J = 9.0, 6.9 Hz, 2H), 7.69 (t, J = 7.8 Hz, 1H), 6.90 (dd, J = 18.1, 11.6 Hz, 1H), 5.74 (dd, J = 11.6, 1.3 Hz, 1H), 5.60 (dd, J = 18.1, 1.3 Hz, 1H), 4.78 (s, 2H), 3.94 (s, 3H) | |
| 13 | | | ESIMS m/z 442 ([M + H]$^+$) | $^1$H NMR (400 MHz, DMSO-d$_6$) δ 7.95 (dd, J = 8.1, 6.7 Hz, 1H), 7.47 (dd, J = 9.1, 1.9 Hz, 1H), 7.22 (dd, J = 8.1, 1.9 Hz, 1H), 7.14 (s, 2H), 3.87 (s, 3H) | $^{19}$F NMR (376 MHz, DMSO-d$_6$) δ −95.18 |

TABLE 2-continued

Analytical Data for Compounds in Table 1

| Compd. No. | mp (° C.) | IR (cm⁻¹) | Mass[a] | ¹H NMR[b] | ¹³C or ¹⁹F NMR |
|---|---|---|---|---|---|
| 14 | 178.0-179.7 | | ESIMS m/z 308 ([M + H]⁺) | ¹H NMR (400 MHz, DMSO-$d_6$) δ 7.95 (d, 2H), 7.80 (d, 2H), 7.09 (s, 2H) | |
| 15 | 102.4-103.6 | | ESIMS m/z 363 ([M + H]⁺) | ¹H NMR (400 MHz, CDCl₃) δ 7.72 (d, 2H), 7.24 (d, 2H), 5.42 (s, 2H), 4.02 (s, 3H) | |
| 16 | | | ESIMS m/z 306 ([M + H]⁺) | ¹H NMR (400 MHz, DMSO-$d_6$) δ 8.01 (m, 2H), 7.79 (dd, J = 8.1, 1.5 Hz, 1H), 7.30 (d, J = 1.5 Hz, 1H), 6.96 (s, 2H), 3.89 (s, 3H) | |
| 17 | | | ESIMS m/z 385 ([M + H]⁺) | ¹H NMR (400 MHz, DMSO-$d_6$) δ 13.12 (s, 1H), 7.87 (d, J = 8.4 Hz, 2H), 7.66 (d, J = 7.6 Hz, 2H), 6.75 (dd, J = 17.8, 11.5 Hz, 1H), 6.41 (s, 2H), 5.55 (dd, J = 14.2, 1.1 Hz, 1H), 5.52 (dd, J = 7.8, 1.1 Hz, 1H) | ¹⁹F NMR (376 MHz, DMSO-$d_6$) δ -145.75 |
| 18 | | | ESIMS m/z 387 ([M + H]⁺) | ¹H NMR (400 MHz, CDCl₃) δ 8.04 (m, 2H), 7.77 (m, 2H), 5.36 (br s, 2H), 4.01 (s, 3H), 3.91 (s, 3H) | |
| 19 | 113-115 | IR (thin film) 1025.80, 1047.25, 1126.02, 1225.15, 1266.03, 1299.98, 1386.12, 1481.90, 1515.13, 1585.75, 1633.93, 1721.56, 2536.01, 3199.39, 3331.39, 3471.03 cm⁻¹ | ESIMS m/z 369 ([M + H]⁺) | ¹H NMR (400 MHz, DMSO-$d_6$) δ 13.70 (s, 1H), 7.47 (ddd, J = 9.2, 7.2, 2.0 Hz, 1H), 7.40 (d, J = 3.0 Hz, 1H), 7.37 (t, J = 72.3 Hz, 1H), 7.07 (s, 2H) | |
| 20 | 149-152 | | ESIMS m/z 347 ([M + H]⁺) | NMR (400 MHz, DMSO) δ 7.85-7.77 (m, 2H), 7.75-7.68 (m, 2H), 6.94 (s, 2H) | |
| 21 | 117-120 | IR (thin film) 3468 (s), 3334 (s), 3198 (s), 1717 (w), 1629 (m), 1573 (w) cm⁻¹ | ESIMS m/z 365 ([M + H]⁺) | ¹H NMR (400 MHz, DMSO-$d_6$) δ 7.88 (dd, J = 9, 8 Hz, 1H), 7.82 (dd, J = 9, 1.5 Hz, 1H), 7.70 (d, J = 9 Hz, 1H), 6.73 (br s, 2H) | |
| 22 | 190-192 | IR (thin film) 3512 (m), 3411 (s), 3248 (s), 2954 (w), 1730 (m), 1616 (m) cm⁻¹ | ESIMS m/z 341 ([M + H]⁺) | ¹H NMR (400 MHz, CDCl₃) δ 7.33-7.35 (m, 2H), 4.98 (br s, 2H), 3.98 (s, 3H), 3.43 (s, 1H) | |
| 23 | 166.4-169.0 | | ESIMS m/z 329 ([M + H]⁺) | ¹H NMR (400 MHz, CDCl₃) δ 7.95 (d, 2H), 7.31 (m, 3H), 6.85 (s, 2H), 3.92 (s, 3H) | |
| 24 | 169-170 | | ESIMS m/z 422 ([M + H]⁺) | ¹H NMR (400 MHz, CDCl₃) δ 7.58-7.43 (m, 2H), 5.53 (s, 2H), 4.00 (s, 3H), 3.95 (s, 3H) | |
| 25 | 185.2-186.1 | | ESIMS m/z 271 ([M + H]⁺) | ¹H NMR (400 MHz, DMSO-$d_6$) δ 13.6 (s, 1H), 8.40 (d, 2H), 7.96 (d, 2H), 7.46 (s, 2H), 3.79 (s, 3H) | |
| 26 | | IR (thin film) 3401, 1739, 1638 cm⁻¹ | ESIMS m/z 346 ([M + H]⁺) | ¹H NMR (400 MHz, DMSO) δ 8.19 (t, J = 16.1 Hz, 1H), 8.11 (d, J = 12.3 Hz, 1H), 7.92 (t, J = 7.9 Hz, 1H), 7.74-7.46 (m, 2H), 3.92 (s, 3H), 3.76 (s, 3H) | ¹⁹F NMR (376 MHz, DMSO) δ -59.9, -115.7, -116.0. |
| 27 | | | ESIMS m/z 403 ([M + H]⁺) | ¹H NMR (400 MHz, DMSO-$d_6$) δ 8.00-7.87 (m, 2H), 7.82 (dd, J = 8.3, 1.8 Hz, 1H), 7.49 (s, 2H), 3.90 (s, 3H), 3.74 (s, 3H) | ¹⁹F NMR (376 MHz, DMSO-$d_6$) δ -95.51 |
| 28 | 170.7-171.3 | | ESIMS m/z 270 ([M + H]⁺) | ¹H NMR (400 MHz, DMSO-$d_6$) δ 13.6 (s, 1H), 8.25 (d, 2H), 7.59 (d, 2H), 7.36 (s, 2H), 4.35 (s, 1H), 3.77 (s, 3H) | |
| 29 | 145-146 | | ESIMS m/z 349 ([M + H]⁺) | ¹H NMR (400 MHz, CDCl₃) δ 7.79 (dd, J = 15.8, 9.9 Hz, | ¹⁹F NMR (376 MHz, CDCl₃) δ -61.3, -113.9 |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 30 | 122.0-123.6 | | ESIMS m/z 343 ([M + H]$^+$) | 2H), 7.66 (t, J = 7.7 Hz, 1H), 7.12 (s, 1H), 4.90 (s, 2H), 4.02 (s, 3H) $^1$H NMR (400 MHz, CDCl$_3$) δ 8.33 (d, 2H), 7.27 (d, 2H), 5.84 (s, 2H), 4.03 (s, 3H), 3.95 (s, 3H) | |
| 31 | 180-181 | | | $^1$H NMR (400 MHz, DMSO-d$_6$) δ 13.71 (s, 1H), 8.40-8.33 (m, 2H), 8.13 (d, J = 8.3, 2H), 7.07 (s, 2H) | |
| 32 | 168-171 | | ESIMS m/z 328 ([M + H]$^+$) | $^1$H NMR (400 MHz, DMSO-d$_6$) δ 13.68 (s, 1H), 8.28 (d, J = 8.2 Hz, 1H), 8.20 (d, J = 12.2 Hz, 1H), 7.94 (t, J = 7.9 Hz, 1H), 7.35 (d, J = 27.9 Hz, 2H), 6.68 (dd, J = 17.7, 11.5 Hz, 1H), 5.75-5.46 (m, 2H) | $^{19}$F NMR (376 MHz, DMSO-d$_6$) δ −59.97 (d, J = 12.2 Hz), −115.77 (q, J = 12.2 Hz) |
| 33 | 146.3-147.6 | | ESIMS m/z 349 ([M + H]$^+$) | $^1$H NMR (400 MHz, DMSO-d$_6$) δ 13.7 (s, 1H), 7.68 (d, 2H), 7.32 (d, 2H), 6.96 (s, 2H) | |
| 34 | 164.2-166.8 | | ESIMS m/z 321 ([M + H]$^+$) | 6.30 (m, 5H), 5.35 (s, 2H), 3.98 (s, 3H) | |
| 35 | 163-165 | IR (thin film) 3416 (s), 3355 (w), 3300 (m), 3162 (s), 2957 (w), 1730 (s), 1637 (s) cm$^{-1}$ | ESIMS m/z 358 ([M + H]$^+$) | $^1$H NMR (400 MHz, CDCl$_3$) δ 7.84 (t, J = 9 Hz, 1H), 7.31-7.37 (m, 2H), 5.41 (br s, 2H), 3.99 (s, 3H), 3.93 (s, 3H) | |
| 36 | | | ESIMS m/z 282 ([M + H]$^-$) | $^1$H NMR (400 MHz, CDCl$_3$) δ 7.93-7.84 (m, 2H), 7.64-7.54 (m, 2H), 6.75 (dd, J = 17.8, 11.5 Hz, 1H), 6.36 (s, 2H), 5.57 (dd, J = 17.8, 1.4 Hz, 1H), 5.50 (dd, J = 11.5, 1.4 Hz, 1H), 4.31 (s, 1H) | $^{19}$F NMR (376 MHz, CDCl$_3$) δ−141.43 |
| 37 | | | ESIMS m/z 390 ([M + H]$^+$) | $^1$H NMR (400 MHz, DMSO-d$_6$) δ 13.57 (s, 1H), 8.02-7.92 (m, 2H), 7.85 (dd, J = 8.2, 1.8 Hz, 1H), 7.41 (s, 2H), 3.75 (s, 3H) | $^{19}$F NMR (376 MHz, DMSO-d$_6$) δ −95.59. |
| 38 | 288-293 (dec) | IR (thin film) 3473 (s), 1588 (m) cm$^{-1}$ | ESIMS m/z 411 ([M + H]$^+$) | $^1$H NMR (400 MHz, DMSO-d$_6$) δ 7.74 (m, 1H), 7.55 (m, 1H), 7.02 (d, J = 1.5 Hz, 1H), 6.30 (br s, 2H) | |
| 39 | | | ESIMS m/z 292 ([M + H]$^+$) | $^1$H NMR (400 MHz, DMSO-d$_6$) δ 8.08-7.92 (m, 4H), 7.03 (s, 2H) | |
| 40 | | | ESIMS m/z 301 ([M + H]$^+$) | $^1$H NMR (400 MHz, CDCl$_3$) δ 7.55 (d, J = 8.4 Hz, 2H), 7.42 (d, J = 8.5 Hz, 2H), 4.83 (s, 2H), 3.96 (s, 3H), 3.12 (s, 1H), 2.16 (s, 3H) | $^{13}$C NMR (101 MHz, CDCl$_3$) δ 165.71, 155.51, 149.15, 145.10, 140.11, 132.02, 129.34, 122.02, 116.77, 113.59, 83.42, 77.90, 52.87, 14.65 |
| 41 | 155-165 (dec) | IR (thin film) 3297 (s), 3218 (s), 2938 (w), 1618 (s), 1576 (m) cm$^{-1}$ | ESIMS m/z 288 ([M + H]$^+$) | $^1$H NMR (400 MHz, DMSO-d$_6$) δ 7.80 (t, J = 8 Hz, 1H), 7.35-7.40 (m, 2H), 6.66 (br s, 2H), 4.41 (s, 1H), 3.76 (s, 3H) | |
| 42 | 156-157 | | ESIMS m/z 382 ([M + H]$^+$) | $^1$H NMR (400 MHz, DMSO-d$_6$) δ 13.63 (s, 1H), 7.92 (dd, J = 9.0, 5.7 Hz, 1H), 7.61 (dd, J = 8.4, 6.3 Hz, 1H), 7.06 (s, 2H) | $^{19}$F NMR (376 MHz, DMSO-d$_6$) δ −113.46, −113.50, −117.37, −117.41, −117.45, −117.49, −138.28, −138.36. |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 43 | | | ESIMS m/z 381 ([M + H]$^+$) | $^1$H NMR (400 MHz, DMSO-d$_6$) δ 13.72 (s, 1H), 7.82 (dd, J = 8.3, 7.3 Hz, 1H), 7,60 (dd, J = 9.8, 2.0 Hz, 1H), 7.40 (dd, J = 8.3, 2.0 Hz, 1H), 7.06 (s, 2H) | $^{19}$F NMR (376 MHz, DMSO-d$_6$) δ −108.25. |
| 44 | | | ESIMS m/z 324 ([M + H]$^+$) | $^1$H NMR (400 MHz, DMSO-d$_6$) δ, 8.05 (dd, J = 10.0, 1.5 Hz, 1H), 7.85 (dd, J = 8.0, 1.5 Hz, 1H), 7.73-7.81 (m, 1H) 7.18 (s, 2H), 3.87 (s, 3H) | $^{19}$F NMR (376 MHz, DMSO-d$_6$) δ −112.13 (d, J = 28.4 Hz), −137.43 (d, J = 28.4 Hz) |
| 45 | 148-150 | | ESIMS m/z 393 ([M + H]$^+$) | $^1$H NMR (300 MHz, DMSO-d$_6$) δ 7.87 (m, 2H), 7.62 (m, 2H), 6.91 (br s, 2H) | |
| 46 | 133-135 | IR (thin film) 3490 (s), 3350 (s), 1753 (w), 1634 (m), 1607 (m) cm$^{-1}$ | ESIMS m/z 344 ([M + H]$^+$) | $^1$H NMR (400 MHz, DMSO-d$_6$) δ 13.60 (br s, 1H), 7.81 (t, J = 9 Hz, 1H), 7.63 (dd, J = 11, 2 Hz, 1H), 7.52 (dd, J = 9, 2 Hz, 1H), 7.38 (br s, 2H), 3.76 (s, 3H) | |
| 47 | 159.6-161.1 | | ESIMS m/z 377 ([M + H]$^+$) | $^1$H NMR (400 MHz, CDCl$_3$) δ 7.58 (m, 4H), 5.36 (s, 2H), 3.99 (s, 3H) | |
| 48 | 204.2-205.9 | | ESIMS m/z 273 ([M + H]$^+$) | $^1$H NMR (400 MHz, DMSO-d$_6$) δ 13.5 (s, 1H), 7.94 (d, 2H), 7.60 (d, 2H), 7.30 (s, 1H), 6.69 (s, 2H) | |
| 49 | 114-116 | IR (thin film) 3492 (s), 3378 (s), 3235 (w), 2955 (w), 2927 (w), 1736 (s), 1621 (s) cm$^{-1}$ | ESIMS m/z 379 ([M + H]$^+$) | $^1$H NMR (300 MHz, CDCl$_3$) δ 7.76 (m, 1H), 7.60-7.68 (m, 2H), 4.94 (br s, 2H), 3.99 (s, 3H) | |
| 50 | 174-176 | IR (thin film) 3305 (s), 1720 (w), 1634 (m), 1586 (w) cm$^{-1}$ | ESIMS m/z 327 ([M + H]$^+$) | $^1$H NMR (400 MHz, DMSO-d$_6$) δ 7.53 (dd, J = 8, 7 Hz, 1H), 7.41 (m, 1H), 6.93 (br s, 2H), 4.81 (s, 1H) | |
| 51 | 153-154 | | ESIMS m/z 394 ([M − H]−) | $^1$H NMR (400 MHz, CDCl$_3$) δ 7.42-7.38 (m, 2H), 4.98 (s, 2H), 3.99 (s, 3H) | $^{19}$F NMR (376 MHz, CDCl$_3$) δ −112.74, −112.78, −116.99, −117.03, −117.09, −117.13, −137.28, −137.38. |
| 52 | 146-148 | IR (neat film) 3519 (m), 3473 (m), 3420 (s), 3379 (s), 3196 (w), 3075 (w), 2955 (w), 2852 (w), 1736 (s), 1616 (s) cm$^{-1}$ | ESIMS m/z 379 ([M + H]$^+$) | $^1$H NMR (400 MHz, CDCl$_3$) δ 7.50 (dd, J = 8, 7 Hz, 1H), 7.42 (dd, J = 8, 2 Hz, 1H), 7.36 (dd, J = 10, 2 Hz, 1H), 4.93 (br s, 2H), 3.96 (s, 3H) | |
| 53 | 118-120 | | ESIMS m/z 377 ([M + H]$^+$) | $^1$H NMR (400 MHz, CDCl$_3$) δ 7.53-7.45 (m, 2H), 6.91 (dd, J = 18.1, 11.6 Hz, 1H), 5.76 (dd, J = 11.6, 1.3 Hz, 1H), 5.61 (dd, J = 18.1, 1.3 Hz, 1H), 4.81 (s, 2H), 3.92 (s, 3H) | $^{19}$F NMR (376 MHz, CDCl$_3$) δ −61.16, −61.20, −135.77, −135.83, −135.86, −135.92, −138.61, −138.65, −138.67, −138.68, −138.70, −138.72, −138.74, −138.77, −140.73, −140.82. |
| 54 | | | ESIMS m/z 326.07 ([M + H]$^+$) | $^1$H NMR (400 MHz, DMSO-d$_6$) δ 8.15 (m, 2H), 7.67 (m, 2H), 7.45 (br s, 2H), 3.75 (s, 3H) | |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 55 | 142-144 | | ESIMS m/z 443 ([M + H]$^+$) | $^1$H NMR (400 MHz, CDCl$_3$) δ 7.56 (dd, J = 8.5, 4.9 Hz, 1H), 7.32 (dd, J = 7.6, 5.8 Hz, 1H), 4.97 (s, 2H), 3.98 (s, 3H) | $^{19}$F NMR (376 MHz, CDCl$_3$) δ −99.87, −99.91, −117.70, −117.74, −117.80, −117.84, −137.25, −137.35. |
| 56 | 142-144 | | ESIMS m/z 425 ([M + H]$^+$) | $^1$H NMR (400 MHz, CDCl$_3$) δ 7.80 (dd, J = 8.5, 6.5 Hz, 1H), 7.53 (dd, J = 10.0, 5.0 Hz, 1H), 7.25 (d, J = 1.2 Hz, 1H), 4.86 (s, 2H), 4.01 (s, 3H) | $^{19}$F NMR (376 MHz, CDCl$_3$) δ −100.00, −100.05, −120.62, −120.66. |
| 57 | 93-94 | | ESIMS m/z 352 ([M + H]$^+$) | $^1$H NMR (400 MHz, CDCl$_3$) δ 7.86-7.79 (m, 2H), 7.62-7.56 (m, 2H), 6.89 (dd, J = 18.1, 11.5 Hz, 1H), 5.71 (dd, J = 11.6, 1.4 Hz, 1H), 5.58 (dd, J = 18.1, 1.4 Hz, 1H), 4.71 (s, 2H), 3.93 (s, 3H) | $^{19}$F NMR (376 MHz, CDCl$_3$) δ −144.04. |
| 58 | | IR (thin film) 3367, 1735, 1608 cm$^{-1}$. | ESIMS m/z 381 ([M + H]$^+$) | $^1$H NMR (400 MHz, DMSO) δ 7.91 (t, J = 7.8 Hz, 1H), 7.74 (d, J = 11.6 Hz, 1H), 7.62 (d, J = 8.1 Hz, 1H), 7.20 (d, J = 21.4 Hz, 2H), 3.87 (s, 3H) | $^{19}$F NMR (376 MHz, DMSO) δ −59.9, −115.6, −116.3. |
| 59 | 203-205 | IR (thin film) 3425 (m), 3297 (m), 3245 (s), 3158 (m), 3008 (w), 2956 (w), 1729 (m), 1637 (m) cm$^{-1}$ | ESIMS m/z 302 ([M + H]$^+$) | $^1$H NMR (400 MHz, CDCl$_3$) δ 7.91 (t, J = 8 Hz, 1H), 7.32 (dd, J = 8, 1.5 Hz, 1H), 7.26 (dd, J = 12, 1.5 Hz, 1H), 5.40 (br s, 2H), 3.99 (s, 3H), 3.93 (s, 3H), 3.15 (s, 1H) | |
| 60 | | | ESIMS m/z 297 ([M + H] + 1) | $^1$H NMR (400 MHz, CDCl$_3$) δ 7.93 (ddd, J = 8.2, 1.6, 0.7 Hz, 2H), 7.65-7.54 (m, 2H), 6.90 (ddd, J = 18.1, 11.6, 0.5 Hz, 1H), 5.71 (dd, J = 11.5, 1.4 Hz, 1H), 5.58 (dd, J = 18.1, 1.4 Hz, 1H), 4.71 (s, 2H), 3.93 (s, 3H) | $^{19}$F NMR (376 MHz, CDCl$_3$) δ −143.86 |
| 61 | | | ESIMS m/z 361 ([M − H]$^−$) | $^1$H NMR (400 MHz, CDCl$_3$) δ 7.55-7.45 (m, 2H), 7.25 (dd, J = 18.3, 11.6 Hz, 1H), 5.85 (dd, J = 11.7, 1.2 Hz, 1H), 5.64 (dd, J = 18.4, 1.2 Hz, 1H), 5.11 (s, 2H) | −61.22, −61.25, −135.48, −135.54, −135.57, −135.62, −137.62, −137.66, −137.68, −137.69, −137.71, −137.73, −137.75, −137.78, −137.87, −137.95. |
| 62 | 142-147 (dec) | IR (thin film) 3317 (s), 3199 (s), 2955 (w), 2924 (w), 2870 (w), 2256 (w), 1721 (m), 1634 (m) cm$^{-1}$ | ESIMS m/z 291 ([M + H]$^+$) | $^1$H NMR (300 MHz, DMSO-d$_6$) δ 7.86 (m, 2H), 7.61 (m, 2H), 6.93 (br s, 2H), 4.33 (s, 1H) | |
| 63 | | IR (thin film) 2979, 1715 cm$^{-1}$ | ESIMS m/z 332 ([M + H]$^+$) | $^1$H NMR (400 MHz, DMSO) δ 8.22 (t, J = 10.7 Hz, 1H), 8.17 (d, J = 12.3 Hz, 1H), 7.90 (dd, J = 21.3, 13.4 Hz, 1H), 7.56 (d, J = 44.0 Hz, 3H), 3.77 (s, 3H) | $^{19}$F NMR (376 MHz, DMSO) δ −59.9, −115.3, −116.7. |
| 64 | 140-141 | | ESIMS m/z 364 ([M + H]$^+$) | $^1$H NMR (400 MHz, DMSO-d$_6$) δ 7.87 (t, J = 7.5 Hz, 1H), 7.72-7.66 (m, 1H), 7.58 (s, 2H), 3.90 (s, 3H), 3.78 (s, 3H) | |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 65 | | | ESIMS m/z 310 ([M + H]$^+$) | $^1$H NMR (400 MHz, DMSO-d$_6$) δ 13.71 (s, 1H), 8.05 (dd, J = 9.9, 1.4 Hz, 1H), 7.86 (dd, J = 8.0, 1.5 Hz, 1H), 7.75-7.81 (m, 1H), 7.09 (s, 2H) | $^{19}$F NMR (376 MHz, DMSO-d$_6$) δ −112.04 (d, J = 29.9 Hz), −138.35 (d, J = 29.6 Hz) |
| 66 | 141-143 | | ESIMS m/z 407 ([M + H]$^+$) | $^1$H NMR (400 MHz, DMSO-d$_6$) δ 7.95 (dd, 1H), 7.77 (dd, 1H), 7.52 (dd, 1H), 7.32 (s, 1H), 6.81 (s, 2H), 3.89 (s, 3H) | $^{19}$F NMR (376 MHz, DMSO-d$_6$) δ −95.03 |
| 67 | | | ESIMS m/z 341 ([M − H]$^+$) | $^1$H NMR (400 MHz, CDCl$_3$) δ 7.77 (m, 2H), 7.55 (m, 2H), 7.1 (s, 1H), 4.84 (br s, 2H), 4.00 (s, 3H) | |
| 68 | 170.1-172.6 | | ESIMS m/z 431 ([M + 3H]$^+$) | $^1$H NMR (400 MHz, DMSO-d$_6$) δ 6.85-6.77 (m, 3H), 7.79 (m, 1H) | |
| 69 | 159-161 | | ESIMS m/z 429 ([M + H]$^+$) | $^1$H NMR (400 MHz, CDCl$_3$) δ 11.14 (s, 1H), 7.63 (dd, J = 8.6, 4.9 Hz, 1H), 7.27 (dd, J = 7.5, 5.7 Hz, 1H), 5.21 (s, 2H) | $^{19}$F NMR (376 MHz, CDCl$_3$) δ −99.15, −99.20, −117.70, −117.74, −117.79, −117.83, −134.64, −134.71. |
| 70 | 114-116 | | ESIMS m/z 367 ([M + H]$^+$) | $^1$H NMR (400 MHz, CDCl$_3$) δ 7.97 (dd, J = 10.6, 6.3 Hz, 1H), 7.39 (dd, J = 10.5, 5.6 Hz, 1H), 7.30 (d, J = 1.2 Hz, 1H), 4.91 (s, 2H), 4.02 (s, 3H) | $^{19}$F NMR (376 MHz, CDCl$_3$) δ −61.69, −61.73, −119.19, −119.22, −119.24, −119.27, −120.01, −120.06. |
| 71 | 157-160 (dec) | IR (thin film) 3400 (s), 3300 (s), 3200 (m), 1711 (w), 1630 (m) cm$^{-1}$ | ESIMS m/z 309 ([M + H]$^+$) | $^1$H NMR (400 MHz, DMSO-d$_6$) δ 7.68-7.78 (m, 3H), 6.76 (br s, 2H), 4.66 (s, 1H) | |
| 72 | 95-98 | IR (thin film) 3327 (s), 2941 (w), 1718 (w), 1629 (m), 1603 (m) cm$^{-1}$ | ESIMS m/z 390 ([M + H]$^+$) | $^1$H NMR (400 MHz, DMSO-d$_6$) δ 13.67 (br s, 1H), 7.73 (dd, J = 11, 1.5 Hz, 1H), 7.68 (dd, J = 8.5, 1.5 Hz, 1H), 7.63 (t, J = 8.5 Hz, 1H), 7.33 (br s, 2H), 3.76 (s, 3H) | |
| 73 | | | ESIMS m/z 395 ([M + H]$^+$) | $^1$H NMR (400 MHz, DMSO-d$_6$) δ 7.82 (dd, J = 8.3, 7.3 Hz, 1H), 7.60 (dd, J = 9.8, 2.0 Hz, 1H), 7.40 (dd, J = 8.3, 2.0 Hz, 1H), 7.16 (s, 2H), 3.87 (s, 3H) | $^{19}$F NMR (376 MHz, DMSO-d$_6$) δ 108.20 |
| 74 | 186.0-187.3 | | ESIMS m/z 345 ([M + H]$^+$) | $^1$H NMR (400 MHz, DMSO-d$_6$) δ 13.6 (s, 1H), 7.87 (m, 1H), 7.72 (m, 1H), 7.57 (m, 1H), 7.23 (s, 1H), 6.18 (s, 2H) | |
| 76 | 169-170 | | ESIMS m/z 350 ([M + H]$^+$) | $^1$H NMR (400 MHz, DMSO-d$_6$) δ 13.63 (s, 1H), 7.89 (t, J = 7.5 Hz, 1H), 7.69 (t, J = 7.0 Hz, 1H), 7.48 (s, 2H), 3.79 (s, 3H) | |
| 77 | | | ESIMS m/z 393 ([M + H]$^+$) | $^1$H NMR (400 MHz, DMSO-d$_6$) δ 13.57 (s, 1H), 7.95 (dd, J = 8.2, 6.8 Hz, 1H), 7.74 (dd, J = 9.8, 2.0 Hz, 1H), 7.53 (dd, J = 8.3, 2.0 Hz, 1H), 7.28 (s, 1H), 6.71 (s, 2H) | $^{19}$F NMR (376 MHz, DMSO-d$_6$) δ −95.12 |
| 78 | 185.5-187.0 | | ESIMS m/z 342 ([M + H]$^+$) | $^1$H NMR (400 MHz, DMSO-d$_6$) δ 7.64 (d, J = 8.5 Hz, 2H), 7.40 (d, J = 8.5 Hz, 2H), 6.47 (s, 2H), 2.07 (s, 3H) | $^{13}$C NMR (101 MHz, DMSO) δ 166.57, 153.45, 150.28, 138.92, 131.35, |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 79 | 121-124 | | ESIMS m/z 421 ([M + H]$^+$) | $^1$H NMR (400 MHz, CDCl$_3$) δ 7.80 (dd, J = 8.1, 6.5 Hz, 1H), 7.19 (dd, J = 8.6, 1.9 Hz, 1H), 7.00 (dd, J = 8.1, 1.9 Hz, 1H), 4.86 (s, 2H), 3.96 (s, 3H), 2.17 (s, 3H) | 130.86, 121.35, 115.84, 109.91, 99.49, 14.91 $^{19}$F NMR (376 MHz, CDCl$_3$) δ −93.62 |
| 80 | 170-171 | | ESIMS m/z 344 ([M + H]$^+$) | $^1$H NMR (400 MHz, DMSO-d$_6$) δ 8.30 (dd, J = 9.8, 2.1 Hz, 1H), 8.22 (dd, J = 8.5, 2.2 Hz, 1H), 7.87 (m, 1H), 7.22 (s, 2H), 3.88 (s, 3H) | |
| 81 | 128-130 | | ESIMS m/z 354 ([M − H]$^−$) | $^1$H NMR (400 MHz, CDCl$_3$) δ 7.56 (d, J = 8.5 Hz, 2H), 7.33 (d, J = 8.5 Hz, 2H), 4.84 (s, 2H), 3.96 (s, 3H), 2.15 (s, 3H) | $^{13}$C NMR (101 MHz, CDCl$_3$) δ 165.68, 155.19, 149.18, 145.09, 138.57, 131.42, 131.00, 122.60, 116.69, 113.59, 52.88, 14.65 |
| 82 | 159-162 | IR (thin film) 3493 (s), 3352 (s), 2943 (w), 2853 (w), 1725 (m), 1602 (m) cm$^{-1}$ | ESIMS m/z 404 ([M + H]$^+$) | $^1$H NMR (400 MHz, CDCl$_3$) δ 7.68 (t, J = 8 Hz, 1H), 7.50-7.58 (m, 2H), 5.40 (br s, 2H), 4.00 (s, 3H), 3.94 (s, 3H) | |
| 83 | 145-148, 220 | | ESIMS m/z 302 ([M + H]$^+$) | $^1$H NMR (400 MHz, CDCl$_3$) δ 7.73 (d, J = 8.5 Hz, 2H), 7.58 (d, J = 8.5 Hz, 2H), 4.90 (s, 2H), 3.96 (s, 3H), 2.16 (s, 3H) | $^{13}$C NMR (101 MHz, CDCl$_3$) δ 165.50, 154.25, 149.37, 145.36, 144.19, 132.09, 130.18, 118.67, 116.71, 114.01, 112.06, 52.95, 14.58 |
| 84 | 214-217 | IR (thin film) 3453 (m), 3302 (m), 3242 (s), 3170 (m), 2963 (w), 2852 (w), 2112 (w), 1732 (m), 1631 (m) cm$^{-1}$ | ESIMS m/z 320 ([M + H]$^+$) | $^1$H NMR (400 MHz, CDCl$_3$) δ 7.69 (ddd, J = 9, 7, 2 Hz, 7.27 (m, 1H), 5.42 (br s, 2H), 4.00 (s, 3H), 3.95 (s, 3H), 3.42 (s, 1H) | |
| 85 | 126-125 | | ESIMS m/z 347 ([M + H]$^+$) | $^1$H NMR (400 MHz, DMSO) δ 7.88 (dd, J = 8.8, 1.3, 2H), 7.34 (t, J = 73.8, 1H), 7.31 (d, J = 8.9, 2H), 7.01 (br s, 2H), 3.88 (s, 1H) | |
| 86 | 120-22 | | ESIMS m/z 345 ([M + H]$^+$) | $^1$H NMR (400 MHz, DMSO-d$_6$) δ 13.22 (s, 1H), 8.02-7.94 (m, 3H), 6.78 (dd, J = 17.7, 11.6 Hz, 1H), 6.56 (s, 2H), 5.65-5.52 (m, 2H) | $^{19}$F NMR (376 MHz, CDCl$_3$) δ −61.37, −61.41, −114.17, −114.20, −114.24, −114.27, −143.61. |
| 87 | 171-172 | | ESIMS m/z 407 ([M + H]$^+$) | $^1$H NMR (400 MHz, DMSO-d$_6$) δ 13.36 (s, 1H), 7.91 (dd, J = 8.0, 6.8 Hz, 1H), 7.35 (dd, J = 9.1, 1.9 Hz, 1H), 7.10 (dd, J = 8.1, 1.9 Hz, 1H), 6.49 (s, 2H), 2.09 (s, 3H) | $^{19}$F NMR (376 MHz, DMSO-d$_6$) δ −95.45 |
| 88 | | | ESIMS m/z 372 ([M + H]$^+$) | $^1$H NMR (400 MHz, DMSO-d$_6$) δ 8.00 (m, 2H), 7.84 (m, 2H) 7.35 (br s, 2H), 3.11 (s, 3H) | |
| 89 | 119-121 | | | $^1$H NMR (400 MHz, DMSO-d$_6$) δ 13.63 (s, 1H), 7.72 (ddd, J = 8.3, 5.7, 1.8 Hz, 1H), 7.51 (ddd, J = 8.6, 7.0, 1.8 Hz, 1H), 7.43 (s, 2H), 3.76 (s, 3H) | |

TABLE 2-continued

Analytical Data for Compounds in Table 1

| Compd. No. | mp (° C.) | IR (cm⁻¹) | Mass[a] | ¹H NMR[b] | ¹³C or ¹⁹F NMR |
|---|---|---|---|---|---|
| 90 | 176.2-178.7 | | ESIMS m/z 445 ([M + 2H]+) | ¹H NMR (400 MHz, DMSO-d₆) δ 3.86 (s, 3H), 6.98-6.94 (m, 3H), 7.89-7.85 (m, 1H) | |
| 91 | 173-175 | | ESIMS m/z 363 ([M − H]⁻) | ¹H NMR (300 MHz, DMSO-d₆) δ 7.76-7.56 (m, 2H), 7.22 (d, J = 1.7, 1H), 6.84 (s, 2H) | |
| 92 | 147-149 | IR (thin film) 778.80, 822.34, 879.66, 973.14, 1006.40, 1026.12, 1056.64, 1120.85, 1214.80, 1276.30, 1389.19, 1409.98, 1459.47, 1496.89, 1519.03, 1592.79, 1627.42 1720.12, 1769.38, 2535.30, 3199.10, 3386.23, 3501.86 cm⁻¹ | ESIMS m/z 351 ([M + H]⁺) | ¹H NMR (400 MHz, DMSO-d₆) δ 13.63 (s, 1H), 7.83 (dd, J = 11.8, 2.1 Hz, 1H), 7.75 (t, J = 72.0 Hz, 1H), 7.52 (d, J = 8.0 Hz, 1H), 7.50-7.14 (m, 1H), 6.99 (s, 2H) | |
| 93 | 98.9-101.6 | | ESIMS m/z 359 ([M + H]⁺) | ¹H NMR (400 MHz, CDCl₃) δ 7.93 (m, 1H), 7.34 (m, 2H), 7.22 (s, 1H), 4.85 (s, 2H), 4.00 (s, 3H) | |
| 94 | 158.5-159.5 | | ESIMS m/z 329 ([M + H]⁺) | ¹H NMR (400 MHz, DMSO-d₆) δ 7.51 (d, J = 8.6 Hz, 2H), 7.33-7.14 (m, 3H), 6.61 (s, 2H), 2.09 (s, 3H) | ¹⁹F NMR (376 MHz, DMSO-d₆) δ −82.20 |
| 95 | | | ESIMS m/z 326 ([M + H]⁺) | ¹H NMR (300 MHz, CDCl₃) δ 8.32 (d, J = 9.0, 2H), 8.13 (dd, J = 9.0, 1.4, 2H), 5.02 (s, 2H), 4.01 (s, 3H) | |
| 96 | 187.2-189.9 | | ESIMS m/z 423 ([M + H]⁺) | ¹H NMR (400 MHz, CDCl₃) δ 7.80 (d, 2H), 7.42 (d, 2H), 5.35 (s, 2H), 3.98 (s, 3H) | |
| 97 | | | ESIMS m/z 340 ([M + H]⁺) | ¹H NMR (400 MHz, CDCl₃) δ 8.19 (m, 2H), 7.55 (m, 2H), 5.35 (br s, 2H), 4.01 (s, 3H), 3.92 (s, 3H) | |
| 98 | | | ESIMS m/z 299 ([M + H]⁺) | ¹H NMR (400 MHz, DMSO-d₆) δ 8.13-7.90 (m, 2H), 7.80 (dd, J = 8.0, 1.6 Hz, 1H), 7.46 (s, 2H), 6.66 (dd, J = 17.6, 11.5 Hz, 1H), 5.63-5.43 (m, 2H), 3.82 (s, 3H) | ¹⁹F NMR (376 MHz, DMSO-d₆) δ −111.51. |
| 99 | 168-170 | IR (thin film) 3502 (m), 3378 (s), 2953 (w), 1739 (m), 1726 (m), 1617 (m) cm⁻¹ | ESIMS m/z 443 ([M + H]⁺) | ¹H NMR (400 MHz, CDCl₃) δ 7.62 (ddd, J = 9, 6, 2 Hz, 1H), 7.16 (ddd, J = 9, 6.5, 2 Hz, 1H), 4.97 (br s, 2H), 3.96 (s, 3H) | |
| 100 | 145-147 | | ESIMS m/z 502 ([M − H]⁻) | ¹H NMR (400 MHz, CDCl₃) δ 7.54 (dd, J = 8.2, 4.9 Hz, 1H), 7.12 (dd, J = 7.4, 5.8 Hz, 1H), 5.44 (s. 2H), 3.97 (s, 3H) | −99.80, −99.84, −116.84, −116.89. |
| 101 | 193-194 | | ESIMS m/z 422 ([M + H]⁺) | ¹H NMR (400 MHz, CDCl₃) δ 7.69 (dd, J = 8.3, 6.3 Hz, 1H), 7.54 (dd, J = 9.5, 5.0 Hz, 1H), 5.43 (s, 2H), 4.00 (s, 3H), 3.94 (s, 3H) | ¹⁹F NMR (376 MHz, CDCl₃) δ −100.82, −100.86, −118.25, −118.29. |
| 102 | 171.0-172.1 | | ESIMS m/z 330 ([M + H]⁺) | ¹H NMR (400 MHz, DMSO-d₆) δ 7.35 (d, 2H), 7.47 (d, 2H), 7.39 (s, 2H), 3.78 (s, 3H) | |
| 103 | | IR (thin film) 708.67, 786.89, 824.69, 939.95, 1032.81, 1120.09, 1153.46, 1204.33, 1225.97, 1263.98, | ESIMS m/z 383 ([M + H]⁺) | ¹H NMR (400 MHz, CDCl₃) δ 7.37 (ddd, J = 8.7, 7.0, 2.3 Hz, 1H), 7.19-7.11 (m, 1H), 6.61 (t, J = 72.5 Hz, 1H), 4.99 (s, 2H), 3.98 (s, 3H) | |

TABLE 2-continued

Analytical Data for Compounds in Table 1

| Compd. No. | mp (° C.) | IR (cm⁻¹) | Mass[a] | ¹H NMR[b] | ¹³C or ¹⁹F NMR |
|---|---|---|---|---|---|
| | | 1424.87, 1375.02, 1445.12, 1481.84, 1518.14, 1615.72, 1739.13, 2959.84, 3195.90, 3378.30, 3486.20 cm⁻¹ | | | |
| 104 | 127-129 | IR (thin film) 758.08, 793.58, 824.98, 856.60, 919.36, 972.37, 1014.89, 1053.05, 1122.86, 1162.89, 1203.20, 1241.89, 1276.59, 1369.66, 1439.27, 1480.39, 1512.36 1611.65, 1732.10, 2957.77, 3021.70, 3389.26, 3506.76 cm⁻¹ | ESIMS m/z 366 ([M + H]⁺) | ¹H NMR (400 MHz, CDCl₃) δ 7.61 (t, J = 8.3 Hz, 1H), 7.04 (ddd, J = 8.6, 2.3, 0.8 Hz, 1H), 6.96 (dd, J = 10.5, 2.3 Hz, 1H), 6.55 (t, J = 73.0 Hz, 1H), 4.96 (s, 2H), 3.97 (s, 3H) | ¹³C NMR (101 MHz, CDCl₃) δ 164.70, 161.50, 158.98, 152.94, 152.84, 147.17, 144.60, 143.59, 143.54, 140.22, 140.08, 137.91, 137.78, 132.54, 132.53, 132.49, 119.75, 119.71, 119.60, 119.56, 118.02, 115.77, 115.75, 115.42, 115.40, 115.37, 112.81, 107.69, 107.43, 53.07. |
| 105 | 141.9-143.1 | | ESIMS m/z 367 ([M + H]⁺) | ¹H NMR (400 MHz, DMSO-d₆) δ 13.7 (s, 1H), 7.75 (d, 2H), 7.49 (d, 2H), 7.01 (s, 2H) | |
| 106 | 183-184 | IR (thin film) 861.93, 886.37, 962.21, 984.56, 1035.97, 1010.25, 1113.86, 1143.26, 1173.58, 1222.01, 1251.67, 1294.93, 1438.95, 1397.88, 1514.76, 1486.42, 1595.67, 1568.01, 1608.88, 1645.71, 1735.15, 2693.18, 2860.72, 2960.57, 3179.92, 3320.20, 3406.42 cm⁻¹ | ESIMS m/z 326 ([M + H]⁺) | ¹H NMR (400 MHz, CDCl₃) δ 8.35-8.29 (m, 2H), 7.19-7.10 (m, 2H), 6.56 (t, 1H, J = 72 Hz), 5.33 (s, 3H), 4.02 (s, 3H), 3.92 (s, 3H) | |
| 107 | | | ESIMS m/z 298 ([M + H]⁺) | ¹H NMR (400 MHz, CDCl₃) δ 8.08 (dd, J = 8.6, 1.5 Hz, 2H), 7.78-7.71 (m, 2H), 6.89 (dd, J = 18.1, 11.6 Hz, 1H), 5.73 (dd, J = 11.6, 1.4 Hz, 1H), 5.59 (dd, J = 18.1, 1.4 Hz, 1H), 4.78 (s, 2H), 3.93 (s, 3H) | ¹⁹F NMR (376 MHz, CDCl₃) δ −143.64 |
| 108 | 165-175 (dec) | IR (thin film) 3468 (s), 1621 (m) cm⁻¹ | ESIMS m/z 309 ([M + H]⁺) | ¹H NMR (400 MHz, DMSO-d₆) δ 7.55 (t, J = 8 Hz, 1H), 7.50 (dd, J = 11, 1.5 Hz, 1H), 7.46 (dd, J = 8, 1.5 Hz, 1H), 6.47 (br s, 2H), 4.45 (s, 1H) | |
| 109 | 184-186 | | ESIMS m/z 393 ([M − H]⁻) | ¹H NMR (300 MHz, CDCl₃) δ 7.48-7.40 (m, 1H), 7.33-7.26 (m, 1H), 4.99 (br s, 2H), 3.98 (s, 3H) | |
| 110 | | | ESIMS m/z 345 ([M + H]⁺) | ¹H NMR (400 MHz, DMSO-d₆) δ 13.33 (s, 1H), 7.70-7.52 (m, 2H), 7.45 (dd, J = 8.4, 2.0 Hz, 1H), 7.06 (s, 1H), 6.52 (s, 2H) | ¹⁹F NMR (376 MHz, DMSO-d₆) δ −107.95. |
| 111 | | | ESIMS m/z 341 ([M − H]⁻) | ¹H NMR (400 MHz, CDCl₃) 7.46 (d, J = 8.7 Hz, 2H), 7.18 (d, J = 8.7 Hz, 2H), 6.53 (t, J = 73.8 Hz, 1H), 4.84 (s, 2H), 3.95 (s, 3H), 2.16 (s, 3H) | ¹⁹F NMR (376 MHz, CDCl₃) δ −80.81 |
| 112 | 134-137 | | ESIMS m/z 375 ([M + H]⁺) | ¹H NMR (400 MHz, CDCl₃) δ 7.61 (dd, J = 8.2, 7.1 Hz, 1H), 7.27-7.25 (m, 1H), 7.13 (ddd, J = 8.2, 1.9, 0.6 Hz, | ¹⁹F NMR (376 MHz, CDCl₃) δ −107.04 |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 113 | | | ESIMS m/z 344 ([M + H]$^+$) | 1H), 4.86 (s, 2H), 3.96 (s, 3H), 2.17 (s, 3H) $^1$H NMR (400 MHz, DMSO-d$_6$) δ 13.63 (s, 1H), 8.07 (dd, J = 10.3, 1.9 Hz, 1H), 8.01 (dd, J = 8.5, 2.0 Hz, 1H), 7.81 (dd, J = 8.4, 7.2 Hz, 1H), 7.40 (s, 2H), 3.76 (s, 3H) | $^{19}$F NMR (376 MHz, DMSO-d$_6$) δ −108.44. |
| 114 | 178-180 | | ESIMS m/z 379 ([M + H]$^+$) | $^1$H NMR (400 MHz, DMSO) δ 7.78-7.58 (m, 2H), 7.26 (d, J = 1.6, 1H), 6.95 (s, 2H), 3.89 (s, 3H) | |
| 115 | | | ESIMS m/z 359 ([M + H]$^+$) | $^1$H NMR (400 MHz, DMSO-d$_6$) δ 7.91-7.80 (m, 2H), 7.75-7.67 (m, 1H), 7.35 (s, 1H), 6.86 (s, 2H), 3.93 (s, 3H) | $^{19}$F NMR (376 MHz, DMSO-d$_6$) δ −107.88. |
| 116 | 179.5-181.0 | | ESIMS m/z 389 ([M + H]$^+$) | $^1$H NMR (400 MHz, DMSO) δ 7.81 (d, J = 8.3 Hz, 2H), 7.25 (d, J = 8.3 Hz, 2H), 6.46 (s, 2H), 2.07 (s, 3H) | $^{13}$C NMR (101 MHz, DMSO) δ 166.56, 153.62, 150.28, 139.23, 136.72, 131.38, 115.78, 109.86, 94.48, 48.57, 14.90 |
| 117 | 149-151° C. | | ESIMS m/z 336 ([M − H]$^-$) | $^1$H NMR (400 MHz, DMSO-d$_6$) δ 13.13 (s, 1H), 7.82 (dd, J = 8.5, 0.9 Hz, 2H), 7.74-7.66 (m, 2H), 6.75 (dd, J = 17.8, 11.5 Hz, 1H), 6.42 (s, 2H), 5.56 (dd, J = 12.8, 1.3 Hz, 1H), 5.52 (dd, J = 6.5, 1.3 Hz, 1H) | $^{19}$F NMR (376 MHz, DMSO-d$_6$) δ −145.77. |
| 118 | 133-135 | | ESIMS m/z 407 ([M + H]$^+$) | $^1$H NMR (300 MHz, CDCl$_3$) δ 7.81 (m, 2H), 7.67 (m, 2H), 4.91 (br s, 2H), 3.99 (s, 3H) | |
| 119 | 131-132 | | ESIMS m/z 408 ([M + H]$^+$) | $^1$H NMR (400 MHz, DMSO-d$_6$) δ 7.83 (dd, J = 9.6, 5.1 Hz, 1H), 7.66 (dd, J = 8.5, 6.3 Hz, 1H), 7.42 (s, 2H), 3.75 (s, 3H) | $^{19}$F NMR (376 MHz, DMSO-d$_6$) δ −101.95, −102.00, −117.68, −117.72. |
| 121 | 186-188 | IR (thin film) 3500 (w), 3472 (m), 3370 (s), 3229 (m), 2955 (w), 2921 (w), 2850 (w), 1728 (m), 1622 (m) cm$^{-1}$ | ESIMS m/z 323 ([M + H]$^+$) | $^1$H NMR (400 MHz, CDCl$_3$) δ 7.58 (t, J = 8 Hz, 1H), 7.39 (dd, J = 8, 1.5 Hz, 1H), 7.28 (m, 1H), 4.94 (br s, 2H), 3.97 (s, 3H), 3.17 (s, 1H) | |
| 122 | 171-72 | | ESIMS m/z 374 ([M + H]$^+$) | $^1$H NMR (400 MHz, CDCl$_3$) δ 7.65 (ddd, J = 9.0, 7.1, 2.1 Hz, 1H), 7.40-7.31 (m, 1H), 5.45 (s, 2H), 4.01 (s, 3H), 3.95 (s, 3H) | $^{19}$F NMR (376 MHz, CDCl$_3$) δ −129.82 (s), −129.88 (s), −135.73 (s), −135.79 (s) |
| 123 | 187-190 | | ESIMS m/z 368 ([M + H]$^+$) | $^1$H NMR (400 MHz, DMSO-d$_6$) δ 8.01-8.09 (m, 2H), 7.82-7.90 (m, 2H), 7.16 (s, 1H), 6.65 (dd, J = 17.7, 11.5 Hz, 1H), 5.61 (dd, J = 17.7, 1.3 Hz, 1H), 5.49 (dd, J = 11.4, 1.3 Hz, 1H) | |
| 124 | 208.4-210.2 | | ESIMS m/z 393 ([M + H]$^+$) | $^1$H NMR (400 MHz, DMSO-d$_6$) δ 13.7 (s, 1H), 7.78 (m, 3H), 7.23 (s, 1H), 6.83 (s, 2H) | |
| 125 | 164.9-166.1 | | ESIMS m/z 363 ([M + H]$^+$) | $^1$H NMR (400 MHz, DMSO-d$_6$) δ 13.69 (s, 1H), 7.67 (d, 2H) 7.55 (d, 2H), 6.99 (s, 2H) | |
| 126 | 158.9-161.2 | | ESIMS m/z 287 ([M + H]$^+$) | $^1$H NMR (400 MHz, CDCl$_3$) δ 7.93 (d, 2H), 7.60 (d, 2H), | |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 127 | 174-176 | | ESIMS m/z 376 ([M − H]$^-$) | 7.16 (s, 1H), 4.89 (s, 2H), 4.05 (s, 3H) $^1$H NMR (400 MHz, CDCl$_3$) δ 7.89 (dd, J = 9.2, 6.7 Hz, 1H), 7.36 (dd, J = 10.2, 5.5 Hz, 1H), 7.25 (d, J = 1.2 Hz, 1H), 4.86 (s, 2H), 4.01 (s, 3H) | $^{19}$F NMR (376 MHz, CDCl$_3$) δ −112.80, −112.84, −119.98, −120.02. |
| 128 | | IR (thin film) 3334, 1722 cm$^{-1}$ | ESIMS m/z 336 ([M + H]$^+$) | $^1$H NMR (400 MHz, DMSO) δ 8.25 (d, J = 8.1 Hz, 2H), 8.17 (d, J = 11.9 Hz, 2H), 7.95 (t, J = 7.9 Hz, 2H), 7.66 (s, 1H) | $^{19}$F NMR (376 MHz, DMSO) δ −60.0, −114.7, −116.5. |
| 129 | 172-174 | IR (thin film) 3481 (m), 3338 (s), 3185 (w), 3096 (w), 2963 (w), 1727 (m), 1608 (m) cm$^{-1}$ | ESIMS m/z 425 ([M + H]$^+$) | $^1$H NMR (400 MHz, CDCl$_3$) δ 7.7.55-7.62 (m, 2H), 7.21 (d, J = 2 Hz, 1H), 4.86 (br s, 2H), 3.99 (s, 3H) | |
| 130 | 185.1-186.9 | | ESIMS m/z 285 ([M + H]$^+$) | $^1$H NMR (400 MHz, CDCl$_3$) δ 8.45 (d, 2H), 7.75 (s, 2H), 5.84 (s, 2H), 4.03 (s, 3H), 3.96 (s, 3H) | |
| 131 | 173-175 | | ESIMS m/z 411 ([M + H]$^+$) | $^1$H NMR (400 MHz, DMSO-d$_6$) δ 7.90 (dd, J = 10.2, 5.1 Hz, 1H), 7.73 (dd, J = 8.6, 6.6 Hz, 1H), 7.26 (s, 1H), 6.83 (s, 2H) | $^{19}$F NMR (376 MHz, DMSO-d$_6$) δ −96.56, −96.61, −115.34, −115.38. |
| 132 | 138-140 | IR (thin film) 3437 (w), 3352 (s), 3197 (w), 2949 (w), 1737 (m), 1614 (m) cm$^{-1}$ | ESIMS m/z 425 ([M + H]$^+$) | $^1$H NMR (400 MHz, CDCl$_3$) δ 7.88 (dd, J = 9, 7 Hz, 1H), 7.73 (ddd, J = 9, 2, 1 Hz, 1H), 7.55 (dt, J = 8.5, 2 Hz, 1H), 4.94 (br s, 2H), 4.00 (s, 3H) | |
| 133 | 141-143 | IR (thin film) 3385 (s), 3242 (m), 2955 (w), 2918 (w), 2856 (w), 1734 (m), 1622 (m) cm$^{-1}$ | ESIMS m/z 323 ([M + H]$^+$) | $^1$H NMR (400 MHz, CDCl$_3$) δ 7.75 (d, J = 9.5 Hz, 2H), 7.57 (t, J = 7 Hz, 1H), 4.93 (br s, 2H), 3.98 (s, 3H), 3.37 (s, 1H) | |
| 134 | 124-126 | | ESIMS m/z 353 ([M + H]$^+$) | $^1$H NMR (400 MHz, DMSO-d$_6$) δ 7.92 (d, J = 12.8 Hz, 3H), 7.01 (s, 3H) | |
| 135 | | | ESIMS m/z 324 ([M + H]$^+$) | $^1$H NMR (400 MHz, CDCl$_3$) δ 7.98-7.83 (m, 1H), 7.72 (dd, J = 8.4, 6.6, 1H), 5.01 (s, 1H), 4.01 (s, 2H) | |
| 136 | 115-118 | | ESIMS m/z 403 ([M + H]$^+$) | $^1$H NMR (400 MHz, CDCl$_3$) δ 7.77 (d, J = 8.5 Hz, 2H), 7.20 (d, J = 8.5 Hz, 2H), 4.83 (s, 2H), 3.95 (s, 3H), 2.15 (s, 3H) | $^{13}$C NMR (101 MHz, CDCl$_3$) δ 165.69, 155.29, 149.17, 145.12, 139.19, 137.39, 131.16, 116.65, 113.57, 94.30, 52.86, 14.64 |
| 137 | | | ESIMS m/z 342 ([M + H]$^+$) | $^1$H NMR (400 MHz, DMSO-d$_6$) δ 8.26 (d, J = 8.2 Hz, 1H), 8.17 (d, J = 12.2 Hz, 1H), 7.94 (t, J = 7.9 Hz, 1H), 7.35 (s, 2H), 6.67 (dd, J = 17.7, 11.5 Hz, 1H), 5.52 (m, 2H), 3.85 (s, 3H) | $^{19}$F NMR (376 MHz, DMSO-d$_6$) δ −59.99 (d, J = 12.2 Hz), −115.72 (d, J = 12.2 Hz) |
| 138 | | | ESIMS m/z 361 ([M + H]$^+$) | $^1$H NMR (400 MHz, CDCl$_3$) δ 7.81 (m, 2H), 7.60 (m, 2H), 7.40 (d, J = 2 Hz, 2H), 4.91 (br s, 2H), 3.99 (s, 3H) | |
| 139 | 95-96 | | ESIMS m/z 399 ([M + H]$^+$) | $^1$H NMR (400 MHz, CDCl$_3$) δ 7.84-7.75 (m, 2H), 7.73-7.66 (m, 2H), 6.89 (dd, J = 18.1, 11.6 Hz, 1H), 5.71 (dd, J = 11.6, 1.4 Hz, 1H), 5.58 (dd, J = 18.1, 1.4 Hz, 1H), 4.71 (s, 2H), 3.92 (s, 3H) | $^{19}$F NMR (376 MHz, CDCl$_3$) δ −143.98. |
| 140 | 149-151 | IR (thin film) 698.09, 825.26, 869.29, 998.15, | ESIMS m/z 351 ([M + H]$^+$) | $^1$H NMR (400 MHz, DMSO-d$_6$) δ 18.40 (s, 1H), 12.39 (t, J = 8.4 Hz, 1H), | |

TABLE 2-continued

Analytical Data for Compounds in Table 1

| Compd. No. | mp (° C.) | IR (cm⁻¹) | Mass$^a$ | $^1$H NMR$^b$ | $^{13}$C or $^{19}$F NMR |
|---|---|---|---|---|---|
| | | 1025.59, 1050.34, 1098.57, 1129.54, 1167.58, 1246.97, 1386.17, 1435.44, 1481.70, 1515.78, 3590.42, 1628.74, 1720.93, 2535.45, 3198.03, 3327.36, 3469.29 cm⁻¹ | | 12.16 (t, J = 72.0 Hz, 1H), 12.05 (dd, J = 11.1, 2.4 Hz, 1H), 11.94 (dd, J = 8.5, 2.4 Hz, 1H), 11.75 (s, 2H) | |
| 141 | 155-157 | IR (thin film) 3325 (s), 3193 (s), 1625 (m) cm⁻¹ | ESIMS m/z 429 ([M + H]⁺) | $^1$H NMR (400 MHz, DMSO-d$_6$) δ 7.81 (br t, J = 7 Hz, 1H), 7.20 (br t, J = 7 Hz, 1H), 6.64 (br s, 2H) | |
| 142 | 164-167 | | ESIMS m/z 306 ([M + H]⁺) | $^1$H NMR (400 MHz, DMSO) δ 8.06-7.94 (m, 4H), 7.12 (br s, 2H), 3.89 (s, 3H) | |
| 143 | 137-139 | | ESIMS m/z 333 ([M + H]⁺) | $^1$H NMR (300 MHz, DMSO-d$_6$) δ 7.90 (dd, J = 8.8, 1.3, 2H), 7.34 (t, J = 73.8, 1H), 7.30 (d, J = 8.8, 2H), 6.90 (s, 2H) | |
| 144 | 124-126 | | ESIMS m/z 385 ([M + H]⁺) | $^1$H NMR (400 MHz, CDCl$_3$) δ 7.50 (dd, J = 9.8, 5.3 Hz, 1H), 7.42 (dd, J = 8.9, 5.6 Hz, 1H), 5.03 (s, 2H), 3.99 (s, 3H) | $^{19}$F NMR (376 MHz, CDCl$_3$) δ −61.82, −61.85, −116.72, −116.76, −116.81, −116.86, −119.30, −119.33, −119.35, −119.38, −137.15, −137.24. |
| 145 | | | ESIMS m/z 427 ([M + H]⁺) | $^1$H NMR (400 MHz, DMSO-d$_6$) δ 13.75 (s, 1H), 7.95 (dd, J = 8.1, 6.7 Hz, 1H), 7.48 (dd, J = 9.1, 1.9 Hz, 1H), 7.25 (dd, J = 8.1, 1.9 Hz, 1H), 7.04 (s, 2H) | $^{19}$F NMR (376 MHz, DMSO-d$_6$) δ −95.25. |
| 146 | | IR (thin film) 3359, 1719, 1619 cm⁻¹. | ESIMS m/z 369 ([M + H]⁺) | $^1$H NMR (400 MHz, DMSO) δ 7.90 (t, J = 7.9 Hz, 2H), 7.75 (d, J = 11.8 Hz, 2H), 7.64 (d, J = 8.1 Hz, 2H) | $^{19}$F NMR (376 MHz, DMSO) δ −59.9, −115.3, −116.6. |
| 147 | 168-170 | | ESIMS m/z 381 ([M − H]⁻) | $^1$H NMR (400 MHz, DMSO-d$_6$) δ 7.74-7.65 (m, 1H), 7.43-7.32 (m, 1H), 7.00 (br s, 2H) | |
| 148 | 96-98 | | ESIMS m/z 364 ([M + H]⁺) | $^1$H NMR (400 MHz, CDCl$_3$) δ 7.84 (dd, J = 10.6, 5.9 Hz, 1H), 7.39 (dd, J = 9.8, 5.6 Hz, 1H), 5.46 (s, 2H), 4.01 (s, 3H), 3.96 (s, 3H) | $^{19}$F NMR (376 MHz, CDCl$_3$) δ −61.73, −61.76, −117.59, −117.64, −120.18, −120.21, −120.23, −120.26. |
| 149 | 131-132 | | ESIMS m/z 385 ([M + H]⁺) | $^1$H NMR (400 MHz, DMSO-d$_6$) δ 7.77 (t, J = 7.2, 1H), 7.63 (t, J = 7.0, 1H), 7.25 (s, 2H), 3.88 (s, 3H) | |
| 150 | | | ESIMS m/z 284 ([M + H]⁺) | $^1$H NMR (400 MHz, CDCl$_3$) δ 11.46 (s, 1H), 8.05-7.98 (m, 2H), 7.84-7.75 (m, 2H), 7.26 (ddd, J = 18.4, 11.7, 1.4 Hz, 1H), 5.85 (dd, J = 11.7, 1.4 Hz, 1H), 5.63 (dd, J = 18.4, 1.4 Hz, 1H), 5.06 (s, 2H) | $^{19}$F NMR (376 MHz, CDCl$_3$) δ −140.74 |
| 151 | 130-132 | | ESIMS m/z 319 ([M + H]⁺) | $^1$H NMR (400 MHz, CDCl$_3$) δ 7.53 (dd, J = 7.9, 7.3 Hz, 1H), 7.22 (ddd, J = 7.3, 6.7, | $^{19}$F NMR (376 MHz, CDCl$_3$) δ −110.01 |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| | | | | 1.5 Hz, 2H), 4.87 (s, 2H), 3.96 (s, 3H), 3.35 (s, 1H), 2.17 (s, 3H) | |
| 152 | 112-114 | IR (thin film) 751.85, 792.16, 879.37, 933.73, 1013.05, 1094.15, 1058.41, 1117.03, 1200.23, 1247.75, 1267.53, 1375.51, 1432.34, 1476.69, 1516.02, 1611.65, 1725.02, 2961.33, 3378.00, 3505.09 cm$^{-1}$ | ESIMS m/z 366 ([M + H]$^+$) | $^1$H NMR (400 MHz, CDCl$_3$) δ 7.86-7.68 (m, 2H), 7.36-7.29 (m, 1H), 6.60 (t, J = 73.3 Hz, 1H), 4.95 (s, 2H), 4.00 (s, 3H) | |
| 153 | 160.9-162.6 | | ESIMS m/z 307 ([M + H]$^+$) | $^1$H NMR (400 MHz, DMSO-d$_6$) δ 13.72 (s, 1H), 7.61 (m, 5H), 7.04 (s, 2H) | |
| 154 | 142-144 | IR (thin film) 3486 (m), 3378 (s), 3225 (s), 2940 (w), 1768 (w), 1719 (w), 1625 (m) cm$^{-1}$ | ESIMS m/z 306 ([M + H]$^+$) | $^1$NMR (400 MHz, DMSO-d$_6$) δ 7.72 (m, 1H), 7.46 (m, 1H), 7.11 (br s, 2H), 4.80 (s, 1H), 3.79 (m, 3H) | |
| 155 | 177-180 | | ESIMS m/z 318 ([M − H]−) | $^1$H NMR (400 MHz, CDCl$_3$) δ 7.78-7.61 (m, 1H), 7.42-7.29 (m, 2H), 4.92 (s, 2H), 3.97 (s, 3H), 2.17 (s, 3H) | $^{13}$C NMR (101 MHz, CDCl$_3$) δ 165.33, 164.23, 161.59, 152.85, 149.49, 145.46, 133.27, 125.88, 117.79, 117.58, 116.64, 114.32, 113.80, 53.01, 14.55; $^{19}$F NMR (376 MHz, CDCl$_3$) δ −105.97 |
| 156 | | | ESIMS m/z 310 ([M + H]$^+$) | $^1$H NMR (300 MHz, DMSO-d$_6$) δ 8.07 (dd, J = 8.1, 7.0, 1H), 7.96-7.85 (m, 2H), 7.08 (s, 2H) | |
| 157 | 140-150 (dec) | IR (thin film) 3462 (s), 3194 (s), 1610 (m) cm$^{-1}$ | ESIMS m/z 411 ([M + H]$^+$) | $^1$H NMR (400 MHz, DMSO-d$_6$) δ 7.99 (dd, J = 8, 7 Hz, 1H), 7.68 (dd, J = 10, 1 Hz, 1H), 7.53 (dt, J = 9, 1.5 Hz, 1H), 6.39 (br s, 2H) | |
| 158 | | | ESIMS m/z 387 ([M − H]$^+$) | $^1$H NMR (400 MHz, CDCl$_3$) δ 7.75 (m, 2H), 7.63 (m, 2H), 7.08 (s, 1H), 4.87 (br s, 2H), 4.00 (s, 3H) | |
| 159 | 139.8-141.2 | | ESIMS m/z 407 ([M + H]$^+$) | $^1$H NMR (400 MHz, CDCl$_3$) δ 7.60 (m, 3H), 7.39 (s, 1H), 5.53 (s, 2H), 4.04 (s, 3H) | |
| 160 | 163-164 | | ESIMS m/z 342 ([M + H]$^+$) | $^1$H NMR (400 MHz, DMSO-d$_6$) δ 7.90 (m, 1H), 7.59 (t, J = 6.8 Hz, 1H), 7.25 (s, 2H), 3.87 (s, 3H) | |
| 161 | 170.0-171.5 | | ESIMS m/z 349 ([M]$^+$) | $^1$H NMR (400 MHz, CDCl$_3$) δ 7.73 (t, J = 7.7 Hz, 1H), 7.32 (t, J = 8.9 Hz, 2H), 5.15 (s, 2H), 2.23 (s, 3H) | $^{19}$F NMR (400 MHz, CDCl$_3$) δ −61.4, −113.3 |
| 162 | | | ESIMS m/z 383 ([M + 2H]$^+$) | $^1$H NMR (400 MHz, DMSO-d$_6$) δ 6.90-6.70 (br s, 3H), 7.88 (d, J = 8.96 Hz, 1H) | |
| 163 | 162-164 | IR (thin film) 3467 (s), 1609 (m) cm$^{-1}$ | ESIMS m/z 365 ([M + H]$^+$) | $^1$H NMR (400 MHz, DMSO-d$_6$) δ 7.75 (dd, J = 10, 2 Hz, 1H), 7.60 (dd, J = 8, 2 Hz, 1H), 7.52 (t, J = 8 Hz, 1H), 6.55 (br s, 2H) | |
| 164 | 142-144 | | ESIMS m/z 382 ([M + H]$^+$) | $^1$H NMR (400 MHz, DMSO-d$_6$) δ 3.83 (s, 3H), 5.38-5.58 (m, 2H), 6.65 (dd, J = 17.6, 11.5 Hz, 1H), 6.98-7.65 (m, 2H), 7.86 (d, | |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 165 | 133-135 | | ESIMS m/z 368 ([M + H]$^+$) | J = 8.5 Hz, 2H), 8.03 (d, J = 8.5 Hz, 2H) $^1$H NMR (400 MHz, DMSO-d$_6$) δ 7.92 (m, 3H), 7.17 (s, 2H), 3.90 (s, 3H) | |
| 166 | 148.2-150.9 | | ESIMS m/z 284 ([M + H]$^+$) | $^1$H NMR (400 MHz, CDCl$_3$) δ 7.29 (d, 2H), 7.56 (d, 2H), 5.37 (s, 2H), 4.02 (s, 3H), 3.93 (s, 3H) 3.18 (s, 1H) | |
| 167 | 69-70 | | ESIMS m/z 369 ([M − H]$^-$) | $^1$H NMR (400 MHz, DMSO-d$_6$) δ 13.75 (s, 1H), 7.77 (m, 1H), 7.64 (m, 1H), 7.16 (s, 2H) | |
| 168 | | $^1$H NMR (400 MHz, DMSO-d$_6$) δ 7.84 (m, 2H), 7.68 (m, 2H), 7.25 (s, 1H), 6.72 (br s, 2H) | ESIMS m/z 329 ([M + H]$^+$) | | |
| 169 | 152-155 | IR (thin film) 3470 (s), 1716 (w), 1629 (m), 1606 (m) cm$^{-1}$ | ESIMS m/z 411 ([M + H]$^+$) | $^1$H NMR (400 MHz, DMSO-d$_6$) δ 7.84 (dd, J = 10, 1.5 Hz, 1H), 7.76 (dd, J = 8, 1.5 Hz, 1H), 7.33 (t, J = 8 Hz, 1H), 6.61 (br s, 2H) | |
| 170 | 178.9-180.2 | | ESIMS m/z 381 ([M + H]$^+$) | $^1$H NMR (400 MHz, CDCl$_3$) δ 7.75 (d, 2H), 7.32 (d, 2H), 5.40 (s, 2H), 4.02 (s, 3H) | |
| 171 | | | ESIMS m/z 356 ([M + H]$^+$) | $^1$H NMR (400 MHz, DMSO-d$_6$) δ 8.11-7.90 (m, 2H), 7.82 (dd, J = 8.3, 7.2 Hz, 1H), 7.67-7.39 (m, 2H), 3.91 (s, 3H), 3.75 (s, 3H) | $^{19}$F NMR (376 MHz, DMSO-d$_6$) δ −108.34. |
| 172 | 161 | | ESIMS m/z 353 ([M + H]$^+$) | $^1$H NMR (400 MHz, DMSO-d$_6$) δ 13.69 (s, 1H), 7.91 (t, J = 7.5 Hz, 1H), 7.71 (t, J = 7.2 Hz, 1H), 7.30 (d, J = 1.7 Hz, 1H), 6.93 (s, 2H) | |
| 173 | 188.7-190.3 | | ESIMS m/z 409 ([M + H]$^+$) | $^1$H NMR (400 MHz, DMSO-d$_6$) δ 13.79 (s, 1H), 7.87 (d, 2H), 7.42 (d, 2H), 7.01 (s, 2H) | |
| 174 | 171.8-173.9 | | ESIMS m/z: 337 [(M + 3H)$^+$] | 1H-NMR (400 MHz, DMSO-d$_6$): δ 6.91 (brs, 2H), 7.26 (t, J = 53.88 Hz, 1H), 7.45-7.47 (m, 1H), 7.68 (dd, J = 5.60, 10.64 Hz, 1H), 7.87 (dd, J = 5.88, 10.74 Hz, 1H), 13.68 (brs, 1H) | |
| 175 | 123-124 | | ESIMS m/z 260 ([M + H]$^+$) | $^1$H NMR (400 MHz, CDCl$_3$) δ 8.34-8.24 (m, 2H), 7.49-7.38 (m, 3H), 5.33 (s, 2H), 4.02 (s, 3H), 3.92 (s, 3H) | |
| 176 | 135.2-136.9 | | ESIMS m/z 367 ([M + H]$^+$) | $^1$H NMR (400 MHz, CDCl$_3$) δ 7.41 (m, 2H), 6.91 (t, 1H), 5.02 (s, 2H), 4.00 (s, 3H) | |
| 177 | 107.5-110.3 | | ESIMS m/z 365 ([M + H]$^+$) | $^1$H NMR (400 MHz, CDCl$_3$) δ 7.95 (m, 1H), 7.26 (s, 1H), 7.08 (m, 1H), 6.61 (t, 1H), 4.91 (s, 2H), 4.02 (s, 3H) | |
| 178 | 86.1-88.4 | | ESIMS m/z: 354 [(M + 2H)$^+$] | $^1$H NMR (400 MHz, DMSO-d$_6$): δ 6.99 (brs, 2H), 7.28 (t, J = 54.00 Hz, 1H), 7.60-7.70 (m, 2H) | |
| 179 | 137.2-138.8 | | ESIMS m/z 313 ([M + H]$^+$) | $^1$H NMR (400 MHz, CDCl$_3$) δ 7.73 (m, 1H), 7.76 (s, 1H), 6.95 (m, 1H), 4.85 (s, 2H), 4.01 (s, 3H), 2.30 (s, 3H) | |
| 180 | | | ESIMS m/z 267 ([M + H]$^+$) | $^1$H NMR (400 MHz, DMSO-d$_6$) δ 7.82 (m, 2H), 7.55-7.44 (m, 3H), 6.88 (s, 2H) | |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 181 | 105-108 | | ESIMS m/z 281 ([M + H]$^+$) | $^1$H NMR (400 MHz, DMSO-d$_6$) δ 7.82 (m, 2H), 7.55-7.44 (m, 3H), 6.88 (s, 2H), 3.98 (s, 3H) | |
| 183 | | | ESIMS m/z 299 ([M + H]$^+$) | $^1$H NMR (400 MHz, DMSO-d$_6$) δ 7.68 (dq, J = 7.9, 1.3 Hz, 1H), 7.58 (m, 2H), 7.33 (m, 1H), 7.06 (s, 2H), 3.89 (s, 3H) | $^{19}$F NMR (376 MHz, DMSO) δ −112.86, −140.06. |
| 184 | 116.5-118.8 | | ESIMS m/z 331 ([M + H]$^+$) | $^1$H NMR (400 MHz, CDCl$_3$) δ 7.26 (m, 1H), 6.99 (m, 1H), 4.95 (s, 2H), 3.99 (s, 3H), 2.32 (s, 3H) | |
| 185 | 163.4-164.8 | | ESIMS m/z 310 ([M + H]$^+$) | $^1$H NMR (400 MHz, CDCl$_3$) δ 7.62 (m, 1H), 6.97 (m, 1H), 5.45 (s, 2H), 4.01 (s, 3H), 3.95 (s, 3H), 2.30 (s, 3H) | |
| 186 | 147-148 | | | $^1$H NMR (400 MHz, DMSO-d$_6$) δ 7.46 (m, 2H), 7.17 (s, 2H), 3.87 (s, 3H) | |
| 187 | 167.4-170.2 | | ESIMS m/z: 351 [(M + H)$^+$] | 1H-NMR (400 MHz, MeOD): δ 4.89 (s, 2H), 7.02 (t, J = 72.80 Hz, 1H), 7.33 (dd, J = 6.40, 10.80 Hz, 1H), 7.80 (dd, J = 7.20, 11.00 Hz, 1H) | |
| 188 | 172.9-175.0 | | ESIMS m/z 301 [(M + 2H)$^+$] | 1H-NMR (400 MHz, DMSO-d$_6$): δ 2.28 (s, 3H), 6.80 (brs, 2H), 7.25 (s, 1H), 7.31 (dd, J = 6.32, 11.58 Hz, 1H), 7.65 (dd, J = 6.60, 10.36 Hz, 1H), 13.54 (brs, 1H) | |
| 189 | | IR (thin film) 3376, 1737, 1615 cm$^{-1}$ | ESIMS m/z 317 ([M + H]$^+$) | $^1$H NMR (400 MHz, DMSO) δ 7.50-7.32 (m, 3H), 7.13 (s, 2H), 3.87 (d, J = 2.3 Hz, 3H) | |
| 190 | 163-165 | | ESIMS m/z 339 ([M + H]$^+$) | $^1$H NMR (400 MHz, DMSO-d$_6$) δ 8.13-8.04 (m, 2H), 8.02-7.92 (m, 2H), 7.08 (s, 2H), 3.89 (s, 6H) | |
| 191 | 154-157 | | ESIMS m/z 296 ([M + H]$^+$) | $^1$H NMR (400 MHz, DMSO-d$_6$) δ 7.86-7.70 (m, 1H), 7.41 (tdd, J = 9.5, 7.3, 2.1 Hz, 3H), 6.66 (dd, J = 17.6, 11.5 Hz, 1H), 5.63-5.38 (m, 2H), 3.82 (s, 3H) | $^{19}$F NMR (376 MHz, DMSO-d$_6$) δ −132.72 (dd, J = 21.4, 8.8 Hz), −135.29 (dd, J = 21.0, 8.7 Hz), −161.04 (t, J = 21.3 Hz) |
| 192 | 192-195 | | ESIMS m/z 324 ([M + H]$^+$) | $^1$H NMR (400 MHz, DMSO) δ 8.08 (br s, 1H), 7.99 (m, 2H), 7.87 (m, 2H), 7.47 (br s, 1H), 7.03 (br s, 2H), 3.89 (s, 3H) | |
| 193 | 127.9-129.2 | | ESIMS m/z 346 ([M + H]$^+$) | $^1$H NMR (400 MHz, CDCl$_3$) δ 7.77 (m, 1H), 7.39 (m, 1H), 6.89 (t, 1H), 5.49 (s, 2H), 4.02 (s, 3H), 3.97 (s, 3H) | |
| 194 | 167.4-170.2 | | ESIMS m/z 317 ([M + H]$^+$) | 1H-NMR (400 MHz, DMSO-d$_6$): δ 2.30 (s, 3H), 6.41 (brs, 2H), 7.28-0.00 (m, 2H) | |
| 195 | 162.0-165.0 | | ESIMS m/z 369 ([M + H]$^+$) | 1H-NMR (400 MHz, MeOD): δ 4.90 (s, 2H), 7.01 (t, J = 72.72 Hz, 1H), 7.29 (dd, J = 6.52, 9.76 Hz, 1H), 7.55 (dd, J = 6.36, 10.52 Hz, 1H) | |
| 196 | 127-129 | IR (thin film) 3480 (s), 3345 (s), 3186 (w), 2961 (w), | ESIMS m/z 331 ([M + H]$^+$) | $^1$H NMR (300 MHz, CDCl$_3$) δ 7.75-7.81 (m, 2H), 7.67 (t, J = 8 Hz, 1H), 7.14 (s, 1H), | |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 197 | 156-158 | 1717 (s), 1614 (s) cm$^{-1}$ | ESIMS m/z 309 ([M + H]$^+$) | 6.94 (t, J = 55 Hz, 1H), 4.90 (br s, 2H), 4.04 (s, 3H) $^1$H NMR (400 MHz, DMSO-d$_6$) δ 7.86-7.70 (m, 1H), 7.41 (tdd, J = 9.5, 7.3, 2.1 Hz, 3H), 6.66 (dd, J = 17.6, 11.5 Hz, 1H), 5.63-5.38 (m, 2H), 3.82 (s, 3H) | $^{19}$F NMR (376 MHz, DMSO-d$_6$) δ −132.72 (dd, J = 21.4, 8.8 Hz), −135.29 (dd, J = 21.0, 8.7 Hz), −161.04 (t, J = 21.3 Hz) |
| 198 | No | | ESIMS m/z 342 ([M + H]$^+$) | $^1$H NMR (400 MHz, CDCl$_3$) δ 7.54 (m, 1H), 7.44 (m, 1H), 5.06 (s, 2H), 4.00 (s, 3H) | $^{19}$F NMR (376 MHz, CDCl$_3$) δ −111.33, −111.38, −115.73, −115.77, −115.83, −115.89, −136.82, −136.92. |
| 199 | 145-147 | | ESIMS m/z 317 ([M + H]$^+$) | $^1$H NMR (400 MHz, CDCl$_3$) δ 7.36 (tt, J = 5.8, 1.7 Hz, 1H), 7.29-7.15 (m, 2H), 4.97 (s, 2H), 3.98 (s, 3H) | |
| 200 | 143.5-144.5 | IR (thin film) 3498, 3374, 1731, 1621, 1520, 1232 cm$^{-1}$ | ESIMS m/z 335 ([M + H]$^+$) | $^1$H NMR (400 MHz, CDCl$_3$) δ 7.57-7.39 (m, 1H), 7.09-6.96 (m, 1H), 4.96 (s, 2H), 4.00 (s, 3H) | $^{19}$F NMR (400 MHz, CDCl$_3$) δ −114.6, −131.0, −137.5, −142.0 |
| 201 | 135.9-137.7 | | ESIMS m/z 297 ([M + H]$^+$) | 1H-NMR (400 MHz, DMSO-d$_6$): δ 2.28 (s, 3H), 3.75 (s, 3H), 7.24 (dd, J = 6.24, 10.98 Hz, 1H), 7.36 (brs, 2H), 7.58 (dd, J = 6.32, 10.20 Hz, 1H), 13.5 (s, 1H) | |
| 202 | 209.7-211.9 | | ESIMS m/z 324 ([M + H]$^+$) | $^1$H NMR (400 MHz, CDCl$_3$) δ 8.03 (m, 1H), 7.42 (m, 1H), 7.32 (s, 1H), 4.96 (s, 2H), 4.03 (s, 3H) | $^{19}$F NMR (376 MHz, CDCl$_3$) δ −111.15, −119.08. |
| 203 | 143.7-145.5 | | ESIMS m/z 332 ([M + H]$^+$) | 1H-NMR (400 MHz, DMSO-d$_6$): δ 3.76 (s, 3H), 7.24 (t, J = 54.00 Hz, 1H), 7.43 (brs, 2H), 7.59 (dd, J = 5.60, 10.00 Hz, 1H), 7.78 (dd, J = 5.60, 10.40 Hz, 1H) | |
| 204 | 131 | | | $^1$H NMR (400 MHz, DMSO-d$_6$) δ 7.87 (m, 2H), 7.35 (m, 2H), 7.01 (s, 2H), 3.89 (s, 3H) | |
| 205 | 141.8-145 | | ESIMS m/z 349 ([M + H]$^+$) | $^1$H NMR (400 MHz, CDCl$_3$) δ 7.91 (m, 1H), 7.38 (m, 1H), 7.35 (s, 1H) 6.90 (t, 1H)), 4.90 (s, 2H), 4.03 (s, 3H) | |
| 206 | 159-161 | | ESIMS m/z 299 ([M + H]$^+$) | $^1$H NMR (400 MHz, DMSO-d$_6$) δ 7.55 (m, 2H), 7.39-7.30 (m, 2H), 7.05 (s, 2H), 3.86 (s, 3H) | |
| 207 | 130-132 | | ESIMS m/z 246 ([M + H]$^+$) | $^1$H NMR (400 MHz, CDCl$_3$) δ 8.29-8.21 (m, 2H), 7.48 (m, 3H), 5.66 (s, 2H), 4.06 (s, 3H) | |
| 208 | 165.0-166.5 | | ESIMS m/z 321 ([M + H]$^+$) | $^1$H NMR (400 MHz, CDCl$_3$) δ 7.88 (m, 1H), 7.42 (m, 1H), 5.51 (s, 2H), 4.03 (s, 3H), 3.98 (s, 3H) | |
| 209 | 113-115 | IR (thin film) 3496 (s), 3377 (s), 2954 (w), 1726 (s), 1611 (s) cm$^{-1}$ | ESIMS m/z 331 ([M + H]$^+$) | $^1$H NMR (300 MHz, CDCl$_3$) δ 8.01 (br d, J = 8 Hz, 2H), 7.61 (br d, J = 8 Hz, 2H), 6.70 (t, J = 56 Hz, 1H), 4.93 (br s, 2H), 3.99 (s, 3H) | |
| 210 | 159 decomp | | ESIMS m/z 317 ([M + H]$^+$) | $^1$H NMR (400 MHz, DMSO-d$_6$) δ 7.26 (m, 2H), | |

TABLE 2-continued

Analytical Data for Compounds in Table 1

| Compd. No. | mp (° C.) | IR (cm$^{-1}$) | Mass$^a$ | $^1$H NMR$^b$ | $^{13}$C or $^{19}$F NMR |
|---|---|---|---|---|---|
| 211 | 167-168 | | ESIMS m/z 329 ([M − H]$^−$) | 7.02 (s, 2H), 2.35 (d, J = 1.7 Hz, 3H) $^1$H NMR (300 MHz, DMSO-d$_6$) δ 7.23 (m, 2H), 7.08 (s, 2H), 3.85 (s, 3H), 2.33 (d, J = 2.1 Hz, 3H) | |
| 212 | 145-146 | | ESIMS m/z 299 ([M + H]$^+$) | $^1$H NMR (400 MHz, DMSO-d$_6$) δ 13.59 (s, 1H), 7.60 (m, 2H), 7.42 (m, 1H), 6.94 (s, 2H), 2.30 (s, 3H) | |
| 213 | 127 | | ESIMS m/z 313 ([M + H]$^+$) | $^1$H NMR (400 MHz, DMSO-d$_6$) δ 7.57 (dd, J = 14.6, 9.7 Hz, 2H), 7.42 (t, J = 8.1 Hz, 1H), 7.02 (s, 2H), 3.89 (s, 3H), 2.30 (s, 3H) | |
| 214 | 151-154 | | ESIMS m/z 311 ([M + H]$^+$) | $^1$H NMR (400 MHz, DMSO-d$_6$) δ 7.87 (dd, J = 11.2, 1.6 Hz, 1H), 7.80-7.68 (m, 2H), 6.76 (dd, J = 17.6, 11.7 Hz, 1H), 6.50 (br s, 2H), 5.57 (dd, J = 7.3, 0.9 Hz, 1H), 5.53 (s, 1H) | |
| 215 | 97-101 | | ESIMS m/z 325 ([M + H]$^+$) | $^1$H NMR (300 MHz, CDCl$_3$) δ 7.83-7.77 (m, 1H), 7.76-7.69 (m, 1H), 7.48 (dd, J = 8.4, 7.6 Hz, 1H), 6.89 (dd, J = 18.0, 11.7 Hz, 1H), 5.73 (dd, J = 11.5, 1.4 Hz, 1H), 5.59 (dd, J = 18.1, 1.4 Hz, 1H), 4.78 (br s, 2H), 3.93 (s, 3H) | |
| 216 | 111-114 | | | | |
| 217 | 159-161 | | | $^1$H NMR (400 MHz, CDCl$_3$) δ 7.80 (d, J = 10.4 Hz, 1H), 7.72 (d, J = 8.4 Hz, 1H), 7.48 (m, 1H), 4.93 (s, 2H), 4.00 (s, 3H) | |

$^a$Mass spectrometry data are electrospray ionization mass spectrometry (ESIMS) unless otherwise noted.
$^b$All $^1$H NMR data measured in CDCl$_3$ at 400 MHz unless otherwise noted.

Examples of Herbicidal Activities

TABLE A

Percent Control Rating Conversion Table

| Rating | Control |
|---|---|
| A | 95-100 |
| B | 85-94 |
| C | 75-84 |
| D | 60-74 |
| E | 45-59 |
| F | 30-44 |
| G | 0-29 |

Example A

Evaluation of Postemergent Herbicidal Activity

Post-emergent Test I Seeds test species were obtained from commercial suppliers and planted into a 13 cm diameter-round pot containing soil-less media mix (metro-mix 360®, Sun Gro Horticulture). Postemergence treatments were planted 8-12 days prior to application and cultured in a greenhouse equipped with supplemental light sources to provide a 16 h photoperiod at 24-29° C. All pots were surface irrigated.

A weighted amount, determined by the highest rate to be tested, of each compound was dissolved in 1.3 mL acetone-DMSO (97:3, v/v) and diluted with 4.1 mL water-isopropanol-crop oil concentrate (78:20:2, v/v/v) containing 0.02% Triton X-155 to obtain concentrated stock solutions. Additional application rates were obtained by serial dilution of the high rate solution into a solution containing appropriate volume of 97:3 v/v mixture of acetone and DMSO and appropriate volume of an aqueous mixture of water, isopropyl alcohol, crop oil concentrate (78:20:2, v/v/v) containing 0.02% Triton X-155.

Formulated compounds were applied using a DeVilbiss® compressed air sprayer at 2-4 psi. Following treatment, pots were returned to the greenhouse for the duration of the experiment. All pots were sub-irrigated as need to provide optimum growing conditions. All pots were fertilized one time per week by subirrigating with Peters Peat-Lite Special® fertilizer (20-10-20).

Phytotoxicity ratings were obtained 10 days after treatment postemergence applications. All evaluations were made visually on a scale of 0 to 100 where 0 represents no activity and 100 represents complete plant death. Visual assessments of plant injury were made based on growth reduction, discoloration, leaf deformity and necrosis.

Some of the compounds tested, application rates employed, plant species tested, and results are given in Table 3.

TABLE 3

Post-emergent Test I Herbicidal Activity on Key Broadleaf and Grass Weed as well as Crop Species

| Compound No. | Application Rate (kg ai/ha) | Visual Growth Reduction (%) 14 Days After Application | | | | | |
|---|---|---|---|---|---|---|---|
| | | AMARE | AVEFA | ECHCG | HELAN | IPOHE | SETFA |
| 138 | 4 | A | C | A | A | A | A |
| 20 | 4 | n/t | C | A | A | B | A |
| 135 | 4.04 | A | D | A | A | B | C |
| 156 | 4.04 | A | C | A | A | A | B |
| 16 | 3.84 | A | G | E | A | A | D |
| 114 | 3.92 | A | G | A | A | B | C |
| 85 | 3.76 | A | F | A | A | F | B |
| 142 | 3.84 | A | E | A | A | A | D |
| 118 | 2.32 | A | A | A | A | A | A |
| 45 | 3.96 | A | A | A | A | B | A |
| 143 | 4 | A | n/t | A | A | E | A |
| 39 | 2 | A | C | B | A | D | n/t |
| 209 | 4 | A | B | A | A | B | A |
| 199 | 4 | A | n/t | D | A | C | B |
| 206 | 4.04 | A | n/t | G | A | C | G |
| 196 | 3.84 | A | D | A | A | B | A |
| 181 | 1.76 | A | G | G | A | C | G |
| 109 | 4 | n/t | C | A | A | B | A |
| 147 | 3.96 | A | C | A | A | A | A |
| 215 | 3.96 | n/t | F | B | A | A | G |
| 214 | 4.04 | n/t | D | A | A | A | B |

AMARE: redroot pigweed (*Amaranthus retroflexus*)
AVEFA: wild oats (*Avena fatua*)
ECHCG: barnyardgrass (*Echinochloa crus-galli*)
HELAN: sunflower (*Helianthus annuus*)
IPOHE: ivyleaf morningglory (*Ipomoea hederecea*)
SETFA: giant foxtail (*Setaria faberi*)
kg ai/ha: kilograms active ingredient per hectare
n/t: not tested Example B Evaluation of Preemergent Herbicidal Activity Pre-emergent Test I Seeds of test species were planted into round plastic pots (5-inch diameter) containing sandy loam soil. After planting, all pots were sub-irrigated 16 h prior to compound application.

Compounds were dissolved in a 97:3 v/v (volume/volume) mixture of acetone and dimethyl sulfoxide (DMSO) and diluted to the appropriate concentration in a final application solution containing water, acetone, isopropanol, DMSO and Agri-dex (crop oil concentrate) in a 59:23:15:1.0:1.5 v/v ratio and 0.02% w/v (weight/volume) of Triton X-155 to obtain the spray solution containing the highest application rate. Additional application rates were obtained by serial dilution of the high rate solution with the above application solution.

Formulated compound (2.7 mL) was applied pipetted evenly over the soil surface followed by incorporation with water (15 mL). Following treatment, pots were returned to the greenhouse for the duration of the experiment. The greenhouse was programmed for an approximate 15 h photoperiod which was maintained at about 23-29° C. during the day and 22-28° C. during the night. Nutrients and water were added on a regular basis through surface irrigation and supplemental lighting was provided with overhead metal halide 1000-Watt lamps as necessary.

Herbicidal effect ratings were obtained 14 days after treatment. All evaluations were made relative to appropriate controls on a scale of 0 to 100 where 0 represents no herbicidal effect and 100 represents plant death or lack of emergence from the soil. Some of the compounds tested, application rates employed, plant species tested, and results are given in Table 4.

TABLE 4

Pre-emergent Test I Herbicidal Activity on Key Broadleaf and Grass Weed as well as Crop Species

| Compound No. | Application Rate (kg ai/ha) | Visual Growth Reduction (%) 14 Days After Application | | | | | |
|---|---|---|---|---|---|---|---|
| | | AMARE | AVEFA | ECHCG | HELAN | IPOHE | SETFA |
| 138 | 4 | A | A | A | A | A | A |
| 20 | 4 | n/t | A | A | A | A | A |
| 135 | 4.04 | A | F | F | A | A | F |
| 156 | 4.04 | A | C | A | A | A | A |
| 16 | 3.84 | A | F | F | A | A | G |
| 114 | 3.92 | A | A | C | A | A | B |
| 85 | 3.76 | A | C | A | A | F | n/t |
| 142 | 3.84 | A | A | F | A | A | n/t |
| 118 | 2.32 | A | A | A | A | A | n/t |

TABLE 4-continued

Pre-emergent Test I Herbicidal Activity on Key Broadleaf and Grass Weed as well as Crop Species

| Compound No. | Application Rate (kg ai/ha) | Visual Growth Reduction (%) 14 Days After Application | | | | | |
|---|---|---|---|---|---|---|---|
| | | AMARE | AVEFA | ECHCG | HELAN | IPOHE | SETFA |
| 45 | 3.96 | A | A | A | A | A | A |
| 143 | 4 | B | D | B | A | B | A |
| 39 | 2 | A | B | A | A | A | n/t |
| 209 | 4 | A | A | A | A | A | A |
| 199 | 4 | n/t | n/t | G | D | C | E |
| 206 | 4.04 | n/t | n/t | G | A | A | C |
| 196 | 3.84 | A | n/t | B | A | A | A |
| 181 | 1.76 | A | G | n/t | B | B | C |
| 109 | 4 | n/t | B | A | C | A | A |
| 147 | 3.96 | n/t | A | A | A | A | A |
| 215 | 3.96 | A | B | A | A | A | B |
| 214 | 4.04 | n/t | B | A | A | A | A |

AMARE: redroot pigwseed (*Amaranthus retroflexus*)
AVEFA: wild oats (*Avena fatua*)
ECHCG: barnyardgrass (*Echinochloa crus-galli*)
HELAN: sunflower (*Helianthus annuus*)
IPOHE: ivyleaf morningglory (*Ipomoea hederecea*)
SETFA: giant foxtail (*Setaria faberi*)
kg ai/ha: kilograms active ingredient per hectare
n/t: not tested Example C Evaluation of Postemergent Herbicidal Activity Post-emergent Test II: Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 d in a greenhouse with an approximate 15 h photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO. Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½×, ¼×, ⅛× and 1/16× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 5.

TABLE 5

Post-emergent Test II Herbicidal Activity on Key Broadleaf Weed and Crop Species

| Compound No. | Application Rate (g ai/ha) | Visual Growth Reduction (%) 14 Days After Application | | | | | | |
|---|---|---|---|---|---|---|---|---|
| | | ABUTH | AMARE | BRSNN | CHEAL | EPHHL | HELAN | VIOTR |
| 20 | 70 | A | A | A | A | A | A | A |
| | 140 | A | A | A | A | A | A | A |
| 216 | 70 | A | A | C | A | A | A | B |
| | 140 | A | A | B | A | A | A | A |

TABLE 5-continued

Post-emergent Test II Herbicidal Activity on Key Broadleaf Weed and Crop Species

| Compound No. | Application Rate (g ai/ha) | Visual Growth Reduction (%) 14 Days After Application | | | | | | |
|---|---|---|---|---|---|---|---|---|
| | | ABUTH | AMARE | BRSNN | CHEAL | EPHHL | HELAN | VIOTR |
| 217 | 70 | A | A | B | A | A | A | A |
|  | 140 | A | A | A | A | A | A | A |
| 135 | 70 | A | A | D | A | A | A | D |
|  | 140 | A | A | D | A | A | A | D |
| 156 | 70 | D | A | C | A | B | A | D |
|  | 140 | C | A | B | A | B | A | D |
| 16 | 70 | B | n/t | G | A | A | A | F |
|  | 140 | A | A | G | A | A | A | F |
| 95 | 70 | D | A | G | A | A | A | G |
|  | 140 | C | A | F | A | A | A | G |
| 31 | 70 | G | A | F | D | G | A | G |
|  | 140 | G | A | E | B | G | A | G |
| 149 | 70 | A | A | B | A | A | A | B |
|  | 140 | A | A | A | A | A | A | B |
| 114 | 70 | A | A | B | A | A | A | A |
|  | 140 | A | A | A | A | A | A | A |
| 85 | 70 | A | A | E | B | A | B | G |
|  | 140 | A | A | D | A | A | A | G |
| 142 | 70 | A | A | G | A | A | A | C |
|  | 140 | A | A | G | A | A | A | B |
| 118 | 70 | A | A | A | A | A | A | B |
|  | 140 | A | A | A | A | A | A | A |
| 45 | 70 | A | A | A | A | A | A | B |
|  | 140 | A | A | A | A | A | A | A |
| 91 | 70 | B | A | C | B | A | B | A |
|  | 140 | A | A | B | B | A | B | A |
| 143 | 70 | B | D | D | B | A | D | F |
|  | 140 | B | B | B | B | A | B | F |
| 190 | 70 | G | G | G | D | G | G | G |
|  | 140 | G | F | G | F | G | G | G |
| 39 | 70 | F | G | G | B | B | A | F |
|  | 140 | D | G | F | A | A | A | F |
| 165 | 70 | B | B | C | A | A | A | E |
|  | 140 | A | B | B | A | A | A | A |
| 160 | 70 | F | B | G | D | E | B | G |
|  | 140 | E | A | G | C | D | A | G |
| 204 | 70 | A | A | B | A | A | A | C |
|  | 140 | A | A | A | A | A | A | A |
| 186 | 70 | A | A | B | A | A | B | B |
|  | 140 | A | A | A | A | A | A | A |
| 209 | 70 | A | A | B | A | A | A | G |
|  | 140 | A | A | B | A | A | A | G |
| 134 | 70 | B | B | A | A | A | A | A |
|  | 140 | B | A | A | A | A | A | A |
| 80 | 70 | G | D | G | A | C | D | G |
|  | 140 | G | B | G | A | C | C | G |
| 199 | 70 | A | A | B | B | D | C | G |
|  | 140 | A | A | A | A | B | A | F |
| 206 | 70 | A | A | C | B | A | D | E |
|  | 140 | A | A | B | B | A | B | D |
| 180 | 70 | B | E | B | A | D | B | G |
|  | 140 | A | C | A | A | C | B | G |
| 213 | 66 | A | A | B | A | A | A | G |
|  | 132 | A | A | B | A | A | A | G |
| 196 | 70 | A | A | F | A | A | A | G |
|  | 140 | A | A | F | A | A | A | G |
| 181 | 70 | A | B | B | A | B | A | G |
|  | 140 | A | A | A | A | A | A | G |
| 212 | 70 | A | A | A | A | A | A | G |
|  | 140 | A | A | A | A | A | A | G |
| 211 | 70 | A | A | D | A | A | A | G |
|  | 140 | A | A | B | A | A | A | G |
| 109 | 70 | A | A | A | A | A | G | A |
|  | 140 | A | A | A | A | A | A | A |
| 147 | 70 | A | A | A | A | A | A | A |
|  | 140 | G | A | A | A | A | A | A |
| 210 | 70 | B | A | C | A | A | A | G |
|  | 140 | A | A | C | A | A | A | G |
| 167 | 70 | B | A | A | A | A | A | A |
|  | 140 | A | A | A | A | A | A | B |
| 215 | 70 | A | A | A | A | A | A | G |
|  | 140 | A | A | A | A | A | A | n/t |

TABLE 5-continued

Post-emergent Test II Herbicidal Activity on Key Broadleaf Weed and Crop Species

| Compound No. | Application Rate (g ai/ha) | Visual Growth Reduction (%) 14 Days After Application ||||||| 
|---|---|---|---|---|---|---|---|---|
| | | ABUTH | AMARE | BRSNN | CHEAL | EPHHL | HELAN | VIOTR |
| 214 | 70 | A | A | A | A | A | A | C |
| | 140 | A | A | A | A | A | A | C |
| 175 | 70 | E | E | G | G | B | E | G |
| | 140 | E | A | G | F | B | D | G |
| 7 | 70 | A | A | B | A | B | B | G |
| | 140 | A | A | B | A | A | A | G |
| 62 | 70 | C | A | A | B | A | B | G |
| | 140 | C | n/t | A | B | A | A | G |
| 64 | 70 | A | E | C | A | A | A | D |
| | 140 | A | C | B | A | A | A | D |
| 76 | 70 | A | A | B | B | A | B | E |
| | 140 | A | A | A | A | n/t | A | D |
| 172 | 70 | A | A | C | B | A | A | E |
| | 140 | A | A | C | B | A | A | D |
| 106 | 70 | G | G | G | G | G | G | G |
| | 140 | G | G | G | G | G | G | G |
| 49 | 70 | A | A | A | A | n/t | A | A |
| | 140 | A | A | A | A | n/t | A | A |
| 21 | 70 | A | A | A | A | A | A | A |
| | 140 | A | A | A | A | A | A | A |
| 132 | 70 | A | A | A | A | A | A | A |
| | 140 | A | A | A | A | A | A | A |
| 157 | 70 | B | A | A | A | A | A | A |
| | 140 | B | A | A | A | A | A | A |
| 152 | 70 | B | B | B | B | A | C | G |
| | 140 | B | B | B | B | A | B | G |
| 103 | 70 | E | G | G | G | G | C | G |
| | 140 | E | G | F | B | G | C | G |
| 99 | 70 | A | A | A | A | A | A | A |
| | 140 | A | A | A | A | A | A | A |
| 67 | 70 | A | A | G | A | A | B | G |
| | 140 | A | A | D | A | A | A | G |
| 158 | 70 | A | A | D | A | A | C | G |
| | 140 | A | A | C | A | A | C | G |
| 141 | 70 | B | A | A | B | A | A | A |
| | 140 | B | A | A | B | A | A | A |
| 104 | 70 | E | G | G | G | C | C | G |
| | 140 | E | G | G | G | B | C | G |
| 133 | 70 | B | C | C | A | B | A | G |
| | 140 | A | C | A | A | A | A | F |
| 71 | 70 | G | D | E | B | A | D | G |
| | 140 | E | C | E | B | A | C | G |
| 121 | 70 | B | G | B | C | E | B | G |
| | 140 | B | G | A | A | A | A | G |
| 168 | 70 | A | A | A | A | A | A | G |
| | 140 | A | A | A | A | A | A | F |
| 4 | 70 | A | B | A | A | A | C | G |
| | 140 | A | B | A | A | A | B | G |
| 97 | 70 | B | A | B | B | A | C | D |
| | 140 | A | A | A | A | A | A | A |
| 18 | 70 | C | G | C | B | A | A | G |
| | 140 | C | G | A | A | A | A | E |
| 54 | 70 | B | A | A | A | A | B | F |
| | 140 | B | A | A | A | A | A | E |
| 88 | 70 | C | B | A | n/t | A | B | E |
| | 140 | A | B | A | A | A | B | D |
| 59 | 70 | G | G | F | G | G | D | G |
| | 140 | G | G | E | D | G | D | G |
| 41 | 70 | G | G | G | G | G | D | G |
| | 140 | G | G | E | D | G | C | G |
| 108 | 70 | E | C | B | D | B | B | G |
| | 140 | C | A | B | C | A | A | E |
| 122 | 70 | A | A | A | A | A | B | A |
| | 140 | A | A | A | A | A | A | B |
| 24 | 70 | A | C | A | A | A | B | E |
| | 140 | A | B | A | A | A | A | A |
| 52 | 70 | A | A | A | A | A | A | A |
| | 140 | A | A | A | A | A | A | A |
| 9 | 70 | G | G | G | G | G | G | G |
| | 140 | G | G | G | G | G | G | G |
| 163 | 70 | B | A | A | A | A | A | A |
| | 140 | B | A | A | A | A | A | A |

TABLE 5-continued

Post-emergent Test II Herbicidal Activity on Key Broadleaf Weed and Crop Species

| Compound No. | Application Rate (g ai/ha) | Visual Growth Reduction (%) 14 Days After Application | | | | | | |
|---|---|---|---|---|---|---|---|---|
| | | ABUTH | AMARE | BRSNN | CHEAL | EPHHL | HELAN | VIOTR |
| 169 | 70 | B | A | A | A | A | A | A |
| | 140 | B | A | A | A | A | A | A |
| 22 | 70 | G | G | G | E | G | E | G |
| | 140 | G | G | D | C | A | C | G |
| 50 | 70 | D | G | G | G | E | E | G |
| | 140 | D | G | G | G | A | D | G |
| 82 | 70 | A | A | B | B | A | A | D |
| | 140 | A | A | B | A | A | A | C |
| 72 | 70 | B | A | B | A | A | A | D |
| | 140 | B | A | B | A | A | A | D |
| 35 | 70 | A | C | A | A | A | A | B |
| | 140 | A | A | A | A | A | A | A |
| 46 | 70 | A | B | A | A | A | B | E |
| | 140 | A | A | A | A | A | A | A |
| 89 | 70 | B | B | A | A | A | A | A |
| | 140 | A | A | A | A | A | A | A |
| 84 | 70 | G | G | G | G | G | n/t | G |
| | 140 | G | G | G | G | G | D | G |
| 154 | 70 | G | G | G | G | A | C | G |
| | 140 | E | G | D | E | A | C | G |
| 129 | 70 | A | A | B | A | A | C | A |
| | 140 | A | A | A | A | A | B | A |
| 38 | 70 | A | B | A | B | A | C | A |
| | 140 | A | A | A | A | A | B | A |
| 183 | 70 | C | A | D | A | A | B | G |
| | 140 | A | A | B | A | A | B | G |
| 92 | 70 | G | E | F | B | A | D | G |
| | 140 | G | D | E | B | A | C | G |
| 140 | 70 | G | G | G | G | B | D | G |
| | 140 | G | G | G | G | B | C | G |
| 19 | 70 | G | G | G | G | G | C | G |
| | 140 | G | G | D | G | F | C | G |
| 8 | 70 | A | A | A | A | A | A | A |
| | 140 | A | A | A | A | A | A | A |
| 26 | 70 | B | D | F | G | A | B | G |
| | 140 | B | C | F | G | A | B | G |
| 29 | 70 | B | D | E | A | A | B | G |
| | 140 | B | D | D | A | A | B | G |
| 63 | 70 | D | D | C | B | A | B | C |
| | 140 | B | C | B | A | A | B | A |
| 128 | 70 | G | E | F | E | E | E | G |
| | 140 | F | E | E | E | E | E | G |
| 58 | 70 | B | B | D | A | G | A | G |
| | 140 | A | A | C | A | G | A | G |
| 146 | 70 | C | C | B | B | G | A | G |
| | 140 | B | B | B | B | G | A | G |
| 47 | 70 | A | A | A | A | B | A | G |
| | 140 | A | A | A | A | A | A | G |
| 125 | 70 | A | A | A | A | F | A | G |
| | 140 | A | A | A | A | E | A | G |
| 189 | 70 | C | A | E | B | G | B | n/t |
| | 140 | C | A | D | B | G | B | G |
| 200 | 70 | A | A | A | A | A | B | C |
| | 140 | A | A | A | A | A | A | A |
| 12 | 70 | C | G | G | G | E | G | G |
| | 140 | B | E | G | G | A | G | G |
| 126 | 70 | A | A | C | A | A | B | G |
| | 140 | A | A | B | A | A | A | F |
| 48 | 140 | A | A | B | B | A | A | G |
| 23 | 70 | A | A | G | B | A | G | G |
| | 140 | A | A | G | A | A | B | G |
| 10 | 140 | A | A | D | C | A | B | G |
| 34 | 70 | A | A | B | A | C | A | G |
| | 140 | A | A | A | A | B | A | G |
| 153 | 140 | A | A | A | A | G | A | G |
| 15 | 140 | B | G | G | F | G | A | G |
| 33 | 140 | D | G | F | G | G | A | G |
| 170 | 140 | G | G | G | D | G | B | G |
| 105 | 140 | G | G | G | G | G | A | G |
| 1 | 140 | D | D | G | B | G | A | G |
| 14 | 140 | G | G | G | A | G | A | G |
| 51 | 70 | A | A | A | A | A | A | A |
| | 140 | A | A | A | A | A | A | A |

TABLE 5-continued

Post-emergent Test II Herbicidal Activity on Key Broadleaf Weed and Crop Species

| Compound No. | Application Rate (g ai/ha) | Visual Growth Reduction (%) 14 Days After Application | | | | | | |
|---|---|---|---|---|---|---|---|---|
| | | ABUTH | AMARE | BRSNN | CHEAL | EPHHL | HELAN | VIOTR |
| 42 | 70 | B | A | A | A | A | A | A |
| | 140 | A | A | A | A | A | A | A |
| 55 | 70 | A | A | A | A | A | A | A |
| | 140 | A | A | A | A | A | A | A |
| 69 | 70 | B | A | A | A | A | A | A |
| | 140 | B | A | A | A | A | A | A |
| 86 | 70 | A | n/t | C | A | A | A | A |
| | 140 | A | n/t | A | A | A | A | A |
| 100 | 70 | B | B | D | A | E | B | G |
| | 140 | B | A | D | A | E | B | G |
| 166 | 140 | G | A | G | D | A | B | G |
| 30 | 140 | E | G | G | G | A | G | G |
| 102 | 140 | G | G | G | G | A | D | G |
| 25 | 140 | G | G | G | G | G | G | G |
| 127 | 70 | A | A | B | A | A | B | A |
| | 140 | A | A | A | A | A | A | A |
| 56 | 70 | A | A | B | A | A | C | A |
| | 140 | A | A | B | A | A | B | A |
| 3 | 70 | A | A | B | A | A | B | A |
| | 140 | A | A | A | A | A | B | A |
| 131 | 70 | A | A | A | A | A | B | A |
| | 140 | A | A | A | A | A | A | A |
| 159 | 70 | A | A | B | A | A | C | G |
| | 140 | A | A | B | A | A | A | E |
| 124 | 70 | B | A | A | A | A | B | A |
| | 140 | B | A | A | A | A | B | A |
| 96 | 70 | A | B | C | A | C | A | G |
| | 140 | A | A | B | A | E | A | G |
| 173 | 70 | D | B | B | B | G | A | G |
| | 140 | B | A | B | B | E | A | G |
| 28 | 140 | G | A | G | A | A | B | G |
| 130 | 140 | G | G | G | G | A | B | G |
| 161 | 70 | C | E | A | A | G | A | G |
| | 140 | B | A | A | A | G | A | G |
| 53 | 70 | G | G | G | G | A | G | G |
| | 140 | G | G | G | G | A | G | G |
| 93 | 70 | A | A | G | B | A | B | F |
| | 140 | A | A | D | A | A | B | n/t |
| 74 | 70 | A | A | B | A | A | A | A |
| | 140 | A | A | B | A | A | A | A |
| 61 | 70 | B | A | G | C | A | A | G |
| | 140 | A | A | G | B | A | A | G |
| 81 | 140 | A | A | D | A | C | A | G |
| 136 | 70 | A | B | B | A | G | A | G |
| | 140 | A | B | B | A | G | A | G |
| 78 | 70 | A | B | B | B | G | A | G |
| | 140 | A | A | A | B | G | A | G |
| 116 | 70 | A | C | B | B | G | A | G |
| | 140 | A | B | A | B | G | A | G |
| 2 | 70 | A | B | A | A | A | A | F |
| | 140 | A | B | A | A | A | A | A |
| 101 | 70 | B | B | A | B | A | B | G |
| | 140 | B | B | A | B | A | B | G |
| 11 | 70 | A | A | A | A | A | A | G |
| | 140 | A | A | A | A | A | A | E |
| 119 | 70 | C | B | A | A | A | B | G |
| | 140 | B | A | A | A | A | B | G |
| 107 | 70 | C | G | G | A | A | C | G |
| | 140 | C | G | G | A | A | B | G |
| 40 | 66 | C | G | E | E | G | B | G |
| | 132 | A | E | E | D | G | A | G |
| 150 | 70 | E | A | E | B | A | A | G |
| | 140 | D | A | D | B | A | A | G |
| 60 | 70 | G | G | G | G | G | E | G |
| | 140 | G | G | G | G | G | C | G |
| 36 | 70 | G | A | G | B | A | B | G |
| | 140 | G | A | G | B | A | B | G |
| 57 | 70 | B | B | D | B | B | B | G |
| | 140 | B | A | C | B | B | B | G |
| 17 | 70 | A | A | A | B | A | B | G |
| | 140 | A | A | A | A | A | A | G |
| 117 | 70 | A | A | C | A | A | B | G |
| | 140 | A | A | C | A | A | B | G |

TABLE 5-continued

Post-emergent Test II Herbicidal Activity on Key Broadleaf Weed and Crop Species

| Compound No. | Application Rate (g ai/ha) | Visual Growth Reduction (%) 14 Days After Application | | | | | | |
|---|---|---|---|---|---|---|---|---|
| | | ABUTH | AMARE | BRSNN | CHEAL | EPHHL | HELAN | VIOTR |
| 83 | 70 | G | G | G | G | G | B | G |
| | 140 | F | G | G | G | G | B | G |
| 111 | 70 | F | G | G | F | G | C | G |
| | 140 | D | G | G | D | G | B | G |
| 94 | 70 | G | G | G | B | G | B | G |
| | 140 | G | E | G | B | G | B | G |
| 192 | 70 | G | G | G | G | G | G | G |
| | 140 | G | G | G | G | G | G | G |
| 112 | 70 | A | A | B | B | G | A | G |
| | 140 | A | A | B | B | G | A | G |
| 79 | 66 | B | D | B | A | G | A | G |
| | 132 | A | C | B | A | G | A | G |
| 155 | 70 | G | G | E | B | G | B | G |
| | 140 | G | G | D | A | G | B | G |
| 66 | 70 | B | A | E | B | A | B | G |
| | 140 | B | A | E | B | A | B | G |
| 13 | 70 | B | B | B | A | G | A | G |
| | 140 | A | A | B | A | F | A | G |
| 27 | 70 | D | D | D | B | A | B | A |
| | 140 | C | C | D | B | A | B | A |
| 77 | 70 | B | A | C | A | A | B | G |
| | 140 | A | A | B | A | A | B | G |
| 145 | 70 | E | C | A | A | D | A | G |
| | 140 | D | A | A | A | D | A | G |
| 37 | 70 | E | B | A | A | A | B | A |
| | 140 | D | B | A | A | A | B | A |
| 73 | 70 | B | A | A | B | E | A | E |
| | 140 | B | A | A | B | D | A | E |
| 171 | 70 | C | B | B | B | A | B | A |
| | 140 | B | A | B | B | A | B | A |
| 43 | 70 | B | A | A | C | D | A | A |
| | 140 | B | A | A | C | D | A | A |
| 113 | 70 | B | A | A | A | A | A | A |
| | 140 | B | A | A | A | A | A | A |
| 115 | 70 | B | A | D | A | A | B | A |
| | 140 | B | A | C | A | A | A | A |
| 110 | 70 | A | A | A | A | A | A | E |
| | 140 | A | A | A | A | A | A | E |
| 197 | 70 | A | A | A | A | A | B | D |
| | 140 | A | A | B | A | A | B | C |
| 191 | 70 | D | A | A | A | A | A | E |
| | 140 | A | A | A | A | A | A | E |
| 137 | 70 | C | G | G | G | G | E | G |
| | 140 | B | G | G | E | D | D | G |
| 98 | 70 | G | G | G | G | G | G | G |
| | 140 | G | G | G | G | G | G | G |
| 32 | 70 | D | C | G | A | A | B | G |
| | 140 | D | A | E | A | A | B | G |
| 5 | 70 | G | G | G | G | G | B | G |
| | 140 | G | G | G | G | G | B | G |
| 151 | 70 | A | n/t | C | A | G | B | G |
| | 140 | A | n/t | B | A | G | B | G |
| 87 | 70 | B | n/t | A | B | G | B | D |
| | 140 | B | n/t | A | B | G | B | B |
| 123 | 70 | G | A | G | G | A | C | G |
| | 140 | G | A | D | G | A | C | E |
| 70 | 70 | A | A | C | A | A | B | D |
| | 140 | A | A | B | A | A | A | C |
| 44 | 70 | F | C | G | C | B | B | G |
| | 140 | D | A | G | B | A | A | G |
| 65 | 70 | G | A | G | D | A | B | G |
| | 140 | G | A | F | C | A | A | F |
| 144 | 70 | B | A | B | B | C | B | C |
| | 140 | A | A | A | A | B | A | B |
| 148 | 70 | C | G | E | B | B | E | E |
| | 140 | C | G | D | A | C | D | D |
| 90 | 70 | B | A | A | A | A | F | A |
| | 140 | B | A | A | A | A | C | A |
| 162 | 70 | B | A | A | A | A | B | A |
| | 140 | B | A | A | A | A | B | A |
| 68 | 70 | B | A | A | A | A | D | A |
| | 140 | B | A | A | A | A | G | A |

TABLE 5-continued

Post-emergent Test II Herbicidal Activity on Key Broadleaf Weed and Crop Species

| Compound No. | Application Rate (g ai/ha) | Visual Growth Reduction (%) 14 Days After Application | | | | | | |
|---|---|---|---|---|---|---|---|---|
| | | ABUTH | AMARE | BRSNN | CHEAL | EPHHL | HELAN | VIOTR |
| 202 | 70 | A | A | C | A | A | A | D |
| | 140 | A | A | B | A | A | A | D |
| 198 | 70 | D | D | C | B | E | A | F |
| | 140 | C | A | C | A | D | A | D |
| 208 | 70 | G | G | G | G | F | G | G |
| | 140 | G | G | G | G | E | E | G |
| 205 | 70 | A | A | D | A | A | B | E |
| | 140 | A | A | B | A | A | A | D |
| 176 | 70 | A | A | A | B | A | A | F |
| | 140 | A | A | A | B | A | A | E |
| 193 | 70 | D | C | D | B | B | D | G |
| | 140 | C | A | D | A | A | C | F |
| 177 | 70 | B | C | F | C | A | F | G |
| | 140 | B | B | C | B | A | G | G |
| 179 | 70 | A | A | F | A | A | B | G |
| | 140 | A | A | E | A | A | B | G |
| 184 | 70 | A | B | B | B | B | A | G |
| | 140 | A | A | A | A | A | A | G |
| 185 | 70 | F | G | F | D | C | C | G |
| | 140 | E | G | E | A | B | B | G |
| 174 | 70 | C | A | A | A | A | A | E |
| | 140 | C | A | A | A | A | A | D |
| 178 | 70 | C | A | A | A | B | A | F |
| | 140 | C | A | A | A | A | A | E |
| 203 | 70 | F | E | F | B | A | D | G |
| | 140 | F | A | E | A | A | C | F |
| 187 | 70 | E | A | C | C | A | E | G |
| | 140 | D | A | C | A | A | D | G |
| 195 | 70 | G | G | E | E | F | D | G |
| | 140 | G | E | D | C | F | B | G |
| 188 | 70 | C | A | D | A | A | C | G |
| | 140 | A | A | D | B | A | C | G |
| 194 | 70 | D | A | D | C | B | B | G |
| | 140 | C | A | C | B | B | A | G |
| 201 | 70 | F | F | A | B | E | D | G |
| | 140 | D | D | A | C | B | C | G |

ABUTH: velvetleaf (*Abutilon theophrasti*)
AMARE: redroot pigweed (*Amaranthus retroflexus*)
BRSNN: oilseed-rape, canola (*Brassica napus*)
CHEAL: lambsquarters (*Chenopodium album*)
EPHHL: wild poinsettia (*Euphorbia heterophylla*)
HELAN: sunflower (*Helianthus annuus*)
VIOTR: wild pansy (*Viola tricolor*)
g ai/ha: grams active ingredient per hectare
n/t: not tested

TABLE 6

Post-emergent Test II Herbicidal Activity on Key Grass and Sedge Weeds as well as Grass Crops

| Compound No. | Application Rate (g ai/ha) | Visual Growth Reduction (%) 14 Days After Application | | | | | | | |
|---|---|---|---|---|---|---|---|---|---|
| | | CYPES | DIGSA | ECHCG | SETFA | SORVU | ORYSA | TRZSS | ZEAMX |
| 20 | 70 | A | A | A | A | A | D | C | A |
| | 140 | A | A | A | A | A | D | C | A |
| 216 | 70 | B | F | A | F | B | G | G | B |
| | 140 | A | C | A | E | B | G | F | B |
| 217 | 70 | B | B | A | A | B | D | C | B |
| | 140 | B | B | A | A | B | C | C | A |
| 135 | 70 | B | D | A | D | C | G | F | C |
| | 140 | A | C | A | C | B | G | F | C |
| 156 | 70 | D | D | C | B | D | G | E | C |
| | 140 | B | C | B | A | D | G | D | C |
| 16 | 70 | A | D | C | E | D | G | F | B |
| | 140 | A | C | A | D | D | G | E | B |
| 95 | 70 | E | G | B | G | D | G | G | G |
| | 140 | C | G | A | G | D | G | G | G |

TABLE 6-continued

Post-emergent Test II Herbicidal Activity on Key Grass and Sedge Weeds as well as Grass Crops

| Compound No. | Application Rate (g ai/ha) | Visual Growth Reduction (%) 14 Days After Application | | | | | | | |
|---|---|---|---|---|---|---|---|---|---|
| | | CYPES | DIGSA | ECHCG | SETFA | SORVU | ORYSA | TRZSS | ZEAMX |
| 31 | 70 | G | D | C | G | G | G | G | G |
| | 140 | G | D | B | G | G | G | G | G |
| 149 | 70 | A | F | A | F | A | G | F | C |
| | 140 | A | F | A | F | A | G | E | B |
| 114 | 70 | A | D | A | D | A | G | F | B |
| | 140 | A | D | A | C | A | G | E | B |
| 85 | 70 | B | F | A | E | C | G | F | C |
| | 140 | B | F | A | C | B | G | F | C |
| 142 | 70 | C | D | C | G | E | G | G | E |
| | 140 | B | D | B | G | E | G | F | D |
| 118 | 70 | A | C | A | E | A | F | C | D |
| | 140 | A | B | A | D | A | E | C | B |
| 45 | 70 | B | B | A | B | D | E | D | B |
| | 140 | A | B | A | B | A | D | C | A |
| 91 | 70 | A | B | A | C | C | G | E | B |
| | 140 | A | B | A | B | C | G | E | B |
| 143 | 70 | B | C | A | C | B | G | E | B |
| | 140 | B | C | A | C | B | F | D | B |
| 190 | 70 | G | G | G | G | G | G | G | G |
| | 140 | G | G | G | G | G | G | G | G |
| 39 | 70 | D | F | B | G | F | G | F | D |
| | 140 | C | E | B | F | D | G | E | D |
| 165 | 70 | A | D | B | D | D | G | E | C |
| | 140 | A | D | A | B | D | G | E | A |
| 160 | 70 | G | G | G | G | G | G | G | G |
| | 140 | G | G | G | G | G | G | G | G |
| 204 | 70 | B | D | A | G | C | G | E | C |
| | 140 | B | D | A | E | B | G | D | C |
| 186 | 70 | B | E | B | G | D | G | D | C |
| | 140 | B | D | A | D | C | F | D | B |
| 209 | 70 | B | E | A | E | A | G | G | C |
| | 140 | B | D | A | C | A | G | G | B |
| 134 | 70 | A | C | A | A | B | E | D | E |
| | 140 | A | B | A | A | B | E | C | D |
| 80 | 70 | G | G | G | G | G | G | G | G |
| | 140 | G | G | G | G | G | G | G | G |
| 199 | 70 | G | G | G | G | G | G | G | G |
| | 140 | G | G | G | G | G | G | G | G |
| 206 | 70 | G | G | G | G | G | G | G | G |
| | 140 | G | G | G | G | G | G | G | G |
| 180 | 70 | F | G | G | G | G | G | G | G |
| | 140 | E | G | G | G | F | G | G | G |
| 213 | 66 | G | G | B | G | C | G | G | D |
| | 132 | E | G | B | G | A | G | G | C |
| 196 | 70 | B | E | A | G | C | G | G | G |
| | 140 | B | E | A | G | C | G | G | C |
| 181 | 70 | A | G | G | G | G | G | G | G |
| | 140 | A | G | G | G | F | G | G | F |
| 212 | 70 | G | G | C | E | D | D | D | C |
| | 140 | F | F | B | C | C | D | D | B |
| 211 | 70 | E | G | E | E | G | G | G | F |
| | 140 | D | G | B | D | F | G | G | E |
| 109 | 70 | A | B | A | A | B | E | E | B |
| | 140 | A | A | A | A | A | E | D | B |
| 147 | 70 | A | B | A | G | A | D | D | A |
| | 140 | A | A | A | A | A | C | D | A |
| 210 | 70 | G | G | D | C | G | G | G | G |
| | 140 | G | G | C | B | G | F | G | E |
| 167 | 70 | B | C | A | B | B | G | D | C |
| | 140 | A | C | A | A | B | G | D | B |
| 215 | 70 | A | G | G | G | E | G | G | F |
| | 140 | A | G | A | G | D | G | G | E |
| 214 | 70 | A | G | A | G | C | G | G | B |
| | 140 | A | G | A | F | B | E | G | B |
| 175 | 70 | G | G | G | G | G | G | G | G |
| | 140 | G | G | G | G | G | G | G | G |
| 7 | 70 | C | C | C | D | B | G | F | A |
| | 140 | B | B | A | A | B | G | E | A |
| 62 | 70 | A | B | A | A | C | G | E | C |
| | 140 | A | B | A | A | C | G | E | B |
| 64 | 70 | E | D | E | F | F | G | F | A |
| | 140 | D | B | B | D | E | G | E | A |

TABLE 6-continued

Post-emergent Test II Herbicidal Activity on Key Grass and Sedge Weeds as well as Grass Crops

| Compound No. | Application Rate (g ai/ha) | Visual Growth Reduction (%) 14 Days After Application | | | | | | | |
|---|---|---|---|---|---|---|---|---|---|
| | | CYPES | DIGSA | ECHCG | SETFA | SORVU | ORYSA | TRZSS | ZEAMX |
| 76 | 70 | G | C | B | E | E | G | E | G |
| | 140 | F | B | A | D | E | F | E | A |
| 172 | 70 | A | C | A | A | C | G | E | A |
| | 140 | A | C | A | A | C | G | D | A |
| 106 | 70 | G | G | G | G | G | G | G | G |
| | 140 | G | G | G | G | G | G | G | G |
| 49 | 70 | A | D | B | D | A | G | E | A |
| | 140 | B | C | A | A | A | G | D | A |
| 21 | 70 | A | C | A | A | A | G | D | A |
| | 140 | A | C | A | A | A | G | D | A |
| 132 | 70 | E | B | B | G | B | G | G | A |
| | 140 | B | B | C | D | A | G | F | A |
| 157 | 70 | E | C | A | A | B | G | E | A |
| | 140 | E | B | A | A | A | G | E | A |
| 152 | 70 | D | E | n/t | G | E | G | G | A |
| | 140 | A | C | B | E | E | G | G | A |
| 103 | 70 | G | G | G | G | G | G | G | G |
| | 140 | E | G | G | G | G | G | G | G |
| 99 | 70 | n/t | C | A | A | A | G | E | A |
| | 140 | A | B | A | A | A | G | D | A |
| 67 | 70 | A | D | B | G | B | G | G | G |
| | 140 | A | C | A | G | B | G | G | E |
| 158 | 70 | E | D | D | G | B | G | G | G |
| | 140 | E | D | C | G | B | G | E | G |
| 141 | 70 | G | C | B | C | B | G | D | A |
| | 140 | A | C | A | A | B | G | D | A |
| 104 | 70 | G | G | G | G | G | G | G | E |
| | 140 | E | G | G | G | E | G | G | A |
| 133 | 70 | F | G | G | E | D | G | F | A |
| | 140 | E | D | D | C | C | G | F | A |
| 71 | 70 | G | D | B | D | F | G | F | A |
| | 140 | G | E | B | D | E | G | E | A |
| 121 | 70 | E | G | G | G | E | G | G | A |
| | 140 | E | G | G | G | D | G | G | A |
| 168 | 70 | A | C | A | A | A | G | D | A |
| | 140 | A | C | A | A | A | G | D | A |
| 4 | 70 | E | D | C | D | C | G | C | G |
| | 140 | A | C | B | D | C | G | C | G |
| 97 | 70 | A | E | G | G | G | G | F | A |
| | 140 | A | E | D | F | F | G | D | A |
| 18 | 70 | A | G | G | G | F | G | F | A |
| | 140 | A | F | E | G | G | G | F | A |
| 54 | 70 | E | G | A | C | D | G | E | A |
| | 140 | A | D | A | C | C | G | E | A |
| 88 | 70 | B | G | C | D | C | G | D | E |
| | 140 | A | G | C | B | B | G | D | E |
| 59 | 70 | G | G | G | G | G | G | G | G |
| | 140 | G | G | G | G | G | G | G | G |
| 41 | 70 | G | G | G | G | G | G | G | G |
| | 140 | G | G | G | G | G | G | G | G |
| 108 | 70 | E | D | E | E | G | G | F | G |
| | 140 | F | D | C | F | F | G | F | E |
| 122 | 70 | A | E | B | n/t | A | G | E | A |
| | 140 | A | E | A | A | B | G | E | A |
| 24 | 70 | A | E | A | D | B | G | G | A |
| | 140 | A | D | A | B | B | G | F | A |
| 52 | 70 | A | B | D | n/t | A | G | F | A |
| | 140 | A | B | C | B | A | G | F | A |
| 9 | 70 | G | G | G | G | G | G | G | G |
| | 140 | G | G | G | G | G | G | G | G |
| 163 | 70 | A | C | B | B | B | G | D | E |
| | 140 | A | B | B | A | B | G | D | D |
| 169 | 70 | A | C | C | A | A | F | F | A |
| | 140 | A | B | C | A | A | F | E | A |
| 22 | 70 | G | G | G | G | G | G | G | G |
| | 140 | G | G | E | G | G | G | G | E |
| 50 | 70 | G | G | E | F | G | G | G | A |
| | 140 | G | E | C | E | G | G | G | A |
| 82 | 70 | A | G | E | G | G | G | F | A |
| | 140 | A | G | B | G | E | G | F | A |
| 72 | 70 | G | E | A | E | B | G | D | D |
| | 140 | A | D | A | C | A | G | D | D |

TABLE 6-continued

Post-emergent Test II Herbicidal Activity on Key Grass and Sedge Weeds as well as Grass Crops

| Compound No. | Application Rate (g ai/ha) | CYPES | DIGSA | ECHCG | SETFA | SORVU | ORYSA | TRZSS | ZEAMX |
|---|---|---|---|---|---|---|---|---|---|
| 35 | 70 | A | E | F | G | E | G | F | A |
|  | 140 | A | B | B | E | D | G | E | A |
| 46 | 70 | A | E | B | C | E | G | E | E |
|  | 140 | A | D | B | B | D | G | D | E |
| 89 | 70 | E | E | B | B | B | G | G | E |
|  | 140 | A | D | B | B | A | D | E | A |
| 84 | 70 | G | G | G | G | G | G | G | G |
|  | 140 | G | G | G | G | G | G | G | G |
| 154 | 70 | G | G | E | G | G | G | G | G |
|  | 140 | G | G | E | G | G | G | G | G |
| 129 | 70 | A | D | C | n/t | A | G | E | D |
|  | 140 | n/t | D | C | n/t | A | G | E | C |
| 38 | 70 | A | C | A | A | B | G | D | B |
|  | 140 | A | C | A | A | B | G | D | A |
| 183 | 70 | G | G | n/t | G | F | G | G | G |
|  | 140 | G | G | n/t | G | E | G | G | G |
| 92 | 70 | G | D | n/t | n/t | F | G | F | D |
|  | 140 | G | D | n/t | n/t | E | G | E | D |
| 140 | 70 | G | G | n/t | n/t | G | G | G | G |
|  | 140 | G | G | n/t | n/t | G | G | G | G |
| 19 | 70 | G | G | G | G | G | G | G | G |
|  | 140 | G | G | G | G | G | G | G | G |
| 8 | 70 | A | C | B | C | A | F | D | D |
|  | 140 | A | B | B | A | A | E | C | B |
| 26 | 70 | n/t | G | G | G | G | G | E | G |
|  | 140 | n/t | G | G | G | G | G | E | E |
| 29 | 70 | F | F | G | G | E | G | G | G |
|  | 140 | E | D | G | G | E | G | G | G |
| 63 | 70 | n/t | D | C | n/t | G | G | D | D |
|  | 140 | n/t | D | A | A | F | G | D | D |
| 128 | 70 | G | F | E | C | G | G | G | G |
|  | 140 | G | F | E | C | G | G | G | G |
| 58 | 70 | A | D | G | n/t | E | G | E | D |
|  | 140 | A | C | C | n/t | E | G | D | D |
| 146 | 70 | A | D | C | n/t | F | G | D | D |
|  | 140 | A | D | B | n/t | F | G | C | D |
| 47 | 70 | B | C | B | B | B | G | E | B |
|  | 140 | A | C | B | A | B | G | E | B |
| 125 | 70 | A | D | n/t | B | D | G | D | D |
|  | 140 | A | D | n/t | A | B | G | D | D |
| 189 | 70 | G | G | n/t | G | G | G | G | G |
|  | 140 | G | G | n/t | G | G | G | G | G |
| 200 | 70 | G | C | C | E | G | G | F | E |
|  | 140 | E | C | C | C | G | G | F | D |
| 12 | 70 | F | G | G | G | G | G | G | G |
|  | 140 | E | G | G | G | G | G | G | G |
| 126 | 70 | D | C | A | G | C | G | G | G |
|  | 140 | F | B | A | C | B | G | G | D |
| 48 | 140 | G | D | C | G | G | G | F | G |
| 23 | 70 | E | C | B | G | B | G | G | G |
|  | 140 | C | C | A | E | A | G | G | G |
| 10 | 140 | G | C | B | A | C | G | D | D |
| 34 | 70 | D | G | G | C | F | G | D | D |
|  | 140 | D | E | G | B | E | G | D | D |
| 153 | 140 | E | E | G | C | G | G | D | D |
| 15 | 140 | G | G | G | G | G | G | G | G |
| 33 | 140 | G | G | G | G | G | G | G | G |
| 170 | 140 | G | G | G | G | G | G | G | G |
| 105 | 140 | G | G | G | G | G | G | G | G |
| 1 | 140 | F | G | G | G | G | G | G | G |
| 14 | 140 | G | G | G | G | G | G | G | G |
| 51 | 70 | A | A | A | A | A | G | D | B |
|  | 140 | A | n/t | A | A | A | G | B | B |
| 42 | 70 | A | C | A | A | A | F | D | C |
|  | 140 | A | B | A | A | A | F | C | D |
| 55 | 70 | A | B | A | A | B | G | n/t | D |
|  | 140 | A | B | A | A | A | G | A | B |
| 69 | 70 | E | A | A | A | A | G | D | C |
|  | 140 | A | A | A | A | A | G | B | C |
| 86 | 70 | A | G | C | G | C | F | G | D |
|  | 140 | A | G | B | G | n/t | E | G | D |
| 100 | 70 | G | E | G | G | G | G | F | G |
|  | 140 | G | D | G | G | G | G | D | E |

TABLE 6-continued

Post-emergent Test II Herbicidal Activity on Key Grass and Sedge Weeds as well as Grass Crops

| Compound No. | Application Rate (g ai/ha) | Visual Growth Reduction (%) 14 Days After Application | | | | | | | |
|---|---|---|---|---|---|---|---|---|---|
| | | CYPES | DIGSA | ECHCG | SETFA | SORVU | ORYSA | TRZSS | ZEAMX |
| 166 | 140 | E | G | G | G | G | G | G | E |
| 30 | 140 | G | G | G | G | G | G | G | G |
| 102 | 140 | G | G | G | G | G | G | G | G |
| 25 | 140 | G | G | G | G | G | G | G | G |
| 127 | 70 | A | B | A | A | A | G | D | B |
| | 140 | A | A | A | A | A | G | C | B |
| 56 | 70 | A | C | A | A | C | G | D | B |
| | 140 | A | B | A | A | B | G | D | B |
| 3 | 70 | A | C | B | A | B | F | D | B |
| | 140 | A | B | B | A | B | E | D | B |
| 131 | 70 | B | C | A | A | D | G | D | B |
| | 140 | B | C | A | A | C | F | C | B |
| 159 | 70 | A | B | B | C | A | G | D | D |
| | 140 | A | B | A | A | A | G | D | C |
| 124 | 70 | A | C | B | D | A | F | E | C |
| | 140 | A | B | B | A | A | F | D | C |
| 96 | 70 | A | D | G | D | B | G | D | C |
| | 140 | A | C | D | C | B | G | C | C |
| 173 | 70 | A | D | C | C | C | G | D | D |
| | 140 | A | C | C | B | B | G | D | C |
| 28 | 140 | G | D | G | E | G | G | G | D |
| 130 | 140 | G | G | G | G | G | G | G | G |
| 161 | 70 | A | F | E | B | G | G | D | D |
| | 140 | n/t | E | D | B | G | G | D | D |
| 53 | 70 | G | G | G | G | G | G | G | G |
| | 140 | G | G | G | G | G | G | G | G |
| 93 | 70 | A | C | B | C | B | G | E | D |
| | 140 | A | A | B | C | A | G | E | C |
| 74 | 70 | A | B | B | C | B | G | E | C |
| | 140 | A | B | B | B | B | F | D | C |
| 61 | 70 | E | G | E | G | E | G | F | D |
| | 140 | E | G | D | G | D | G | F | D |
| 81 | 140 | G | E | G | D | C | G | E | C |
| 136 | 70 | A | D | G | F | D | G | E | D |
| | 140 | A | D | G | E | D | G | E | C |
| 78 | 70 | G | G | G | E | G | G | E | G |
| | 140 | A | G | G | D | G | G | E | F |
| 116 | 70 | G | E | E | E | F | G | E | E |
| | 140 | G | D | D | D | E | G | E | D |
| 2 | 70 | D | n/t | D | E | F | G | E | C |
| | 140 | D | D | D | D | D | G | E | C |
| 101 | 70 | E | E | G | G | F | G | F | D |
| | 140 | E | D | B | D | E | G | F | D |
| 11 | 70 | E | D | B | D | D | G | E | D |
| | 140 | E | D | B | D | C | G | D | D |
| 119 | 70 | E | E | B | D | D | G | E | D |
| | 140 | E | D | B | D | D | G | D | D |
| 107 | 70 | G | G | G | G | G | G | G | G |
| | 140 | D | G | G | G | G | G | G | G |
| 40 | 66 | G | G | G | G | G | G | G | G |
| | 132 | G | G | G | G | G | G | G | G |
| 150 | 70 | G | G | G | G | E | G | F | E |
| | 140 | E | G | G | D | E | G | E | D |
| 60 | 70 | G | G | G | G | G | G | G | G |
| | 140 | G | G | G | G | G | G | G | G |
| 36 | 70 | G | G | D | G | D | G | E | F |
| | 140 | A | G | C | G | D | G | E | E |
| 57 | 70 | A | G | G | G | C | G | G | G |
| | 140 | A | G | G | G | A | G | G | G |
| 17 | 70 | A | G | C | G | B | D | F | D |
| | 140 | A | G | B | E | A | B | E | C |
| 117 | 70 | A | G | C | G | B | E | G | E |
| | 140 | A | G | C | E | B | E | G | D |
| 83 | 70 | G | G | G | G | G | G | G | G |
| | 140 | G | G | G | G | G | G | G | G |
| 111 | 70 | G | G | G | G | G | G | G | G |
| | 140 | G | G | G | G | G | G | G | G |
| 94 | 70 | G | G | G | G | G | G | G | G |
| | 140 | G | G | G | G | G | G | G | G |
| 192 | 70 | G | G | G | G | G | G | G | G |
| | 140 | G | G | G | G | G | G | G | G |
| 112 | 70 | A | D | D | B | B | G | E | D |
| | 140 | A | D | D | A | B | G | D | D |

TABLE 6-continued

Post-emergent Test II Herbicidal Activity on Key Grass and Sedge Weeds as well as Grass Crops

| Compound No. | Application Rate (g ai/ha) | Visual Growth Reduction (%) 14 Days After Application | | | | | | |
|---|---|---|---|---|---|---|---|---|
| | | CYPES | DIGSA | ECHCG | SETFA | SORVU | ORYSA | TRZSS | ZEAMX |
| 79 | 66 | A | D | D | C | D | G | G | D |
| | 132 | A | D | D | C | C | G | F | D |
| 155 | 70 | G | G | G | G | G | G | G | G |
| | 140 | G | G | G | G | G | G | G | G |
| 66 | 70 | E | D | G | G | C | G | G | G |
| | 140 | A | D | D | G | B | G | G | G |
| 13 | 70 | C | D | D | E | B | G | E | D |
| | 140 | C | C | C | C | B | G | D | D |
| 27 | 70 | G | G | G | G | G | G | E | G |
| | 140 | A | G | G | G | F | G | E | G |
| 77 | 70 | G | C | D | G | E | G | E | G |
| | 140 | E | B | D | G | E | G | E | G |
| 145 | 70 | E | B | C | C | B | G | D | C |
| | 140 | E | B | C | C | B | G | D | C |
| 37 | 70 | G | E | C | G | C | G | E | G |
| | 140 | G | D | C | D | B | G | D | E |
| 73 | 70 | A | G | G | D | B | G | D | D |
| | 140 | A | E | D | D | B | G | D | D |
| 171 | 70 | E | G | F | G | G | G | F | D |
| | 140 | E | D | D | G | E | G | F | C |
| 43 | 70 | A | C | C | D | A | G | D | C |
| | 140 | A | C | D | D | A | F | D | C |
| 113 | 70 | A | C | B | C | B | F | D | B |
| | 140 | A | C | B | C | B | D | C | B |
| 115 | 70 | A | B | B | G | B | G | G | G |
| | 140 | A | B | B | G | A | G | G | G |
| 110 | 70 | E | C | D | D | B | G | E | E |
| | 140 | E | C | C | D | B | G | E | D |
| 197 | 70 | D | E | G | G | D | G | G | D |
| | 140 | D | D | C | G | D | G | G | D |
| 191 | 70 | G | D | B | C | E | G | G | E |
| | 140 | D | C | C | C | E | G | F | D |
| 137 | 70 | E | G | G | G | G | G | G | G |
| | 140 | E | G | G | G | G | G | G | G |
| 98 | 70 | G | G | G | G | G | G | G | G |
| | 140 | G | G | G | G | G | G | G | G |
| 32 | 70 | G | G | C | G | D | G | G | E |
| | 140 | E | G | C | G | D | G | G | D |
| 5 | 70 | G | G | G | G | G | G | G | G |
| | 140 | G | G | G | G | G | G | G | G |
| 151 | 70 | G | G | G | G | D | G | G | D |
| | 140 | C | G | E | D | D | G | G | C |
| 87 | 70 | G | D | C | D | D | G | D | D |
| | 140 | E | D | C | C | D | G | D | D |
| 123 | 70 | G | G | C | G | F | G | G | E |
| | 140 | E | G | B | G | F | G | G | D |
| 70 | 70 | A | B | B | F | B | G | C | A |
| | 140 | A | A | A | D | A | G | B | A |
| 44 | 70 | F | G | G | G | G | G | F | G |
| | 140 | E | G | G | G | G | G | F | G |
| 65 | 70 | G | G | G | G | G | G | G | G |
| | 140 | G | G | G | G | G | G | G | G |
| 144 | 70 | B | D | E | D | C | G | D | D |
| | 140 | A | C | C | C | B | G | C | C |
| 148 | 70 | D | G | G | G | G | G | F | G |
| | 140 | C | G | G | G | G | F | D | F |
| 90 | 70 | A | B | B | B | A | F | F | D |
| | 140 | A | C | B | B | A | G | E | D |
| 162 | 70 | A | C | B | B | B | E | E | D |
| | 140 | E | C | C | C | A | E | E | C |
| 68 | 70 | A | C | B | B | A | E | F | G |
| | 140 | A | C | C | C | A | E | E | C |
| 202 | 70 | B | F | D | D | D | G | D | F |
| | 140 | B | D | A | D | B | G | C | E |
| 198 | 70 | D | G | G | G | G | G | F | G |
| | 140 | D | G | G | G | G | G | E | G |
| 208 | 70 | G | G | G | G | G | G | G | G |
| | 140 | G | G | G | G | G | G | G | G |
| 205 | 70 | B | F | B | E | D | G | G | F |
| | 140 | A | E | B | C | C | G | F | D |
| 176 | 70 | B | E | B | B | D | G | F | G |
| | 140 | A | D | B | B | B | G | E | B |

TABLE 6-continued

Post-emergent Test II Herbicidal Activity on Key Grass and Sedge Weeds as well as Grass Crops

| Compound No. | Application Rate (g ai/ha) | Visual Growth Reduction (%) 14 Days After Application | | | | | | | |
|---|---|---|---|---|---|---|---|---|---|
| | | CYPES | DIGSA | ECHCG | SETFA | SORVU | ORYSA | TRZSS | ZEAMX |
| 193 | 70 | F | G | G | G | G | G | G | G |
| | 140 | E | G | G | E | E | G | F | G |
| 177 | 70 | E | G | G | F | G | G | F | G |
| | 140 | E | G | D | E | E | G | F | G |
| 179 | 70 | G | G | G | G | G | G | G | G |
| | 140 | G | G | F | G | E | G | G | G |
| 184 | 70 | G | G | E | G | G | G | G | G |
| | 140 | G | G | D | G | F | G | G | G |
| 185 | 70 | G | G | G | G | G | G | G | G |
| | 140 | G | G | G | G | G | G | G | G |
| 174 | 70 | D | G | D | G | G | G | G | G |
| | 140 | B | E | B | E | G | G | G | G |
| 178 | 70 | B | G | D | B | E | G | F | G |
| | 140 | B | E | B | B | D | G | E | F |
| 203 | 70 | G | G | G | G | G | G | G | G |
| | 140 | C | G | G | C | G | G | G | G |
| 187 | 70 | G | G | D | D | G | G | G | G |
| | 140 | F | G | D | C | G | G | E | G |
| 195 | 70 | G | G | G | G | G | G | G | G |
| | 140 | G | G | G | G | G | G | G | G |
| 188 | 70 | G | G | C | G | E | G | G | G |
| | 140 | G | G | D | F | G | G | G | G |
| 194 | 70 | G | G | G | E | G | G | G | G |
| | 140 | G | G | G | D | G | G | G | G |
| 201 | 70 | G | G | D | G | G | G | G | G |
| | 140 | G | G | E | F | E | G | G | G |

ECHCG: barnyardgrass (*Echinochloa crus-galli*)
CYPES: yellow nutsedge (*Cyperus esculentus*)
DIGSA: crabgrass (*Digitaria sanguinalis*)
ORYSA: rice (*Oryza sativa*)
SETFA: giant foxtail (*Setaria faberi*)
SORVU: johnsongrass (*Sorghum vulgare*)
TRZAS: wheat, spring (*Triticum aestivum*)
ZEAMX: maize, corn (*Zea mays*)
g ai/ha: grams active ingredient per hectare
n/t: not tested Example D Evaluation of Postemergent Herbicidal Activity in Wheat and Barley Post-emergent Test III. Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14 hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Agri-Dex crop oil concentrate, and X-77 surfactant in a 48:39:10:1.5:1.5:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Agri-Dex crop oil concentrate, and X-77 surfactant in a 48:39:10:1.5:1.5:0.02 v/v ratio to obtain ½×, ¼×, ⅛× and ¹⁄₁₆× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 21 d, the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in *"Probit Analysis"* Cambridge University Press (1952), herbicidal injury of a specific compound at various rates can be used to calculate $GR_{20}$, $GR_{50}$, $GR_{80}$ and $GR_{90}$ values, which are defined as growth reduction factors that correspond to the effective dose of herbicide required to provide plant growth reduction (GR) of 20 percent, 50 percent, 80 percent and 90 percent, respectively. Probit analysis was applied to data collected from multiple dose rates of individual compounds utilizing the procedures explained in the following examples. The analysis of those dose rates is captured in the following tables.

Some of the compounds tested, application rates employed, plant species tested, and results are given in Tables 7 through 11.

TABLE 7

Activity of Herbicidal Compounds in Wheat and Barley

| Compd. No. | Application Rate (g ai/ha) | Visual Growth Reduction (%) 21 Days After Application | | | | | | |
|---|---|---|---|---|---|---|---|---|
| | | ALOMY | APESV | BROTE | KCHSC | LAMSS | LOLSS | MATSS |
| 138 | 35 | C | B | C | A | A | D | D |
| | 70 | B | B | B | A | A | C | B |
| | 140 | A | A | B | A | A | B | B |
| | GR20 | — | — | — | — | — | — | — |
| | GR50 | 11 | 2 | 12 | 1 | 1 | 20 | 16 |
| | GR80 | 30 | 12 | 42 | 4 | 1 | 66 | 51 |
| 20 | 35 | C | B | C | A | A | E | A |
| | 70 | C | B | B | A | A | D | A |
| | 140 | C | B | B | A | A | D | A |
| | GR20 | — | — | — | — | — | — | — |
| | GR50 | 21 | 2 | 3 | 2 | 1 | 25 | 1 |
| | GR80 | 72 | 12 | 87 | 5 | 1 | >140 | 1 |
| 216 | 35 | E | B | F | A | A | G | C |
| | 70 | D | B | E | A | A | F | C |
| | 140 | C | A | E | A | A | E | B |
| | GR20 | — | — | — | — | — | — | — |
| | GR50 | 54 | 6 | 136 | 1 | 1 | 137 | 10 |
| | GR80 | >140 | 20 | >140 | 2 | 1 | >140 | 62 |
| 217 | 35 | C | B | C | B | A | E | B |
| | 70 | B | B | B | A | A | D | B |
| | 140 | B | A | B | A | A | D | B |
| | GR20 | — | — | — | — | — | — | — |
| | GR50 | 12 | 6 | 15 | 2 | 1 | 32 | 34 |
| | GR80 | 31 | 15 | 33 | 6 | 2 | >140 | >140 |
| 114 | 35 | G | G | G | D | B | G | G |
| | 70 | G | G | G | D | B | G | G |
| | 140 | G | G | G | C | A | G | G |
| | GR20 | — | — | — | — | — | — | — |
| | GR50 | >140 | >140 | >140 | 3 | 1 | >140 | >140 |
| | GR80 | >140 | >140 | >140 | >140 | 4 | >140 | >140 |
| 85 | 35 | G | G | G | G | B | G | G |
| | 70 | G | G | G | G | B | G | G |
| | 140 | G | G | G | G | B | G | G |
| | GR20 | — | — | — | — | — | — | — |
| | GR50 | >140 | >140 | >140 | >140 | 0 | 0 | 88 |
| | GR80 | >140 | >140 | >140 | >140 | 6 | 0 | >140 |
| 142 | 35 | G | G | G | E | B | G | G |
| | 70 | G | G | G | D | B | G | G |
| | 140 | G | G | G | D | B | G | F |
| | GR20 | — | — | — | — | — | — | — |
| | GR50 | >140 | >140 | >140 | 17 | 0 | >140 | >140 |
| | GR80 | >140 | >140 | >140 | >140 | 5 | >140 | >140 |
| 118 | 35 | D | D | D | B | A | F | D |
| | 70 | C | C | B | B | A | D | C |
| | 140 | B | B | B | A | A | C | B |
| | GR20 | — | — | — | — | — | — | — |
| | GR50 | 25 | 22 | 31 | 3 | 1 | 49 | 14 |
| | GR80 | 60 | 60 | 64 | 17 | 0 | 121 | 60 |
| 45 | 35 | C | B | B | B | B | D | B |
| | 70 | B | B | B | A | A | C | A |
| | 140 | A | A | A | A | A | B | A |
| | GR20 | — | — | — | — | — | — | — |
| | GR50 | 9 | 8 | 13 | 2 | 1 | 20 | 2 |
| | GR80 | 27 | 25 | 36 | 9 | 6 | 69 | 29 |
| 91 | 35 | E | E | E | C | A | G | D |
| | 70 | E | E | E | B | A | G | C |
| | 140 | E | D | F | B | A | G | B |
| | GR20 | — | — | — | — | — | — | — |
| | GR50 | 98 | 67 | 29 | 2 | 1 | >140 | 11 |
| | GR80 | >140 | >140 | >140 | 47 | 3 | >140 | 75 |
| 143 | 35 | G | D | G | F | B | G | G |
| | 70 | D | D | E | F | B | F | D |
| | 140 | D | C | E | E | B | E | D |
| | GR20 | — | — | — | — | — | — | — |

TABLE 7-continued

Activity of Herbicidal Compounds in Wheat and Barley

|  |  |  |  |  |  |  |  |  |
|---|---|---|---|---|---|---|---|---|
|  | GR50 | 71 | 31 | 95 | >140 | 1 | 116 | 67 |
|  | GR80 | >140 | 129 | >140 | >140 | 1 | >140 | >140 |
| 39 | 35 | G | F | G | C | A | F | A |
|  | 70 | E | E | G | B | A | E | A |
|  | 140 | E | D | G | B | A | D | A |
|  | GR20 | — | — | — | — | — | — | — |
|  | GR50 | 111 | 70 | 0 | 3 | 1 | 82 | 1 |
|  | GR80 | >140 | >140 | 0 | 40 | 1 | >140 | 1 |
| 204 | 35 | G | G | G | B | B | G | G |
|  | 70 | E | F | G | A | A | G | G |
|  | 140 | E | D | F | A | A | G | G |
|  | GR20 | — | — | — | — | — | — | — |
|  | GR50 | 105 | 106 | >140 | 2 | 1 | 0 | >140 |
|  | GR80 | >140 | >140 | >140 | 9 | 8 | 0 | >140 |
| 186 | 35 | G | G | G | D | C | G | G |
|  | 70 | G | G | G | D | B | G | G |
|  | 140 | G | G | G | D | B | G | G |
|  | GR20 | — | — | — | — | — | — | — |
|  | GR50 | >140 | >140 | >140 | 1 | 1 | >140 | >140 |
|  | GR80 | >140 | >140 | >140 | >140 | 25 | >140 | >140 |
| 209 | 35 | G | G | G | D | B | G | G |
|  | 70 | G | G | F | B | B | F | G |
|  | GR20 | — | — | — | — | — | — | — |
|  | GR50 | >140 | >140 | 88 | 12 | 7 | 93 | >140 |
|  | GR80 | >140 | >140 | >140 | 42 | 29 | >140 | >140 |
| 109 | 35 | D | B | C | B | A | E | F |
|  | 70 | C | B | B | B | A | E | E |
|  | GR20 | — | — | — | — | — | — | — |
|  | GR50 | 22 | 1 | 14 | 3 | 1 | 34 | 72 |
|  | GR80 | 88 | 6 | 41 | 19 | 1 | >140 | >140 |
| 147 | 35 | D | B | C | B | B | F | A |
|  | 70 | B | B | B | A | B | E | A |
|  | 140 | B | B | B | B | B | D | A |
|  | GR20 | — | — | — | — | — | — | — |
|  | GR50 | 20 | 5 | 6 | 4 | 1 | 71 | 6 |
|  | GR80 | 47 | 16 | 28 | 19 | 8 | >140 | 14 |
| 167 | 35 | F | C | F | D | A | G | C |
|  | 70 | D | B | C | C | A | G | B |
|  | GR20 | — | — | — | — | — | — | — |
|  | GR50 | 57 | 20 | 43 | 23 | 1 | >140 | 24 |
|  | GR80 | 119 | 46 | 81 | 52 | 1 | >140 | 48 |
| 214 | 35 | F | G | G | C | C | F | C |
|  | 70 | E | F | G | B | C | E | B |
|  | 140 | F | E | G | A | B | B | B |
|  | GR20 | — | — | — | — | — | — | — |
|  | GR50 | 95 | 110 | >140 | 7 | 12 | 59 | 4 |
|  | GR80 | >140 | >140 | >140 | 52 | 33 | >140 | 41 |

| Compd. No. | Application Rate (g ai/ha) | Visual Growth Reduction (%) 21 Days After Application | | | | | |
|---|---|---|---|---|---|---|---|
|  |  | PAPRH | PHAMI | SETVI | STEME | VERPE | HORSS | TRZSS |
| 138 | 35 | A | E | B | F | D | B | B |
|  | 70 | A | C | B | F | B | B | B |
|  | 140 | A | B | A | E | B | A | B |
|  | GR20 | — | — | — | — | — | 1 | 1 |
|  | GR50 | 1 | 31 | 8 | 125 | 15 | — | — |
|  | GR80 | 1 | 78 | 32 | >140 | 49 | — | — |
| 20 | 35 | A | B | A | C | D | B | B |
|  | 70 | A | B | A | A | D | A | B |
|  | 140 | A | B | A | A | C | A | B |
|  | GR20 | — | — | — | — | — | 1 | 1 |
|  | GR50 | 1 | 5 | 4 | 8 | 33 | — | — |
|  | GR80 | 1 | 25 | 10 | 25 | >140 | — | — |
| 216 | 35 | A | G | D | F | E | B | C |
|  | 70 | A | F | C | F | D | B | B |
|  | 140 | A | C | B | C | C | B | B |
|  | GR20 | — | — | — | — | — | 1 | 1 |
|  | GR50 | 1 | >140 | 20 | 52 | 32 | — | — |
|  | GR80 | 1 | >140 | 64 | >140 | >140 | — | — |
| 217 | 35 | A | B | C | D | D | C | C |
|  | 70 | A | B | C | C | D | C | C |
|  | 140 | A | B | C | C | D | C | B |
|  | GR20 | — | — | — | — | — | 7 | 2 |
|  | GR50 | 1 | 11 | 46 | 28 | 19 | — | — |
|  | GR80 | 1 | 30 | >140 | 88 | 73 | — | — |

TABLE 7-continued

Activity of Herbicidal Compounds in Wheat and Barley

| | | | | | | | | |
|---|---|---|---|---|---|---|---|---|
| 114 | 35 | A | G | G | G | F | G | F |
| | 70 | A | G | G | G | F | F | E |
| | 140 | A | G | G | G | F | F | E |
| | GR20 | — | — | — | — | — | 42 | 16 |
| | GR50 | 1 | >140 | >140 | >140 | >140 | — | — |
| | GR80 | 4 | >140 | >140 | >140 | >140 | — | — |
| 85 | 35 | B | G | G | G | F | G | D |
| | 70 | A | G | G | G | E | F | D |
| | 140 | A | G | G | G | D | D | D |
| | GR20 | — | — | — | — | — | 33 | 1 |
| | GR50 | 1 | >140 | >140 | 57 | 90 | — | — |
| | GR80 | 3 | >140 | >140 | 123 | >140 | — | — |
| 142 | 35 | B | G | G | G | C | G | G |
| | 70 | A | G | G | G | B | G | G |
| | 140 | A | G | G | G | B | G | E |
| | GR20 | — | — | — | — | — | 57 | >140 |
| | GR50 | 1 | >140 | >140 | >140 | 5 | — | — |
| | GR80 | 4 | >140 | >140 | >140 | 40 | — | — |
| 118 | 35 | A | G | G | F | B | B | C |
| | 70 | A | D | F | F | B | B | B |
| | 140 | A | C | D | F | A | B | B |
| | GR20 | — | — | — | — | — | 1 | 0 |
| | GR50 | 1 | 68 | 91 | 1 | 5 | — | — |
| | GR80 | 1 | 126 | 184 | 1 | 17 | — | — |
| 45 | 35 | A | C | D | F | C | B | B |
| | 70 | A | B | B | F | B | B | B |
| | 140 | A | A | A | F | B | A | B |
| | GR20 | — | — | — | — | — | 1 | 1 |
| | GR50 | 1 | 15 | 18 | 75 | 7 | — | — |
| | GR80 | 1 | 32 | 52 | >140 | 30 | — | — |
| 91 | 35 | A | F | D | G | F | C | C |
| | 70 | A | F | C | F | F | C | B |
| | 140 | A | F | C | E | E | B | B |
| | GR20 | — | — | — | — | — | 1 | 1 |
| | GR50 | 1 | >140 | 6 | >140 | 123 | — | — |
| | GR80 | 1 | >140 | 105 | >140 | >140 | — | — |
| 143 | 35 | B | G | E | G | F | D | D |
| | 70 | B | F | E | G | E | C | C |
| | 140 | B | D | D | G | E | B | C |
| | GR20 | — | — | — | — | — | 2 | 0 |
| | GR50 | 1 | 112 | 52 | >140 | 97 | — | — |
| | GR80 | 8 | >140 | >140 | >140 | >140 | — | — |
| 39 | 35 | A | G | F | G | B | F | C |
| | 70 | A | F | E | F | B | E | C |
| | 140 | A | E | D | E | A | D | B |
| | GR20 | — | — | — | — | — | 18 | 1 |
| | GR50 | 0 | 118 | 68 | 111 | 1 | — | — |
| | GR80 | 0 | >140 | >140 | >140 | 12 | — | — |
| 204 | 35 | B | G | G | C | D | F | D |
| | 70 | B | E | F | C | D | D | C |
| | 140 | A | D | F | B | D | D | B |
| | GR20 | — | — | — | — | — | 16 | 7 |
| | GR50 | 3 | 100 | >140 | 7 | 20 | — | — |
| | GR80 | 19 | >140 | >140 | 61 | >140 | — | — |
| 186 | 35 | D | G | G | F | F | G | G |
| | 70 | D | G | G | F | E | G | G |
| | 140 | C | G | G | F | D | G | G |
| | GR20 | — | — | — | — | — | 115 | >140 |
| | GR50 | 1 | >140 | >140 | >140 | 82 | — | — |
| | GR80 | >140 | >140 | >140 | >140 | >140 | — | — |
| 209 | 35 | A | G | F | G | D | E | F |
| | 70 | A | G | E | F | C | D | D |
| | GR20 | — | — | — | — | — | 16 | 25 |
| | GR50 | 2 | >140 | 65 | >140 | 20 | — | — |
| | GR80 | 5 | >140 | >140 | >140 | 86 | — | — |
| 109 | 35 | A | A | C | D | B | C | D |
| | 70 | A | A | C | D | A | B | C |
| | GR20 | — | — | — | — | — | 2 | 4 |
| | GR50 | 1 | 6 | 15 | 11 | 2 | — | — |
| | GR80 | 1 | 14 | 42 | >140 | 13 | — | — |
| 147 | 35 | A | A | D | F | E | B | C |
| | 70 | A | A | B | D | C | B | B |
| | 140 | A | A | B | D | D | B | B |
| | GR20 | — | — | — | — | — | 0 | 0 |
| | GR50 | 1 | 4 | 16 | 61 | 43 | — | — |
| | GR80 | 1 | 14 | 49 | >140 | >140 | — | — |
| 167 | 35 | A | C | F | F | A | E | E |
| | 70 | A | B | C | F | A | C | D |

TABLE 7-continued

Activity of Herbicidal Compounds in Wheat and Barley

|     |      |   |      |      |      |      |    |    |
|-----|------|---|------|------|------|------|----|----|
|     | GR20 | — | —    | —    | —    | —    | 13 | 14 |
|     | GR50 | 1 | 22   | 40   | >140 | 1    | —  | —  |
|     | GR80 | 1 | 44   | 90   | >140 | 2    | —  | —  |
| 214 | 35   | A | G    | G    | G    | F    | G  | F  |
|     | 70   | A | G    | F    | F    | D    | F  | E  |
|     | 140  | A | G    | E    | C    | C    | D  | D  |
|     | GR20 | — | —    | —    | —    | —    | 24 | 8  |
|     | GR50 | 4 | >140 | >140 | 71   | 62   | —  | —  |
|     | GR80 | 9 | >140 | >140 | >140 | >140 | —  | —  |

TABLE 8

Activity of Herbicidal Compounds in Wheat and Barley

| Compound No | Application Rate (g ai/ha) | Visual Growth Reduction (%) 21 Days After Application ||||||||||
|---|---|---|---|---|---|---|---|---|---|---|---|
| | | CIRAR | GALAP | KCHSC | LAMSS | MATSS | PAPRH | SASKR | VERPE | VIOSS | HORSS | TRZSS |
| 135 | 35   | B   | D    | C   | C  | F    | B | D    | D    | D    | G    | F    |
|     | 70   | B   | A    | C   | B  | F    | B | D    | C    | D    | F    | F    |
|     | 140  | B   | A    | C   | B  | E    | A | C    | B    | C    | D    | E    |
|     | GR20 | —   | —    | —   | —  | —    | — | —    | —    | —    | 37   | 16   |
|     | GR50 | 1   | 12   | 3   | 1  | 125  | 1 | 3    | 24   | 23   | —    | —    |
|     | GR80 | 13  | 38   | 130 | 19 | >140 | 1 | >140 | 78   | >140 | >140 | >140 |
| 3   | 35   | D   | A    | A   | A  | A    | A | C    | E    | A    | B    | B    |
|     | 70   | C   | A    | A   | A  | A    | A | B    | D    | A    | A    | B    |
|     | GR20 | —   | —    | —   | —  | —    | — | —    | —    | —    | 1    | 1    |
|     | GR50 | 18  | 5    | 2   | 1  | 4    | 1 | 2    | 34   | 4    | —    | —    |
|     | GR80 | 53  | 7    | 8   | 1  | 11   | 1 | 28   | 126  | 7    | —    | —    |
| 124 | 35   | D   | B    | B   | A  | C    | A | D    | C    | D    | B    | B    |
|     | 70   | C   | A    | B   | A  | B    | A | B    | B    | A    | A    | B    |
|     | GR20 | —   | —    | —   | —  | —    | — | —    | —    | —    | 1    | 1    |
|     | GR50 | 24  | 6    | 3   | 1  |      | 1 | 12   | 20   | 24   | —    | —    |
|     | GR80 | 91  | 21   | 29  | 1  | 32   | 1 | 53   | 39   | 49   | —    | —    |
| 79  | 35   | A   | A    | D   | D  | C    | A | C    | C    | G    | B    | C    |
|     | 70   | A   | A    | C   | D  | B    | A | B    | B    | G    | B    | B    |
|     | GR20 | —   | —    | —   | —  | —    | — | —    | —    | —    | 1    | 2    |
|     | GR50 | 1   | 4    | 24  | 27 | 13   | 1 | 11   | 2    | >140 | —    | —    |
|     | GR80 | 5   | 6    | 70  | 72 | 46   | 1 | 43   | 37   | >140 | —    | —    |
| 27  | 35   | C   | B    | C   | B  | F    | A | D    | C    | C    | F    | D    |
|     | 70   | C   | B    | C   | B  | F    | A | D    | B    | A    | E    | C    |
|     | GR20 | —   | —    | —   | —  | —    | — | —    | —    | —    | 11   | 11   |
|     | GR50 | 18  | 5    | 18  | 1  | 109  | 1 | 22   | 5    | 8    | —    | —    |
|     | GR80 | 70  | 25   | 61  | 14 | >140 | 1 | 116  | 42   | 27   | —    | —    |
| 145 | 35   | A   | E    | D   | A  | A    | A | D    | B    | G    | B    | B    |
|     | 70   | B   | C    | D   | A  | A    | A | C    | B    | G    | A    | B    |
|     | 140  | A   | A    | C   | A  | A    | A | B    | A    | F    | A    | B    |
|     | GR20 | —   | —    | —   | —  | —    | — | —    | —    | —    | 1    | 1    |
|     | GR50 | 2   | 18   | 37  | 4  | 3    | 1 |      | 1    | >140 | —    | —    |
|     | GR80 | 7   | 54   | 112 | 13 | 10   | 1 | 79   | 10   | >140 | —    | —    |
| 37  | 35   | E   | B    | E   | B  | D    | A | E    | D    | C    | D    | C    |
|     | 70   | C   | A    | D   | A  | D    | A | D    | C    | B    | C    | B    |
|     | GR20 | —   | —    | —   | —  | —    | — | —    | —    | —    | 5    | 3    |
|     | GR50 | 23  | 14   | 34  | 1  | 21   | 1 | 33   | 15   | 12   | —    | —    |
|     | GR80 | 103 | 31   | 119 | 11 | 77   | 1 | 104  | 66   | 35   | —    | —    |
| 171 | 35   | D   | B    | B   | B  | F    | A | D    | B    | A    | E    | C    |
|     | 70   | D   | A    | A   | A  | F    | A | C    | B    | A    | D    | B    |
|     | GR20 | —   | —    | —   | —  | —    | — | —    | —    | —    | 20   | 11   |
|     | GR50 | 17  |      |     | 2  | >140 | 1 | 21   | 4    | 5    | —    | —    |
|     | GR80 | 80  | 23   | 23  | 11 | >140 | 1 | 67   | 27   | 10   | —    | —    |
| 43  | 35   | B   | A    | D   | B  | B    | A | C    | F    | E    | A    | B    |
|     | 70   | B   | A    | B   | B  | A    | A | C    | C    | D    | A    | A    |
|     | GR20 | —   | —    | —   | —  | —    | — | —    | —    | —    | 1    | 1    |
|     | GR50 | 0   | 2    | 11  | 1  | 3    | 1 | 3    | 33   | 37   | —    | —    |
|     | GR80 | 13  | 6    | 41  | 10 | 7    | 1 | 61   | >140 | >140 | —    | —    |
| 113 | 35   | C   | A    | A   | A  | B    | A | C    | B    | A    | B    | B    |
|     | 70   | B   | A    | A   | A  | A    | A | B    | B    | A    | A    | B    |
|     | GR20 | —   | —    | —   | —  | —    | — | —    | —    | —    | 1    | 1    |
|     | GR50 | 7   | 5    | 3   | 1  | 4    | 1 | 5    | 3    | 4    | —    | —    |
|     | GR80 | 33  | 12   | 10  | 4  | 15   | 1 | 36   | 18   | 11   | —    | —    |
| 110 | 35   | C   | A    | A   | A  | D    | A | C    | G    | F    | B    | B    |
|     | 70   | C   | A    | A   | A  | B    | A | B    | G    | D    | A    | B    |

TABLE 8-continued

Activity of Herbicidal Compounds in Wheat and Barley

| Compound No | Application Rate (g ai/ha) | Visual Growth Reduction (%) 21 Days After Application | | | | | | | | | |
|---|---|---|---|---|---|---|---|---|---|---|---|
| | | CIRAR | GALAP | KCHSC | LAMSS | MATSS | PAPRH | SASKR | VERPE | VIOSS | HORSS | TRZSS |
| | GR20 | — | — | — | — | — | — | — | — | — | 1 | 1 |
| | GR50 | 19 | 1 | 1 | 1 | 10 | 1 | 1 | >140 | 51 | — | — |
| | GR80 | 52 | 1 | 1 | 1 | 37 | 1 | 30 | >140 | 144 | — | — |

TABLE 9

Activity of Herbicidal Compounds in Wheat and Barley

| Compound No. | Application Rate (g ai/ha) | Visual Growth Reduction (%) 21 Days After Application | | | | | |
|---|---|---|---|---|---|---|---|
| | | APESV | KCHSC | LOLSS | SETVI | HORSS | TRZSS |
| 76 | 35 | C | G | F | E | D | C |
| | 70 | B | E | E | D | D | B |
| | GR20 | — | — | — | — | 6 | 4 |
| | GR50 | 27 | 74 | 53 | 42 | — | — |
| | GR80 | 52 | 132 | 133 | 87 | — | — |
| 172 | 35 | F | D | G | D | D | C |
| | 70 | D | D | G | C | D | C |
| | GR20 | — | — | — | — | 3 | 1 |
| | GR50 | 53 | 38 | >140 | 25 | — | — |
| | GR80 | 124 | 73 | >140 | 56 | — | — |
| 168 | 35 | C | A | G | E | B | B |
| | 70 | B | A | E | D | A | A |
| | GR20 | — | — | — | — | 1 | 1 |
| | GR50 | 21 | 5 | 108 | 28 | — | — |
| | GR80 | 57 | 15 | >140 | 70 | — | — |
| 35 | 35 | G | C | G | G | D | C |
| | 70 | F | B | F | F | D | C |
| | GR20 | — | — | — | — | 8 | 2 |
| | GR50 | 113 | 8 | 126 | 79 | — | — |
| | GR80 | >140 | 37 | >140 | >140 | — | — |
| 46 | 35 | G | C | G | G | D | C |
| | 70 | G | B | F | F | D | C |
| | 140 | E | B | E | F | B | B |
| | GR20 | — | — | — | — | 8 | 1 |
| | GR50 | >140 | 10 | 118 | >140 | — | — |
| | GR80 | >140 | 45 | >140 | >140 | — | — |
| 154 | 35 | G | G | G | F | G | G |
| | 70 | G | G | G | D | G | F |
| | 140 | G | G | G | C | E | E |
| | GR20 | — | — | — | — | 81 | 49 |
| | GR50 | >140 | 57 | >140 | 56 | — | — |
| | GR80 | >140 | 93 | >140 | 109 | — | — |
| 146 | 35 | A | G | G | E | C | C |
| | 70 | A | G | G | C | B | B |
| | 140 | A | G | G | A | A | B |
| | GR20 | — | — | — | — | 1 | 1 |
| | GR50 | 23 | >140 | >140 | 41 | — | — |
| | GR80 | 34 | >140 | >140 | 76 | — | — |
| 47 | 35 | A | B | G | G | A | B |
| | 70 | A | C | E | C | A | A |
| | 140 | A | A | D | B | A | A |
| | GR20 | — | — | — | — | 1 | 1 |
| | GR50 | 10 | 20 | 80 | 51 | — | — |
| | GR80 | 14 | 45 | >140 | 104 | — | — |
| 125 | 35 | C | D | G | B | B | C |
| | 70 | B | B | G | B | A | C |
| | 140 | A | A | E | B | A | B |
| | GR20 | — | — | — | — | 1 | 1 |
| | GR50 | 10 | 8 | >140 | 2 | — | — |
| | GR80 | 41 | 34 | >140 | 16 | — | — |
| 51 | 35 | B | B | C | C | B | B |
| | 70 | A | A | C | B | A | A |
| | GR20 | — | — | — | — | 1 | 1 |
| | GR50 | 3 | 4 | 3 | 24 | — | — |
| | GR80 | 11 | 14 | 61 | 49 | — | — |
| 42 | 35 | B | B | F | B | B | B |
| | 70 | B | D | E | B | B | B |

TABLE 9-continued

Activity of Herbicidal Compounds in Wheat and Barley

| Compound No. | Application Rate (g ai/ha) | Visual Growth Reduction (%) 21 Days After Application | | | | | |
|---|---|---|---|---|---|---|---|
| | | APESV | KCHSC | LOLSS | SETVI | HORSS | TRZSS |
| | 140 | A | A | C | A | A | A |
| | GR20 | — | — | — | — | 1 | 1 |
| | GR50 | 7 | 1 | 76 | 1 | — | — |
| | GR80 | 22 | 1 | >140 | 19 | — | — |
| 55 | 35 | C | B | D | C | B | B |
| | 70 | A | B | C | B | A | A |
| | GR20 | — | — | — | — | 1 | 1 |
| | GR50 | 4 | 4 | 21 | 29 | — | — |
| | GR80 | 18 | 21 | 50 | 46 | — | — |
| 159 | 35 | B | B | E | E | B | B |
| | 70 | A | A | D | D | A | A |
| | GR20 | — | — | — | — | 1 | 1 |
| | GR50 | 11 | 4 | 36 | 43 | — | — |
| | GR80 | 25 | 19 | 89 | 113 | — | — |
| 96 | 35 | F | G | E | G | B | B |
| | 70 | F | D | D | D | A | B |
| | 140 | E | D | D | C | A | A |
| | GR20 | — | — | — | — | 1 | 1 |
| | GR50 | 125 | 79 | 48 | 72 | — | — |
| | GR80 | >140 | >140 | >140 | 128 | — | — |
| 173 | 35 | D | F | F | F | B | C |
| | 70 | C | E | E | E | A | B |
| | GR20 | — | — | — | — | 1 | 1 |
| | GR50 | 27 | 60 | 119 | 54 | — | — |
| | GR80 | 59 | 131 | >140 | 104 | — | — |
| 28 | 35 | G | G | G | G | G | F |
| | 70 | G | F | G | G | F | D |
| | GR20 | — | — | — | — | 43 | 17 |
| | GR50 | >140 | 88 | >140 | >140 | — | — |
| | GR80 | >140 | >140 | >140 | >140 | — | — |
| 161 | 35 | D | G | G | F | B | C |
| | 70 | C | G | G | D | B | C |
| | GR20 | — | — | — | — | 1 | 1 |
| | GR50 | 30 | >140 | 38 | 53 | — | — |
| | GR80 | 57 | >140 | 82 | 128 | — | — |
| 74 | 35 | B | B | F | C | B | C |
| | 70 | B | A | E | B | B | C |
| | GR20 | — | — | — | — | 1 | 1 |
| | GR50 | 10 | 3 | >140 | 3 | — | — |
| | GR80 | 25 | 11 | >140 | 49 | — | — |
| 150 | 35 | G | D | G | G | F | D |
| | 70 | G | D | G | F | E | D |
| | GR20 | — | — | — | — | 8 | 1 |
| | GR50 | >140 | 7 | >140 | 79 | — | — |
| | GR80 | >140 | >140 | >140 | >140 | — | — |
| 36 | 35 | G | G | G | G | F | C |
| | 70 | G | G | G | F | D | C |
| | GR20 | — | — | — | — | 16 | 1 |
| | GR50 | >140 | >140 | >140 | 126 | — | — |
| | GR80 | >140 | >140 | >140 | >140 | — | — |
| 117 | 35 | E | D | E | G | G | G |
| | 70 | D | C | D | D | G | F |
| | GR20 | — | — | — | — | 73 | 32 |
| | GR50 | 41 | 20 | 41 | 59 | — | — |
| | GR80 | >140 | 67 | >140 | 99 | — | — |

TABLE 10

Activity of Herbicidal Compounds in Wheat and Barley

| Compd. No. | Application Rate (g ai/ha) | Visual Gorowth Reduction (%) 21 days After Application | | | | | | |
|---|---|---|---|---|---|---|---|---|
| | | KCHSC | MATSS | SASKR | VERPE | VIOSS | HORSS | TRZSS |
| 49 | 35 | B | D | C | E | A | C | C |
| | 70 | B | C | B | D | A | B | B |
| | GR20 | — | — | — | — | — | 1 | 1 |
| | GR50 | 4 | 15 | 1 | 37 | 5 | — | — |
| | GR80 | 18 | 93 | 30 | >140 | 8 | — | — |

TABLE 10-continued

Activity of Herbicidal Compounds in Wheat and Barley

| Compd. No. | Application Rate (g ai/ha) | Visual Gorowth Reduction (%) 21 days After Application | | | | | | |
|---|---|---|---|---|---|---|---|---|
| | | KCHSC | MATSS | SASKR | VERPE | VIOSS | HORSS | TRZSS |
| 21 | 35 | A | B | C | F | A | B | C |
| | 70 | A | B | B | G | A | A | B |
| | GR20 | — | — | — | — | — | 1 | 1 |
| | GR50 | 1 | 5 | 1 | 130 | 4 | — | — |
| | GR80 | 1 | 31 | 25 | >140 | 6 | — | — |
| 132 | 35 | B | G | C | G | A | D | D |
| | 70 | B | F | C | C | A | C | D |
| | 140 | A | F | C | B | A | A | C |
| | GR20 | — | — | — | — | — | 9 | 10 |
| | GR50 | 4 | >140 | 1 | 58 | 9 | — | — |
| | GR80 | 20 | >140 | 66 | 99 | 17 | — | — |
| 157 | 35 | B | D | C | F | A | B | C |
| | 70 | B | C | B | D | A | A | C |
| | GR20 | — | — | — | — | — | 1 | 1 |
| | GR50 | 6 | 21 | 11 | 50 | 1 | — | — |
| | GR80 | 18 | 64 | 34 | >140 | 4 | — | — |
| 99 | 35 | C | F | C | A | A | B | B |
| | 70 | B | E | C | A | A | A | B |
| | GR20 | — | — | — | — | — | 1 | 1 |
| | GR50 | 9 | 63 | 10 | 8 | 9 | — | — |
| | GR80 | 27 | >140 | 48 | 17 | 19 | — | — |
| 141 | 35 | C | C | C | C | A | B | C |
| | 70 | B | A | B | B | A | A | B |
| | GR20 | — | — | — | — | — | 1 | 1 |
| | GR50 | 7 | 15 | 4 | 14 | 7 | — | — |
| | GR80 | 28 | 33 | 40 | 43 | 11 | — | — |
| 108 | 35 | G | F | G | D | F | F | C |
| | 70 | G | D | F | C | F | E | C |
| | GR20 | — | — | — | — | — | 16 | 6 |
| | GR50 | >140 | 58 | 136 | 22 | 85 | — | — |
| | GR80 | >140 | >140 | >140 | 67 | >140 | — | — |
| 122 | 35 | B | G | A | A | A | D | C |
| | 70 | A | F | A | A | A | B | B |
| | GR20 | — | — | — | — | — | 3 | 1 |
| | GR50 | 5 | >140 | <17.5 | 1 | 10 | — | — |
| | GR80 | 14 | >140 | <17.5 | 2 | 21 | — | — |
| 52 | 35 | C | G | D | C | A | B | B |
| | 70 | B | D | C | A | A | A | B |
| | GR20 | — | — | — | — | — | 1 | 1 |
| | GR50 | 5 | 62 | 4 | 20 | 12 | — | — |
| | GR80 | 38 | 91 | 84 | 37 | 19 | — | — |
| 163 | 35 | C | C | C | C | C | B | C |
| | 70 | B | A | B | A | A | A | C |
| | GR20 | — | — | — | — | — | 1 | 1 |
| | GR50 | 8 | 5 | 3 | 13 | 14 | — | — |
| | GR80 | 36 | 24 | 27 | 30 | 29 | — | — |
| 169 | 37.1 | D | C | D | B | C | A | C |
| | 74.3 | B | A | C | A | A | A | B |
| | 149 | B | A | B | A | A | A | B |
| | GR20 | — | — | — | — | — | 1 | 1 |
| | GR50 | 8 | 15 | 5 | 19 | 21 | — | — |
| | GR80 | 72 | 35 | 83 | 37 | 36 | — | — |
| 72 | 35 | D | G | F | B | F | E | C |
| | 70 | D | F | D | A | E | D | B |
| | GR20 | — | — | — | — | — | 5 | 1 |
| | GR50 | 27 | 126 | 48 | 1 | 67 | — | — |
| | GR80 | 105 | >140 | 106 | 8 | >140 | — | — |
| 89 | 35 | B | C | B | A | A | D | C |
| | 70 | B | B | B | A | A | D | B |
| | GR20 | — | — | — | — | — | 3 | 1 |
| | GR50 | 12 | 14 | 9 | 3 | 11 | — | — |
| | GR80 | 25 | 36 | 21 | 6 | 19 | — | — |
| 129 | 35 | B | G | C | F | C | B | C |
| | 70 | A | F | B | E | A | B | B |
| | GR20 | — | — | — | — | — | 1 | 1 |
| | GR50 | 7 | 89 | 6 | 92 | 17 | — | — |
| | GR80 | 21 | 131 | 41 | >140 | 34 | — | — |
| 38 | 35 | B | D | D | F | A | B | B |
| | 70 | B | B | D | D | A | B | B |
| | GR20 | — | — | — | — | — | 1 | 1 |
| | GR50 | 1 | 21 | 17 | 42 | 13 | — | — |
| | GR80 | 24 | 56 | 68 | 112 | 26 | — | — |

TABLE 10-continued

Activity of Herbicidal Compounds in Wheat and Barley

| Compd. No. | Application Rate (g ai/ha) | Visual Gorowth Reduction (%) 21 days After Application | | | | | | |
|---|---|---|---|---|---|---|---|---|
| | | KCHSC | MATSS | SASKR | VERPE | VIOSS | HORSS | TRZSS |
| 8 | 35 | A | D | B | A | B | D | C |
| | 70 | A | C | B | A | B | C | B |
| | GR20 | — | — | — | — | — | 1 | 1 |
| | GR50 | 3 | 26 | 1 | 1 | 13 | — | — |
| | GR80 | 6 | 73 | 16 | 1 | 28 | — | — |
| 69 | 35 | B | C | B | B | B | B | B |
| | 70 | B | B | B | A | A | A | B |
| | GR20 | — | — | — | — | — | 1 | 1 |
| | GR50 | 5 | 5 | 7 | 1 | 3 | — | — |
| | GR80 | 19 | 29 | 29 | 4 | 8 | — | — |
| 86 | 35 | C | D | D | B | D | F | D |
| | 70 | C | D | C | B | D | F | D |
| | GR20 | — | — | — | — | — | 14 | 1 |
| | GR50 | 12 | 22 | 18 | 15 | 21 | — | — |
| | GR80 | 55 | 85 | 66 | 34 | 77 | — | — |

TABLE 11

Activity of Herbicidal Compounds in Wheat and Barley

| Compound No. | Application Rate (g ai/ha) | Visual Growth Reduction (%) 21 Days After Application | | | | | |
|---|---|---|---|---|---|---|---|
| | | KCHSC | MATSS | SASKR | VIOSS | HORSS | TRZSS |
| 149 | 35 | F | E | D | F | D | E |
| | 70 | D | D | D | D | C | C |
| | GR20 | 18 | 9 | 6 | 11 | 21 | 20 |
| | GR50 | 56 | 38 | 24 | 44 | — | — |
| | GR80 | >140 | >140 | 100 | >140 | — | — |
| 165 | 35 | B | G | C | F | C | D |
| | 70 | B | E | B | D | B | C |
| | GR20 | — | — | — | — | 9 | 8 |
| | GR50 | 9 | 81 | 4 | 55 | — | — |
| | GR80 | 30 | >140 | 46 | >140 | — | — |

ALOMY: black-grass (*Alopecurus myosuroides*)
APESV: bentgrass (*Apera spica-venti*)
BROTE: downy brome (*Bromus tectorum*)
HORSS: barley, including spring and winter (*Hordeum vulgare*)
TRZSS: wheat, including spring and winter (*Triticum aestivum*)
LOLSS: ryegrass including, Italian ryegrass (*Lolium multiflorum*), rigid ryegrass (*Lolium rigidum*), annual ryegrass (*Lolium multiflorum* subsp. *Gaudini*)
PHAMI: lesser canary grass (*Phalaris minor*)
SETVI: green foxtail (*Setaria viridis*)
KCHSC: kochia (*Kochia scoparia*)
LAMPU: purple deadnettle (*Lamium purpureum*)
GALAP: cleavers (*Galium aparine*)
SINAR: wild mustard (*Sinapis arvensis*)
VERPE: bird's-eye speedwell (*veronica persica*)
PAPRH: common poppy (*Papaver rhoeas*)
SASKR: Russian thistle (*Salsola iberica*)
CIRAR: Canada thistle (*Cirsium arvense*)
VIOSS: wild pansy (*Viola tricolor*), field violet (*Viola arvensis*).
POLCO: wild buckwheat (*Polygonum convolvulus*)
MATSS: scented mayweed (*Matricaria chamomilla*), pineappleweed (*Matricaria matricarioides*)
STEME: common chickweed (*Stellaria media*).
g ai/ha: grams active ingredient per hectare
nt: Not tested
GR10: Growth reduction of 20% of plant growth
GR20: Growth reduction of 20% of plant growth
GR50: Growth reduction of 50% of plant growth
GR80: Growth reduction of 80% of plant growth
GR90: Growth reduction of 90% of plant growth

Example E

Evaluation of Preemergent Herbicidal Activity

Pre-emergent Test III. Seeds of test species were planted into square plastic pots (10 cm wide) containing sandy loam soil. After planting, all pots were sub-irrigated 16 h prior to compound application.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing water and 0.02% w/v (weight/volume) of Triton X-155 to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing water and 0.02% w/v (weight/volume) of Triton X-155 to obtain ½×, ¼×, ⅛× and ¹⁄₁₆× rates of the high rate. Compound requirements are based upon a 12 mL application volume at a rate of 187 liters per hectare (L/ha). Formulated compounds were applied to the soil surface with an overhead Mandel track sprayer equipped with 8002E nozzles calibrated to deliver 187 L/ha over an application area of 0.503 square meters. Control pots were sprayed in the same manner with the solvent blank.

The treated pots and control pots were placed in a greenhouse as described above and watered through surface irrigation. After 21 d, the condition of the test pots as compared with that of the untreated pots was determined visually and scored on a scale of 0 to 100 percent where 0 corresponds to no herbicidal effect and 100 corresponds to plant death or lack of emergence from the soil.

By applying the well-accepted probit analysis as described by J. Berkson in *Journal of the American Statistical Society*, 48, 565 (1953) and by D. Finney in *"Probit Analysis"* Cambridge University Press (1952), the above data can be used to calculate $GR_{20}$, $GR_{50}$, $GR_{80}$ and $GR_{90}$ values, which are defined as growth reduction factors that correspond to the effective dose of herbicide required to kill or control 20 percent, 50 percent, 80 percent or 90 percent, respectively, of a target plant. Some of the compounds tested, application rates employed, plant species tested, and results are given in Table 12.

TABLE 12

Preemergent Activity of Herbicidal Compounds in Wheat and Barley

| Compound No. | Application Rate (g ai/ha) | Visual Growth Reduction (%) 21 Days After Application | | | | | |
|---|---|---|---|---|---|---|---|
| | | APESV | LAMSS | LOLSS | SETVI | HORSS | TRZSS |
| 20 | 35 | A | A | G | F | F | E |
| | 70 | A | A | E | B | E | E |
| | GR20 | — | — | — | — | 17 | 10 |
| | GR50 | 6 | 6 | >70 | 32 | — | — |
| | GR80 | 16 | 9 | >70 | 71 | — | — |
| 147 | 35 | C | A | G | E | G | F |
| | 70 | B | A | G | C | G | F |
| | GR20 | — | — | — | — | 70 | 23 |
| | GR50 | 19 | 1 | 52 | 17 | — | — |
| | GR80 | 33 | 5 | >70 | >70 | — | — |
| 214 | 35 | C | A | G | G | G | G |
| | 70 | A | A | E | G | G | F |
| | GR20 | — | — | — | — | 93 | 28 |
| | GR50 | 13 | 1 | >70 | >70 | — | — |
| | GR80 | 28 | 2 | >70 | >70 | — | — |
| 49 | 35 | F | A | G | F | G | G |
| | 70 | E | A | G | F | G | G |
| | GR20 | — | — | — | — | >70 | >70 |
| | GR50 | >70 | 1 | >70 | >70 | — | — |
| | GR80 | >70 | 3 | >70 | >70 | — | — |
| 42 | 35 | B | A | G | E | F | E |
| | 70 | A | A | G | D | E | E |
| | GR20 | — | — | — | — | 11 | 5 |
| | GR50 | 12 | 1 | >70 | 36 | — | — |
| | GR80 | 27 | 1 | >70 | >70 | — | — |

Example F

Evaluation of Postemergence Herbicidal Activity in Direct Seeded Rice

Seeds or nutlets of the desired test plant species were planted in a soil matrix prepared by mixing a loam soil (43 percent silt, 19 percent clay, and 38 percent sand, with a pH of about 8.1 and an organic matter content of about 1.5 percent) and river sand in an 80 to 20 ratio. The soil matrix was contained in plastic pots with a surface area of 139.7 cm². When required to ensure good germination and healthy plants, a fungicide treatment and/or other chemical or physical treatment was applied. The plants were grown for 10-17 d in a greenhouse with an approximate 14-h photoperiod which was maintained at about 29° C. during the day and 26° C. during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in 25 mL glass vials and dissolved in a volume of 97:3 v/v acetone-DMSO to obtain 12× stock solutions. If the test compound did not dissolve readily, the mixture was warmed and/or sonicated.

The concentrated stock solutions were added to the spray solutions so that the final acetone and DMSO concentrations were 16.2% and 0.5%, respectively. Spray solutions were diluted to the appropriate final concentrations with the addition of 10 mL of an aqueous mixture of 1.5% (v/v) Agri-dex crop oil concentrate. The final spray solutions contained 1.25% (v/v) Agri-dex crop oil concentrate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy height. Control plants were sprayed in the same manner with the solvent blank.

The treated plants and control plants were placed in a greenhouse as described above and watered by sub-irrigation to prevent wash-off of the test compounds. After 20-22 days, the condition of the test plants, compared with that of the untreated plants, was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in *"Probit Analysis"* Cambridge University Press (1952), the above data can be used to calculate $GR_{20}$, $GR_{50}$, $GR_{80}$ and $GR_{90}$ values, which are defined as growth reduction factors that correspond to the effective dose of herbicide required to kill or control 20 percent, 50 percent, 80 percent or 90 percent, respectively, of a target plant.

Some of the application rates and ratios employed, plant species tested, and results are given in Table 13.

TABLE 13

Activity of Herbicidal Compounds in Direct Seeded Rice

| Compound No | Application Rate (g ai/ha) | Visual Growth Reduction (%) 21 Days After Application | | | | | | |
|---|---|---|---|---|---|---|---|---|
| | | BRAPP | CYPSS | ECHSS | LEFSS | SCPJU | SEBEX | ORYSS |
| 216 | 35 | B | B | B | B | A | A | G |
| | 70 | B | B | A | A | A | A | G |
| | GR20 | — | — | — | — | — | — | >70 |
| | GR50 | 8 | 10 | 4 | 8 | 1 | 1 | — |
| | GR80 | 27 | 70 | 15 | 23 | 1 | 1 | — |
| 217 | 35 | A | A | A | A | A | A | E |
| | 70 | A | A | A | A | A | A | C |
| | GR20 | — | — | — | — | — | — | 10 |
| | GR50 | 3 | 5 | 1 | 1 | 1 | 1 | — |
| | GR80 | 5 | 11 | 1 | 3 | 1 | 1 | — |
| 135 | 35 | B | C | C | G | B | A | G |
| | 70 | B | B | C | D | A | A | G |
| | GR20 | — | — | — | — | — | — | >70 |
| | GR50 | 4 | 5 | 17 | 57 | 2 | 1 | — |
| | GR80 | 11 | 49 | 70 | 114 | 5 | 1 | — |
| 165 | 35 | B | C | B | G | FALSE | A | G |
| | 70 | A | C | A | A | FALSE | A | F |
| | GR20 | — | — | — | — | | — | 44 |
| | GR50 | 12 | 19 | 10 | 24 | | 1 | — |
| | GR80 | 27 | 67 | 24 | 56 | | 1 | — |
| 134 | 35 | A | A | A | A | FALSE | A | D |
| | 70 | A | A | A | A | A | A | B |
| | GR20 | — | — | — | — | — | — | 5 |
| | GR50 | 3 | 6 | 1 | 6 | 1 | 1 | — |
| | GR80 | 12 | 13 | 1 | 15 | 1 | 1 | — |
| 122 | 35 | C | A | C | G | A | A | G |
| | 70 | B | A | B | G | A | A | G |
| | GR20 | — | — | — | — | — | — | 70 |
| | GR50 | 5 | 1 | 6 | >70 | 1 | 1 | — |
| | GR80 | 42 | 1 | 47 | >70 | 1 | 1 | — |
| 8 | 35 | A | A | A | G | A | A | C |
| | 70 | A | A | A | F | A | A | B |
| | GR20 | — | — | — | — | — | — | 2 |
| | GR50 | 4 | 1 | 2 | >70 | 1 | 3 | — |
| | GR80 | 9 | 1 | 6 | >70 | 1 | 5 | — |
| 58 | 35 | G | A | G | G | A | A | G |
| | 70 | G | A | G | E | A | A | G |
| | GR20 | — | — | — | — | — | — | >70 |
| | GR50 | >70 | 4 | >70 | >70 | 5 | 2 | — |
| | GR80 | >70 | 8 | >70 | >70 | 8 | 4 | — |
| 146 | 35 | D | A | B | G | A | A | F |
| | 70 | A | A | B | C | A | A | D |
| | GR20 | — | — | — | — | — | — | 18 |
| | GR50 | 8 | 1 | 17 | 44 | 1 | 3 | — |
| | GR80 | 29 | 1 | 32 | 87 | 1 | 4 | — |
| 47 | 35 | F | A | F | C | A | A | G |
| | 70 | F | A | G | G | A | A | G |
| | GR20 | — | — | — | — | — | — | >70 |
| | GR50 | >70 | 1 | >70 | >70 | 1 | 1 | — |
| | GR80 | >70 | 3 | >70 | >70 | 1 | 1 | — |
| 125 | 35 | E | A | E | E | A | A | G |
| | 70 | D | A | D | D | A | A | G |

TABLE 13-continued

Activity of Herbicidal Compounds in Direct Seeded Rice

| Compound No | Application Rate (g ai/ha) | Visual Growth Reduction (%) 21 Days After Application | | | | | | |
|---|---|---|---|---|---|---|---|---|
| | | BRAPP | CYPSS | ECHSS | LEFSS | SCPJU | SEBEX | ORYSS |
| | GR20 | — | — | — | — | — | — | 0 |
| | GR50 | 46 | 4 | 40 | 43 | 1 | 1 | — |
| | GR80 | >70 | 10 | >70 | >70 | 1 | 1 | — |
| 159 | 35 | A | A | A | A | A | A | E |
| | 70 | A | A | A | A | A | A | D |
| | GR20 | — | — | — | — | — | — | 12 |
| | GR50 | 3 | 2 | 2 | 12 | 1 | 1 | — |
| | GR80 | 8 | 5 | 4 | 19 | 1 | 1 | — |
| 124 | 35 | A | A | A | A | A | A | D |
| | 70 | A | A | A | A | A | A | B |
| | GR20 | — | — | — | — | — | — | 1 |
| | GR50 | 4 | 1 | 2 | 7 | 1 | 1 | — |
| | GR80 | 8 | 1 | 6 | 16 | 1 | 1 | — |
| 96 | 35 | D | A | E | B | A | A | G |
| | 70 | B | A | B | C | A | A | G |
| | GR20 | — | — | — | — | — | — | 130 |
| | GR50 | 19 | 3 | 29 | 27 | 1 | 1 | — |
| | GR80 | 58 | 6 | 84 | 58 | 1 | 1 | — |
| 173 | 35 | C | A | C | E | A | A | E |
| | 70 | A | A | A | A | A | A | D |
| | GR20 | — | — | — | — | — | — | 16 |
| | GR50 | 8 | 2 | 12 | 24 | 1 | 1 | — |
| | GR80 | 26 | 4 | 33 | 47 | 1 | 1 | — |
| 93 | 35 | A | A | A | A | A | A | E |
| | 70 | A | A | A | A | A | A | D |
| | GR20 | — | — | — | — | — | — | 13 |
| | GR50 | 1 | 1 | 1 | 6 | 1 | 1 | — |
| | GR80 | 1 | 2 | 1 | 11 | 1 | 1 | — |
| 74 | 35 | A | A | A | A | A | A | D |
| | 70 | A | A | A | A | A | A | D |
| | GR20 | — | — | — | — | — | — | 4 |
| | GR50 | 1 | 5 | 1 | 6 | 1 | 1 | — |
| | GR80 | 5 | 10 | 1 | 13 | 1 | 1 | — |
| 11 | 35 | D | A | B | G | A | A | F |
| | 70 | B | A | A | G | A | A | E |
| | GR20 | — | — | — | — | — | — | 25 |
| | GR50 | 13 | 1 | 11 | 175 | 1 | 3 | — |
| | GR80 | 44 | 1 | 25 | 463 | 1 | 7 | — |

BRAPP: broadleaf signalgrass, *Brachiaria platyphylla*
CYPSS: sedge including small-flower flatsedge (*Cyperus difformis*), yellow nutsedge (*Cyperus esculentus*), rice flatsedge (*Cyperus iria*)
ECHSS: including barnyardgrass, (*Echinochloa crus-galli*), junglerice, (*Echinochloa colonum*)
LEFSS: sprangletop including Chinese sprangletop (*Leptochloa chinensis*), green sprangletop (*Leptochloa dubia*)
SCPJU: Japanese bulrush, *Scirpus juncoides*
SEBEX: hemp sesbania, *Sesbania exaltata*
ORYSS: *Oryza sativa*
g ai/ha: gram active ingredient per hectare

What is claimed is:

1. A compound of Formula (I):

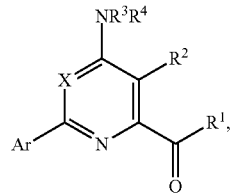

(I)

wherein

X is CY; wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$; wherein $R^{1'}$ is H, $C_1$-$C_8$ alkyl, or $C_7$-$C_{10}$ arylalkyl;

$R^2$ is halogen selected from F, Cl, or Br, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, ($C_1$-$C_3$ alkyl)carbonyl, ($C_1$-$C_3$ haloalkyl)carbonyl, or cyano, with the proviso that $R^2$ is not $SCH_3$;

$R^3$ and $R^4$ are each independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, hydroxy, $C_1$-$C_6$ alkoxy, $C_1$-$C_6$ haloalkoxy, formyl, ($C_1$-$C_3$ alkyl)carbonyl, ($C_1$-$C_3$ haloalkyl)carbonyl, ($C_1$-$C_6$ alkoxy)carbonyl, ($C_1$-$C_6$ alkyl)carbamyl, $C_1$-$C_6$ alkylsulfonyl, tri($C_1$-$C_6$ alkyl)silyl, or di($C_1$-$C_6$ alkyl)phosphonyl, or $R^3$ and $R^4$ together with the nitrogen atom to which they are attached form a 5- or 6-membered saturated ring, or $R^3$ and $R^4$ taken together represent $=CR^{3'}R^{4'}$, wherein $R^{3'}$ and $R^{4'}$ are each independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino, or $R^{3'}$ and $R^{4'}$ together with the carbon atom to which they are attached form a 5- or 6-membered saturated ring;

Ar is Ar2, Ar3, Ar4, Ar5, or Ar6:

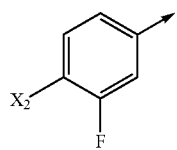
Ar2

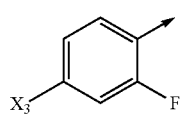
Ar3

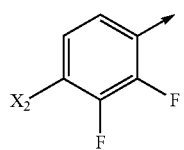
Ar4

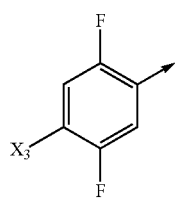
Ar5

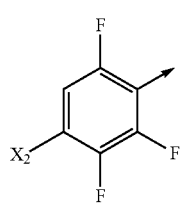
Ar6 wherein $X_2$ is H, F, Cl, Br, I, ethynyl, $CH_3$, $CFH_2$, $CF_2H$, $CF_3$, $OCF_2H$, $OCF_3$, CN, $CONH_2$, $CO_2H$, or $NO_2$;

$X_3$ is H, F, Br, I, ethynyl, $CH_3$, $CFH_2$, $CF_2H$, $CF_3$, $OCF_2H$, $OCF_3$, CN, $CONH_2$, $CO_2H$, or $NO_2$;

wherein a) when Ar is

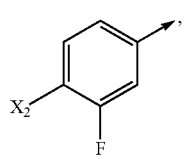

then X is CH, CF, CCl, or $CCH_3$ with the provisos that:
i) $X_2$ is not Cl, when $R_2$ is Cl and X is CH;
ii) $X_2$ is not Cl, Br, I, or $CF_3$, when $R_2$ is $OCH_3$ and X is CF; and b) when Ar is

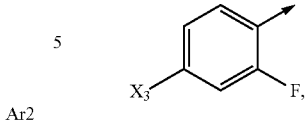

then X is CH or CF
with the provisos that:
i) $X_3$ is not H, F, or $CH_3$, when $R_2$ is Cl and X is CH;
ii) $X_3$ is not Br or I, when $R_2$ is $OCH_3$ and X is CF; and c) when Ar is

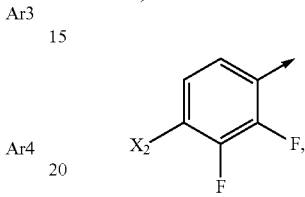

then X is CH or CF
with the provisos that:
i) $X_2$ is not F, when $R_2$ is Cl and X is CH;
ii) $X_2$ is not Cl, Br, I, or $CF_3$, when $R_2$ is $OCH_3$ and X is CF; and d) when Ar is

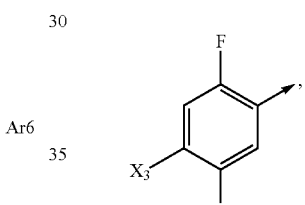

then X is CH or CF
with the provisos that:
i) $X_3$ is not Br or I, when X is CF and $R_2$ is $OCH_3$, and e) when Ar is

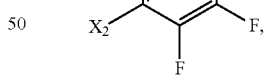

then X is CH, or CF;
or an N-oxide or agriculturally acceptable salt thereof.

2. The compound of claim 1, wherein Ar is Ar2.
3. The compound of claim 1, wherein Ar is Ar3.
4. The compound of claim 1, wherein Ar is Ar4.
5. The compound of claim 1, wherein Ar is Ar5.
6. The compound of claim 1, wherein Ar is Ar6.
7. The compound of claim 1, wherein $R^{1'}$ is H or $C_1$-$C_8$ alkyl.
8. The compound of claim 7, wherein $R^{1'}$ is H or methyl.
9. The compound of claim 1, wherein Y is hydrogen, halogen, or $C_1$-$C_3$ alkyl.
10. The compound of claim 9, wherein Y is H, F, Cl, or $CH_3$.

11. The compound of claim 1, wherein $R^2$ is halogen, $C_2$-$C_4$ alkenyl, $C_2$-$C_4$ haloalkenyl, $C_1$-$C_4$ alkoxy, $C_1$-$C_4$ haloalkoxy, or $C_1$-$C_4$ haloalkylthio, with the proviso that $R^2$ is not $SCH_3$.

12. The compound of claim 11, wherein $R^2$ is halogen, $C_2$-$C_4$ alkenyl, $C_2$-$C_4$ haloalkenyl, or $C_1$-$C_4$ alkoxy.

13. The compound of claim 12, wherein $R^2$ is Cl, $OCH_3$, or vinyl.

14. The compound of claim 1, wherein $R^3$ and $R^4$ are each independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, ($C_1$-$C_3$ alkyl)carbonyl, ($C_1$-$C_3$ haloalkyl)carbonyl, ($C_1$-$C_6$ alkoxy)carbonyl, ($C_1$-$C_6$ alkyl)carbamyl, or tri($C_1$-$C_6$ alkyl)silyl, or $R^3$ and $R^4$ taken together represent =$CR^{3'}R^{4'}$, wherein $R^{3'}$ and $R^{4'}$ are each independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino.

15. The compound of claim 14, wherein $R^3$ and $R^4$ are hydrogen.

16. The compound of claim 1, wherein $X_2$ is H, Cl, Br, I, ethynyl, $CH_3$, $CF_2H$, $CF_3$, $OCF_2H$, or CN.

17. The compound of claim 2, wherein $X_2$ is H, Cl, Br, I, ethynyl, $CH_3$, $CF_2H$, $CF_3$, $OCF_2H$, or CN.

18. The compound of claim 1, wherein $X_3$ is H, Br, I, ethynyl, $OCF_2H$, CN, or $NO_2$.

19. The compound of claim 4, wherein $X_3$ is H, Br, I, ethynyl, $OCF_2H$, CN, or $NO_2$.

20. The compound of claim 1, wherein $X_2$ is H, F, Br, I, ethynyl, $CH_3$, $CF_3$, $OCF_2H$, or CN.

21. The compound of claim 4, wherein $X_2$ is H, F, Br, I, ethynyl, $CH_3$, $CF_3$, $OCF_2H$, or CN.

22. The compound of claim 1, wherein $X_3$ is H, F, Br, I, $CH_3$, $CF_2H$, $CF_3$, $OCF_2H$, or CN.

23. The compound of claim 5, wherein $X_3$ is H, F, Br, I, $CH_3$, $CF_2H$, $CF_3$, $OCF_2H$, or CN.

24. The compound of claim 1, wherein $X_2$ is Br or I.

25. The compound of claim 6, wherein $X_2$ is Br or I.

26. A compound having the formula:

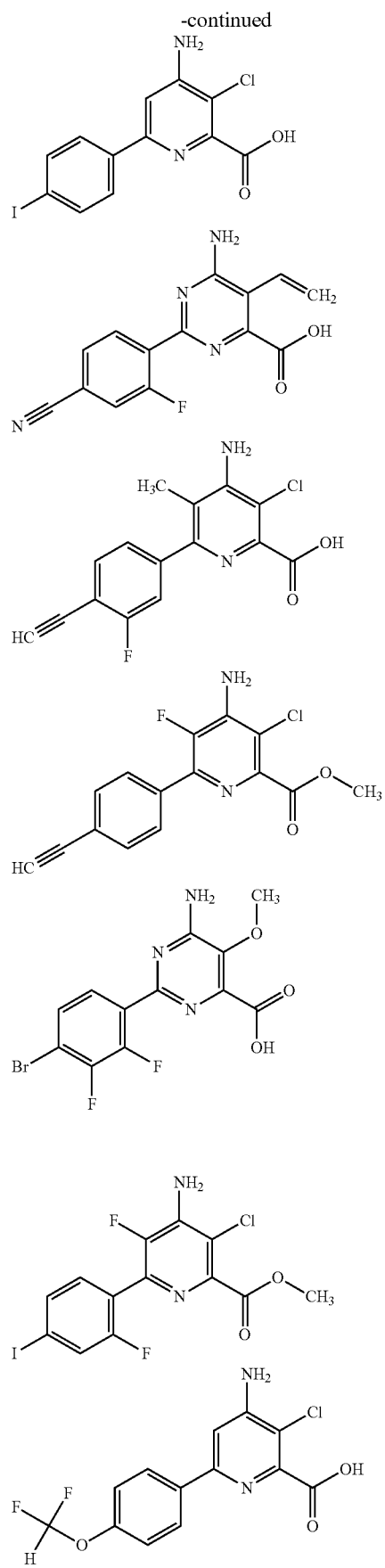

275
-continued
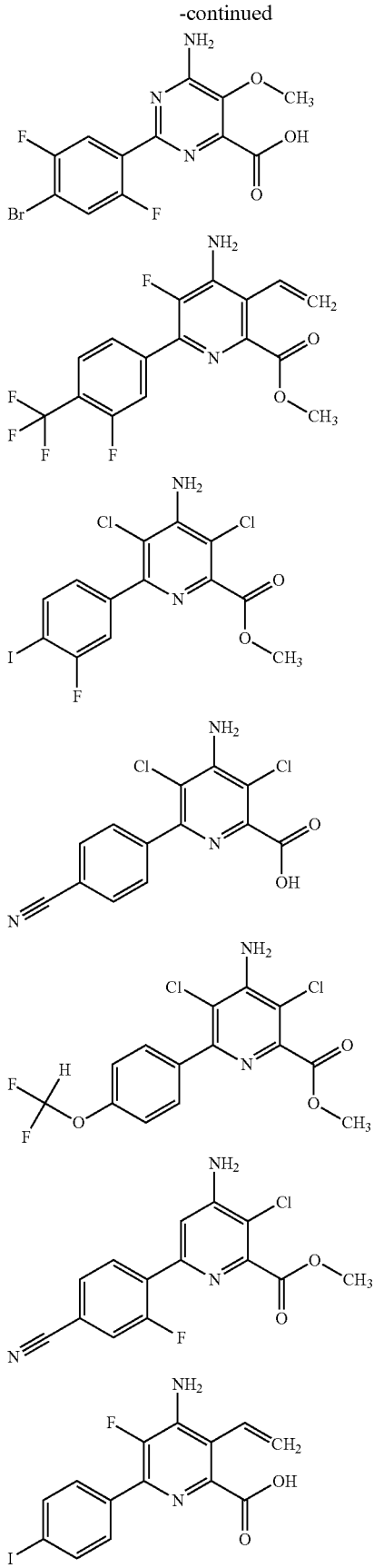
276
-continued
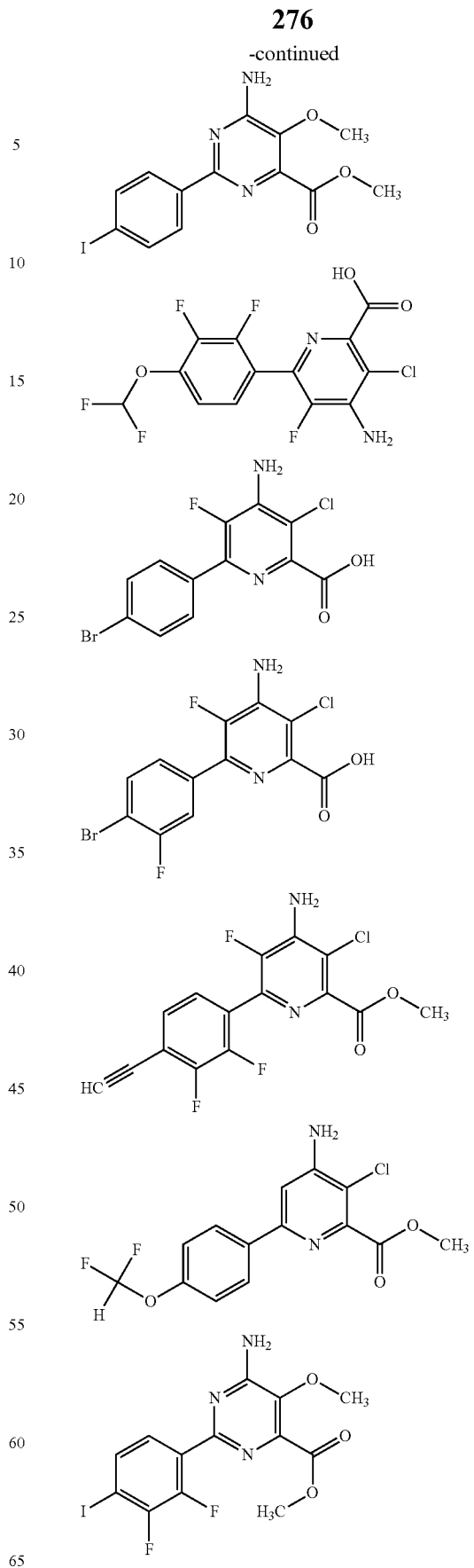

277
-continued
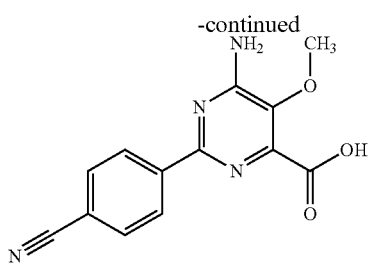
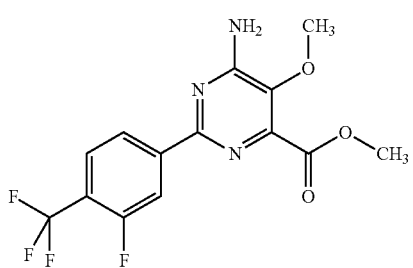
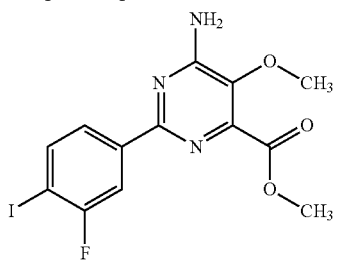
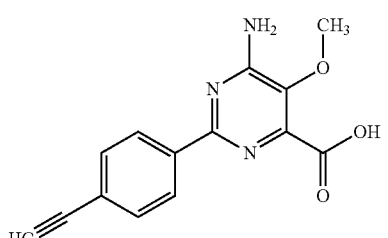
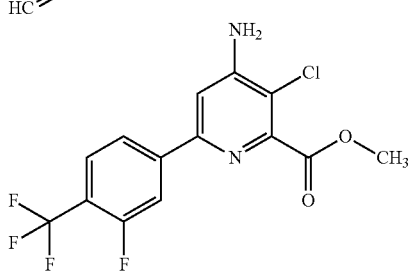
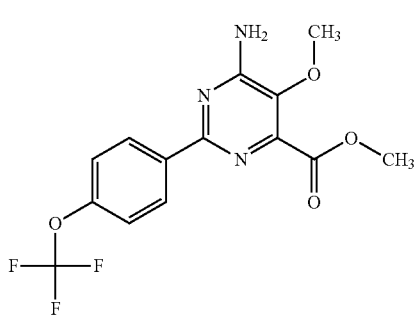
278
-continued
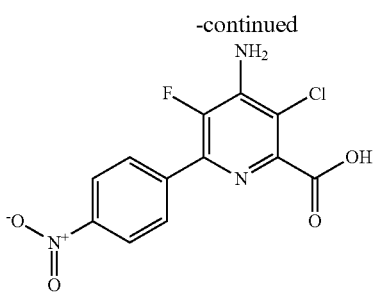
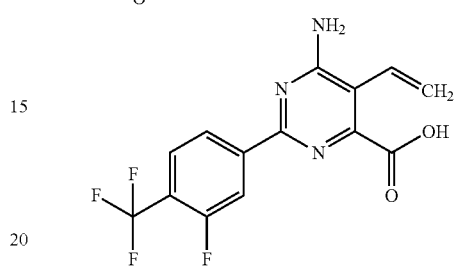
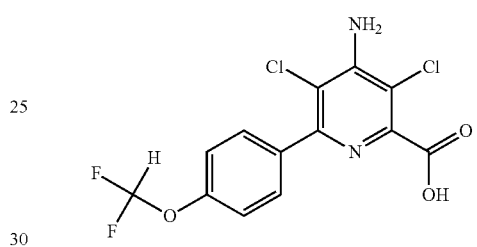
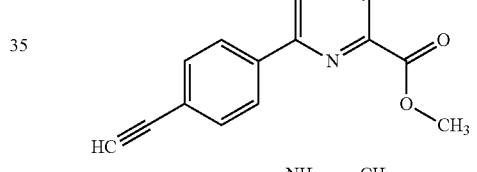
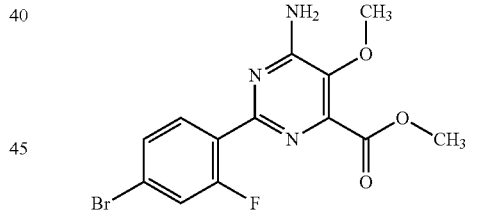
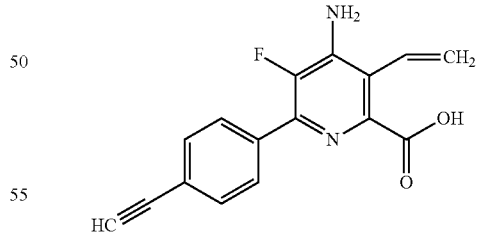
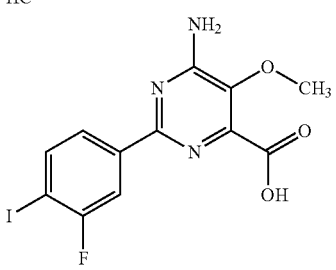

-continued
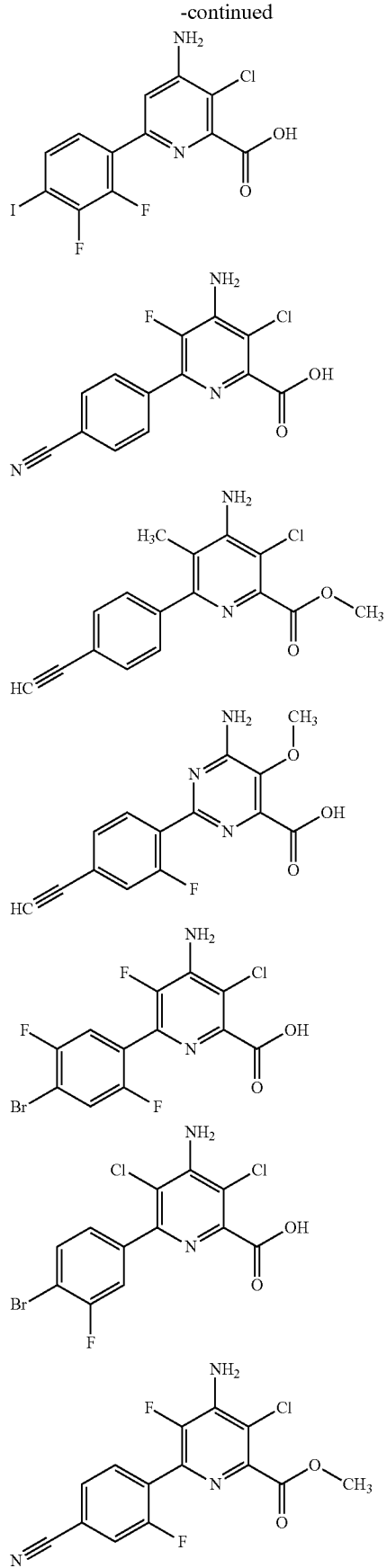
-continued
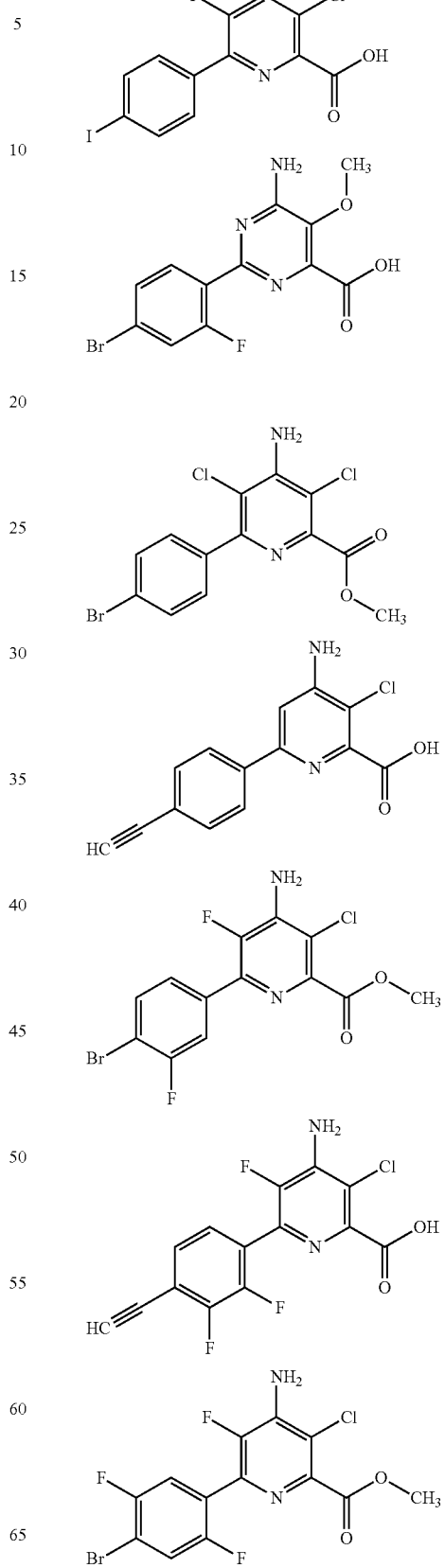

281
-continued
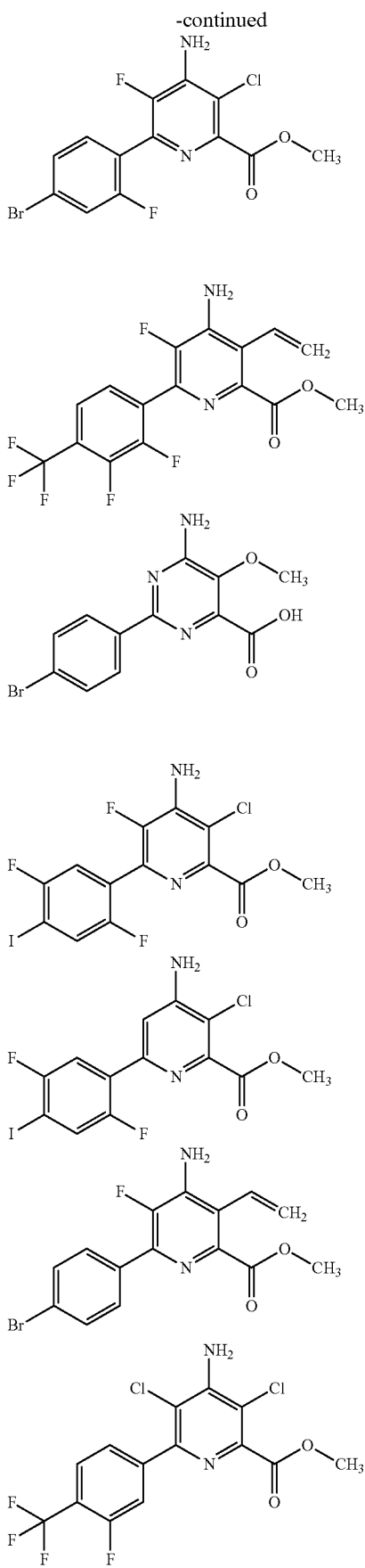
282
-continued
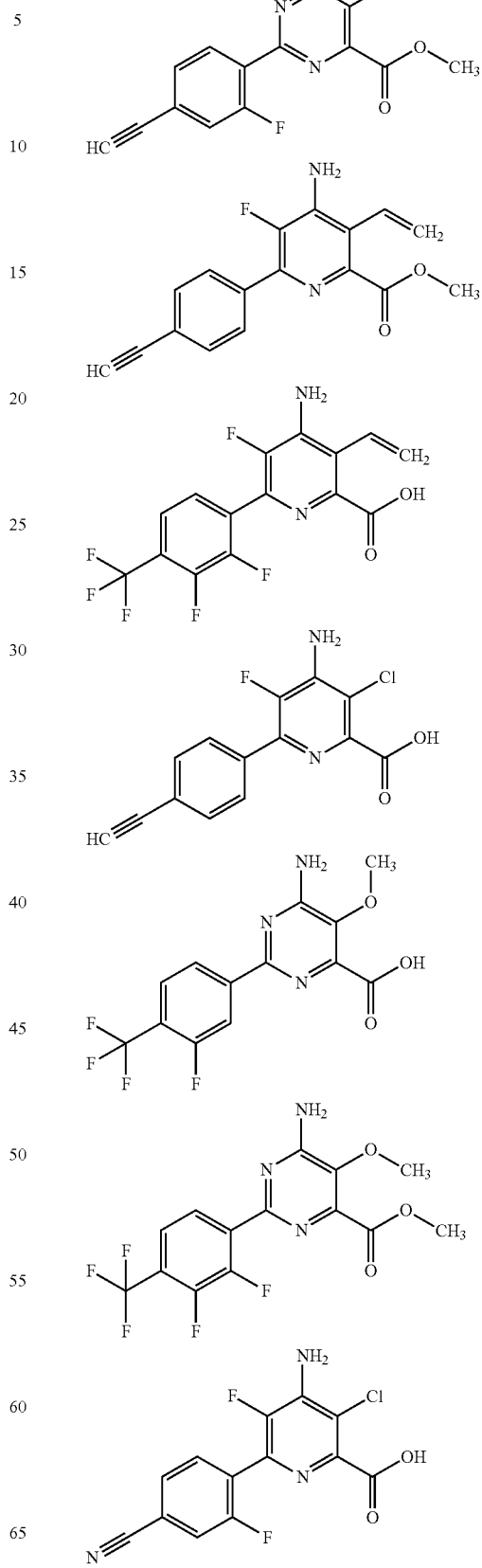

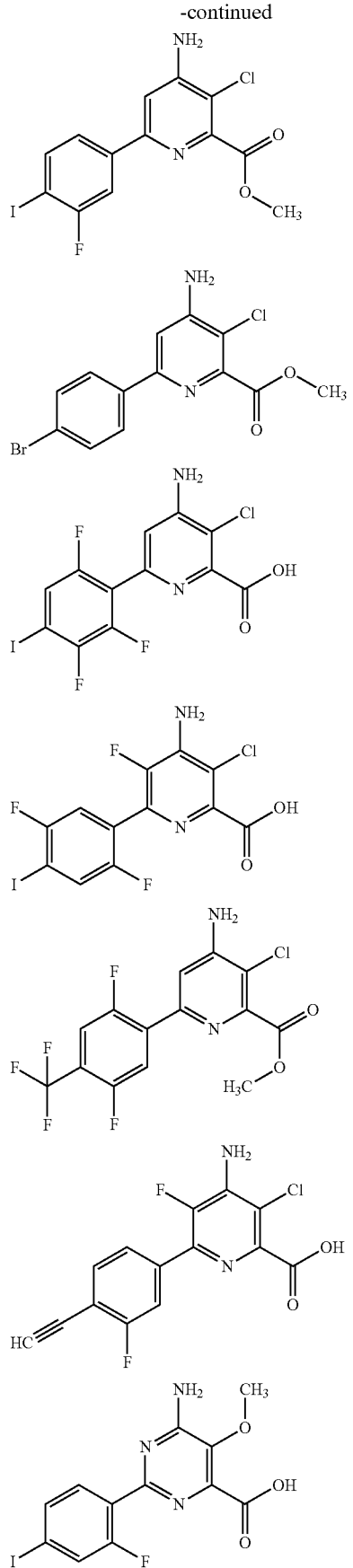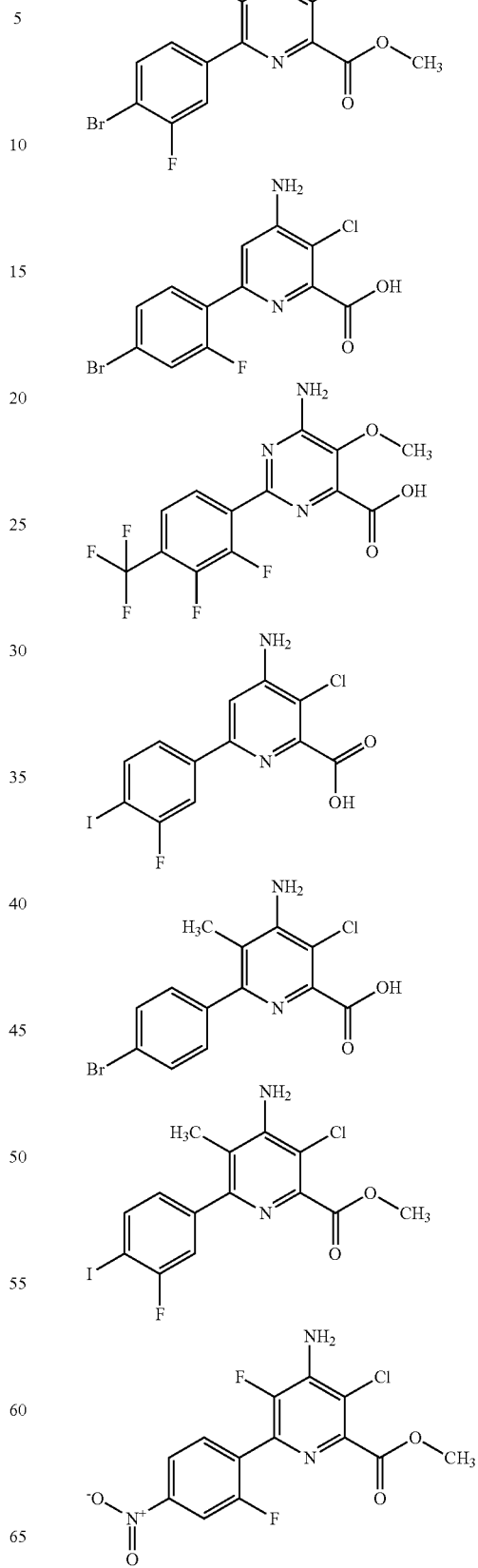

285
-continued
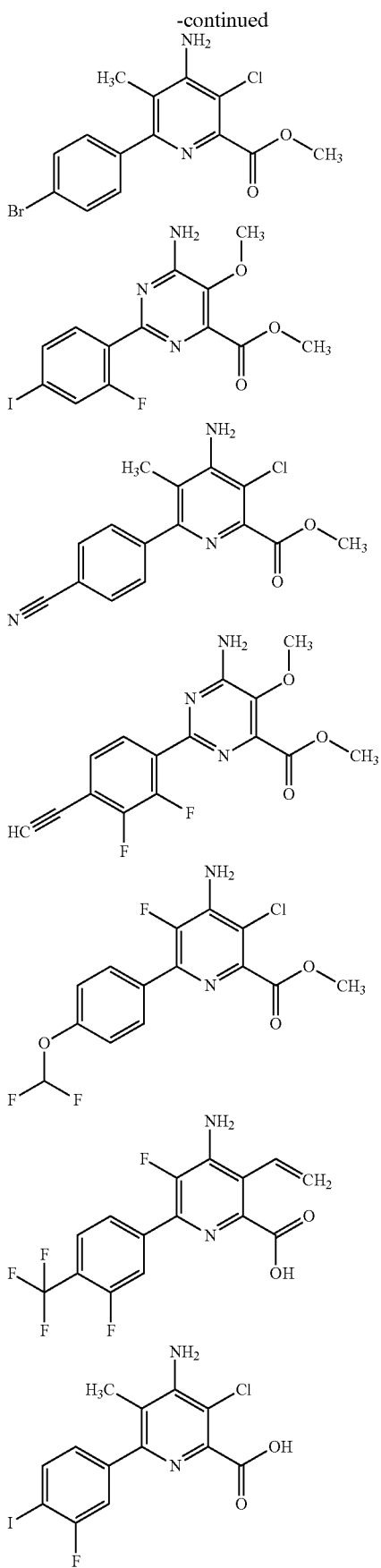
286
-continued
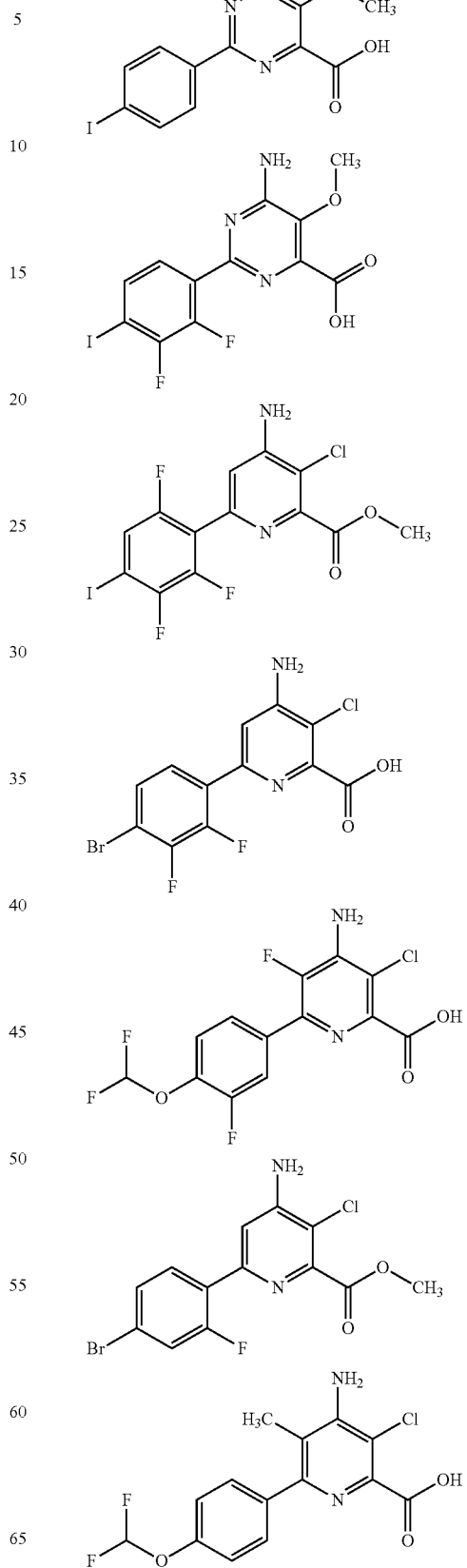

287
-continued
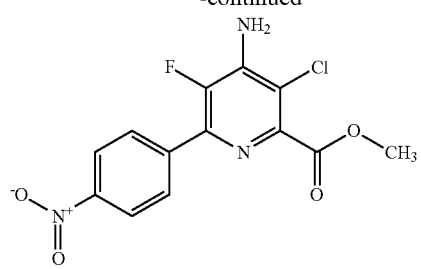
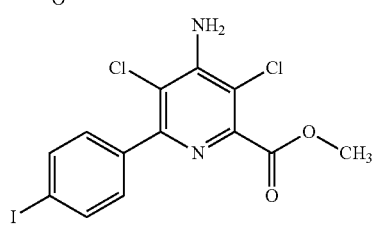
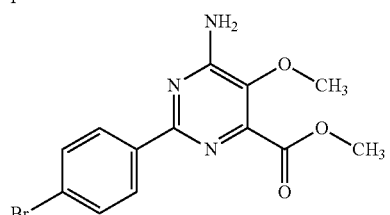
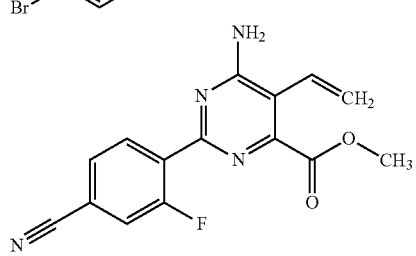
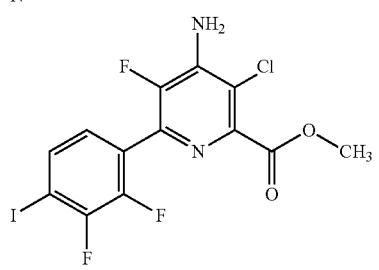
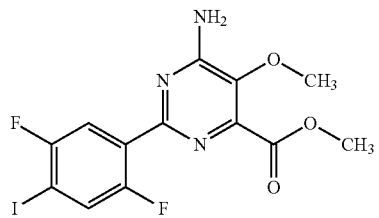
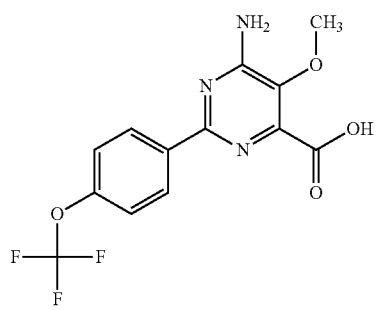
288
-continued
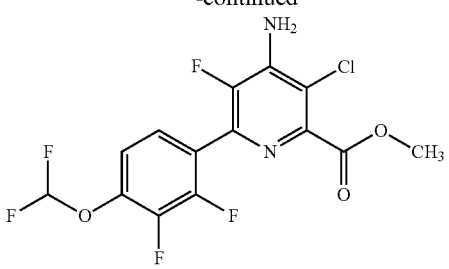
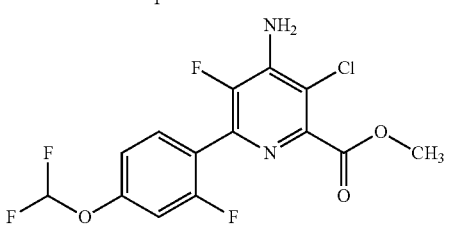
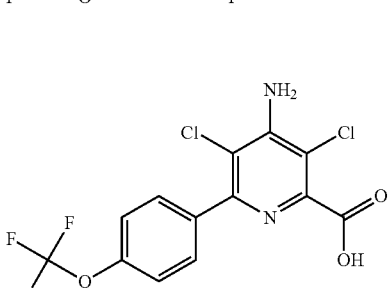
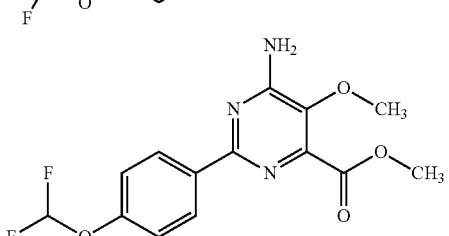
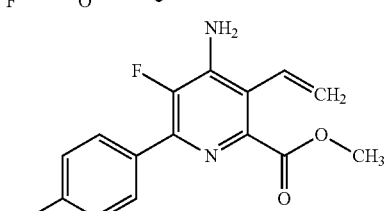
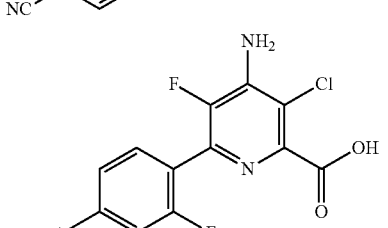
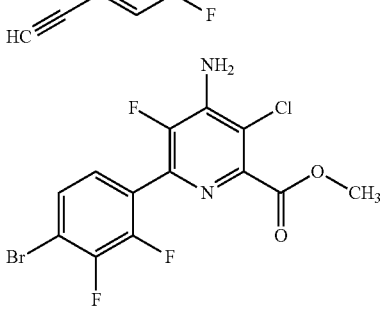

289
-continued
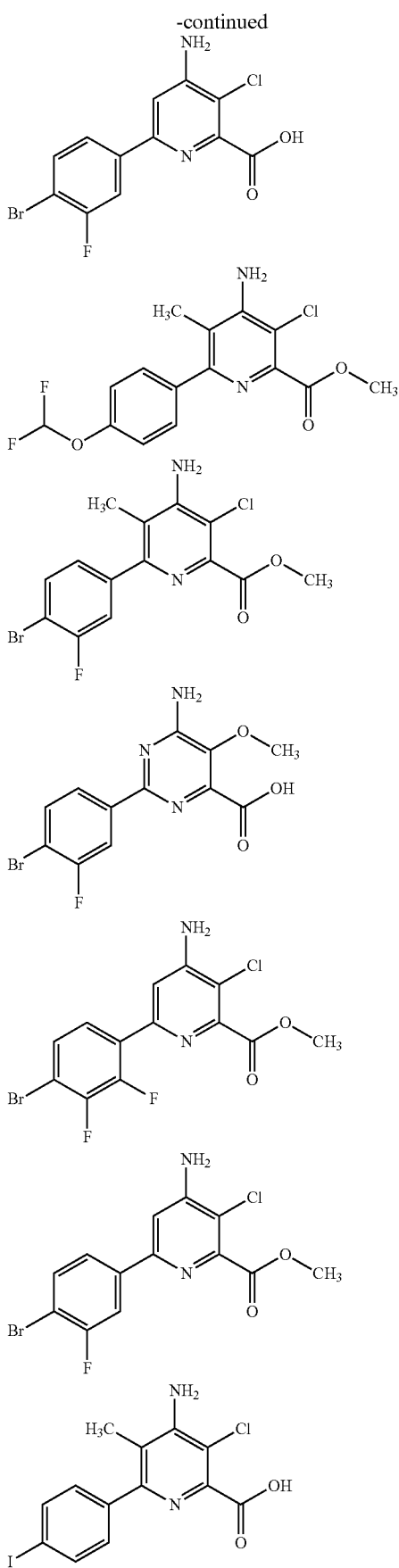
290
-continued
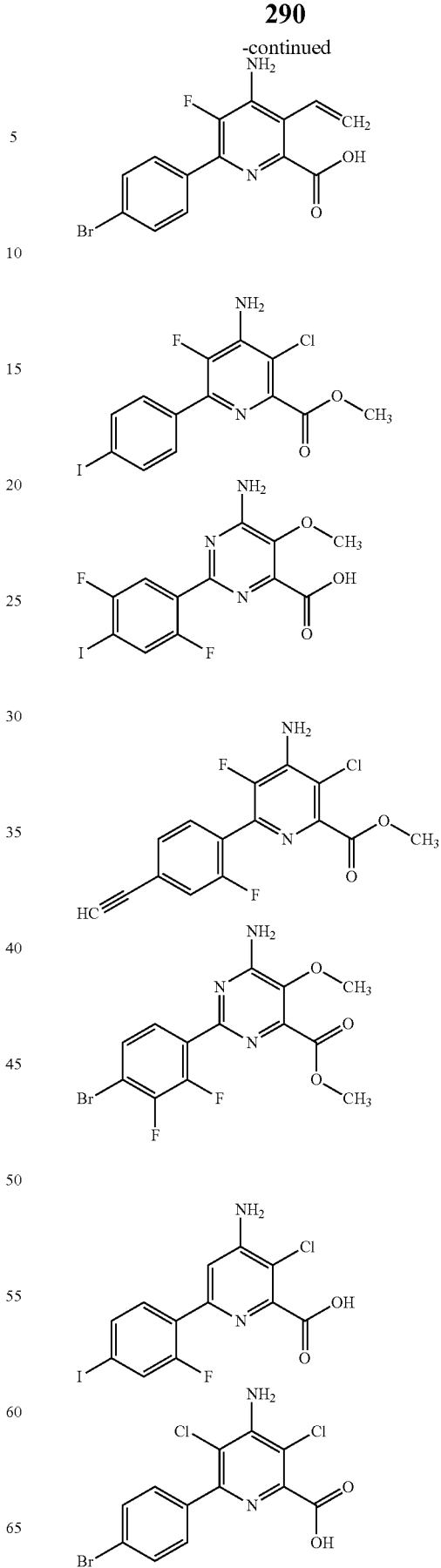

291
-continued
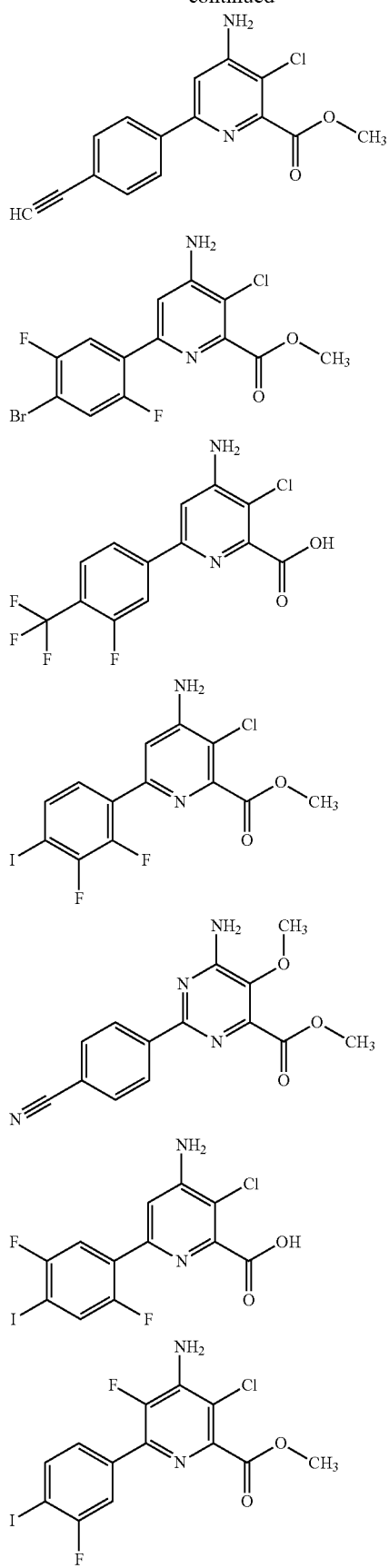
292
-continued
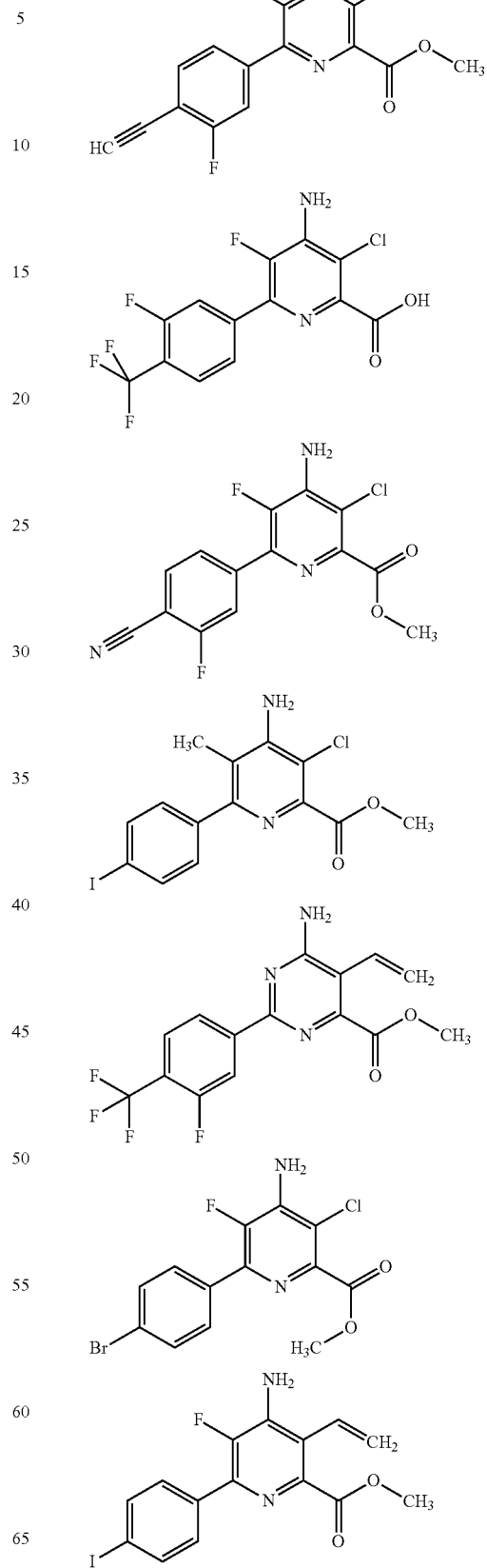

-continued
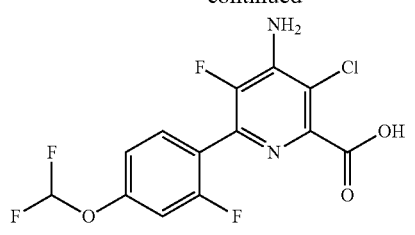
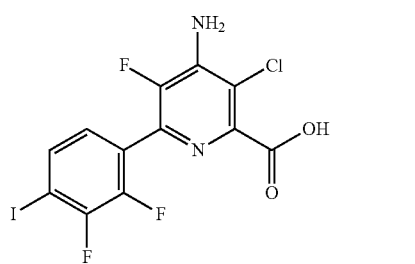
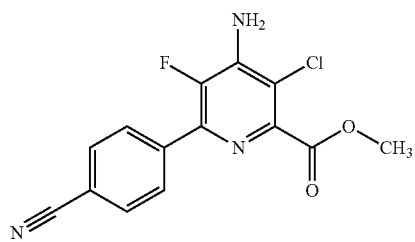
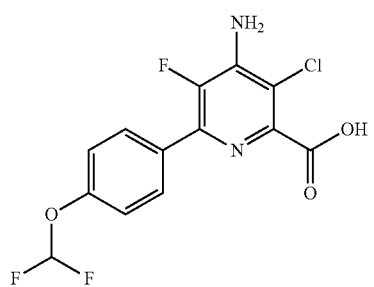
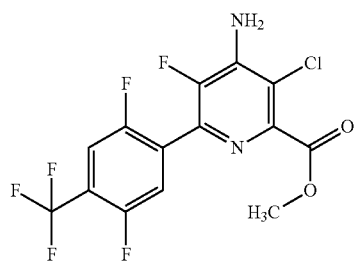
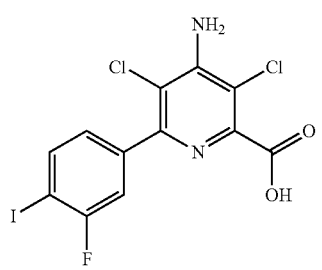
-continued
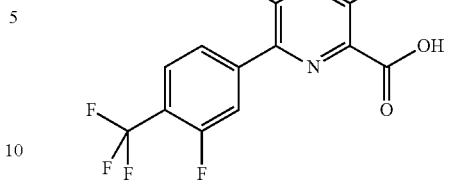
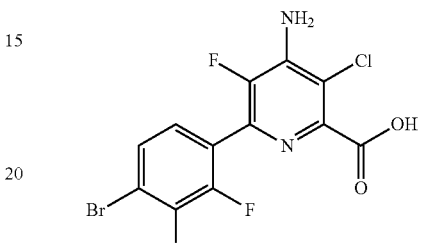
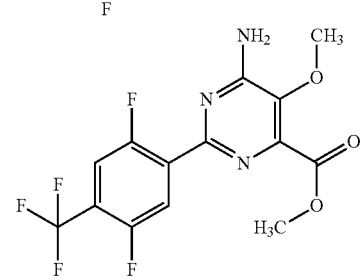
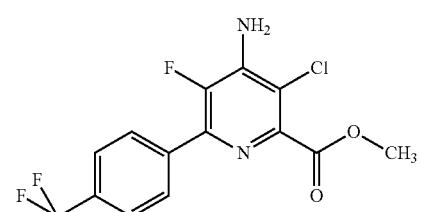
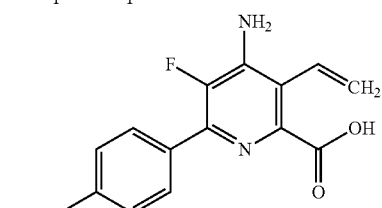
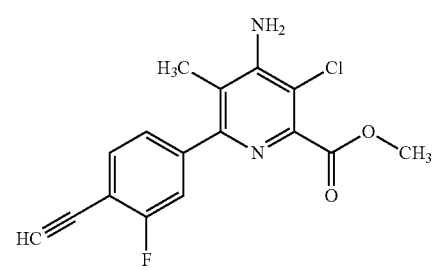

-continued
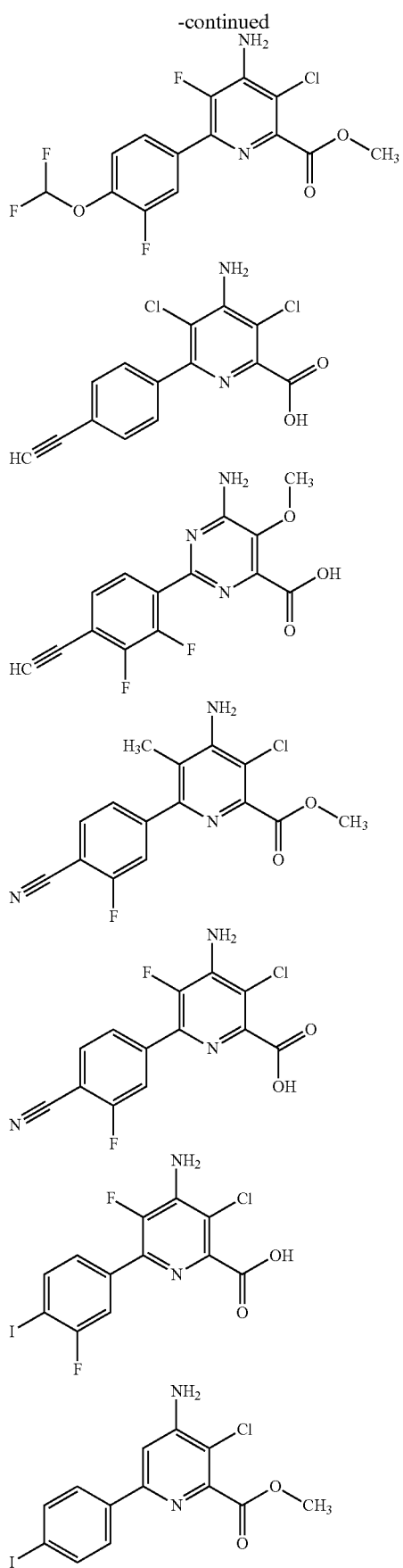
-continued
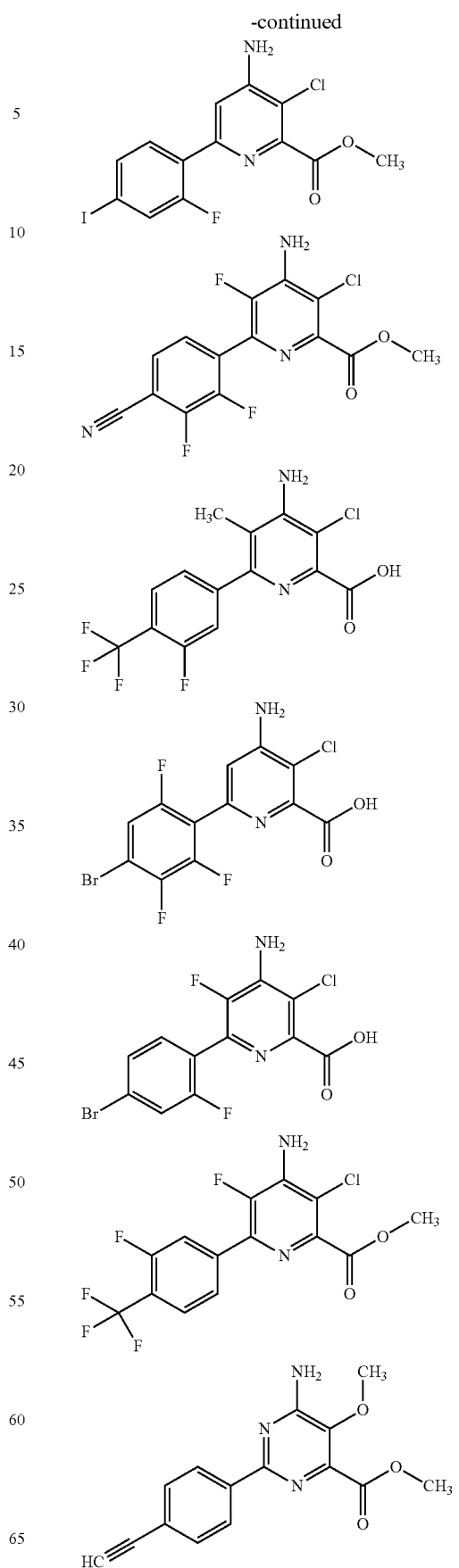

297
-continued
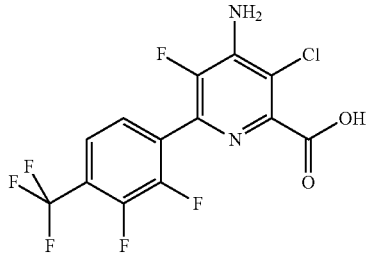
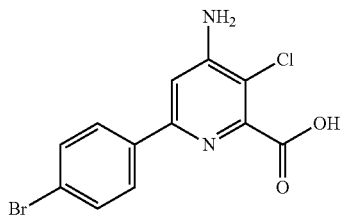
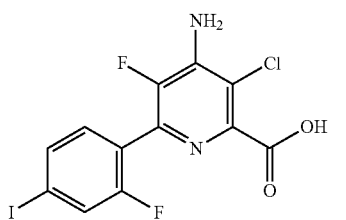
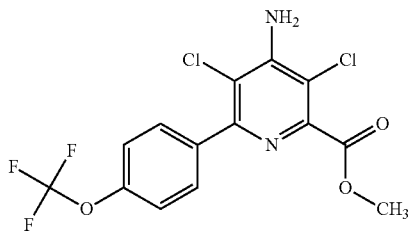
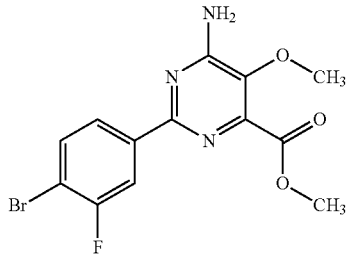
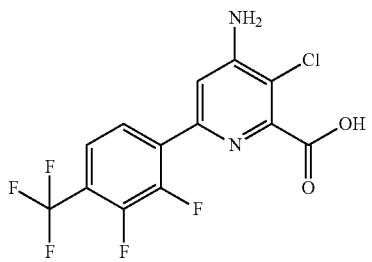
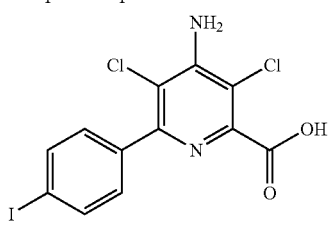
298
-continued
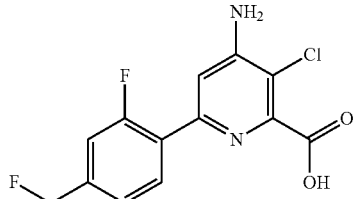
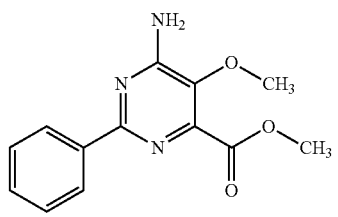
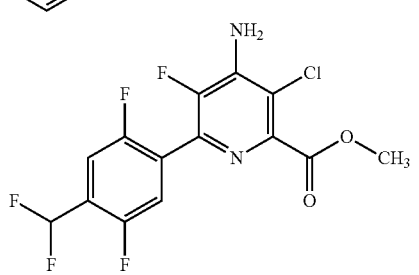
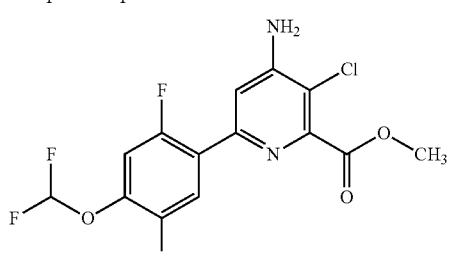
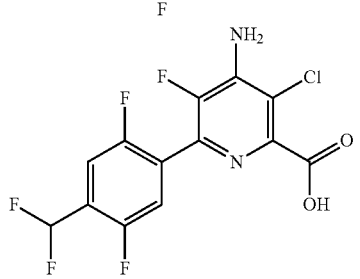
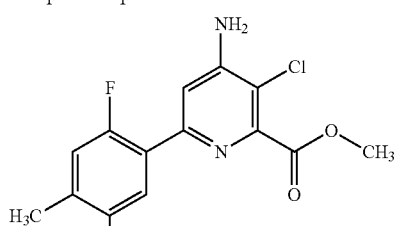
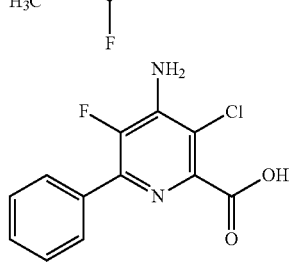

-continued
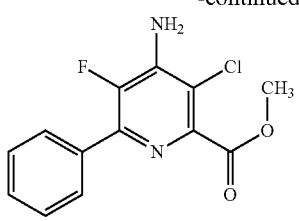
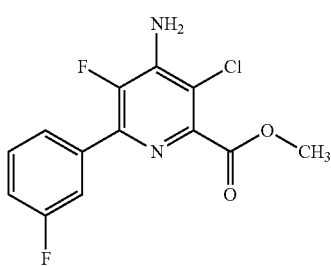
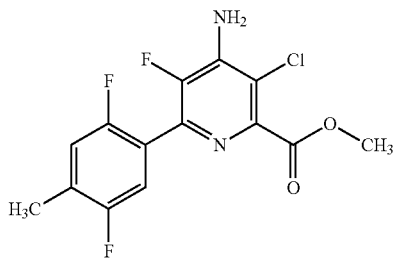
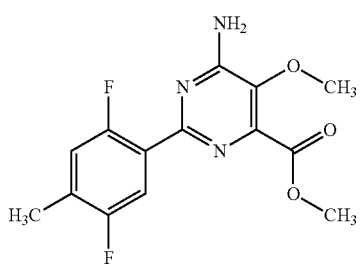
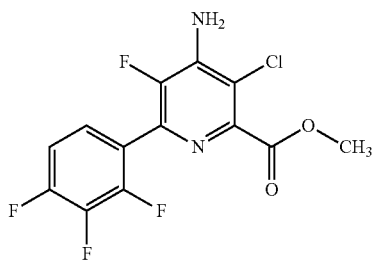
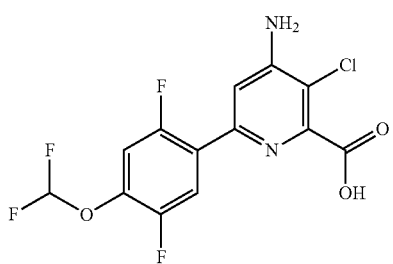
-continued
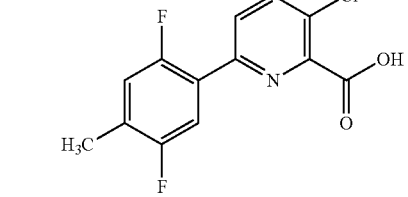
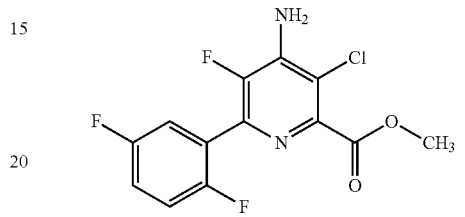
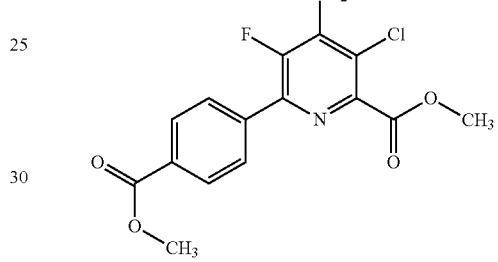
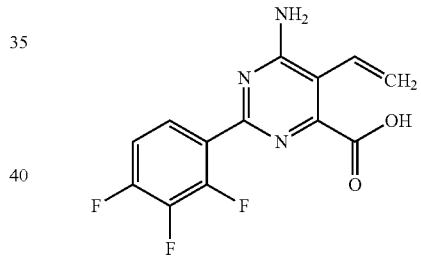
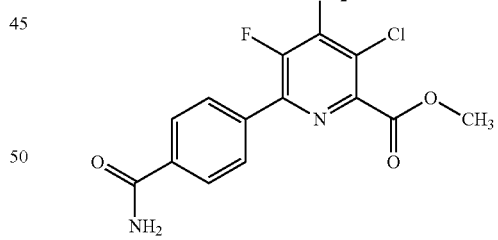
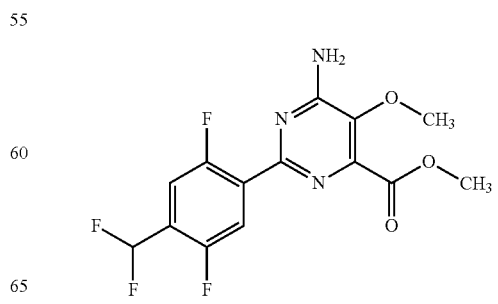

301
-continued
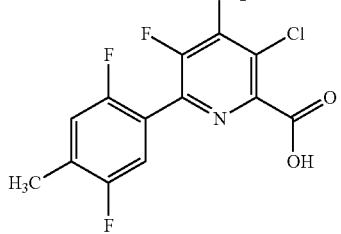
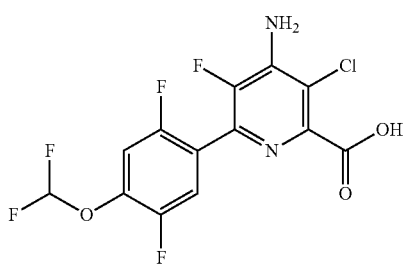
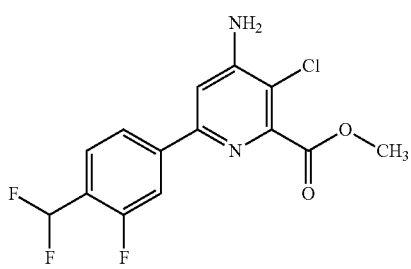
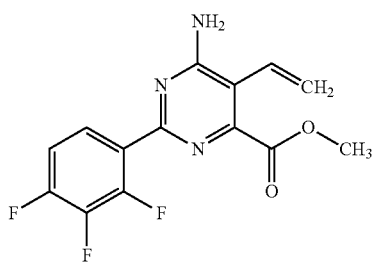
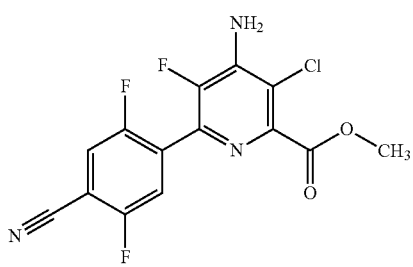
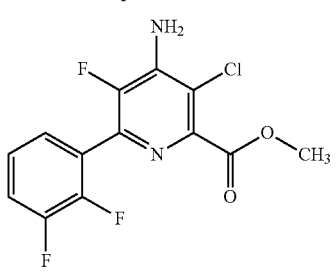
302
-continued
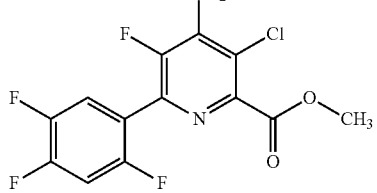
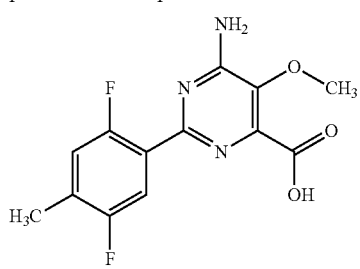
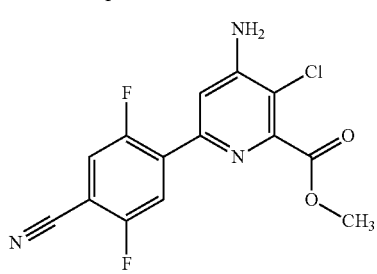
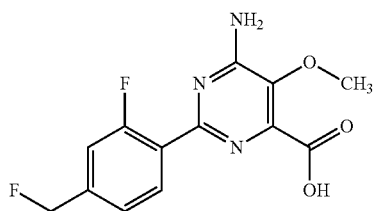
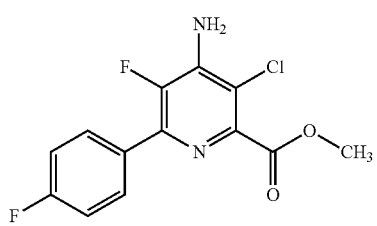
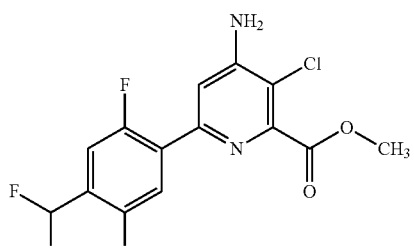
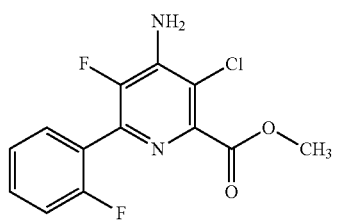

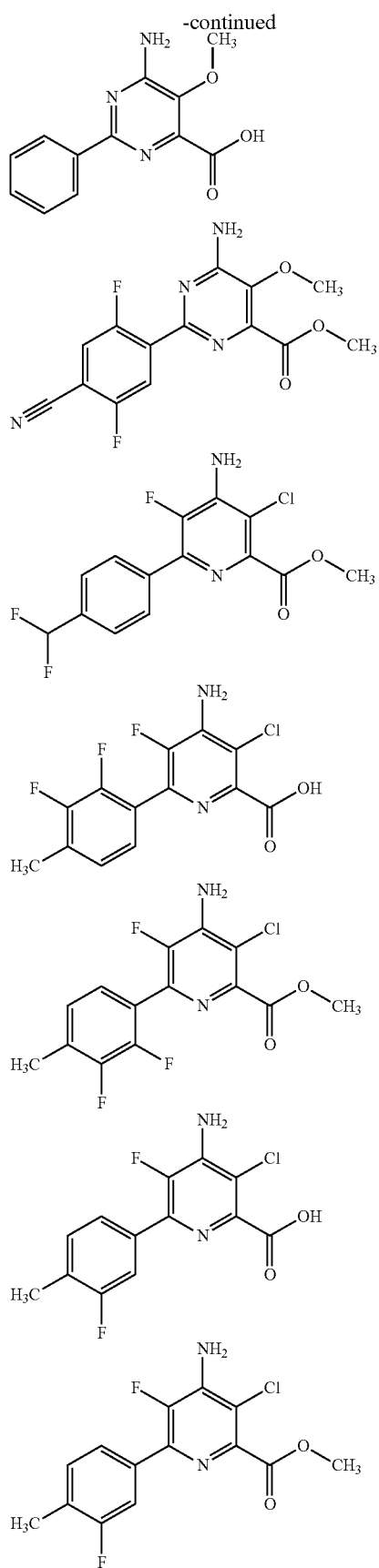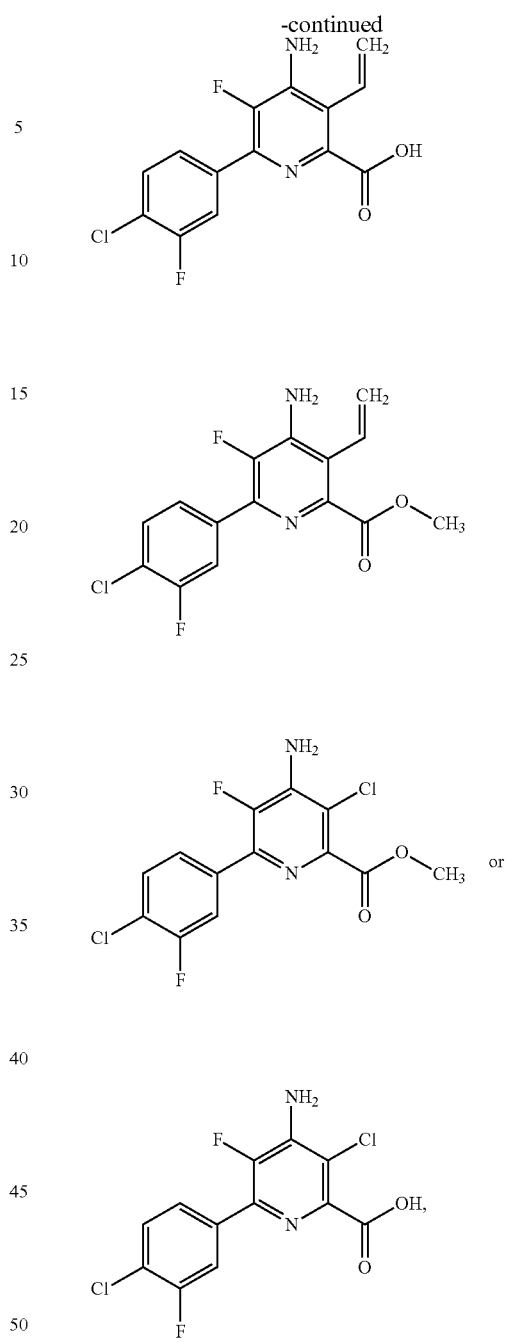

or an N-oxide or agriculturally acceptable salt thereof.

27. A herbicidal composition comprising the compound of claim 1 or an N-oxide or agriculturally acceptable salt thereof, and an agriculturally acceptable adjuvant or carrier.

28. The composition of claim 27, further comprising at one additional herbicidal compound.

29. The composition of claim 27 or 28, further comprising a safener.

30. A method for controlling undesirable vegetation, which comprises applying the compound of claim 1, or the composition of claim 27.

* * * * *